United States Patent
Li et al.

(10) Patent No.: US 10,344,037 B2
(45) Date of Patent: Jul. 9, 2019

(54) USE OF THE FL-ONE HUNDRED EIGHTEEN CORE CHEMICAL STRUCTURE PLATFORM TO GENERATE FL-ONE HUNDRED EIGHTEEN DERIVATIVES FOR TREATMENT OF HUMAN DISEASE

(71) Applicants: Canget Bio Tekpharma, LLC, Buffalo, NY (US); Xiang Ling, Buffalo, NY (US); Fengzhi Li, Buffalo, NY (US)

(72) Inventors: Fengzhi Li, Buffalo, NY (US); Xiang Ling, Buffalo, NY (US)

(73) Assignee: Canget BioTek Pharma LLC, Buffalo, NY (US)

( * ) Notice: Subject to any disclaimer, the term of this patent is extended or adjusted under 35 U.S.C. 154(b) by 150 days.

(21) Appl. No.: 15/128,977

(22) PCT Filed: Mar. 24, 2015

(86) PCT No.: PCT/US2015/022095
§ 371 (c)(1),
(2) Date: Sep. 25, 2016

(87) PCT Pub. No.: WO2015/148415
PCT Pub. Date: Oct. 1, 2015

(65) Prior Publication Data
US 2018/0170944 A1    Jun. 21, 2018

Related U.S. Application Data

(60) Provisional application No. 61/970,572, filed on Mar. 26, 2014.

(51) Int. Cl.
| | | |
|---|---|---|
| C07D 491/22 | (2006.01) | |
| C07D 491/00 | (2006.01) | |
| A61K 45/06 | (2006.01) | |
| A61K 31/4745 | (2006.01) | |
| A61P 35/00 | (2006.01) | |
| A61K 9/19 | (2006.01) | |
| A61K 47/02 | (2006.01) | |
| A61K 47/10 | (2017.01) | |
| A61K 47/20 | (2006.01) | |
| A61K 47/34 | (2017.01) | |
| A61K 47/38 | (2006.01) | |
| A61K 47/40 | (2006.01) | |

(52) U.S. Cl.
CPC .............. *C07D 491/22* (2013.01); *A61K 9/19* (2013.01); *A61K 31/4745* (2013.01); *A61K 45/06* (2013.01); *A61K 47/02* (2013.01); *A61K 47/10* (2013.01); *A61K 47/20* (2013.01); *A61K 47/34* (2013.01); *A61K 47/38* (2013.01); *A61K 47/40* (2013.01); *A61P 35/00* (2018.01)

(58) Field of Classification Search
CPC ............................ C07D 491/22; C07D 491/00
See application file for complete search history.

(56) References Cited

U.S. PATENT DOCUMENTS

| | | | | |
|---|---|---|---|---|
| 5,759,767 A | * | 6/1998 | Lakowicz ............ | A61K 41/008 250/200 |
| 2003/0148996 A1 | * | 8/2003 | Rubinfeld ............ | A61K 9/0019 514/58 |
| 2009/0191266 A1 | | 7/2009 | Vandecruys et al. | |
| 2014/0066470 A1 | * | 3/2014 | Li ........................ | A61K 31/475 514/279 |

FOREIGN PATENT DOCUMENTS

| | | | | |
|---|---|---|---|---|
| WO | WO-9104260 A2 | * | 4/1991 | ........... C07D 491/22 |
| WO | WO 95/32207 A1 | | 11/1995 | |
| WO | WO-2008070009 A2 | * | 6/2008 | ............. A61K 9/127 |

OTHER PUBLICATIONS

Arnot et al. J. Pharmacol. Toxicol. Methods, 1996, vol. 36, No. 1, Abstract.*
USPTO, International Search Report, in related application PCTUS15/022095, dated Jun. 18, 2015, 3 pages.
USPTO, Written Opinion of the International Search Authority, in related application PCTUS15/022095, dated Jun. 18, 2015, 9 pages.
Valenti et al, Novel 7-Alkyl Methylenedioxy-qamptothecin Derivatives Exhibit Increased Cytotoxicity and Induce Persistent Cleavable Complexes Both with Purified Mammalian Topoisomerase I and in Human Colon Carcinoma SW620 Cells, 1997, pp. 82-87, vol. 52 Issue 1, Molecular Pharmacology, available at molpharm.aspetjournals.org/content/52/1/82.full.pdf.
Ling et al, A novel small molecule FL118 that selectively inhibits survivin, MCL-1, XIAP and cIAP2 in a p53-independent manner, shows superior antitumor activity, Sep. 19, 2012, pp. 1-17, vol. 7, No. 9, PLOS ONE, available at journals.plos.org/plosone/article?id=10.1371/journal.pone.0045571.
Zhao et al, Antitumor activity of FL118, a survivin, Mcl-1, XIAP, and cIAP2 selective inhibitor, is highly dependent on is primary structure and steric configuration, Feb. 3, 2014, pp. 457-467, vol. 11, No. 2, Molecular Pharmaceutics, available at pubs.acs.org/doi/10.1021/mp4004282.
Takagi et al, Novel E-ring camptothecin keto analogues (S38809 and S39625) are stable, potent, and selective topoisomerase I inhibitors without being substrates of drug efflux transporters, Dec. 2007, pp. 3229-3238, vol. 6, No. 12, Molecular Cancer Therapeutics, available at mct.aacrjournals.org/content/6/12/3229.full-text.pdf.

(Continued)

*Primary Examiner* — Samira J Jean-Louis
(74) *Attorney, Agent, or Firm* — D'Hue Law LLC; Cedric A. D'Hue

(57) ABSTRACT

Described herein, are FL118 core structure platform compounds, matter of compositions, formulation, methods and uses for treating cancer or other human diseases. Chemical modifications of the FL118 structure are employed alone or in combination with other anti-cancer agents to preclude or reverse refractory cancer phenotypes and for unique personalized cancer treatment (personalized medicine or as Obama called precision medicine) through application of a series of structural relevant individual FL118 platform-derived analogs.

12 Claims, 26 Drawing Sheets

(56) References Cited

OTHER PUBLICATIONS

Lansiaux et al, Novel stable camptothecin derivatives replacing the E-ring lactone by a ketone function are potent inhibitors of topoisomerase I and promising antitumor drugs, Aug. 2007, pp. 311-319, vol. 72, No. 2, Molecular Pharmacology, available at molpharm.aspetjournals.org/content/72/2/311.

European Patent Office, European Search Report, in related application EPO 15 769 768.1, dated Jan. 22, 2018, 7 pages.

State Intellectual Property Office of the People's Republic of China, Notification of the First Office Action, in related application CN 201580024524.7, dated Mar. 20, 2018, 18 pages.

State Intellectual Property Office of the People's Republic of China, Search Report, in related application CN 201580024524.7, dated Mar. 20, 2018, 4 pages.

State Intellectual Property Office of the People's Republic of China, Notification of the Second Office Action, in related application CN 201580024524.7, dated Oct. 19, 2018, 14 pages.

\* cited by examiner

FIG. 28

USE OF THE FL-ONE HUNDRED EIGHTEEN CORE CHEMICAL STRUCTURE PLATFORM TO GENERATE FL-ONE HUNDRED EIGHTEEN DERIVATIVES FOR TREATMENT OF HUMAN DISEASE

CROSS-REFERENCE TO RELATED APPLICATIONS

The present application claims priority as a U.S. national stage application of International Application No. PCT/US2015/022095, filed on Mar. 24, 2015, which claims priority to U.S. Provisional Patent Application Ser. No. 61/970,572 filed on Mar. 26, 2014, the entire contents of which are incorporated herein by reference in their entirety.

STATEMENT OF GOVERNMENT-SPONSORED RESEARCH

This invention was made in part with United States government support under Grant Number R44CA176937 awarded by the National Cancer Institute (NCI) to Canget BioTekpharma. In addition, the data of pancreatic cancer patient-derived xenograft tumor related to FL118 is from the support of NCI R21 grant (CA180764) and the data of FL118 biochemical targets identification using FL118 affinity column and protein microarray was supported by DOD grant (PC110408). The United States government has certain rights in the invention.

FIELD OF THE INVENTION

The present disclosure relates generally to the protection and demonstration of the FL118 core chemical structure platform for generation of unique FL118 analogues for the treatment and prevention of disease associated with treatment-resistant pathways and associated target markers. In particular, the present technology relates to therapeutic indications and methods for the treatment or prevention of refractory cancer, and other disorders.

SUMMARY OF THE INVENTION

In one aspect, the present disclosure provides a method of treating a disease in a subject or a biological condition associated with the disease in the subject, which entails administering to the subject a therapeutically effective amount of a compound of Formula 1, a tautomer of the compound, isomers of the compound, a pharmaceutically acceptable salt of the compound, a pharmaceutically acceptable salt of the tautomer, a pharmaceutically acceptable salt of the isomer, or a mixture thereof, wherein Formula 1 has the following formula:

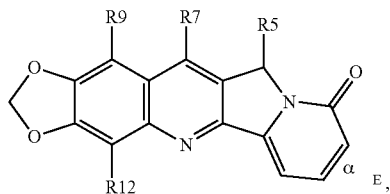

Formula 1 and wherein fused ring E is in the α position, and further wherein E is independently selected from the group consisting of group I structures, group II structures and group III structures:

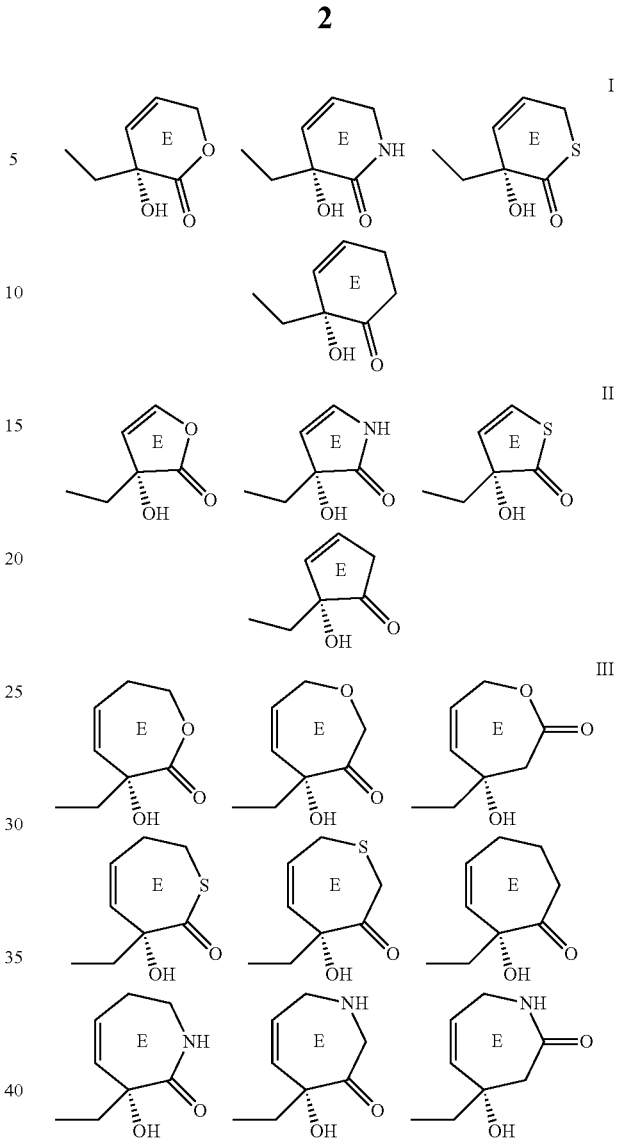

and wherein $R^5$, $R^7$, $R^9$ and $R^{12}$ are independently selected from the group consisting of H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, $—NHC(O)NH_2$, $—C(O)CH_3$, $—CO_2CH_3$, $—C(O)N(CH_2)_2$, and group IV structures:

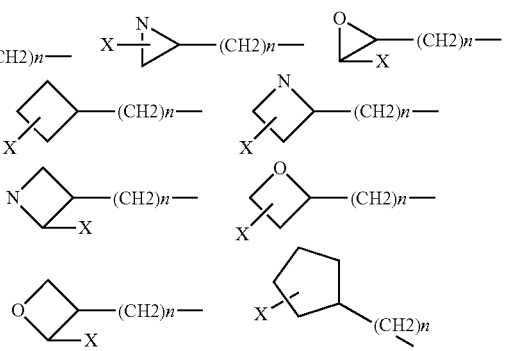

IV

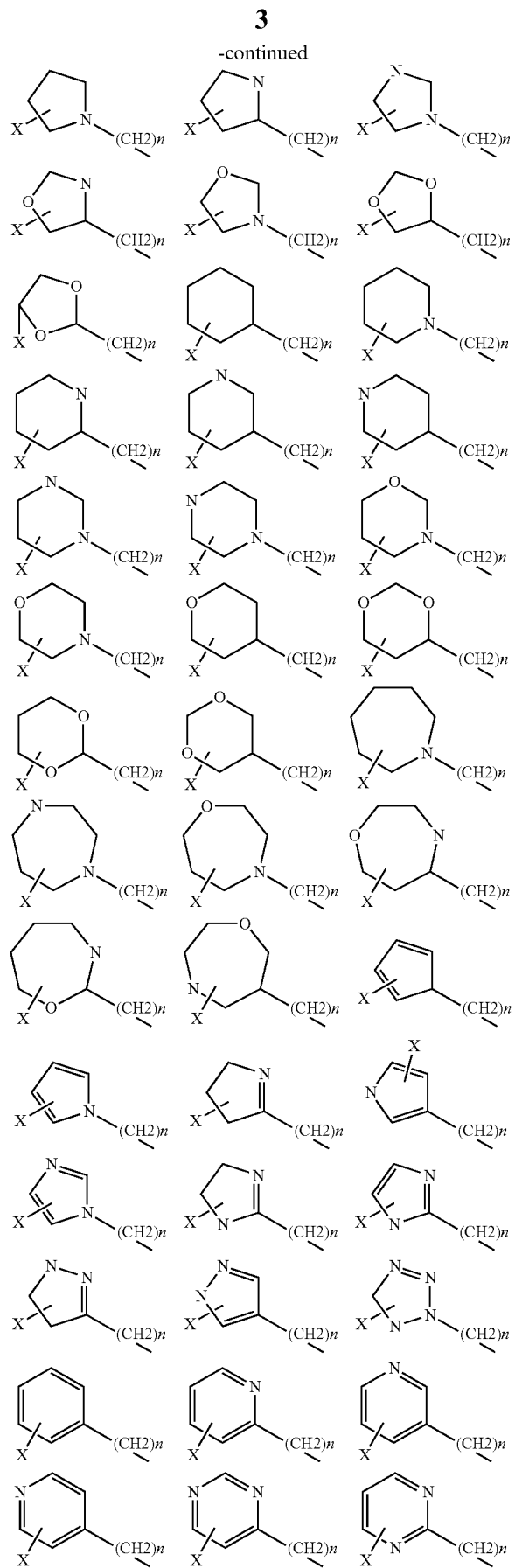

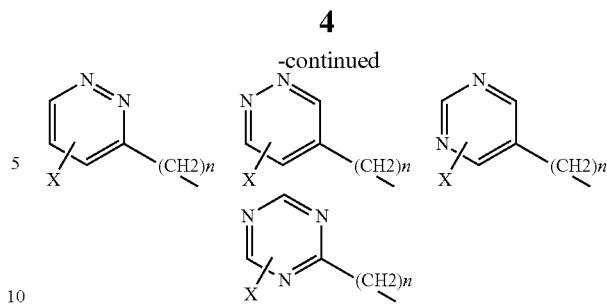

wherein X is independently selected from the group consisting of H—, F—, Cl—, Br—, I—, ClCH$_2$—, BrCH$_2$—, HO—, HONH—, CH$_3$O—, HOCH$_2$—, NH$_2$—, NH$_2$CH$_2$—, CH$_3$, —HOCH$_2$O, and wherein n is 0 or any integer from 1-15.

In illustrative embodiments, at least two functional groups selected from the group consisting of $R^5$, $R^7$, $R^9$ and $R^{12}$ are H, and wherein at least one functional group selected from the group consisting of $R^5$, $R^7$, $R^9$ and $R^{12}$ is selected from the group IV structures, and further wherein at least one functional group selected from the group consisting of $R^5$, $R^7$, $R^9$ and $R^{1-2}$ is selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_2$)$_2$. In illustrative embodiments, the compound of Formula 1 is administered orally, intravenously, subcutaneously, transdermally, intraperitoneally, or by inhalation. In illustrative embodiments, the disease is selected from the group consisting of a neoplastic disease, an autoimmune disease, restenosis, and/or any other human disease relevant to cell proliferation.

In some embodiments, the disease is one or more cancers selected from the group consisting of solid tumors, blood cancers, fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, head and neck cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, glioblastoma, glioblastoma multiforme, astrocytoma, medulloblastoma, craniopharyngioma, ependymoma, pinealoma, hemangioblastoma, acoustic neuroma, oliodendroglioma, Schwannoma, meningioma, melanoma, neuroblastoma, retinoblastoma, leukemia, acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, lymphoma, Hodgkin's disease, non-Hodgkin's disease, multiple myeloma and thymoma or any combination thereof.

In suitable embodiments, the one or more cancers are one or more metastatic cancers, primary tumors, refractory cancers, progressive cancers, invasive cancers, solid tumors, disseminated tumors or hematological cancers. In illustrative embodiments, the one or more cancers are refractory to one or more therapeutic indications. In illustrative embodiments, the refractory cancer phenotype comprises expression of one or more resistance markers selected from the group consisting of survivin, Mcl-1, XIAP, cIAP2, ABC transporter proteins, hypoxia inducing factor 1α (HIF-1α), Hdm2, HdmX, and p53. In illustrative embodiments, the ABC transporter proteins are selected from the group consisting of ABCG2, ABCC4, MDR1 and MRP1. In illustrative embodiments, the p53 is wild-type, null or a p53 mutant, or wherein there is an aberration in a canonical p53 pathway, or any combination thereof.

In illustrative embodiments, the compound of Formula 1 precludes acute treatment resistance. In some embodiments, the compound of Formula 1, the tautomer of the compound, the isomer of the compound, the pharmaceutically acceptable salt of the compound, the pharmaceutically acceptable salt of the tautomer, the pharmaceutically acceptable salt of the isomer or the mixture thereof, is administered to the subject separately, sequentially or simultaneously with one or more agents selected from the group consisting of chemotherapeutic agents, chemopreventive agents, are derived from natural plants, are derived from non-plants, curcumin, resveratrol, vitamin D3, vintain A, vitamin E, vitamin C, isothiocyanates (ITCs), allyl isothiocyanate (AITC), silibinin (silybin), Sulindac, selenium-containing compounds, Methylseleninic acid, *Amoora rohituka*-derived AMR analogs, AMR-Me, AMR-MeOAc, teramoprocol, celecoxib, imatinib, quercetin, Epigallocatechin-3-gallate (EGCG), Deguelin, 3,3'-Diindolylmethane (DIM), Emodin, Genistein, Tolfenamic acid, Simvastatin, Gambogic acid, Docosahexaenoic acid, Ursolic acid, Oleanolic acid, Bufalin, Sulforaphane, Noscapine, Indomethacin (indomethacin), Lupeol, Decursin, Avicin D, Ciglitazone, Bevacizumab (Avastin), crolibulin, Baicalein, Paxilline, Purvalanol A, NU6140, Ardisianone, NVP-BGT226, HDAC inhibitors, MS-275/Entinostat, SAHA, Anacardic acid, Diterpenes, Bufotalin, Withaferin A, Plumbagin, Flavokawain A, Flavokawain B, Ponicidin, Escin, Kuguacin J, LQB-118, Crotepoxide, Kuguaglycoside C, Destruxin B, Evodiamine, Sesamin, prostanoids, endothelin antagonists, cytoplasmic kinase inhibitors, receptor kinase inhibitors, endothelin receptor antagonists, ambrisentan, bosentan, and sitaxsentan, PDE5 (PDE-V) inhibitors, sildenafil, tadalafil, and vardenafil, calcium channel blockers, amlodipine, felodipine, varepamil, diltiazem, menthol, prostacyclin, treprostinil, iloprost, beraprost, nitric oxide, oxygen, heparin, warfarin, diuretics, digoxin, cyclosporins, cyclosporin A, CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, antibodies to CD40, antibodies to gp39, CD154, CD40 fusion proteins, gp39 fusion proteins, CD401g, CD8gp39, nuclear translocation inhibitors of NF-kappa B function, deoxyspergualin (DSG), cholesterol biosynthesis inhibitors, HMG CoA reductase inhibitors, lovastatin, simvastatin, non-steroidal anti-inflammatory drugs (NSAIDs), ibuprofen, aspirin, acetaminophen, leflunomide, deoxyspergualin, cyclooxygenase inhibitors, celecoxib, steroids, prednisolone, dexamethasone, gold compounds, beta-agonists, salbutamol, LABAs, salmeterol, leukotriene antagonists, montelukast, antiproliferative agents, methotrexate, FK506, tacrolimus, Prograf, mycophenolate mofetil, cytotoxic drugs, azathioprine, VP-16, etoposide, fludarabine, doxorubin, adriamycin, amsacrine, camptothecin, cytarabine, gemcitabine, fluorodeoxyuridine, melphalan, cyclophosphamide, antimetabolites, methotrexate, topoisomerase inhibitors, camptothecin, DNA alkylators, cisplatin, kinase inhibitors, sorafenib, microtubule poisons, paclitaxel, TNF-α inhibitors, tenidap, anti-TNF antibodies, soluble TNF receptors, hydroxy urea, rapamycin, sirolimus, and Rapamune, or any combination thereof.

In illustrative embodiments, the compound of Formula 1 is formulated into nanoparticles. In illustrative embodiments, the salt is a chloride, phosphate, mesylate, bismesylate, tosylate, lactate, tartrate, malate, bis-acetate, or citrate salt. In illustrative embodiments, the compound of Formula 1, the tautomer of the compound, the isomer of the compound, the pharmaceutically acceptable salt of the compound, the pharmaceutically acceptable salt of the tautomer, the pharmaceutically acceptable salt of the isomer or the mixture thereof, is administered in a total daily dosage from about 0.01 mg/kg to about 10 mg/kg. In illustrative embodiments, the compound of Formula 1, the tautomer of the compound, the isomer of the compound, the pharmaceutically acceptable salt of the compound, the pharmaceutically acceptable salt of the tautomer, the pharmaceutically acceptable salt of the isomer or the mixture thereof, is administered from one to five times weekly.

In illustrative embodiments, the compound of Formula 1, the tautomer of the compound, the isomer of the compound, the pharmaceutically acceptable salt of the compound, the pharmaceutically acceptable salt of the tautomer, the pharmaceutically acceptable salt of the isomer or the mixture thereof, is administered in unit dosage form, wherein the unit dose comprises from about 0.01 mg/kg to about 1 mg/kg of the compound, tautomer, and/or salts based on the subject's body weight, or from about 0.1 mg/kg to about 20 mg/kg of the compound, tautomer, and/or salts.

In illustrative embodiments, the unit dose is sufficient to provide: (a) a $C_{max}$ of about 10 to 400 ng/mL of the compound in a subject's plasma or a $C_{max}$ of about 10 to 400 ng/mL of the compound in the subject's blood when it is administered to the subject; and/or (b) about 1 to 50 ng/mL of the compound in a subject's plasma 12 hours after administration or about 1 to 50 ng/mL of the compound in the subject's blood 12 hours after administration to the subject; and/or (c) about 0 to 5 ng/mL of the compound in a subject's plasma 24 hours after administration or about 0 to 5 ng/mL of the compound in the subject's blood 24 hours after administration to the subject; and/or (d) active gradients of Formula 1 sustain 1-25 ng/mL (gram) in tumor within 48 hours after administration to the subject. In illustrative embodiments, the subject is a human subject.

In some embodiments, the compound of Formula 1 is a compound of Formula 2:

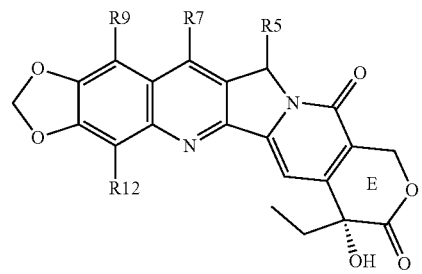

Formula 2

In illustrative embodiments, the compound of Formula 1 is a compound of any of the embodiments described herein.

In one aspect, the present disclosure provides a compound of Formula 1, a tautomer of the compound, an isomer of the compound, a pharmaceutically acceptable salt of the compound, a pharmaceutically acceptable salt of the tautomer, a pharmaceutically acceptable salt of the isomer, or a mixture thereof, wherein Formula 1 has the following formula:

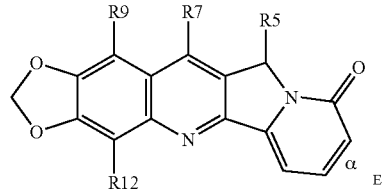

Formula 1 wherein fused ring E is in the α position, and wherein E is independently selected from the group consisting of group I structures, group II structures and group III structures:

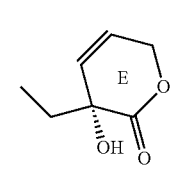
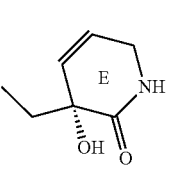
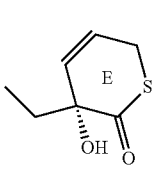
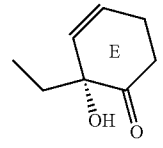

I

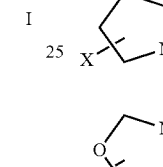
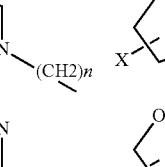

II

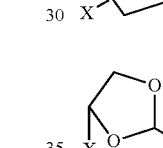

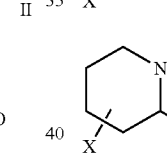
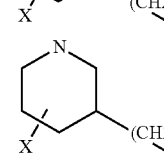
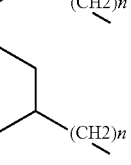

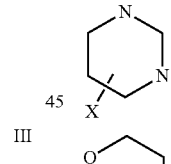

III and wherein $R^5$, $R^7$, $R^9$ and $R^{12}$ are selected from the group consisting of H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, —C(O)N(CH$_2$)$_2$, and group IV structures:

IV

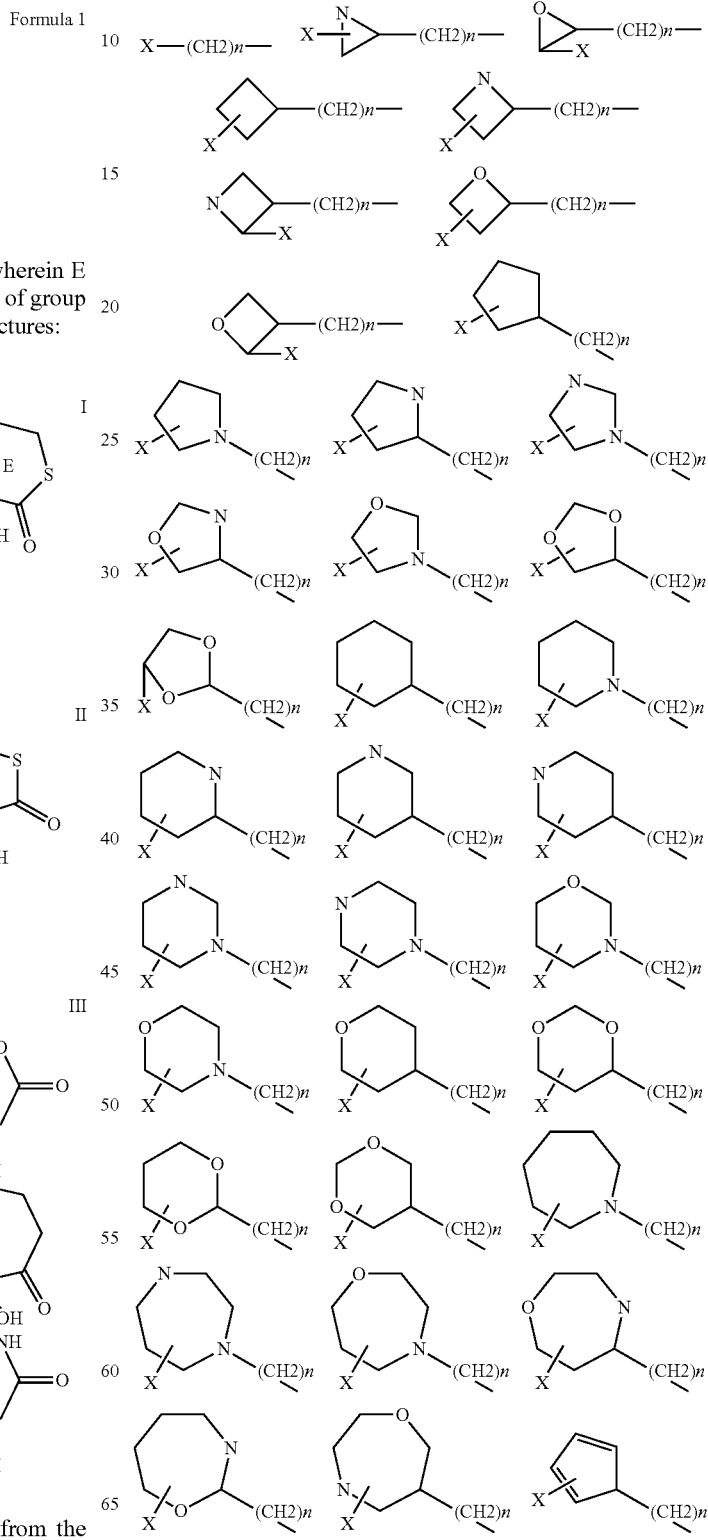

-continued

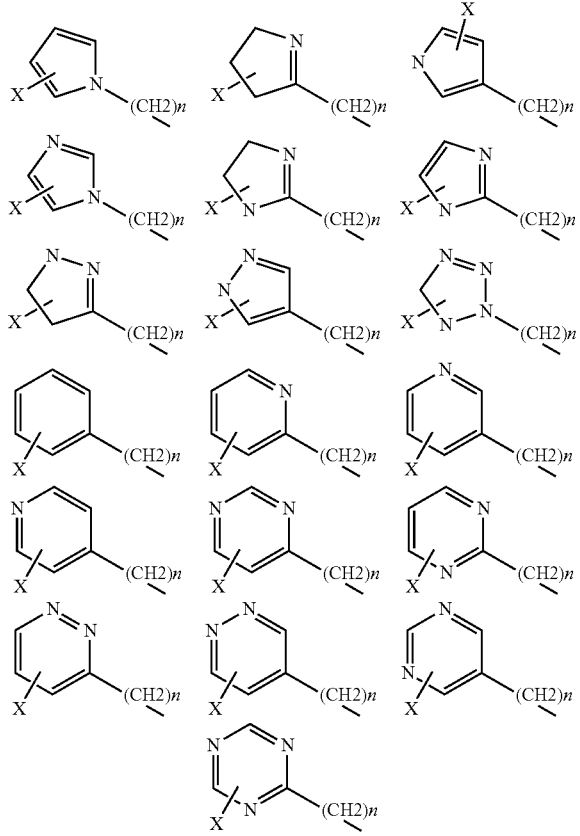

wherein X is independently selected from the group consisting of H—, F—, Cl—, Br—, I—, ClCH$_2$—, BrCH$_2$—, HO—, HONH—, CH$_3$O—, HOCH$_2$—, NH$_2$—, NH$_2$CH$_2$—, CH$_3$, —HOCH$_2$O, and wherein n is 0 or any integer from 1-15.

In illustrative embodiments, at least two functional groups selected from the group consisting of R$^5$, R$^7$, R$^9$ and R$^{12}$ are H, and wherein at least one functional group selected from the group consisting of R$^5$, R$^7$, R$^9$ and R$^{12}$ is selected from the group IV structures, and further wherein at least one functional group selected from the group consisting of R$^5$, R$^7$, R$^9$ and R$^{1-2}$ is selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_2$)$_2$. In illustrative embodiments, the salt is a chloride, phosphate, mesylate, bismesylate, tosylate, lactate, tartrate, malate, bis-acetate, chloride or citrate salt. In some embodiments, the compound of Formula 1 is a compound of Formula 2:

Formula 2

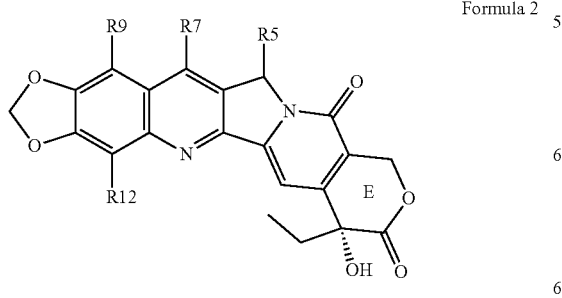

In illustrative embodiments, the compound of Formula 1 is a compound of any of the embodiments described herein.

In illustrative embodiments, a pharmaceutical composition is provided herein, which comprises the compound, the tautomer, the isomer, the pharmaceutically acceptable salt of the compound, the pharmaceutically acceptable salt of the tautomer, the pharmaceutically acceptable salt of the isomer or the mixture thereof of a compound of Formula 1, which further includes a pharmaceutically acceptable carrier. In illustrative embodiments, the present disclosure provides for the use of an active ingredient for the preparation of pharmaceutical compositions for treating a neoplastic disease in a subject or a biological condition associated with the neoplastic disease in the subject, wherein the active ingredient is a compound of Formula 1.

In one aspect, the present disclosure provides for the use of a compound of Formula 1, a tautomer of the compound, an isomer of the compound, a pharmaceutically acceptable salt of the compound, a pharmaceutically acceptable salt of the tautomer, a pharmaceutically acceptable salt of the isomer or a mixture thereof, for treating a disease in a subject or a biological condition associated with the disease in the subject, comprising: administering to the subject a therapeutically effective amount of the compound of Formula 1, the tautomer of the compound, the isomer of the compound, the pharmaceutically acceptable salt of the compound, the pharmaceutically acceptable salt of the tautomer, the pharmaceutically acceptable salt of the isomer or the mixture thereof, wherein Formula 1 has the following formula:

Formula 1

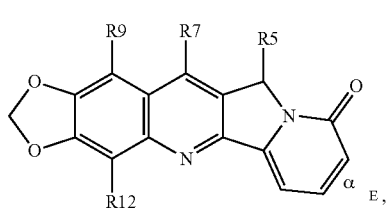

wherein fused ring E is in the α position, and wherein E is independently selected from the group consisting of group I structures, group II structures and group III structures:

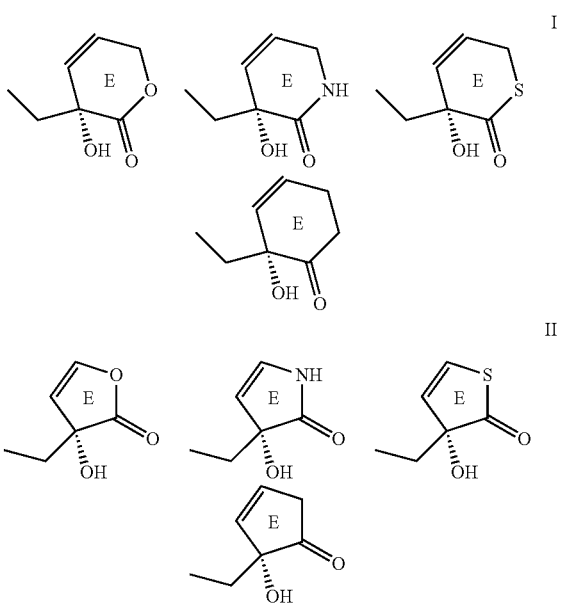

-continued

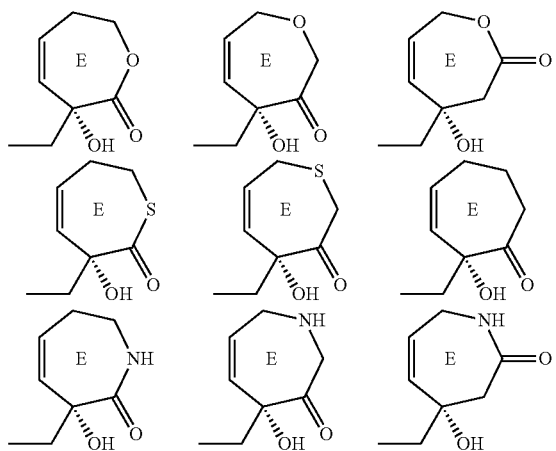

III and wherein $R^5$, $R^7$, $R^9$ and $R^{12}$ are selected from the group consisting of H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$CH$_2$—, CH$_3$NH—, (CH$_3$)$_2$N—, —NHC(O)NH$_2$, —C(O)CH$_3$, —CO$_2$CH$_3$, —C(O)N(CH$_2$)$_2$, and group IV structures:

IV

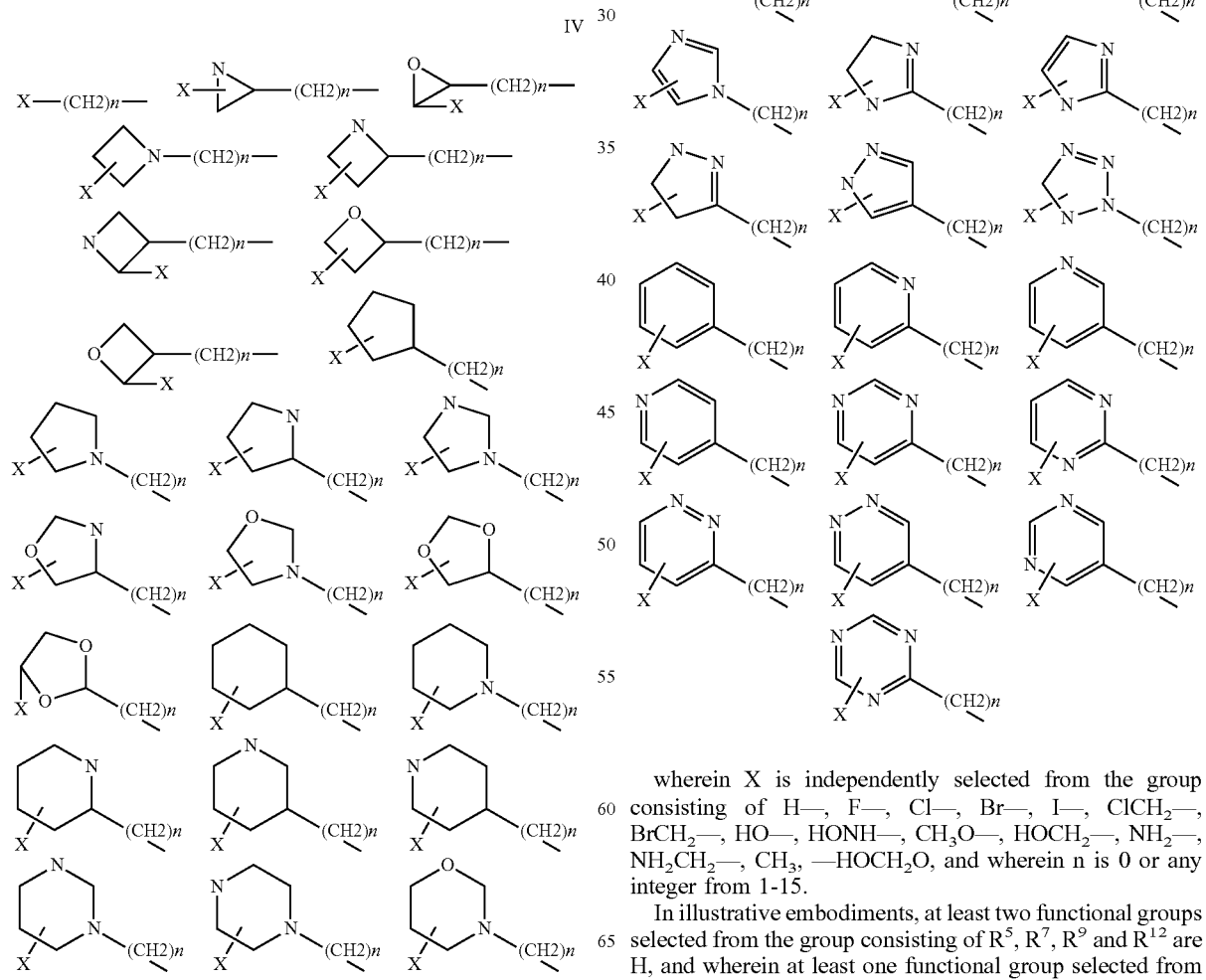

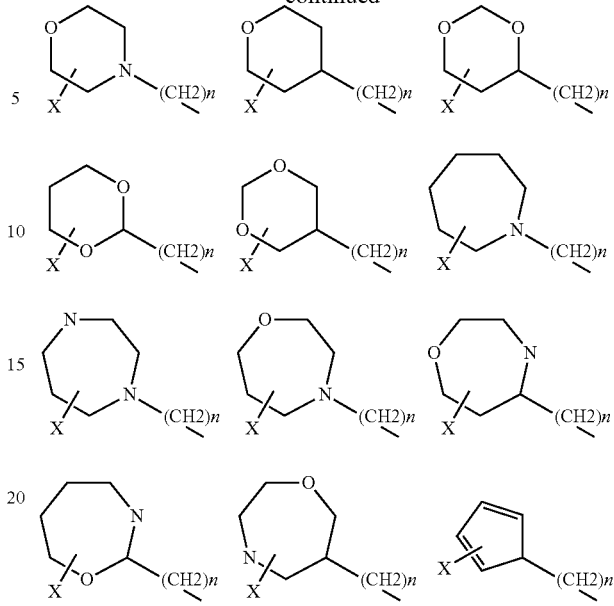

wherein X is independently selected from the group consisting of H—, F—, Cl—, Br—, I—, ClCH$_2$—, BrCH$_2$—, HO—, HONH—, CH$_3$O—, HOCH$_2$—, NH$_2$—, NH$_2$CH$_2$—, CH$_3$, —HOCH$_2$O, and wherein n is 0 or any integer from 1-15.

In illustrative embodiments, at least two functional groups selected from the group consisting of $R^5$, $R^7$, $R^9$ and $R^{12}$ are H, and wherein at least one functional group selected from the group consisting of $R^5$, $R^7$, $R^9$ and $R^{12}$ is selected from the group IV structures, and further wherein at least one functional group selected from the group consisting of $R^5$, $R^7$, $R^9$ and $R^{1-2}$ is selected from H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —$NHC(O)NH_2$, —$C(O)CH_3$, —$CO_2CH_3$, and —$C(O)N(CH_2)_2$. In illustrative embodiments, the compound of Formula 1 is administered orally, intravenously, subcutaneously, transdermally, intraperitoneally, or by inhalation. In illustrative embodiments, the disease is selected from the group consisting of a neoplastic disease, an autoimmune disease, restenosis, and/or any other human disease relevant to cell proliferation.

In illustrative embodiments, the disease is one or more cancers selected from the group consisting of solid tumors, blood cancers, fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, head and neck cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, glioblastoma, glioblastoma multiforme, astrocytoma, medulloblastoma, craniopharyngioma, ependymoma, pinealoma, hemangioblastoma, acoustic neuroma, oliodendroglioma, Schwannoma, meningioma, melanoma, neuroblastoma, retinoblastoma, leukemia, acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, lymphoma, Hodgkin's disease, non-Hodgkin's disease, multiple myeloma and thymoma or any combination thereof.

In illustrative embodiments, the one or more cancers are one or more metastatic cancers, primary tumors, refractory cancers, progressive cancers, invasive cancers, solid tumors, disseminated tumors or hematological cancers. In illustrative embodiments, the one or more cancers are refractory to one or more therapeutic indications. In illustrative embodiments, the refractory cancer phenotype comprises expression of one or more resistance markers selected from the group consisting of survivin, Mcl-1, XIAP, cIAP2, ABC transporter proteins, hypoxia inducing factor $1\alpha$ (HIF-$1\alpha$), Hdm2, HdmX, and p53. In illustrative embodiments, the ABC transporter proteins are selected from the group consisting of ABCG2, ABCC4, MDR1 and MRP1. In illustrative embodiments, the p53 is wild-type, null or a p53 mutant, or wherein there is an aberration in a canonical p53 pathway, or any combination thereof.

In illustrative embodiments, the compound of Formula 1 includes the treatment of one or more of inherent treatment resistance, constitutive treatment resistance, acquired treatment resistance and induced treatment resistance. In illustrative embodiments, the compound of Formula 1, the tautomer of the compound, the pharmaceutically acceptable salt of the compound, the pharmaceutically acceptable salt of the tautomer, or the mixture thereof, is administered to the subject separately, sequentially or simultaneously with one or more agents selected from the group consisting of chemotherapeutic agents, chemopreventive agents, derived from natural plants, derived from non-plants, curcumin, resveratrol, vitamin D3, vintain A, vitamin E, vitamin C, isothiocyanates (ITCs), allyl isothiocyanate (AITC), silibinin (silybin), Sulindac, selenium-containing compounds, Methylseleninic acid, Amoora rohituka-derived AMR analogs, AMR-Me, AMR-MeOAc, terameprocol, celecoxib, imatinib, quercetin, Epigallocatechin-3-gallate (EGCG), Deguelin, 3,3'-Diindolylmethane (DIM), Emodin, Genistein, Tolfenamic acid, Simvastatin, Gambogic acid, Docosahexaenoic acid, Ursolic acid, Oleanolic acid, Bufalin, Sulforaphane, Noscapine, Indomethacin (indomethacin), Lupeol, Decursin, Avicin D, Ciglitazone, Bevacizumab (Avastin), crolibulin, Baicalein, Paxilline, Purvalanol A, NU6140, Ardisianone, NVP-BGT226, HDAC inhibitors, MS-275/Entinostat, SAHA, Anacardic acid, Diterpenes, Bufotalin, Withaferin A, Plumbagin, Flavokawain A, Flavokawain B, Ponicidin, Escin, Kuguacin J, LQB-118, Crotepoxide, Kuguaglycoside C, Destruxin B, Evodiamine, and Sesamin, or any combination thereof.

In illustrative embodiments, the compound of Formula 1 is formulated into nanoparticles. In illustrative embodiments, the salt is a chloride, phosphate, mesylate, bismesylate, tosylate, lactate, tartrate, malate, bis-acetate, or citrate salt. In illustrative embodiments, the compound of Formula 1, the tautomer of the compound, the pharmaceutically acceptable salt of the compound, the pharmaceutically acceptable salt of the tautomer, or the mixture thereof is administered in a total daily dosage from about 0.01 mg/kg to about 10 mg/kg. In illustrative embodiments, the compound of Formula 1, the tautomer of the compound, the pharmaceutically acceptable salt of the compound, the pharmaceutically acceptable salt of the tautomer, or the mixture thereof, is administered from one to five times weekly.

In illustrative embodiments, the compound of Formula 1, the tautomer of the compound, the pharmaceutically acceptable salt of the compound, the pharmaceutically acceptable salt of the tautomer, or the mixture thereof, is administered in unit dosage form, wherein the unit dose comprises from about 0.01 mg/kg to about 1 mg/kg of the compound, tautomer, and/or salts based on the subject's body weight, or from about 0.1 mg/kg to about 10 mg of the compound, tautomer, and/or salts. In illustrative embodiments, the unit dose is sufficient to provide: (a) a $C_{max}$ of about 10 to 400 ng/mL of the compound in a subject's plasma or a $C_{max}$ of about 10 to 400 ng/mL of the compound in the subject's blood when it is administered to the subject; and/or (b) about 1 to 50 ng/mL of the compound in a subject's plasma 12 hours after administration or about 1 to 50 ng/mL of the compound in the subject's blood 12 hours after administration to the subject; and/or (c) about 0 to 5 ng/mL of the compound in a subject's plasma 24 hours after administration or about 0 to 5 ng/mL of the compound in the subject's blood 24 hours after administration to the subject; and/or (d) active gradients of Formula 1 sustain 1-25 ng/mL (gram) in tumor within 48 hours after administration to the subject. In illustrative embodiments, the subject is a human subject.

In illustrative embodiments, the compound of Formula 1 is a compound of Formula 2:

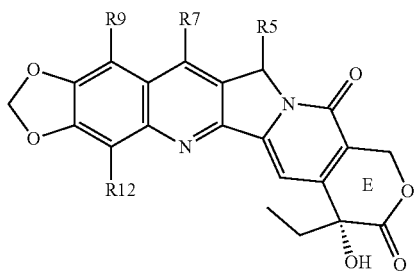

Formula 2

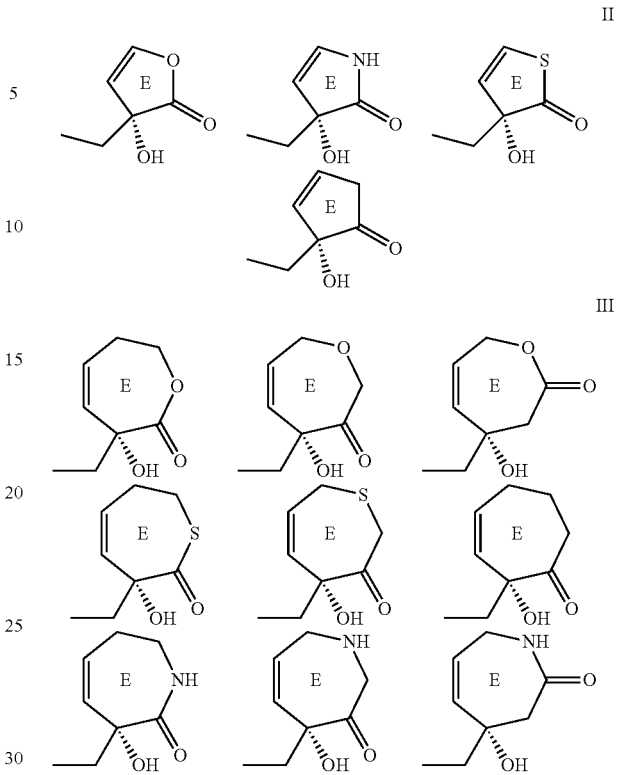

In illustrative embodiments, the compound of Formula 1 is a compound of any of the embodiments described herein.

In one aspect, the present invention provides for a formulation of the foregoing compounds, where the formulation comprises DMSO from about 0.1 to about 5% (w/v) in saline and a type of cyclodextrin such as hydroxypropyl-β-cyclodextrin from about 0.1 to about 2.5% (w/v) in saline. In some embodiments, the formulation is DMSO free. In illustrative embodiments, the formulation entails hydroxypropyl-β-cyclodextrin from 0.1 to 5% (w/v) in saline and from 0.1 to 10% propylene glycol (w/v) or polyethylene glycol 400 (w/v), or both, where the combination of the propylene glycol and polyethylene glycol is from 0.1 to 10% total (w/v).

In one aspect, the present invention entails a method of producing a DMSO-free formulation containing a compound of Formula 1, a tautomer of the compound, an isomer of the compound, a pharmaceutically acceptable salt of the compound, a pharmaceutically acceptable salt of the tautomer, a pharmaceutically acceptable salt of the isomer, or a mixture thereof, where Formula 1 is as follows:

Formula 1

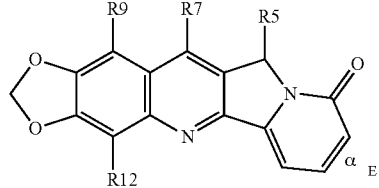

where fused ring E is in the α position, and where E is independently selected from the group consisting of group I structures, group II structures and group III structures as below:

I

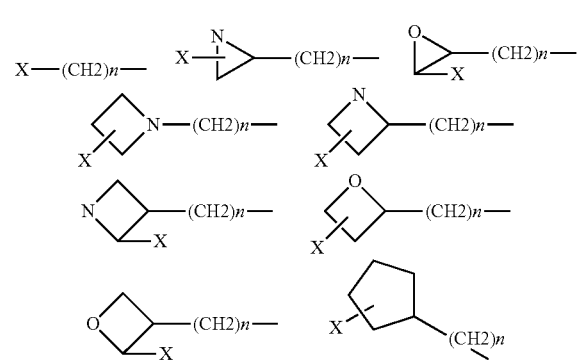

II

III and where $R^5$, $R^7$, $R^9$ and $R^{1-2}$ are selected from H—, F—, Cl—, Br—, I—, FCH$_2$—, ClCH$_2$—, BrCH$_2$—, HO—, HONH—, CH$_3$O—, HOCH$_2$—, NH$_2$—, NH$_2$CH$_2$—, (CH$_3$)$_2$N—, —NHC(O)NH$_2$, —C(O)CH$_3$, —CO$_2$CH$_3$, —C(O)N(CH$_2$)$_2$, and group IV structures as below:

IV

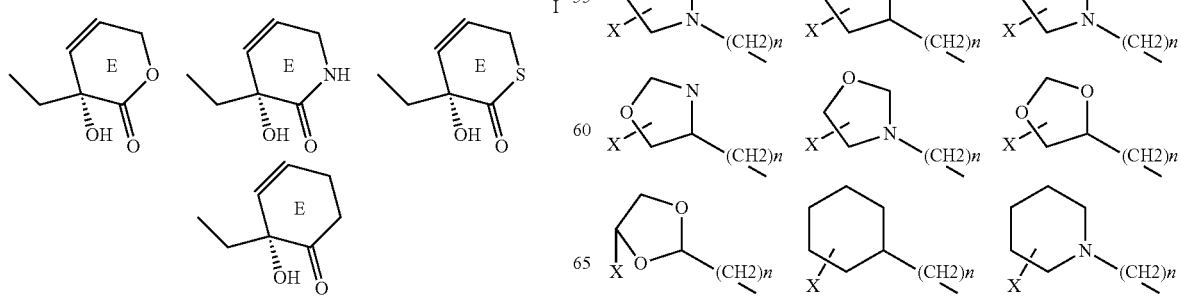

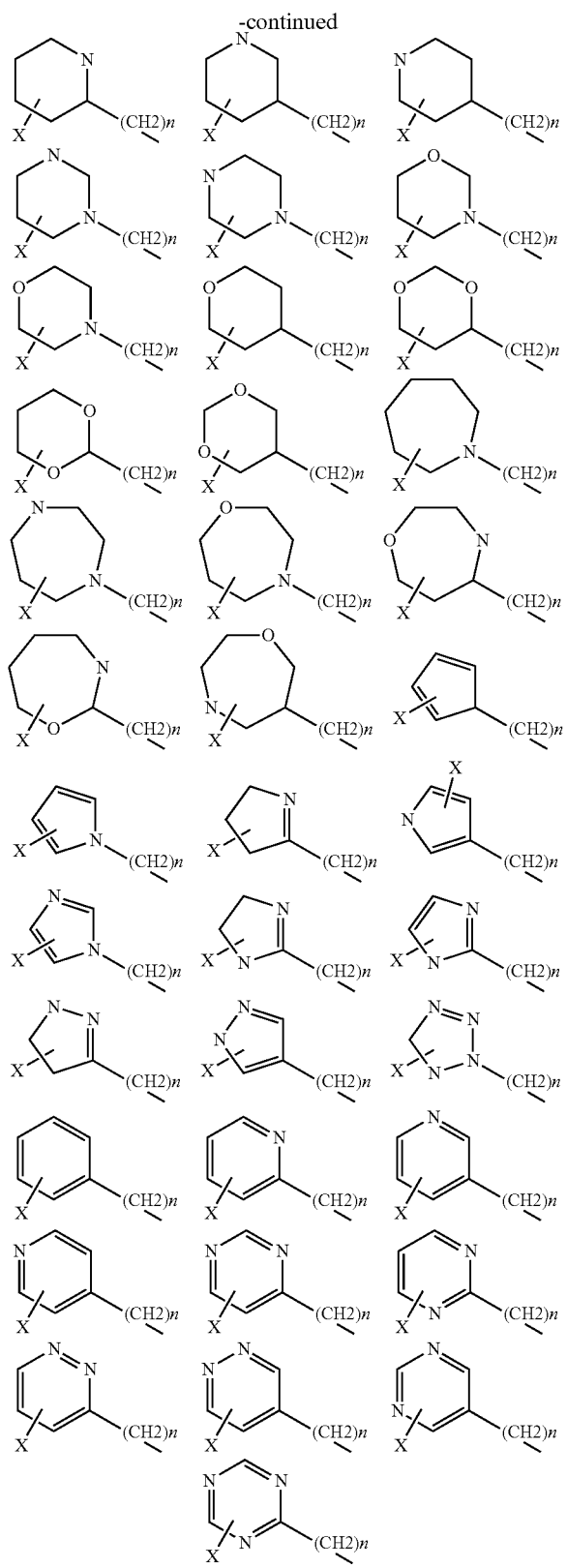

where X is independently selected from the group consisting of H—, F—, Cl—, Br—, I—, ClCH$_2$—, BrCH$_2$—, HO—, HONH—, CH$_3$O—, HOCH$_2$—, NH$_2$—, NH$_2$CH$_2$—, CH$_3$, —HOCH$_2$O, and where n is 0 or any integer from 1-15; the method having the steps of: (a) dissolving a type of cyclodextrin (e.g. β cyclodextrin, hydroxypropyl-β-cyclodextrin, sulfobutylether-β-cyclodextrin, but not limited to) in DMSO to form a solution; (b) adding the compound of Formula I to the solution; (c) lyophilizing the solution to produce a DMSO-free powder; (d) resuspending the powder in a solvent to produce the DMSO-free formulation; and (e) optionally adding an emulsifier.

In illustrative embodiments, the cyclodextrin is hydroxypropyl-β-cyclodextrin. In illustrative embodiments, the hydroxypropyl-β-cyclodextrin is present in the formulation at a final concentration of about from 0.1 to about 5% (w/v) in saline. In illustrative embodiments, the solvent is selected from one or more of propylene glycol, polyethylene glycol 300, and polyethylene glycol 400. In illustrative embodiments, the one or more of propylene glycol, polyethylene glycol 300, and polyethylene glycol 400 is present in the formulation at a concentration of about from 1 to about 10% total (w/v) in saline. In illustrative embodiments, the emulsifier is hydroxypropyl methylcellulose. In some embodiment, the hydroxypropyl methylcellulose is present in the formulation at a final concentration of about from 2 to about 5% (w/v). In illustrative embodiments, the formulation at a final concentration of about from 0.1 to about 5 mg/mL of Formula 1.

The foregoing summary is illustrative only and is not intended to be in any way limiting. In addition to the illustrative aspects, embodiments, and features described above, further aspects, embodiments, and features will become apparent by reference to the following drawings and the detailed description.

Individual tumor curves derived from individual mice are shown. A. Mice with FaDu head-&-neck tumor xenografts were first treated with irinotecan at its maximum tolerated dose (MTD, 100 mg/kg, IP) weekly for 4-5 times (black arrow). After tumor acquired irinotecan resistance, mice were then treated with FL118 (1.5 mg/kg, IP) with every other day for five times (q2d×5, red arrow). If tumors relapse, mice were treated with FL118 again (second cycle, red arrow). B. Mice with FaDu tumor xenografts were first treated with topotecan at its MTD (4 mg/kg, IP) via daily×5 schedules for 4 cycles (each black arrow is one cycle). After mice acquired topotecan resistance, mice were then treated with FL118 as in A (q2d×5, red arrow). C. Mice with SW620 CRC xenografts were first treated with irinotecan at its MTD (IP, weekly×4, black arrow). After tumor acquired irinotecan resistance, mice were then treated (IP) with FL118 at 1 mg/kg (⅔MTD) via q2d×5 (one red arrow as one cycle), and repeat the treatment every 3 weeks for 4 times regardless of tumor status. D. Mice with SW620 xenograft tumors were first treated with topotecan at its MTD. After tumor acquired topotecan resistance, mice were treated with FL118 as in A (q2d×5, red arrow) at 1 mg/kg (⅔MTD). Of note, 12 tumors were tested for A; 10 tumors were tested for B; 14 tumors were tested for C, and 18 tumors were tested for D. Representative tumor curves are shown in A to D. Tumor mice without drug treatment were sacrificed on day 12-15 due to tumor size over 1500 mm$^3$.

Figure 26:
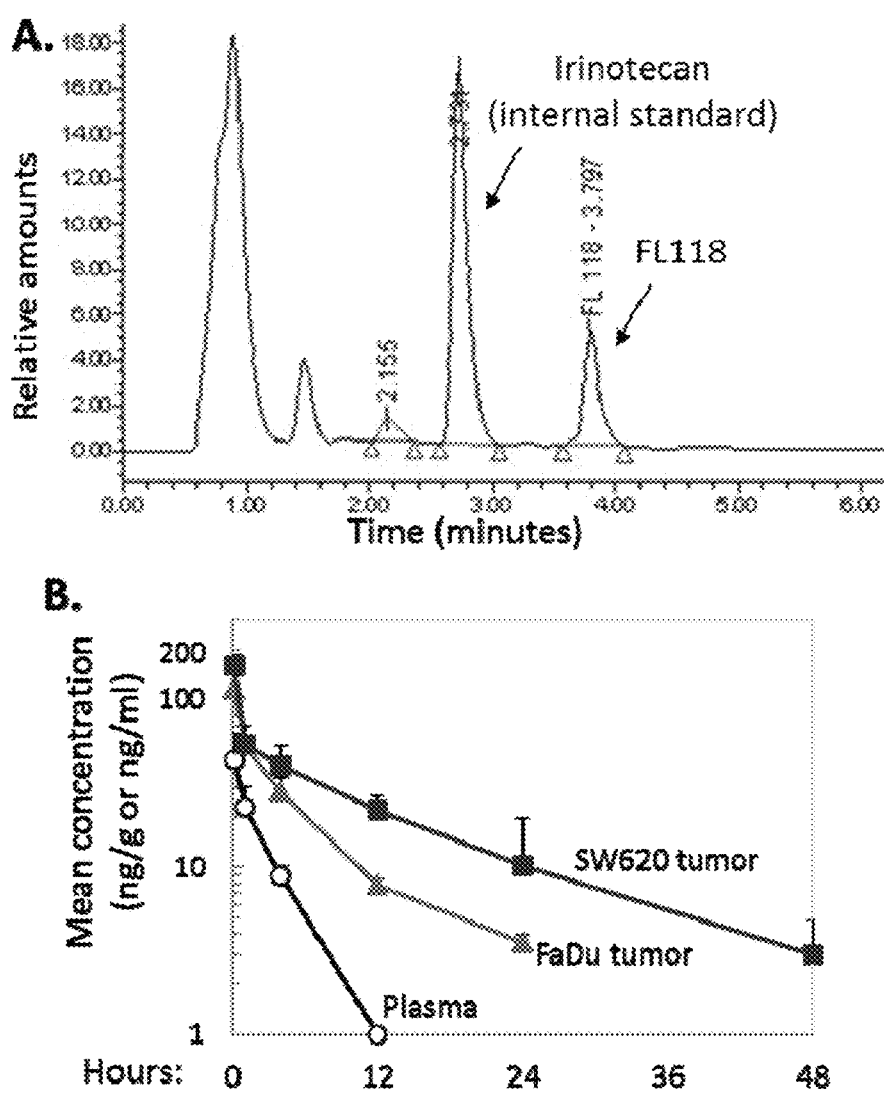

FIG. 26 shows that FL118 exhibits favorable pharmacokinetics profile after IV injection. A. The eluting profile of FL118 and internal standard irinotecan with the established gradient method. B. FL118 IV PK results: SCID mice were subcutaneously implanted with human FaDu (head & neck) and SW620 (colon) tumor. After the implanted tumor grew to 800-1000 mm$^3$, FL118 was IV injected at 1.5 mg/kg. Then, blood and tumor tissues were collected at 10 min, 1 h, 4 h, 12 h, 24, and 48 h. Three SCID mice at each time point were used. Standard deviation (SD) was analyzed using Excel software.

Figure 27:
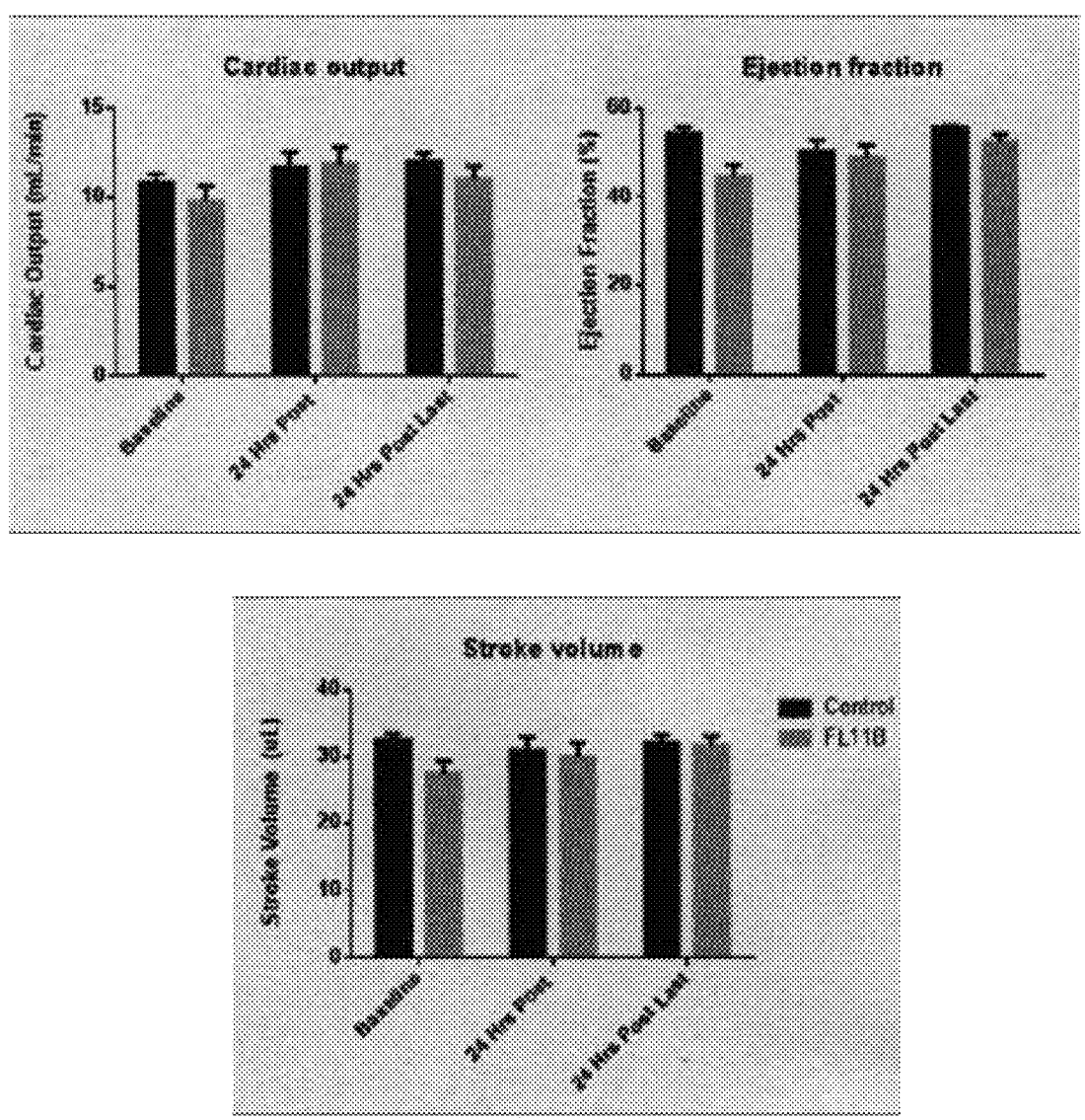

FIG. 27 shows the cardiac measurements related to cardiac output, ejection fraction and stroke volume after FL118 treatment. SCID mice are intravenously administrated with vehicle or FL118 at a half maximal tolerated dose (½MTD, 0.75 mg/kg) via a schedule of q2d×4. Cardiac function is measured at 24 hours after the first injection of vehicle or FL118 and at 24 hours after completion of the fourth injection of vehicle or FL118.

Figure 28:
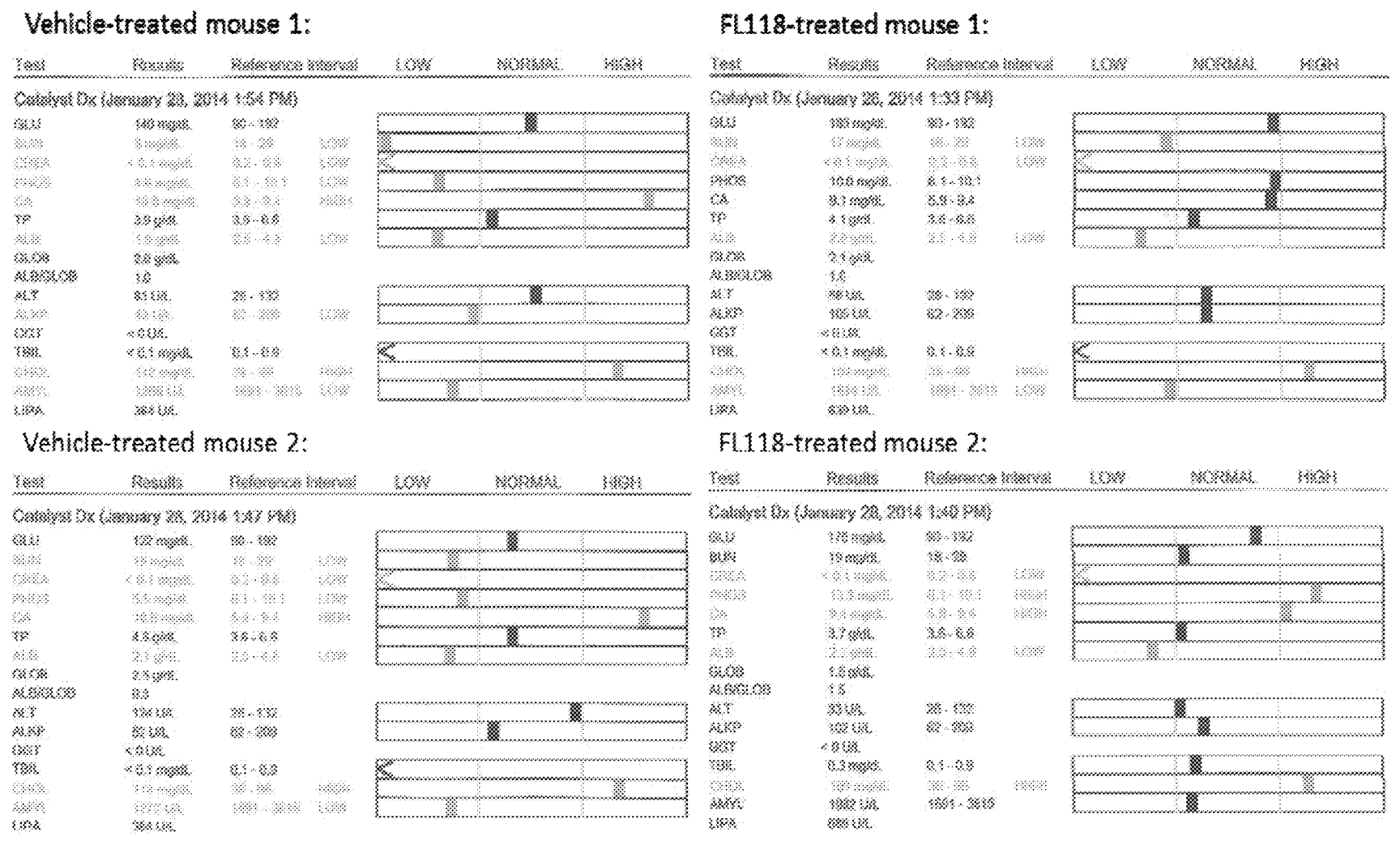

FIG. 28 shows the result derived from analysis of a comprehensive panel of parameters related to metabolic toxicity including renal and kidney toxicity. SCID mice are treated as described in FIG. 27. Blood samples are collected from control vehicle-treated SCID mice and FL118-treated mice after treatment, respectively. A panel of comprehensive parameters is analyzed as shown.

Figure 29:
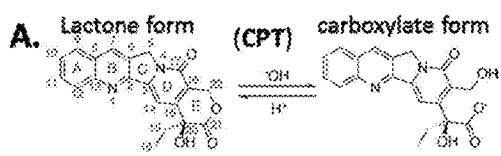
Figure 29:
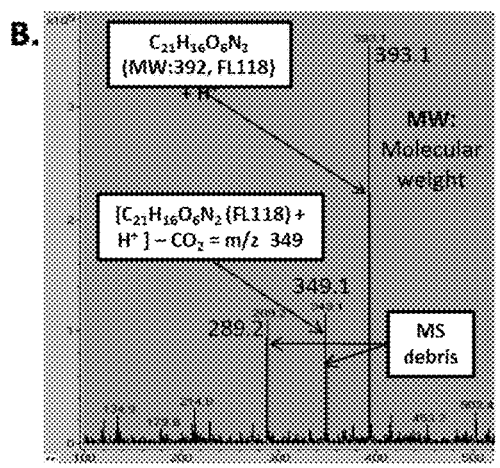
Figure 29:
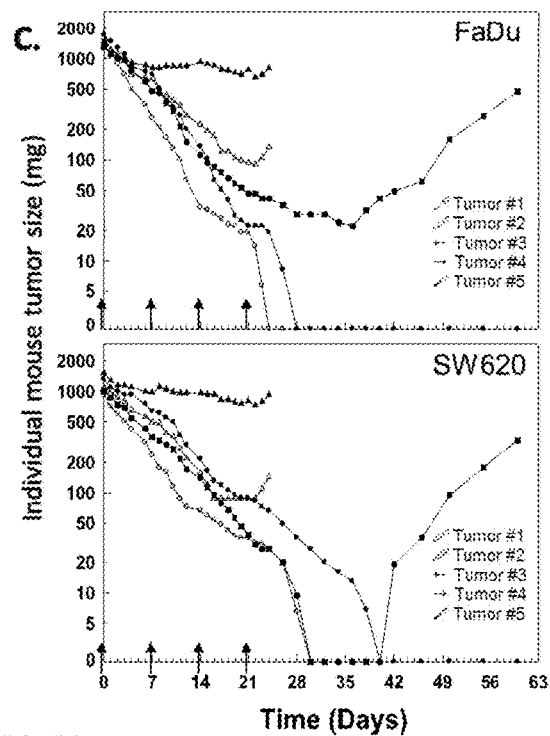

FIG. 29 shows the high stability of FL118 in its lactone ring and its antitumor activity. A shows the formula for reciprocally opening E-ring loop. B shows that FL118 in a formulated solution on shelf for 30 days at room temperature is then analyzed using mass spectrometry (MS) in a positive ion mode. The MS result shows that FL118 is fully in lactone form [MW 393=392 (FL118 MW)+1 (H MW)]. Of note, if carboxylate form exists, we should see a peak signal in a mass of 409 [392 (FL118 MW)+17 (OH MW)]. The masses 289.2 and 349.1 are FL118 debris found in the MS. MW: molecular weight. C. The formulated FL118 shows effectively eradicating large tumors after a long shelf storage period. Of note, the death of two mice on Day 37 with unknown reason is likely due to the rapid tumor breakdown at the early time of FL118 treatment, which is known to be able to cause a life-threatening complication termed Tumor Lysis Syndrome (TLS) due to massive cell necrosis.

Figure 30:
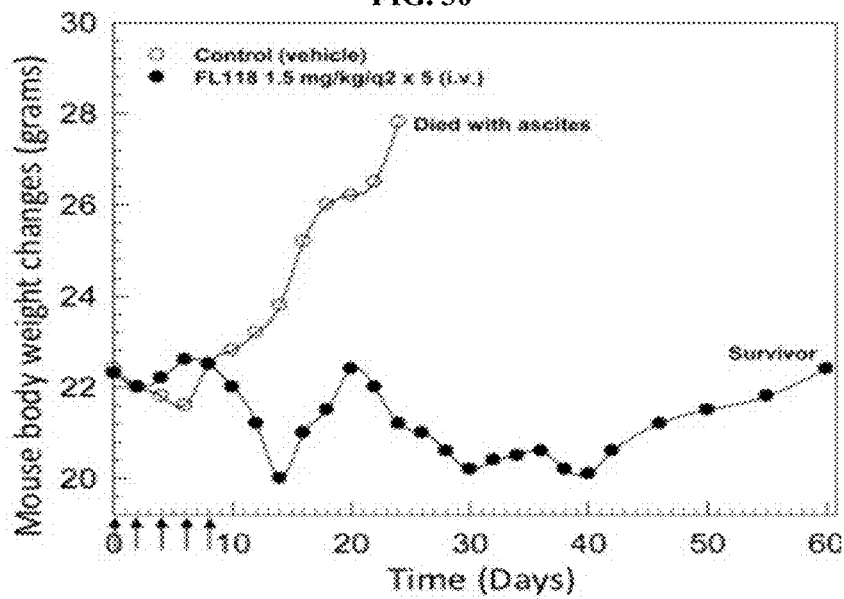

FIG. 30 shows that FL118 effectively inhibits ascites production and extends animal survival in an aggressive human EU-4 acute lymphocytic leukemia (ALL) mouse model. The EU-4 cells are intraperitoneally injected (5×10$^6$ per SCID mouse). Two days later (defined as Day 0), mice are treated with control solution (vehicle) or FL118 every other day from Day 0 for five times (q2×5, arrows) via the clinical compatible IV route. Body weight changes, belly enlargement and overall mouse survival status are documented every 2-3 days throughout the experiment period.

Figure 31:
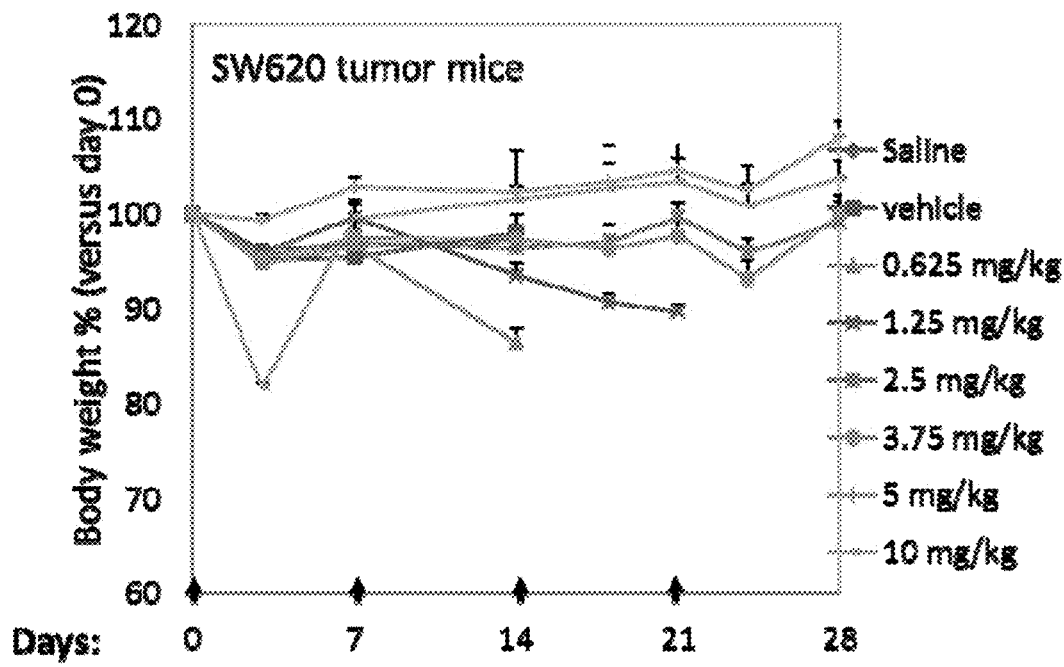

FIG. 31 shows the mouse body weight changes after FL118 oral administration via a schedule of weekly×4 (q7d×4, arrowed). Individual SW620 tumors were subcutaneously inoculated into SCID mice. FL118 treatment was initiated 7 days after the transplanted tumors reached 100-150 mm$^3$ (designated day 0). Each body weight change curve is the mean±SD from the same xenograft tumor of the average on 5 mice.

Figure 32:
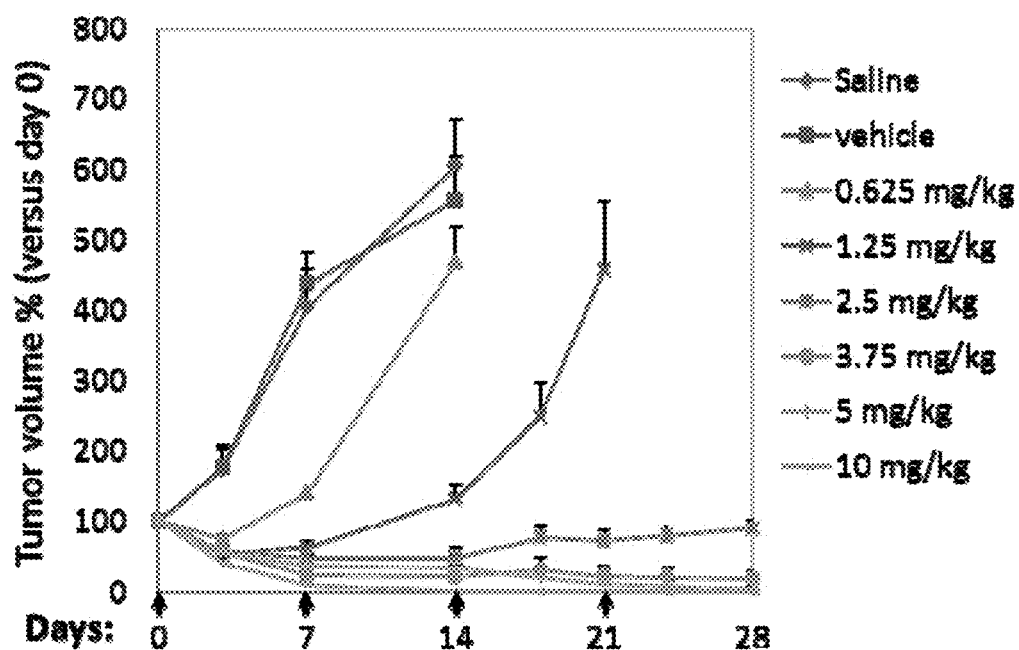

FIG. 32 shows the SW620 tumor changes of the same experiment described in FIG. 31, after FL118 treatment (oral, q7d×4, arrowed). Tumor inoculation and time for FL118 treatment are described in FIG. 31. Each tumor growth curve is the mean±SD from the same xenograft tumor of the average on the corresponding 5 mice.

Figure 33:
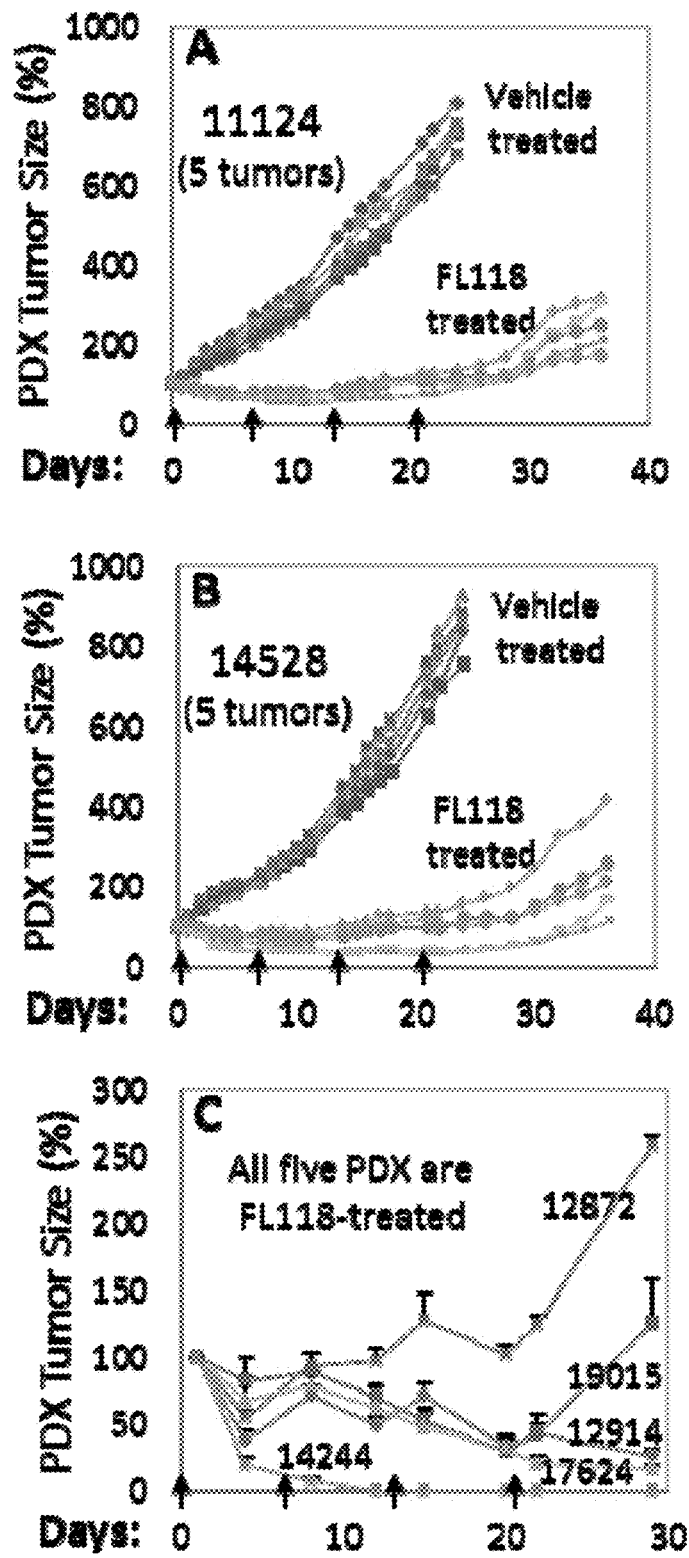

FIG. 33 uses examples of cancer patient-derived tumor xenografts (PDX) to show a concept of using FL118 (or a FL118 platform-derived analogue) for personalized cancer treatment (personalized medicine). Individual PDX were subcutaneously inoculated into SCID mice. FL118 treatment was initiated 7-10 days after the transplanted PDX tumors reached 100-150 mm$^3$ (designated day 0). Individual PDX tumor curves derived from individual mice are shown. A and B show that FL118 exhibits very similar effectiveness to inhibit the same PDX tumor on different mice. Two examples of colorectal cancer PDX (11124, 14528) are shown. C shows that FL118 exhibits very different effectiveness to inhibit five different pancreatic cancer PDX tumors (12872, 12914, 14244, 17624, 19015) on SCID mice. Each curve is the mean±SD from the same PDX of an average tumor on 5 mice. Of note, the corresponding PDX on SCID mice without FL118 treatment had to be euthanized within three weeks due to tumor size reaching 2000 mm³.

Figure 34:
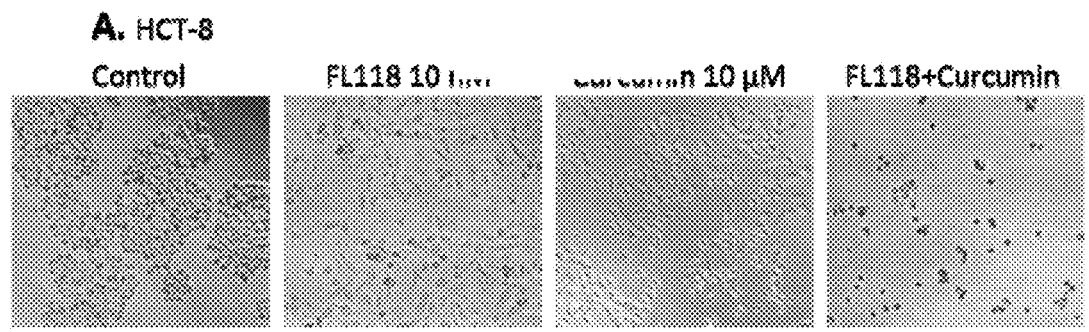
Figure 34:
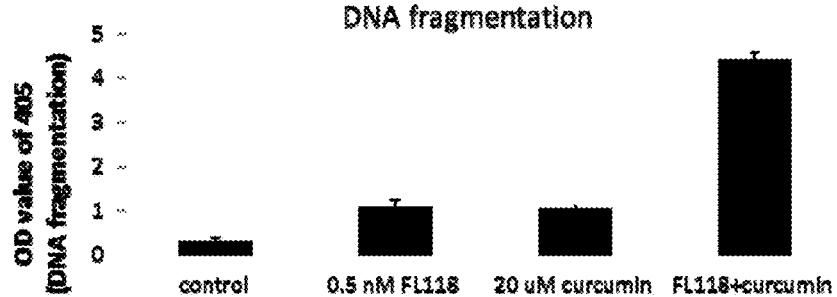

FIG. 34 shows that combination of FL118 and curcumin increase cancer cell death. HCT116 (A) and HCT-8 (B) colon cancer cells are treated with or without FL118 or curcumin alone and in combination as shown for 48 hours. Cell images are taken under microscopy with digital camera (A) or subject to cell death ELISA (DNA fragmentation) analysis (B). Each bar shown in B is the mean±SD from three independent assays.

Figure 35:
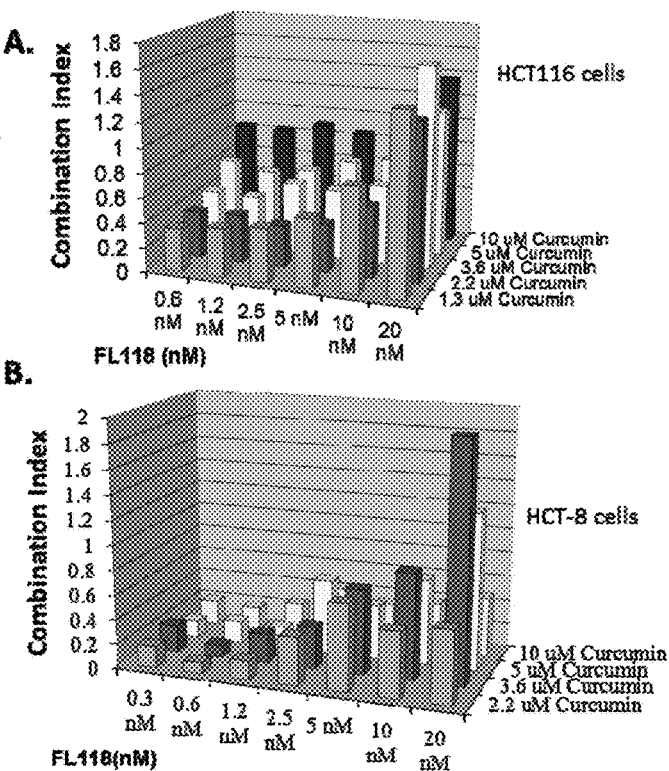

FIG. 35 shows the combination index (CI) of FL118 with curcumin in human colon cancer cells. HCT116 (A) and HCT-8 (B) colon cancer cells are treated with FL118 and curcumin at a series of concentrations as shown for 72 hours and subjected to MTT assays; the obtained results are analyzed and the CI is calculated through a CI equation using CalcuSyn software (Biosoft).

Figure 36:
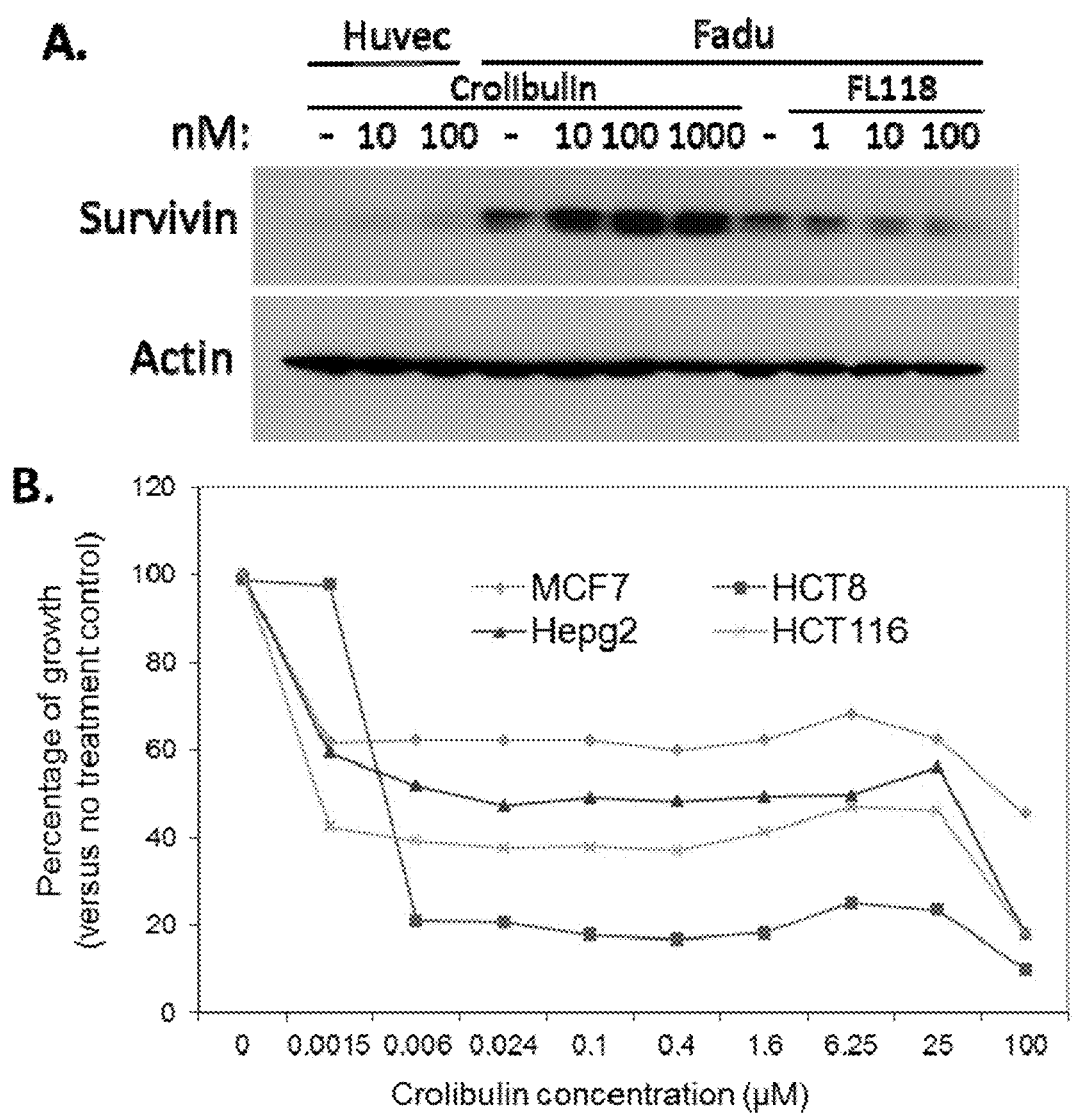

FIG. 36 shows the basis of FL118 in combination of crolibulin, a cancer vascular-disruptive agent (VDA). A. Shows the induction of survivin by crolibulin and inhibition of survivin by FL118 in human head-&-neck FaDu cancer cells. Subconfluent cells are treated with crolibulin and FL118 for 24 hours as shown, followed by Western blots to determine the expression of survivin. Actin is an internal control for equal protein loading. B. Shows the effect of crolibulin treatment on cancer cell growth. Subconfluent cancer cells as shown are treated with a series of concentrations of crolibulin as shown (0-100 µM) for 72 hours. Cell growth and viability are determined via MTT assay. Each curve is the mean±SD from 4 independent assays.

Figure 37:
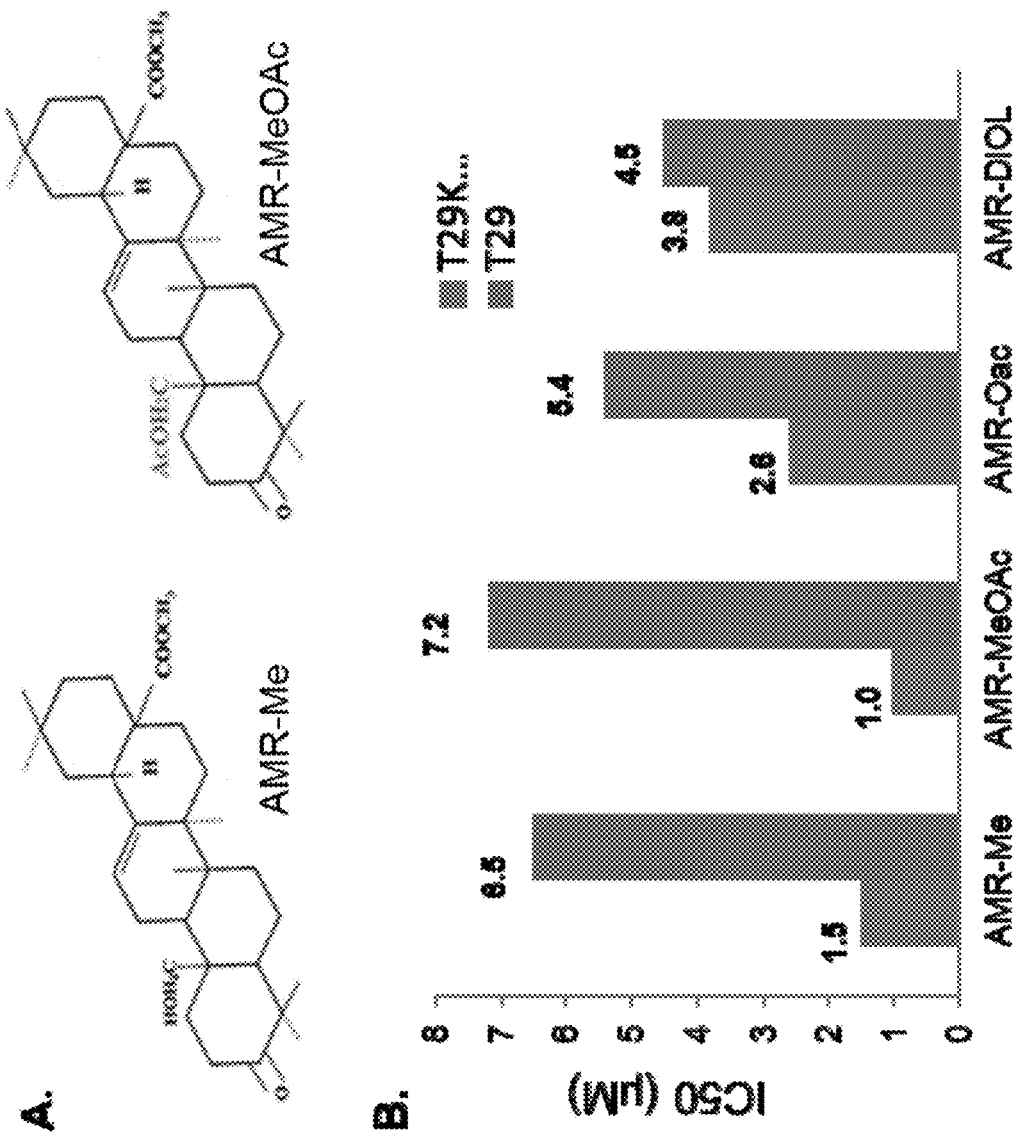

FIG. 37 shows the chemical structure of the plant diet compound-derived AMR-Me and AMR-MeOAc (A) and that these compounds prefer to target cancer cells with K-ras mutations. Subconfluent T29Kt cells with K-Ras mutation and the normal ovarian epithelial T29 cells are treated with a series of concentrations of a plant diet compound-derived compound as shown (AMR-Me, AMR-MeOAc, AMR-Oac or AMR-DIOL) for 72 hours, IC50 are then determined. Relative $IC_{50}$ concentrations of each compound are shown for T29Kt cells versus T29 cells.

Table 1 shows the relative sensitivity and relative potency (RP) of camptothecin (CPT), SN-38 (active metabolite of irinotecan), topotecan and FL118 to DU145 prostate cancer cells and the two DU145 sub-lines with Top1 mutations (RC0.1, RC1).

Table 2 summarizes the pharmacokinetic (PK) results derived from two tumor types (FaDu, SW620) on three SCID mice at each time points after one time intravenous injection of FL118 at a dose of 1.5 mg/kg.

Table 3 shows the differential inhibitory effects of FL118 in comparison with topotecan and SN-38 on cancer cell growth in cancer cells with different genetic backgrounds.

DETAILED DESCRIPTION OF THE INVENTION

The present disclosure relates to, inter alia, a novel class of compounds which function as anti-cancer agents. Likewise, methods for using such compounds in the prevention and treatment of disease conditions are disclosed herein. The present disclosure further relates to pharmaceutical formulations of the compounds, which possess prophylactic and/or therapeutic indications for subjects in need of cancer treatment.

The definitions of certain terms as used in this specification are provided below. Unless defined otherwise, all technical and scientific terms used herein generally have the same meaning as commonly understood by one of ordinary skill in the art to which this invention belongs. As used in this specification and the appended claims, the singular forms "a", "an" and "the" include plural referents unless the content clearly dictates otherwise. For example, reference to "a compound" includes a combination of two or more compounds, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

As used herein, the "administration" of an agent or drug, e.g., one or more antiapoptotic protein inhibitor compounds, to a subject or subjects includes any route of introducing or delivering to a subject a compound to perform its intended function. Administration can be carried out by any suitable route, including orally, intranasally, by inhalation, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment/prevention, and wherein some biologically or medically relevant result is achieved.

As used herein, the terms "assessing," "assaying," "determining," and "measuring" are used interchangeably and include both quantitative and qualitative determinations. These terms refer to any form of measurement, and include determining if a characteristic, trait, or feature is present or not. Assessing may be relative or absolute. "Assessing the presence of" includes determining the amount of something present and/or absent.

As used herein, the term "clinical factors" refers to any data that a medical practitioner may consider in determining a diagnosis, prognosis, or therapeutic regimen for treating or preventing a disease or diseases. Such factors include, but are not limited to, the patient's medical history, a physical examination of the patient, complete blood count, examination of blood cells or bone marrow cells, cytogenetics, pulmonary health, vascular indications of disease, and immunophenotyping of cells.

As used herein, the terms "comparable" or "corresponding" in the context of comparing two or more samples, responses to treatment, or drugs, refer to the same type of sample, response, treatment, and drug respectively used in the comparison. In some embodiments, comparable samples may be obtained from the same individual at different times. In other embodiments, comparable samples may be obtained from different individuals, e.g., a patient and a healthy individual. In general, comparable samples are normalized by a common factor for control purposes.

As used herein, the term "composition" refers to a product with specified ingredients in the specified amounts, as well as any product which results, directly or indirectly, from combination of the specified ingredients in the specified amounts.

As used herein, the term "diagnosis" means detecting a disease or disorder or determining the stage or degree of a disease or disorder. Typically, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease, i.e., there may be differential diagnoses that can be inferred from a diagnostic factor or symptom. Likewise, there may be instances where a factor or symptom that is indicative of a particular disease is present in an individual that does not have the particular disease. The term "diagnosis" also encompasses determining the therapeutic effect of a drug therapy, or predicting the pattern of response to a drug therapy. The diagnostic methods may be used independently, or in combination with other diagnosing and/or staging methods known in the medical art for a particular disease or disorder.

As used herein, the terms "drug," "compound," "active agent," "agent," "actives," "pharmaceutical composition," "pharmaceutical formulation," and "pharmacologically active agent" are used interchangeably and refer to any chemical compound, complex or composition, charged or uncharged, that is suitable for administration and that has a beneficial biological effect, suitably a therapeutic effect in the treatment of a disease or abnormal physiological condition, although the effect may also be prophylactic in nature. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent," and "API" (active pharmaceutical ingredient) are used, then, or when a particular active agent is specifically identified, it is to be understood that applicants intend to include the active agent per se as well as pharmaceutically acceptable, pharmacologically active salts, esters, amides, prodrugs, conjugates, metabolites, analogs, etc.

As used herein, the terms "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds.

As used herein, the term "neoplastic disease" refers to cancers of any kind and origin and precursor stages thereof. Accordingly, the term "neoplastic disease" includes the subject matter identified by the terms "neoplasia", "neoplasm", "cancer", "pre-cancer" or "tumor." A neoplastic disease is generally manifest by abnormal cell division resulting in an abnormal level of a particular cell population. Likewise, the monoclonal expansion of endothelial cells may refer to a "neoplasm" of the pulmonary arteriolar endothelial cells. The abnormal cell division underlying a neoplastic disease, moreover, is typically inherent in the cells and not a normal physiological response to infection or inflammation. In some embodiments, neoplastic diseases for diagnosis using methods provided herein include carcinoma. By "carcinoma," it is meant a benign or malignant epithelial tumor.

As used herein, the term "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, lactic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

As used herein, the term "prognosis" refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average cure rate, a lower propensity for metastasis, a longer than expected life expectancy, differentiation of a benign process from a cancerous process, and the like. For example, a positive prognosis is one where a patient has a 50% probability of being cured of a particular cancer after treatment, while the average patient with the same cancer has only a 25% probability of being cured.

As used herein, the term "reference level" refers to a level of a substance which may be of interest for comparative purposes. In some embodiments, a reference level may be a specified composition dosage as an average of the dose level from samples taken from a control subject. In other embodiments, the reference level may be the level in the same subject at a different time, e.g., a time course of administering the composition, such as the level determined at 2, 4, 6, 8, and 10 minutes (min), etc.

As used herein, the terms "sample" or "test sample" refer to any liquid or solid material containing collected from a subject. In suitable embodiments, a test sample is obtained from a biological source, i.e., a "biological sample," such as cells in culture or a tissue sample from an animal, most preferably, a murine subject, mammal or human subject.

As used herein, the terms "subject" or "individual," refer to a mammal, such as a mouse, rat, or human, but can also be another animal such as a domestic animal, e.g., a dog, cat, or the like, a farm animal, e.g., a cow, a sheep, a pig, a horse, or the like, or a laboratory animal, e.g., a monkey, a rat, a mouse, a rabbit, a guinea pig, or the like. The term "patient" refers to a "subject" who is, or is suspected to be, afflicted with a disease.

As used herein, the terms "treating" or "treatment" or "alleviation" refer to both therapeutic treatment and prophylactic or preventative measures, wherein the objective is to prevent or slow down (lessen) the targeted pathologic condition or disorder. A subject is successfully "treated" for a disorder if, after receiving a therapeutic agent according to the methods of the present invention, the subject shows observable and/or measurable reduction in or absence of one or more signs and symptoms of a particular disease or condition.

As used herein, reference to a certain element such as "hydrogen" or "H" is meant to include all isotopes of that element. For example, if an R group is defined to include hydrogen or H, it also includes deuterium and tritium.

As used herein, the term "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cycloalkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo [2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 5 carbon atoms. In some embodiments, unsubstituted alkyl groups include straight and branched chain alkyl groups having from 1 to 3 carbon atoms and include methyl, ethyl, propyl, and —CH(CH$_3$)$_2$.

As used herein, the term "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. In suitable embodiments, substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

As used herein, the term "unsubstituted aryl" refers to aryl groups that do not contain heteroatoms. Thus the term includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. Unsubstituted aryl groups may be bonded to one or more carbon atom(s), oxygen atom(s), nitrogen atom(s), and/or sulfur atom(s).

As used herein, the term "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the term "substituted aryl" includes, but is not limited to, tolyl and hydroxyphenyl, among others.

As used herein, the term "unsubstituted alkenyl" refers to straight and branched chain and cyclic groups such as those described with respect to unsubstituted alkyl groups as defined above, except that at least one double bond exists between two carbon atoms. Examples include, but are not limited to vinyl, —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, cyclohexenyl, cyclopentenyl, cyclohexadienyl, butadienyl, pentadienyl, and hexadienyl among others.

As used herein, the term "substituted alkenyl" has the same meaning with respect to unsubstituted alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

As used herein, the term "unsubstituted alkynyl" refers to straight and branched chain groups such as those described with respect to unsubstituted alkyl groups as defined above, except that at least one triple bond exists between two carbon atoms. Examples include, but are not limited to, C≡C(H), —C≡C(CH$_3$), —C≡C(CH$_2$CH$_3$), —C(H$_2$)C≡C (H), —C(H)$_2$C≡C(CH$_3$), and —C(H)$_2$C≡C(CH$_2$CH$_3$), among others.

As used herein, the term "substituted alkynyl" has the same meaning with respect to unsubstituted alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

As used herein, the term "unsubstituted aralkyl" refers to unsubstituted alkyl groups as defined above in which a hydrogen or carbon bond of the unsubstituted alkyl group is replaced with a bond to an aryl group as defined above. For example, methyl (—CH$_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group, i.e., a benzyl group. Thus, the term includes, but is not limited to, groups such as benzyl, diphenylmethyl, and 1-phenylethyl (—CH(C$_6$H$_5$)(CH$_3$)), among others.

As used herein, the term "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom. Examples of substituted aralkyl groups include, but are not limited to, —CH$_2$C(=O)(C$_6$H$_5$), and —CH$_2$(2-methylphenyl), among others.

As used herein, the term "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridinyl, dihydropyridinyl, pyrimidyl, pyrazinyl, pyridazinyl, triazolyl, e.g., 4H-1,2,4-triazolyl, 1H-1,2,3-triazolyl, 2H-1,2,3-triazolyl etc., tetrazolyl, e.g., 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl, e.g., 1,2,4-oxadiazolyl, 1,3,4-oxadiazolyl, 1,2,5-oxadiazolyl, etc.; saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl, e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl, e.g., 1,2,3-thiadiazolyl, 1,2,4-thiadiazolyl, 1,3,4-thiadiazolyl, 1,2,5-thiadiazolyl, etc.; saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl, e.g., 2H-3,4-dihydrobenzothiazinyl, etc., unsaturated 3 to 8 membered rings containing oxygen atoms such as, but not limited to furyl; unsaturated condensed heterocyclic rings containing 1 to 2 oxygen atoms such as benzodioxolyl, e.g., 1,3-benzodioxoyl, etc.; unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones).

As used herein, the term "substituted heterocyclyl" refers to an unsubstituted heterocyclyl group as defined above in which one or more of the ring members is bonded to a non-hydrogen atom such as described above with respect to substituted alkyl groups and substituted aryl groups.

As used herein, the term "unsubstituted heterocyclylalkyl" refers to unsubstituted alkyl groups as defined above in which a hydrogen or carbon bond of the unsubstituted alkyl group is replaced with a bond to a heterocyclyl group as defined above. For example, methyl (—CH$_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the aryl.

As used herein, the term "substituted heterocyclylalkyl" has the same meaning with respect to unsubstituted heterocyclylalkyl groups that substituted aralkyl groups had with respect to unsubstituted aralkyl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group. In addition, a substituted heterocyclylalkyl group also includes groups in which a carbon bond or a hydrogen bond of the alkyl part of the group is replaced by a bond to a substituted and unsubstituted aryl or substituted and unsubstituted aralkyl group.

As used herein, the term "unsubstituted alkylaminoalkyl" refers to an unsubstituted alkyl group as defined above in which a carbon or hydrogen bond is replaced by a bond to a nitrogen atom that is bonded to a hydrogen atom and an unsubstituted alkyl group as defined above. For example, methyl (—$CH_3$) is an unsubstituted alkyl group. If a hydrogen atom of the methyl group is replaced by a bond to a nitrogen atom that is bonded to a hydrogen atom and an ethyl group, then the resulting compound is $CH_2$—N(H)($CH_2CH_3$) which is an unsubstituted alkylaminoalkyl group.

As used herein, the term "substituted alkylaminoalkyl" refers to an unsubstituted alkylaminoalkyl group as defined above except where one or more bonds to a carbon or hydrogen atom in one or both of the alkyl groups is replaced by a bond to a non-carbon or non-hydrogen atom as described above with respect to substituted alkyl groups except that the bond to the nitrogen atom in all alkylaminoalkyl groups does not by itself qualify all alkylaminoalkyl groups as being substituted.

As used herein, the term "unsubstituted dialkylaminoalkyl" refers to an unsubstituted alkyl group as defined above in which a carbon bond or hydrogen bond is replaced by a bond to a nitrogen atom which is bonded to two other similar or different unsubstituted alkyl groups as defined above.

As used herein, the term "substituted dialkylaminoalkyl" refers to an unsubstituted dialkylaminoalkyl group as defined above in which one or more bonds to a carbon or hydrogen atom in one or more of the alkyl groups is replaced by a bond to a non-carbon and non-hydrogen atom as described with respect to substituted alkyl groups. The bond to the nitrogen atom in all dialkylaminoalkyl groups does not by itself qualify all dialkylaminoalkyl groups as being substituted.

As used herein, the term "unsubstituted alkoxy" refers to a hydroxyl group (—OH) in which the bond to the hydrogen atom is replaced by a bond to a carbon atom of an otherwise unsubstituted alkyl group as defined above.

As used herein, the term "substituted alkoxy" refers to a hydroxyl group (—OH) in which the bond to the hydrogen atom is replaced by a bond to a carbon atom of an otherwise substituted alkyl group as defined above.

As used herein, the term "unsubstituted heterocyclyloxy" refers to a hydroxyl group (—OH) in which the bond to the hydrogen atom is replaced by a bond to a ring atom of an otherwise unsubstituted heterocyclyl group as defined above.

As used herein, the term "substituted heterocyclyloxy" refers to a hydroxyl group (—OH) in which the bond to the hydrogen atom is replaced by a bond to a ring atom of an otherwise substituted heterocyclyl group as defined above.

As used herein, the term "unsubstituted heterocyclyloxyalkyl" refers to an unsubstituted alkyl group as defined above in which a carbon bond or hydrogen bond is replaced by a bond to an oxygen atom which is bonded to an unsubstituted heterocyclyl group as defined above.

As used herein, the term "substituted heterocyclyloxyalkyl" refers to an unsubstituted heterocyclyloxyalkyl group as defined above in which a bond to a carbon or hydrogen group of the alkyl group of the heterocyclyloxyalkyl group is bonded to a non-carbon and non-hydrogen atom as described above with respect to substituted alkyl groups or in which the heterocyclyl group of the heterocyclyloxyalkyl group is a substituted heterocyclyl group as defined above.

As used herein, the term "unsubstituted heterocyclylalkoxy" refers to an unsubstituted alkyl group as defined above in which a carbon bond or hydrogen bond is replaced by a bond to an oxygen atom which is bonded to the parent compound, and in which another carbon or hydrogen bond of the unsubstituted alkyl group is bonded to an unsubstituted heterocyclyl group as defined above.

As used herein, the term "substituted heterocyclylalkoxy" refers to an unsubstituted heterocyclylalkoxy group as defined above in which a bond to a carbon or hydrogen group of the alkyl group of the heterocyclylalkoxy group is bonded to a non-carbon and non-hydrogen atom as described above with respect to substituted alkyl groups or in which the heterocyclyl group of the heterocyclylalkoxy group is a substituted heterocyclyl group as defined above. Further, a substituted heterocyclylalkoxy group also includes groups in which a carbon bond or a hydrogen bond to the alkyl moiety of the group may be substituted with one or more additional substituted and unsubstituted heterocycles.

As used herein, the term "unsubstituted arylaminoalkyl" refers to an unsubstituted alkyl group as defined above in which a carbon bond or hydrogen bond is replaced by a bond to a nitrogen atom which is bonded to at least one unsubstituted aryl group as defined above.

As used herein, the term "substituted arylaminoalkyl" refers to an unsubstituted arylaminoalkyl group as defined above except where either the alkyl group of the arylaminoalkyl group is a substituted alkyl group as defined above or the aryl group of the arylaminoalkyl group is a substituted aryl group except that the bonds to the nitrogen atom in all arylaminoalkyl groups does not by itself qualify all arylaminoalkyl groups as being substituted. However, substituted arylaminoalkyl groups does include groups in which the hydrogen bonded to the nitrogen atom of the group is replaced with a non-carbon and non-hydrogen atom.

As used herein, the term "unsubstituted heterocyclylaminoalkyl" refers to an unsubstituted alkyl group as defined above in which a carbon or hydrogen bond is replaced by a bond to a nitrogen atom which is bonded to at least one unsubstituted heterocyclyl group as defined above.

As used herein, the term "substituted heterocyclylaminoalkyl" refers to unsubstituted heterocyclylaminoalkyl groups as defined above in which the heterocyclyl group is a substituted heterocyclyl group as defined above and/or the alkyl group is a substituted alkyl group as defined above. The bonds to the nitrogen atom in all heterocyclylaminoalkyl groups does not by itself qualify all heterocyclylaminoalkyl groups as being substituted.

As used herein, the term "unsubstituted alkylaminoalkoxy" refers to an unsubstituted alkyl group as defined above in which a carbon or hydrogen bond is replaced by a bond to an oxygen atom which is bonded to the parent compound and in which another carbon or hydrogen bond of the unsubstituted alkyl group is bonded to a nitrogen atom which is bonded to a hydrogen atom and an unsubstituted alkyl group as defined above.

As used herein, the term "substituted alkylaminoalkoxy" refers to unsubstituted alkylaminoalkoxy groups as defined above in which a bond to a carbon or hydrogen atom of the alkyl group bonded to the oxygen atom which is bonded to the parent compound is replaced by one or more bonds to a non-carbon and non-hydrogen atoms as discussed above with respect to substituted alkyl groups and/or if the hydrogen bonded to the amino group is bonded to a non-carbon and non-hydrogen atom and/or if the alkyl group bonded to the nitrogen of the amine is bonded to a non-carbon and non-hydrogen atom as described above with respect to substituted alkyl groups. The presence of the amine and alkoxy functionality in all alkylaminoalkoxy groups does not by itself qualify all such groups as substituted alkylaminoalkoxy groups.

As used herein, the term "unsubstituted dialkylaminoalkoxy" refers to an unsubstituted alkyl group as defined above in which a carbon or hydrogen bond is replaced by a bond to an oxygen atom which is bonded to the parent compound and in which another carbon or hydrogen bond of the unsubstituted alkyl group is bonded to a nitrogen atom which is bonded to two other similar or different unsubstituted alkyl groups as defined above.

As used herein, the term "substituted dialkylaminoalkoxy" refers to an unsubstituted dialkylaminoalkoxy group as defined above in which a bond to a carbon or hydrogen atom of the alkyl group bonded to the oxygen atom which is bonded to the parent compound is replaced by one or more bonds to a non-carbon and non-hydrogen atoms as discussed above with respect to substituted alkyl groups and/or if one or more of the alkyl groups bonded to the nitrogen of the amine is bonded to a non-carbon and non-hydrogen atom as described above with respect to substituted alkyl groups. The presence of the amine and alkoxy functionality in all dialkylaminoalkoxy groups does not by itself qualify all such groups as substituted dialkylaminoalkoxy groups.

As used herein, the term "protected" with respect to hydroxyl groups, amine groups, and sulfhydryl groups refers to forms of these functionalities which are protected from undesirable reaction with a protecting group known to those skilled in the art such as those set forth in *Protective Groups in Organic Synthesis*, Greene, T. W.; Wuts, P. G. M., John Wiley & Sons, New York, N.Y., (3rd Edition, 1999), which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals, among others.

Overview

Control of human disease to extend quality of life is the goal in clinical practice. In the field of human cancer control, the challenge is the treatment (e.g., chemotherapy and radiation) resistance, which results in untreatable disease or a high rate of recurrence after treatment. Therefore, cancer treatment resistance and recurrence are the primary causes of cancer death and continue to challenge the entire field.

Critical analysis of the peer-reviewed literature indicates that the challenge for overcoming treatment resistance is that the inherent or acquired (induced) resistance to treatment is through diverse mechanisms, often resulting from the fact that cancer cells usually possess diverse genetic and epigenetic alternations. To address the challenge in treatment resistance, the fact that treatment resistance results from diverse mechanisms must be addressed. The prior art is devoid of efficacious strategies to this end.

Using one molecularly targeted agent in concert with one or two traditional cytotoxic drugs as a combination regimen has been previously employed. However, this approach is only able to alleviate the treatment resistance related to toxicity and efficacy for some of cancer patients with particular cancer types and/or favorable genetic background. Another challenging problem of treatment resistance is that cancer is a highly heterogeneous disease (Swanton C: Intratumor heterogeneity: evolution through space and time, Cancer research 2012, 72:4875-4882); gene-expression signatures of favorable versus unfavorable prognosis can be detected in different regions of the same tumor, and a significant percentage of somatic mutations may not be detected across every tumor region of the same tumor (Gerlinger M, et al.: Intratumor heterogeneity and branched evolution revealed by multiregion sequencing, The New England journal of medicine 2012, 366:883-892). This extensive intra-tumor heterogeneity presents difficult challenges with respect to personalized cancer treatment (personalized medicine) and biomarker development. Therefore, new strategies to resolve such challenges are needed.

On aspect of the present invention involves a series of anticancer compounds with a broad spectrum of activity, which were created by the present inventors, but where such compounds nevertheless possess a defined targeting mechanism, quantitatively and/or qualitatively, to combat cancer cell treatment resistance. Among the novel compounds disclosed herein, while each compound can target or bypass multiple resistant factors, individual compounds show distinct selectivity (quantitatively and/or qualitatively) with broad-spectrum overlap. Such a series of compounds impart therapeutic indications, which overcome treatment resistance resulted from diverse genetic and/or epigenetic alternations. Thus, individual compounds target a particular cancer type or the same type of cancer with overlapped but distinct genetic backgrounds. In turn, this imparts a novel strategy of personalized medicine to resolve the treatment resistance challenge. Likewise, from a cost point of view since each anticancer compound has a defined particular target set (quantitatively or qualitatively), in order to save biomarker testing costs for some cancer patients for diagnostic and/or prognostic indications, these individual drugs can be also used for cancer treatment in general without a pre-biomarker testing procedure. For these patients a particular drug selection would be based on general knowledge related to the cancer and the drugs, but not based on biomarker or genetic determinations, although this would compromise the maximal value of these types of drugs. This unprecedented strategy to overcome treatment resistance at a manner of personalized medicine comes out of our unexpected results recently obtained. See Examples.

The anti-cancer drug, camptothecin was initially identified and isolated from plant extracts by Dr. Mansukh Wani and Dr. Monroe Wall in collaboration with National Cancer Institute (NCI) of the United States. While a variety of camptothecin structure-based compounds (camptothecin derivatives) have been synthesized, only two camptothecin analogs, irinotecan and topotecan (both are camptothecin structure-based derivatives, see FIG. 1), were commercialized in clinical practice for cancer treatment. Currently, irinotecan and topotecan represent the best two compounds identified among camptothecin structure-based analogs in terms of their antitumor activity versus their toxicity. However, cancer resistance to irinotecan or topotecan treatment is a common issue in clinical practice, which seriously challenges the scope of their application. Some of our compounds protected in this invention would effectively overcome irinotecan- and topotecan-resistant tumors (see data from FIG. 25).

Figure 25:
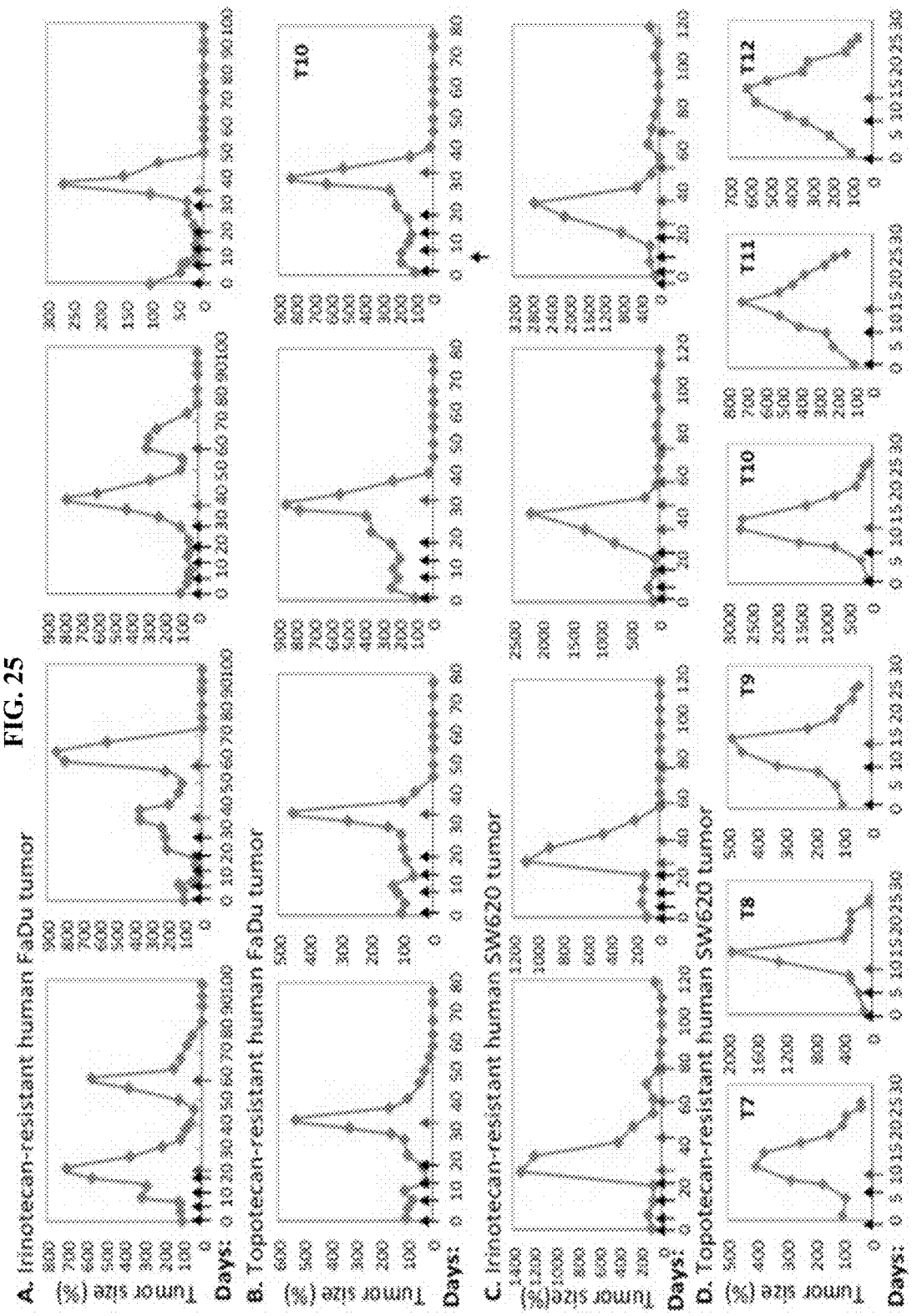
FIG. 25 shows that tumors with acquired irinotecan and topotecan resistance can be effectively regressed by FL118: Tumors were inoculated into SCID mice for each tumor type shown (A to D). Drug treatment was initiated 7 days after the transplanted tumors reached 50-150 mm$^3$ (designated day 0).

A unique camptothecin analog, FL118, targets and bypasses multiple treatment resistant factors and functions to eliminate many types of human tumor xenografts in animal models. See Ling X, et al.: A Novel Small Molecule FL118 That Selectively Inhibits Survivin, Mcl-1, XIAP and cIAP2 in a p53-Independent Manner, Shows Superior Antitumor Activity, PLOS ONE 2012, 7:e45571. These studies also revealed that the antitumor activity of FL118 is highly dependent on its primary structure and steric configuration (Zhao J, et al.: Antitumor activity of FL118, a survivin, Mcl-1, XIAP, cIAP2 selective inhibitor, is highly dependent on its primary structure and steric configuration, Molecular Pharmaceutics 2014; 11: 457-467). Importantly, recent results from the present inventors reveal that FL118 effectively overcomes irinotecan and topotecan-induced treatment resistance in several types of human cancer including head-&-neck and colon cancer xenografts in animal models (FIG. 25). FL118 effectively bypasses the refractory phenotypes emanated from the ATP-binding cassette (ABC) transporters such as ABCG2, while SN-38 (active metabolite of irinotecan) and topotecan were substrates of ABCG2 and unable to bypass ABCG2-induced treatment resistance (FIGS. 15-23).

That is, individual compounds derived from the FL118 core chemical structure platform unexpectedly show distinct anti-cancer selectivity (quantitatively and/or qualitatively) among different cancer types or in the same cancer types with different individual drugs (refer to its sister patent entitled "synthesis and application of FL118 core structure platform-derived analogues for human disease treatment" for details). Such unexpected findings drive us forming the new strategy to overcome treatment resistance using FL118 as a unique core structural platform to generate a series of novel derivatives for personalized medicine (personalized cancer treatment) as well as for cancer treatment in general. The value of the later strategy (cancer treatment in general) is from a treatment cost-saving point of view for some patients, which takes advantage of the overlapped broad-spectrum anticancer feature of individual compounds. In sum, the present invention protects the scope and how to use the FL118 core structure platform to generate a series of novel anticancer compounds that show distinct selectivity (quantitatively and/or qualitatively), but with broad spectrum to inhibit cancers with diverse genetic backgrounds. This invention also includes the discovery of a defined set of combinational targets including survivin, Mcl-1, XIAP, cIAP2, HIF-1a, ATP-binding cassette (ABC) transporter proteins (e.g., ABCG2/BCRP, ABCC4/MRP4, MDR1), HdmX in the Hdm2/HdmX complex, and loss or mutation of functional p53 as essential treatment resistance factors that can be targeted or bypassed by FL118 and its core structure platform-derived analogues. Drugs that target or bypass two or more of this set of treatment resistant factors will effectively overcome treatment resistance for most (if not all) types of cancer, and lead to tumor regression. This invention has also described the further development of the DMSO-containing formulation into DMSO-free formulation of water-insoluble anticancer drugs including FL118 and other FL118 platform-derived analogues for administration, which relates to DMSO-containing formulation of water-insoluble drugs for administration. See, e.g., PCT/US2011/058558 (Formulations of Water-Insoluble Chemical Compounds and Methods of Using a Formulation of Compound FL118 For Cancer Therapy); U.S. patent application Ser. No. 13/881,785; Canadian Patent Application 2,816,418; Chinese Patent Application 201180063530.5; and European Patent Organization Application 11837250.7, all of which are hereby incorporated by reference in their entirety.

In illustrative embodiments, the present invention provides the compositions and general synthesis of a series of compounds based on the core structure platform of FL118 as well as the use of these novel compounds derived from FL118 for cancer treatment. For detailed synthesis of individual FL118 core structure platform-based analogues, please refer to this invention's sister patent entitled "synthesis and application of FL118 core structure platform-derived analogues for human disease treatment"

Compositions of the Compounds

Illustrative embodiments of the present invention described herein concern compounds, methods, compositions and uses of FL118 platform-derived compounds. In some embodiments, the FL118-derived analog has the following formula:

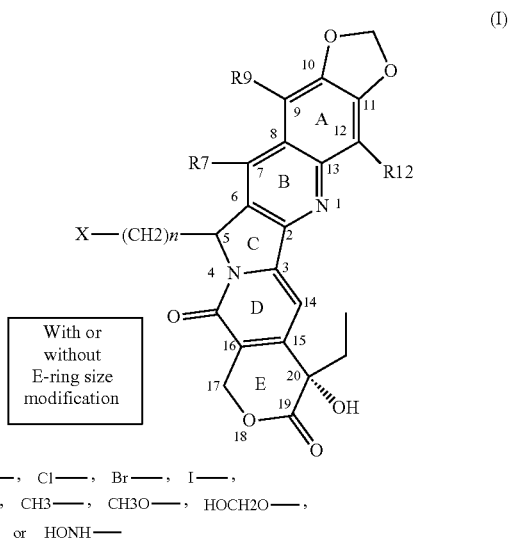

X = F—, Cl—, Br—, I—,
NH2—, CH3—, CH3O—, HOCH2O—,
HO—, or HONH—

In illustrative embodiments, a hydrogen (H) atom at position 5 is substituted with X—(CH$_2$)n- in which n is 0 or an integer 1, 2, 3, 4, 5, 6, 7, 8, 9, 10, 11, 12, 13, 14, or 15. Functional groups $R^7$, $R^9$, and at positions 7, 9 and 12, moreover, are any one of the elements selected from H—, F—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

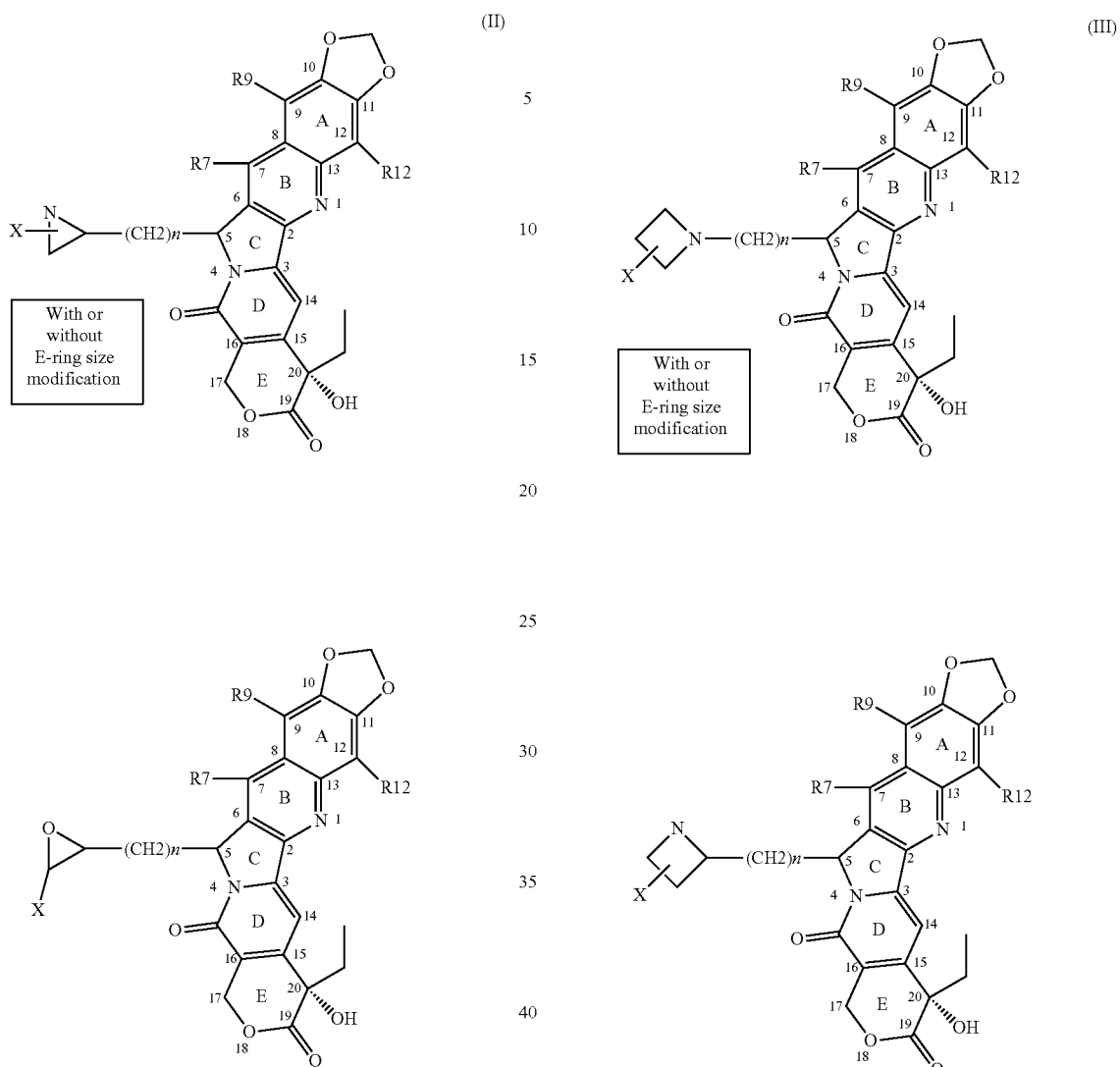

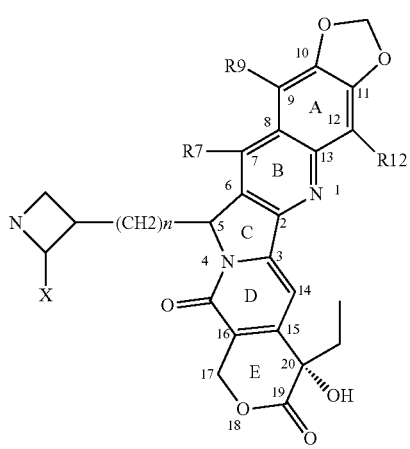

X = H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom at position 5 is substituted with X-cyclopropane-based-(CH$_2$)n-, where n is 0 or an integer selected from 1, 2, 3, 4, 5, 6, 7, 8, 9, 10, 11, 12, 13, 14, to 15. The functional groups $R^7$, $R^9$, and $R^{12}$, at respective positions 7, 9 and 12, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

-continued

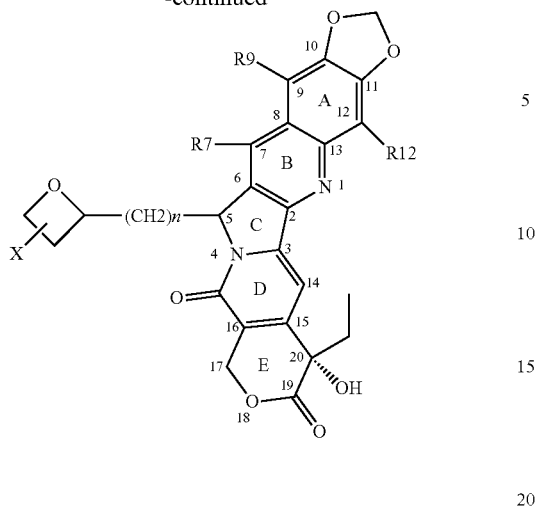

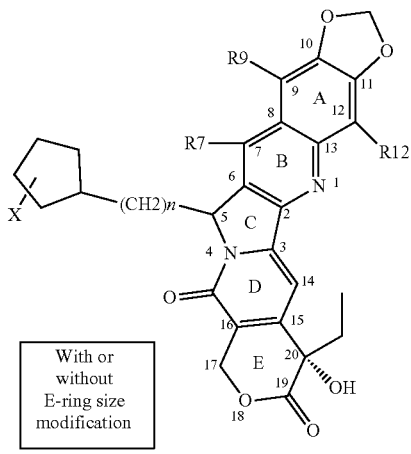

(IV)

With or without E-ring size modification

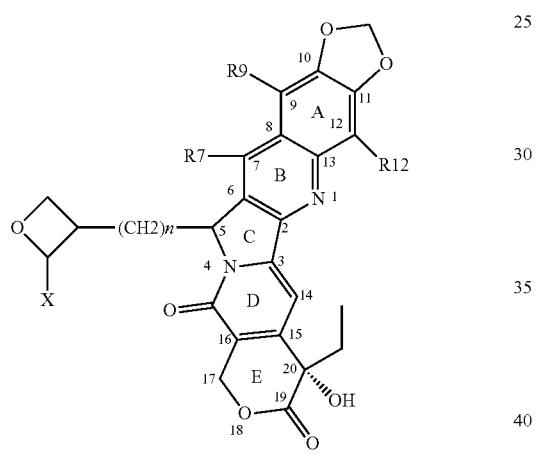

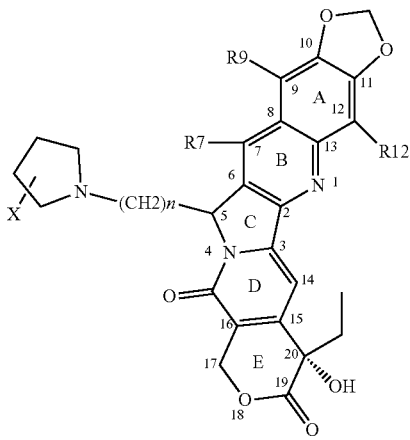

X = H—, F—, Cl—, Br—, I—, ClCH2—, BrCH2—, NH2—, CH3—, CH3O—, HOCH2—, HOCH2O—, NH2CH2—, HO—, or HONH—

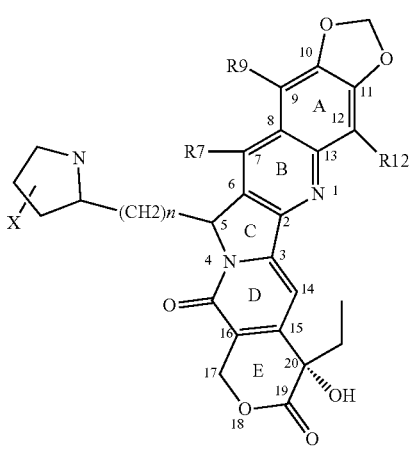

In illustrative embodiments, a hydrogen (H) atom on the position 5 is replaced with the chemical group of "X-cyclobutane-based-$(CH_2)n$-" where n is 0 or an integer selected from 1, 2, 3, 4, 5, 6, 7, 8, 9, 10, 11, 12, 13, 14, to 15. The functional groups $R^7$, $R^9$, and $R^{12}$, at respective positions 7, 9 and 12, are any one of the elements selected from H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —NHC(O)$NH_2$, —C(O)$CH_3$, —$CO_2CH_3$, and —C(O)N$(CH_3)_2$, at the 3 positions, while the remaining two functional group positions are H, in some embodiments. In suitable embodiments, the FL118-derived analogs have the following formulas:

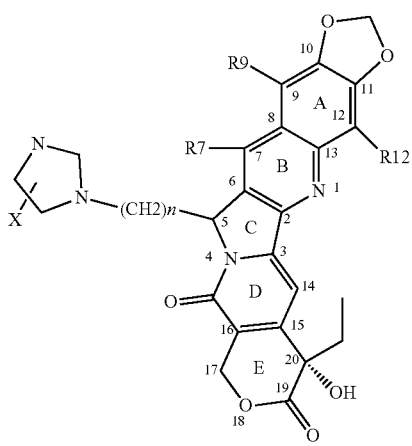

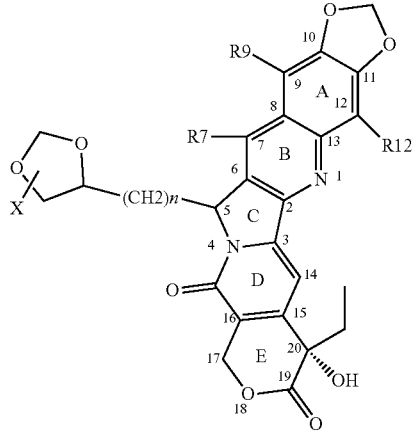

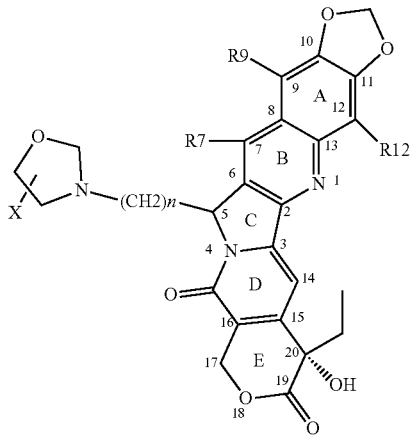

X = H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, a hydrogen (H) atom on the position 5 is replaced with the chemical group of "X-cyclopentane-based-$(CH_2)n$-" where n is 0 or an integer selected from 1, 2, 3, 4, 5, 6, 7, 8, 9, 10, 11, 12, 13, 14, to 15. The functional groups $R^7$, $R^9$, and $R^{12}$, at respective positions 7, 9 and 12, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

(V)
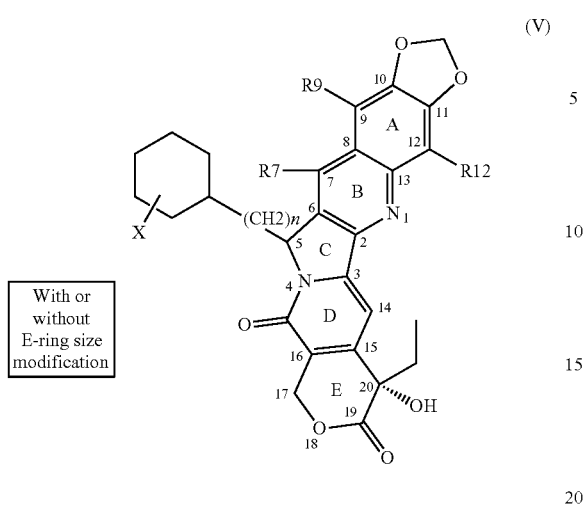
With or without E-ring size modification
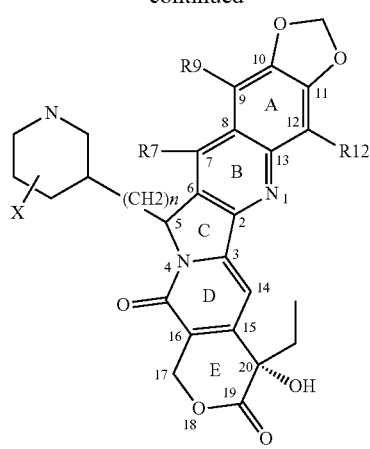
-continued
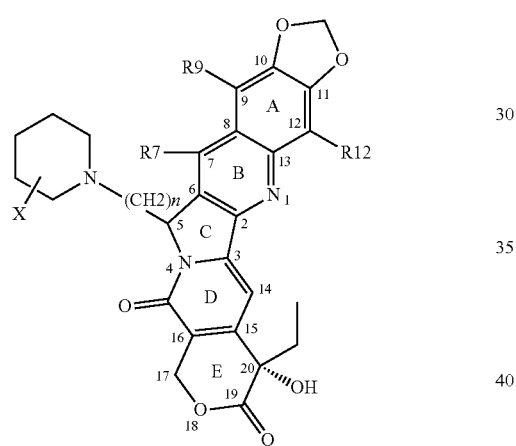
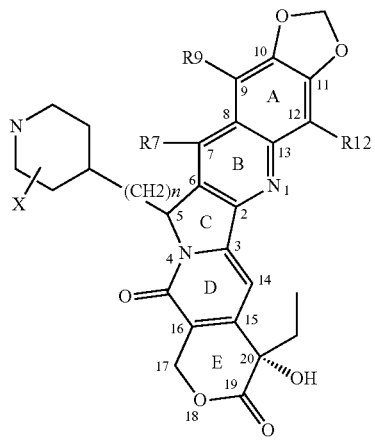
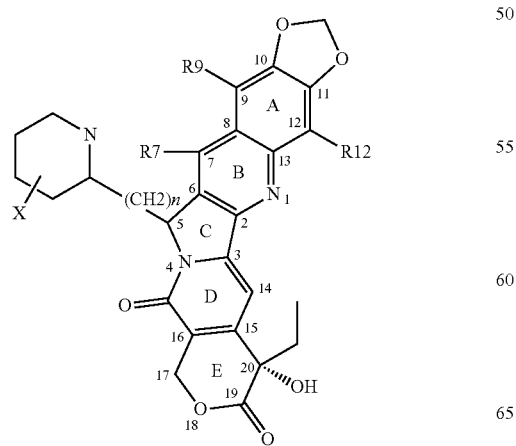
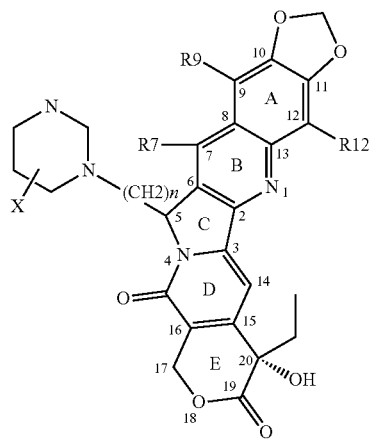

47
-continued
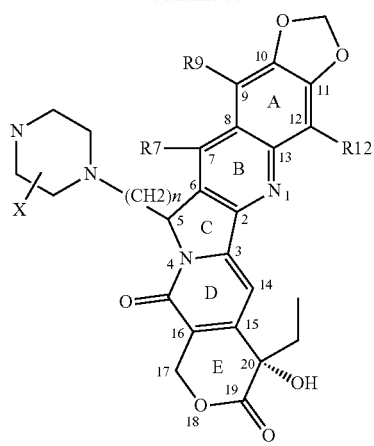
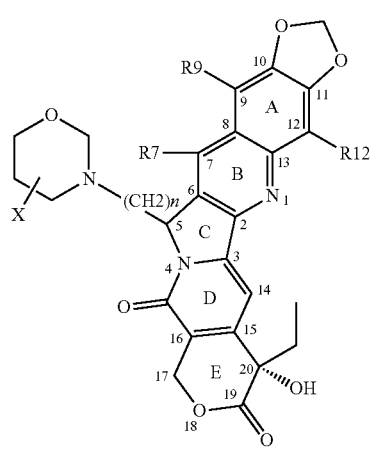
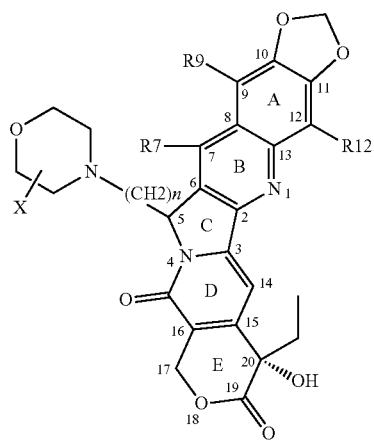
48
-continued
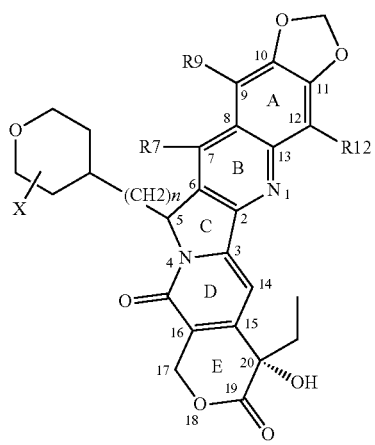
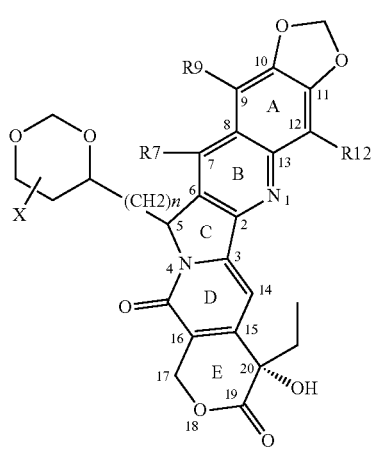
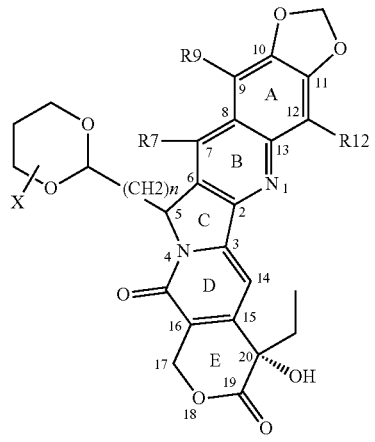

49
-continued

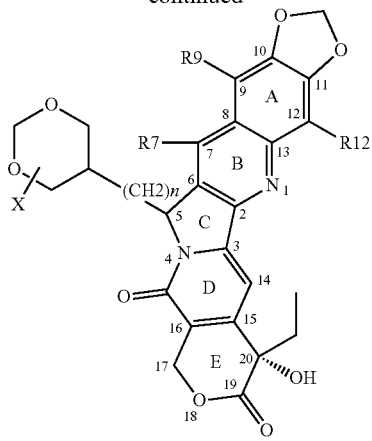

X= H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, a hydrogen (H) atom on the position 5 is replaced with the chemical group of "X-cyclohexane-based-($CH_2$)n-", where n is 0 or an integer selected from 1, 2, 3, 4, 5, 6, 7, 8, 9, 10, 11, 12, 13, 14, to 15. The functional groups $R^7$, $R^9$, and $R^{12}$, at respective positions 7, 9 and 12, are any one of the elements selected from H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —$NHC(O)NH_2$, —$C(O)CH_3$, —$CO_2CH_3$, and —$C(O)N(CH_3)_2$, at the 3 positions, while the remaining two functional group positions are H, in some embodiments. In suitable embodiments, the FL118-derived analogs have the following formulas:

50
-continued

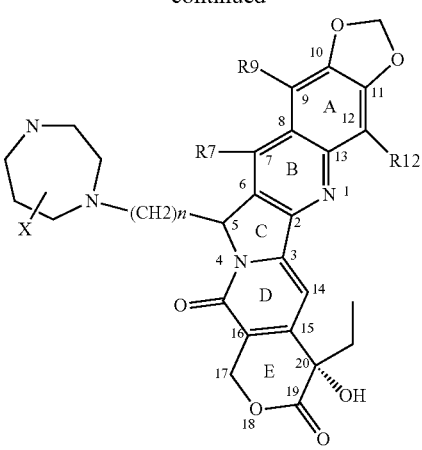

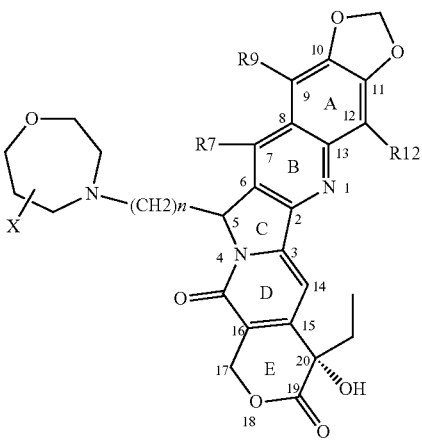

(VI)

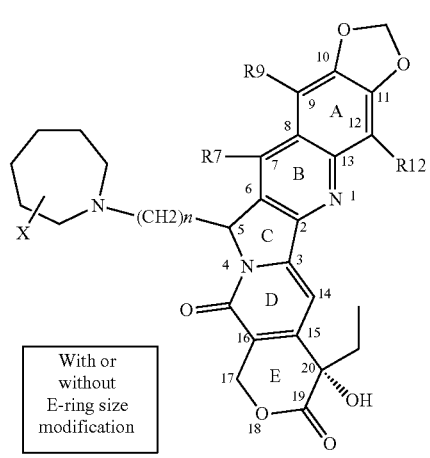

With or without E-ring size modification

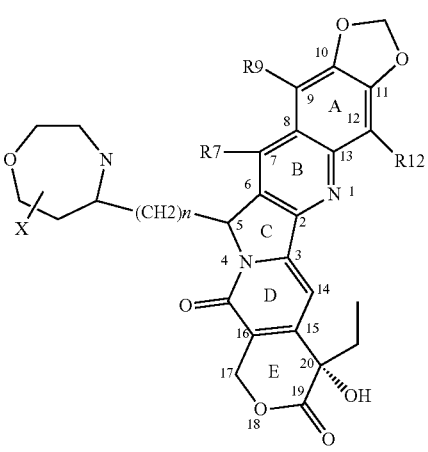

-continued

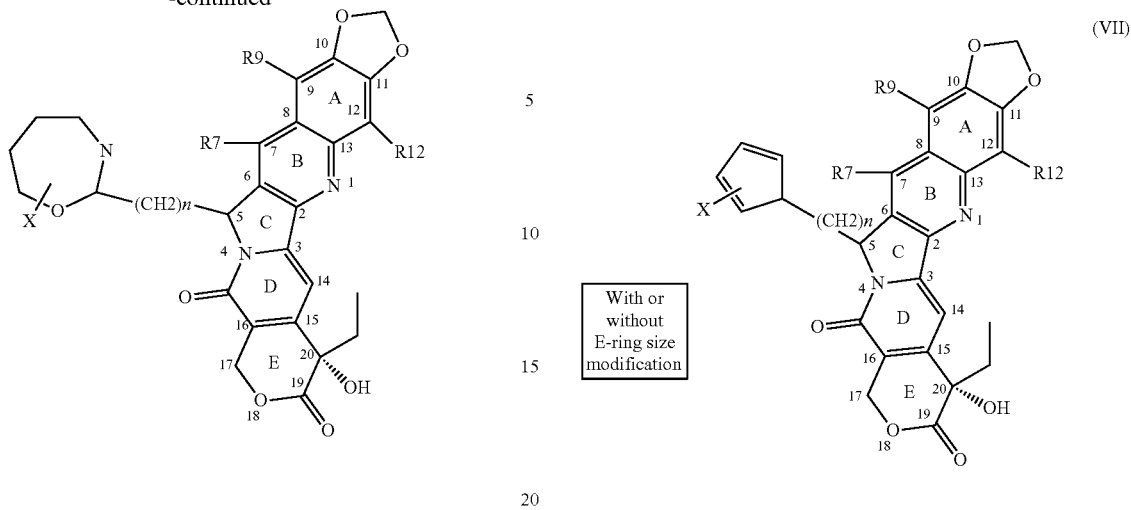

(VII)

With or without E-ring size modification

X = H—, F—, Cl—, Br—, I—, ClCH2—, BrCH2—, NH2—, CH3—, CH3O—, HOCH2—, HOCH2O—, NH2CH2—, HO—, or HONH—

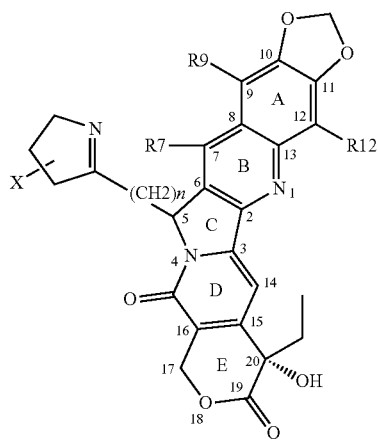

In illustrative embodiments, a hydrogen (H) atom on the position 5 is replaced with the chemical group of "X-cycloheptane-based-(CH$_2$)n-", where n is 0 or an integer selected from 1, 2, 3, 4, 5, 6, 7, 8, 9, 10, 11, 12, 13, 14, to 15. The functional groups R$^7$, R$^9$, and R$^{12}$, at respective positions 7, 9 and 12, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

53
-continued
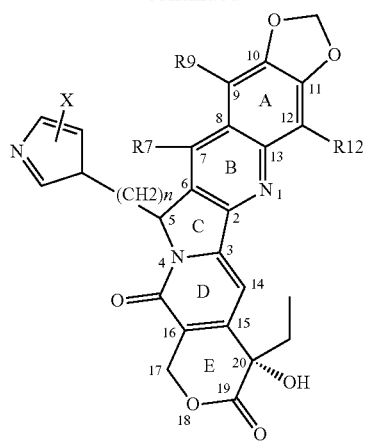
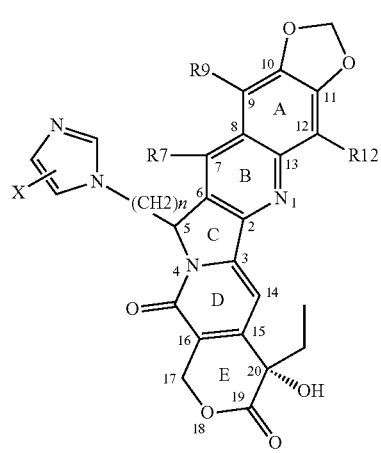
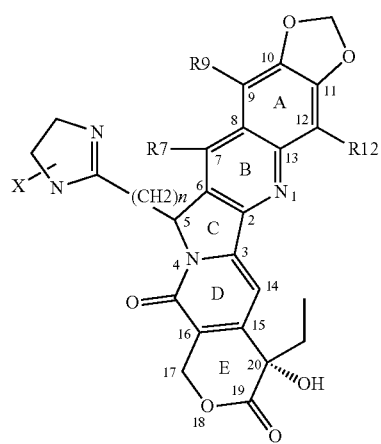
54
-continued
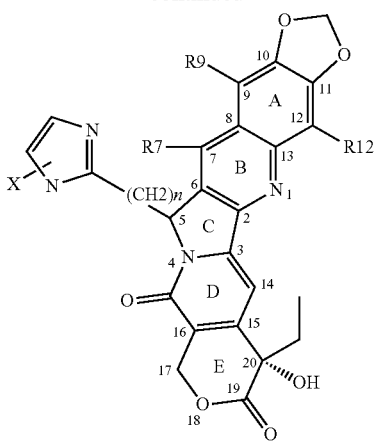
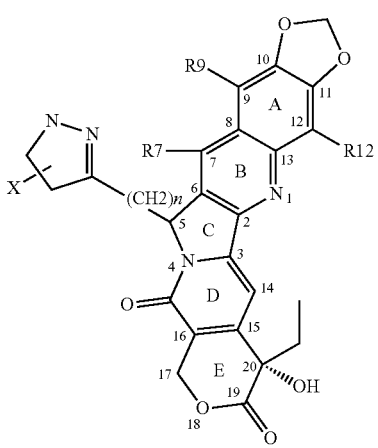
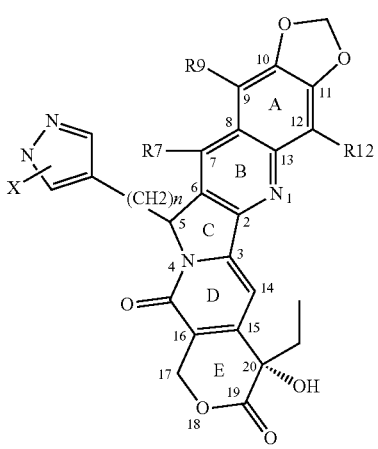

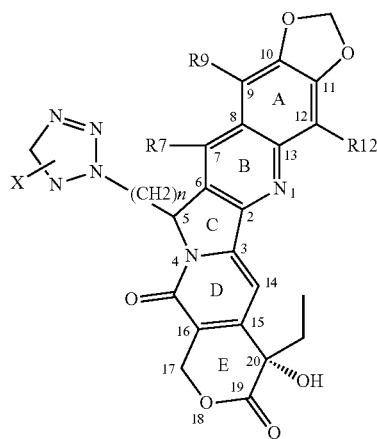

X = H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, a hydrogen (H) atom on the position 5 is replaced with the chemical group of "X-cyclopentadiene-based-(CH2)n-", where n is 0 or an integer selected from 1, 2, 3, 4, 5, 6, 7, 8, 9, 10, 11, 12, 13, 14, to 15. The functional groups $R^7$, $R^9$, and $R^{12}$, at respective positions 7, 9 and 12, are any one of the elements selected from H—, F—, Cl—, Br—, I—, FCH2—, ClCH2—, BrCH2—, ICH2—, HO—, HONH—, CH3O—, HOCH2—, NH2—, NH2CH2—, CH3NH—, (CH3)2N—, —NHC(O)NH2, —C(O)CH3, —CO2CH3, and —C(O)N(CH3)2, at the 3 positions, while the remaining two functional group positions are H, in some embodiments. In suitable embodiments, the FL118-derived analogs have the following formulas:

(VIII)

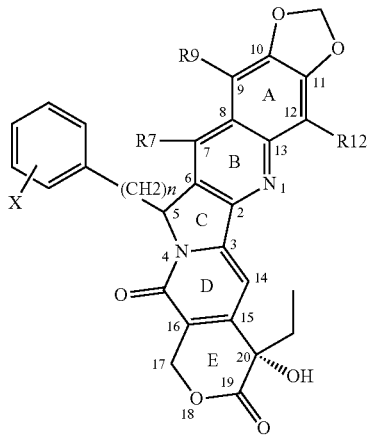

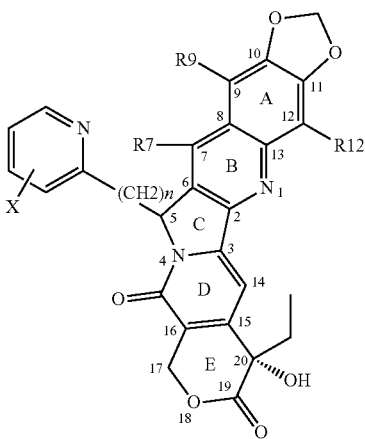

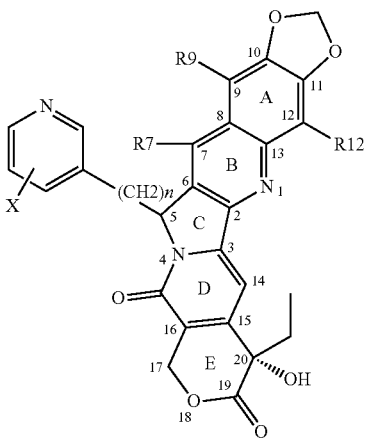

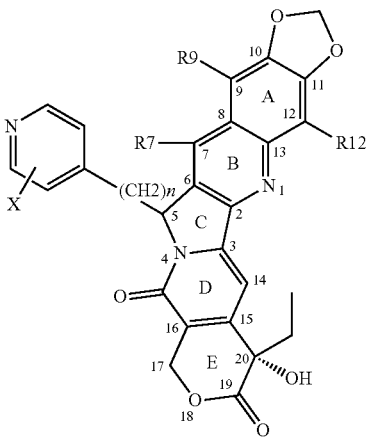

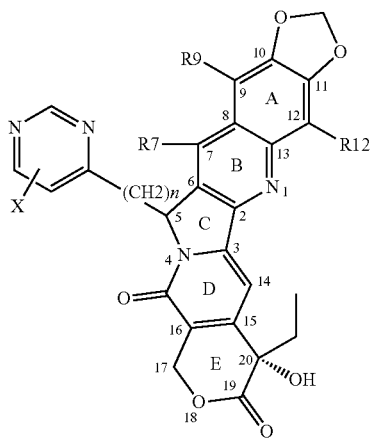

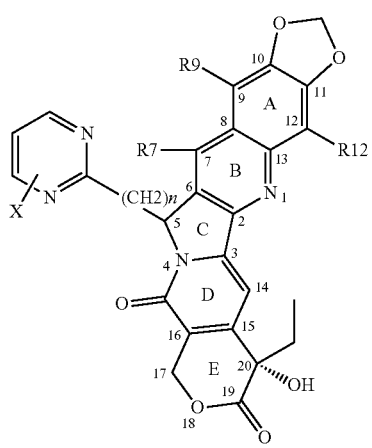

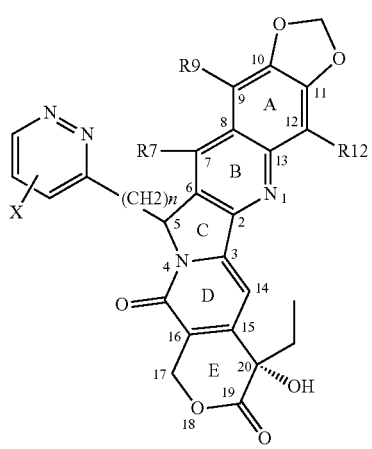

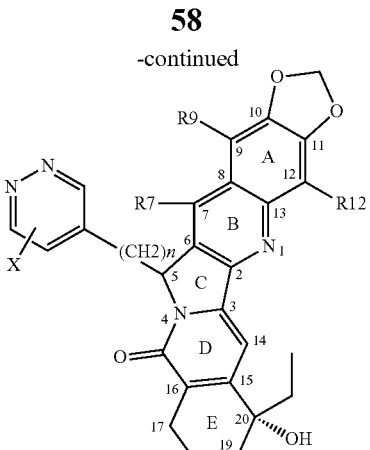

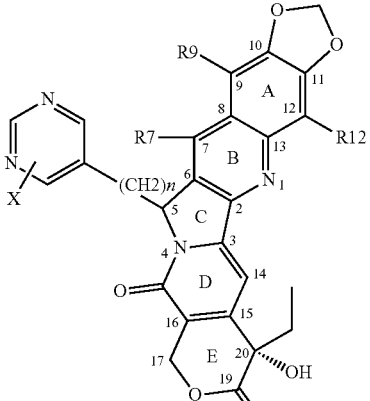

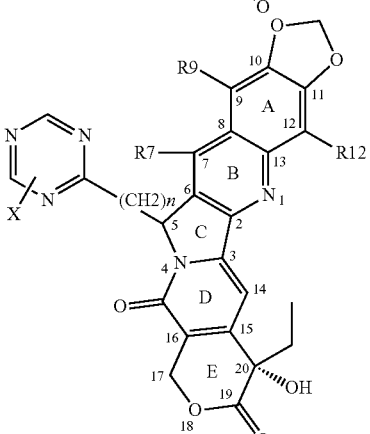

X = H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, a hydrogen (H) atom on the position 5 is replaced with the chemical group of "X-benzene-based-$(CH_2)n$-", where n is 0 or an integer selected from 1, 2, 3, 4, 5, 6, 7, 8, 9, 10, 11, 12, 13, 14, to 15. The functional groups $R^7$, $R^9$, and $R^{12}$, at respective positions 7, 9 and 12, are any one of the elements selected from H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —$NHC(O)NH_2$, —$C(O)CH_3$, —$CO_2CH_3$, and —$C(O)N(CH_3)_2$, at the 3 positions, while the remaining two functional group positions are H, in some embodiments. In suitable embodiments, the FL118-derived analogs have the following formula:

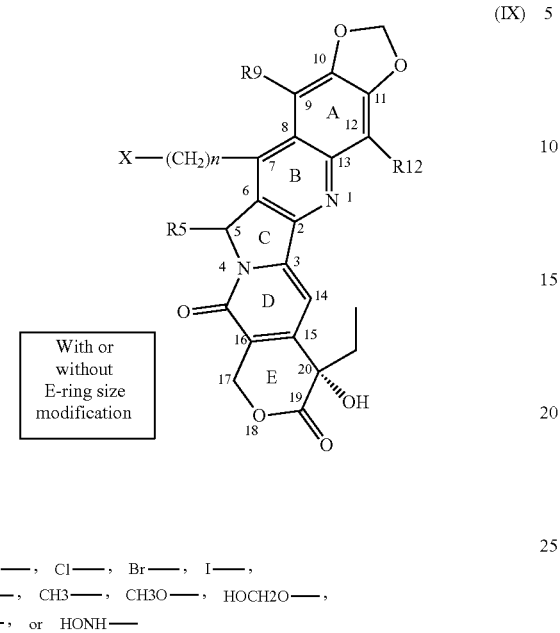

(IX)

X = F—, Cl—, Br—, I—,
NH2—, CH3—, CH3O—, HOCH2O—,
HO—, or HONH—

In illustrative embodiments, the hydrogen (H) atom on the position 7 is replaced with the chemical group of "X—(CH$_2$)n-", where n is 0 or an integer selected from 1, 2, 3, 4, 5, 6, 7, 8, 9, 10, 11, 12, 13, 14, to 15. The functional groups $R^5$, $R^9$, and $R^{12}$, at respective positions 5, 9 and 12, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

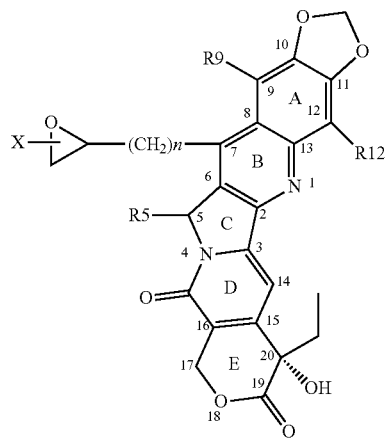

X = H—, F—, Cl—, Br—, I—, ClCH2—, BrCH2—,
NH2—, CH3—, CH3O—, HOCH2—, HOCH2O—,
NH2CH2—, HO—, or HONH—

In illustrative embodiments, the hydrogen (H) atom on the position 7 is replaced with the chemical group of "X-cyclopropane-based-(CH$_2$)n-", where n is 0 or an integer selected from 1, 2, 3, 4, 5, 6, 7, 8, 9, 10, 11, 12, 13, 14, to 15. The functional groups $R^5$, $R^9$, and $R^{12}$, at respective positions 5, 9 and 12, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

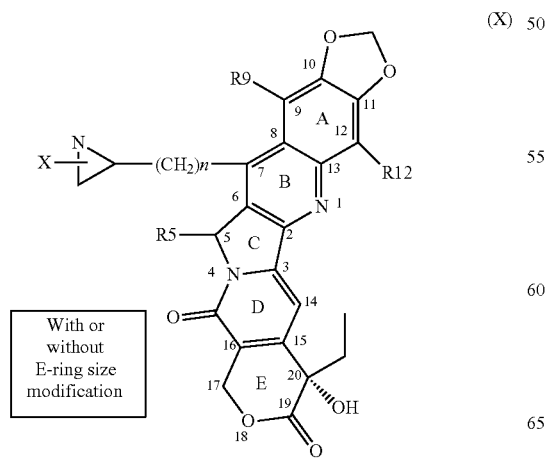

(X)

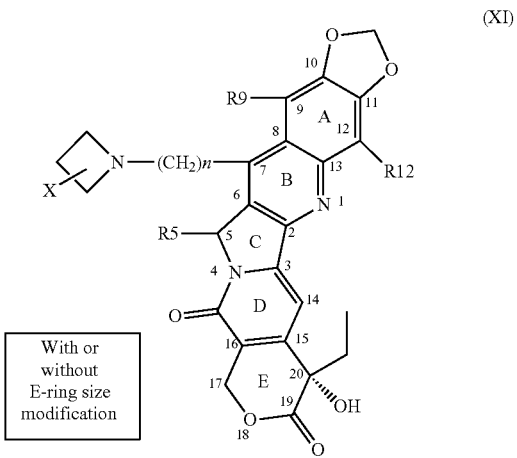

(XI)

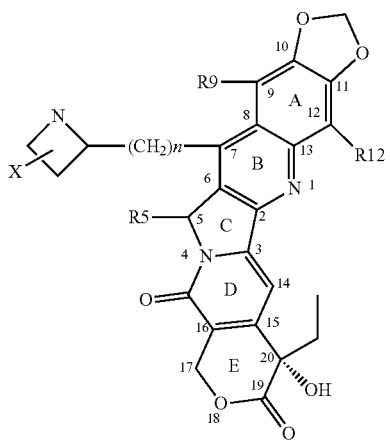

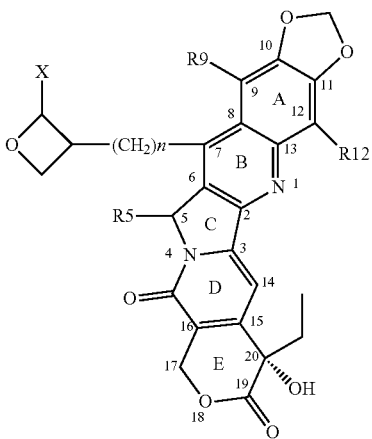

X = H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom on the position 7 is replaced with the chemical group of "X-cyclobutane-based-$(CH_2)n$-", where n is 0 or an integer selected from 1, 2, 3, 4, 5, 6, 7, 8, 9, 10, 11, 12, 13, 14, to 15. The functional groups $R^5$, $R^9$, and $R^{12}$, at respective positions 5, 9 and 12, are any one of the elements selected from H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —NHC(O)$NH_2$, —C(O)$CH_3$, —$CO_2CH_3$, and —C(O)N$(CH_3)_2$, at the 3 positions, while the remaining two functional group positions are H, in some embodiments. In suitable embodiments, the FL118-derived analogs have the following formulas:

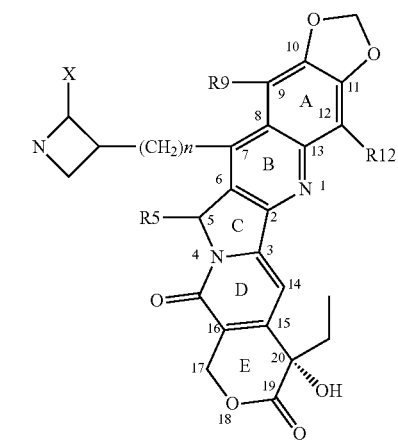

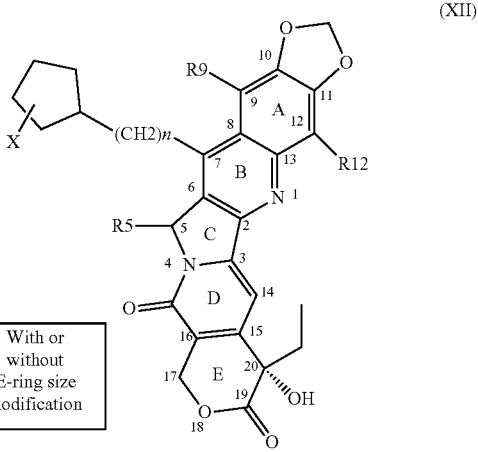

(XII)

With or without E-ring size modification

63
-continued
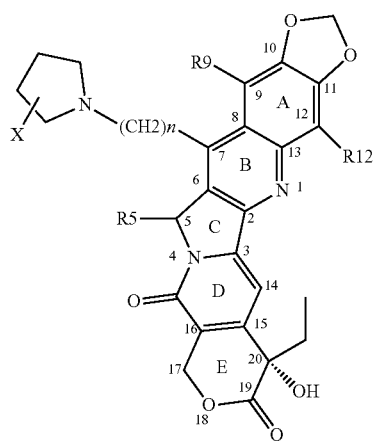
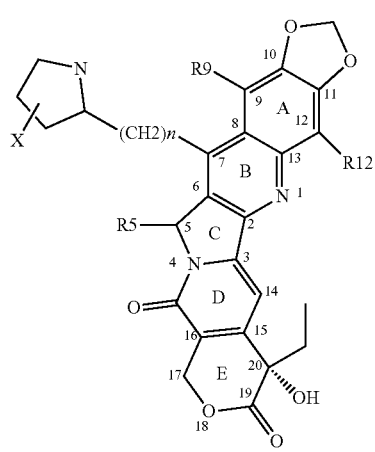
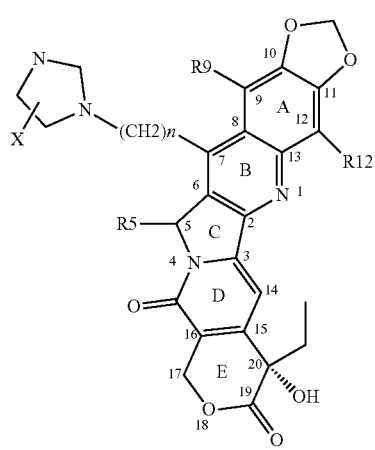
64
-continued
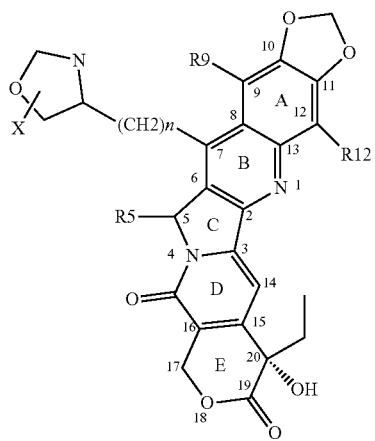
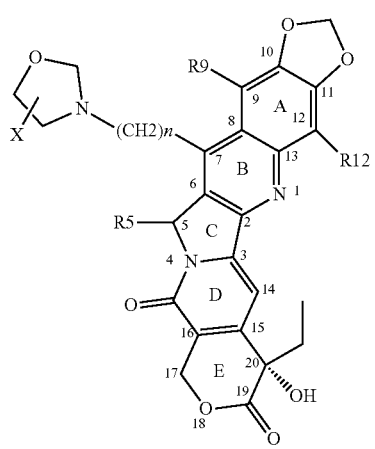
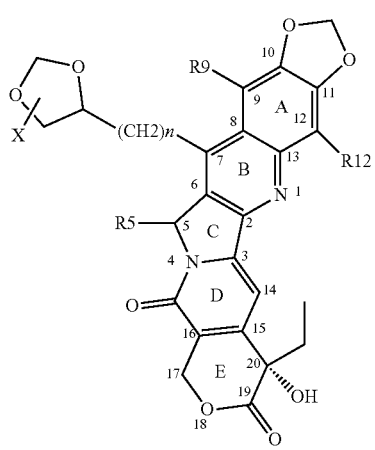

-continued

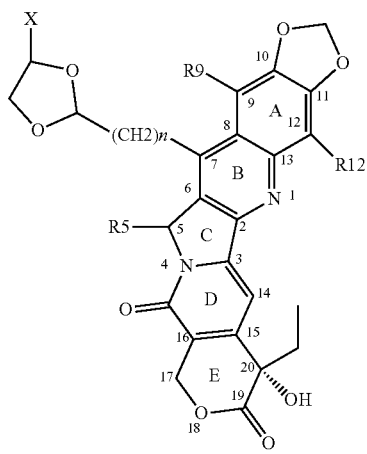

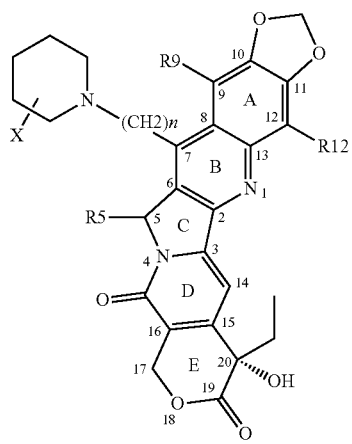

X = H—, F—, Cl—, Br—, I—, ClCH2—, BrCH2—, NH2—, CH3—, CH3O—, HOCH2—, HOCH2O—, NH2CH2—, HO—, or HONH—

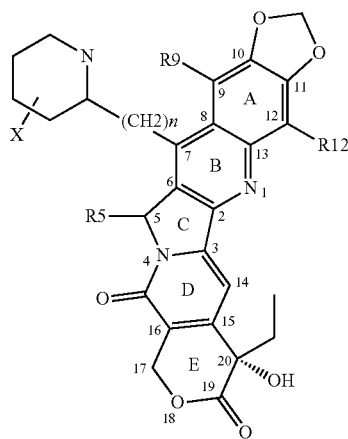

In illustrative embodiments, the hydrogen (H) atom on the position 7 is replaced with the chemical group of "X-cyclopentane-based-(CH$_2$)n-", where n is 0 or an integer selected from 1, 2, 3, 4, 5, 6, 7, 8, 9, 10, 11, 12, 13, 14, to 15. The functional groups $R^5$, $R^9$, and $R^{12}$, at respective positions 5, 9 and 12, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

(XIII)

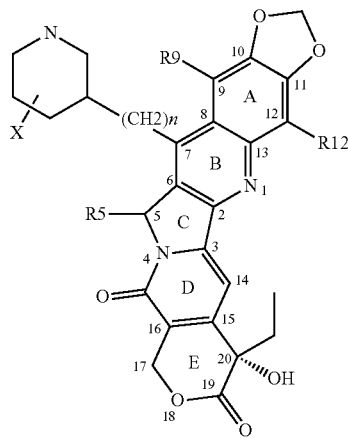

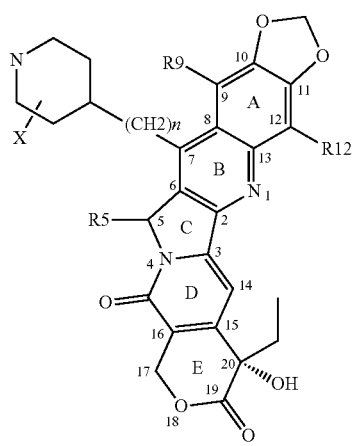
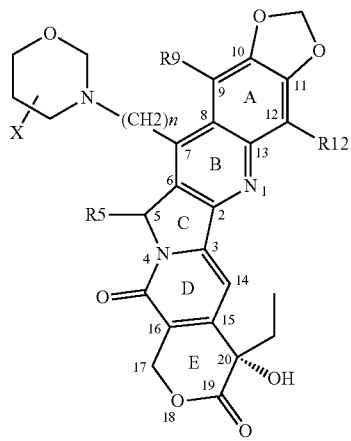
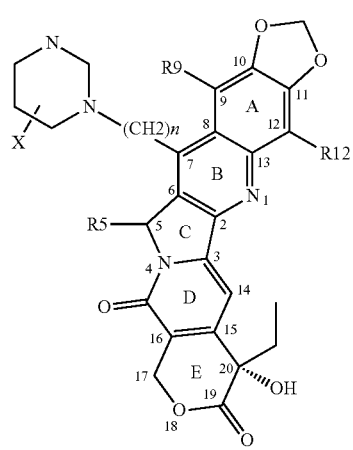
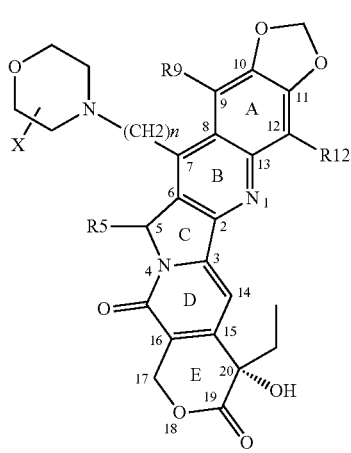
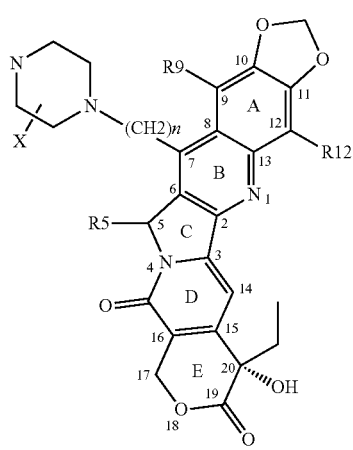
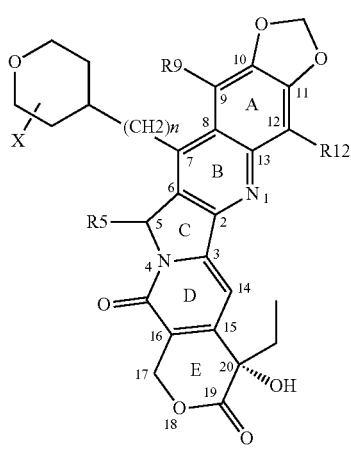

-continued

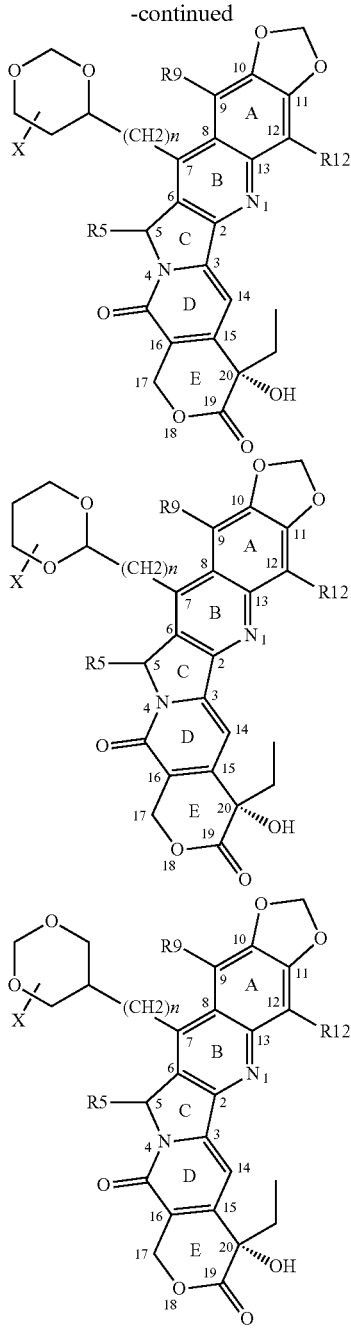

X= H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom on the position 7 is replaced with the chemical group of "X-cyclohexane-based-($CH_2$)n-", where n is 0 or an integer selected from 1, 2, 3, 4, 5, 6, 7, 8, 9, 10, 11, 12, 13, 14, to 15. The functional groups $R^5$, $R^9$, and $R^{12}$, at respective positions 5, 9 and 12, are any one of the elements selected from H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —$NHC(O)NH_2$, —$C(O)CH_3$, —$CO_2CH_3$, and —$C(O)N(CH_3)_2$, at the 3 positions, while the remaining two functional group positions are H, in some embodiments. In suitable embodiments, the FL118-derived analogs have the following formulas:

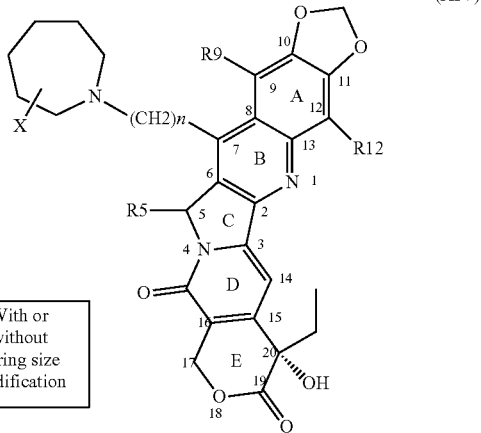

(XIV)

With or without E-ring size modification

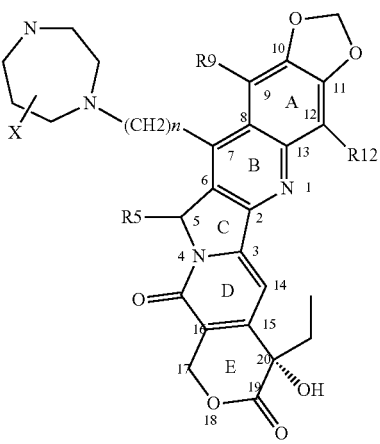

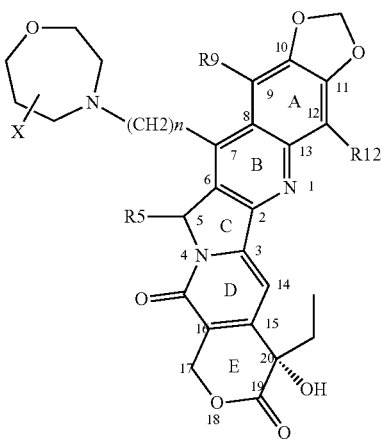

-continued

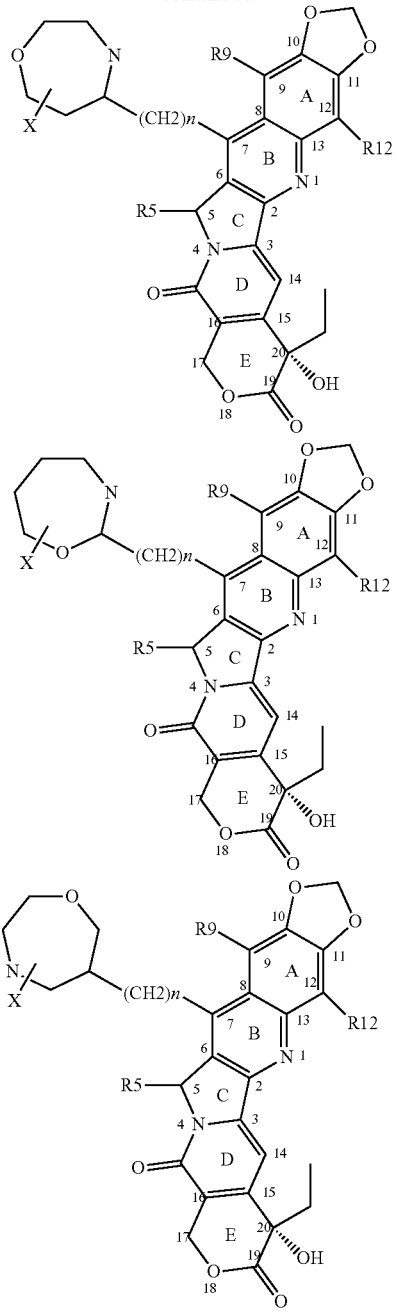

X = H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom on the position 7 is replaced with the chemical group of "X-cyclohexane-based-(CH2)n-", where n is 0 or an integer selected from 1, 2, 3, 4, 5, 6, 7, 8, 9, 10, 11, 12, 13, 14, to 15. The functional groups $R^5$, $R^9$, and $R^{12}$, at respective positions 5, 9 and 12, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

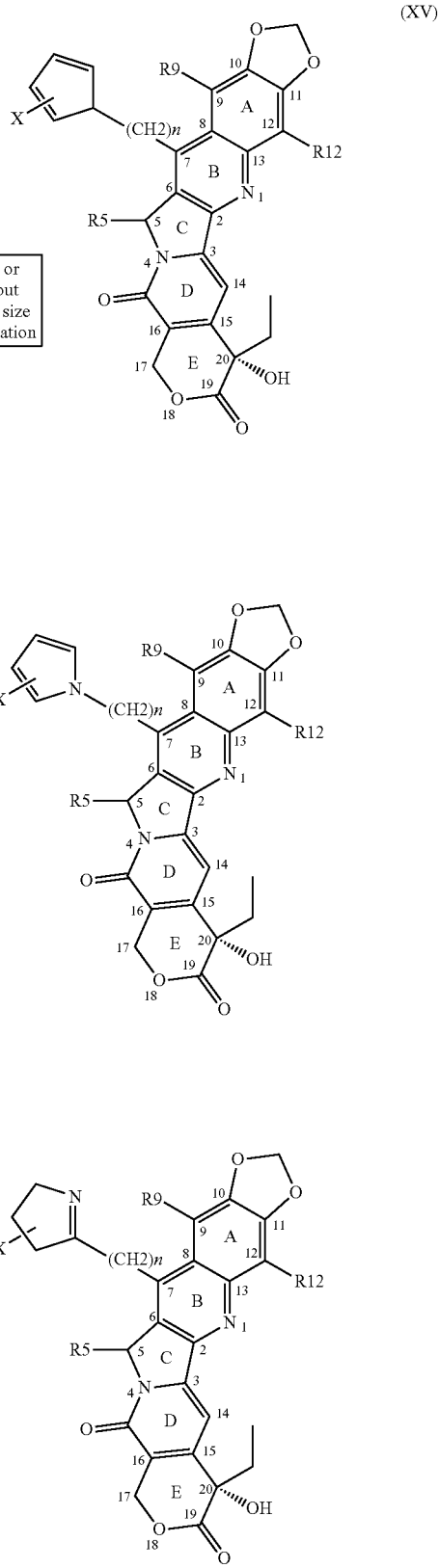

(XV)

With or without E-ring size modification

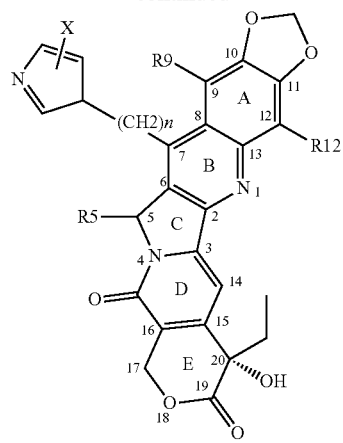
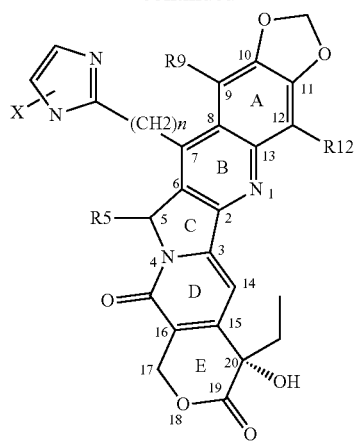
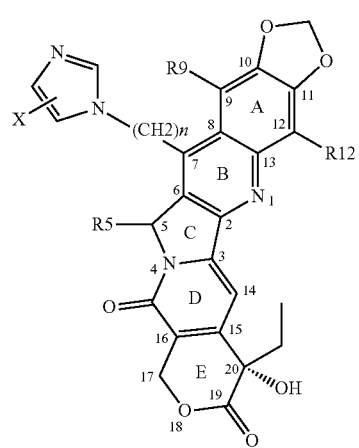
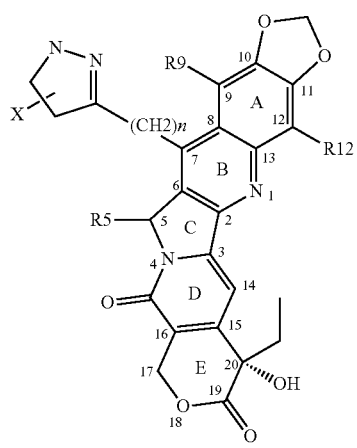
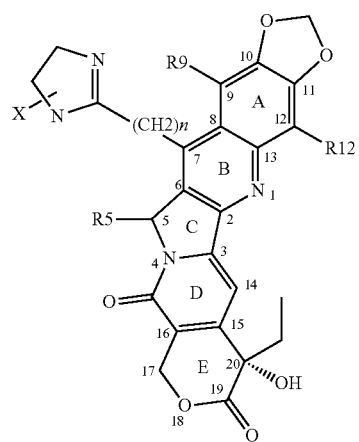
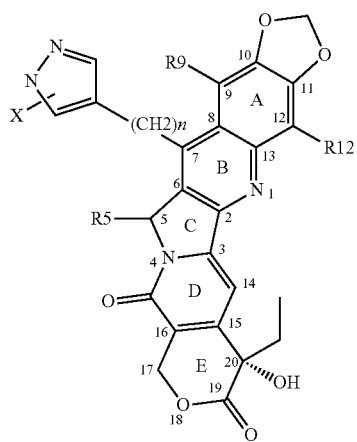

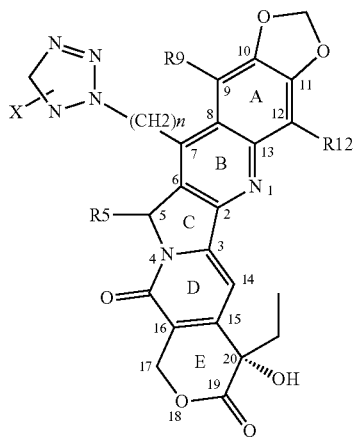

X= H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom on the position 7 is replaced with the chemical group of "X-cyclopentadiene-based-$(CH_2)n$-", where n is 0 or an integer selected from 1, 2, 3, 4, 5, 6, 7, 8, 9, 10, 11, 12, 13, 14, to 15. The functional groups $R^5$, $R^9$, and $R^{12}$, at respective positions 5, 9 and 12, are any one of the elements selected from H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —NHC(O)$NH_2$, —$C(O)CH_3$, —$CO_2CH_3$, and —$C(O)N(CH_3)_2$, at the 3 positions, while the remaining two functional group positions are H, in some embodiments. In suitable embodiments, the FL118-derived analogs have the following formulas:

(XVI)

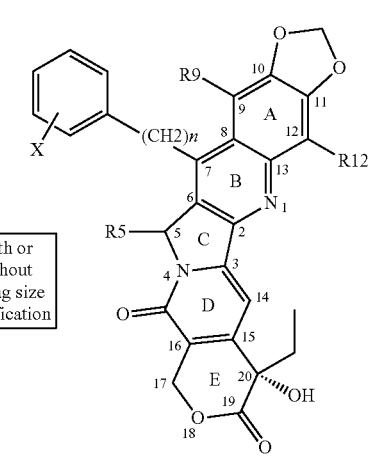

With or without E-ring size modification

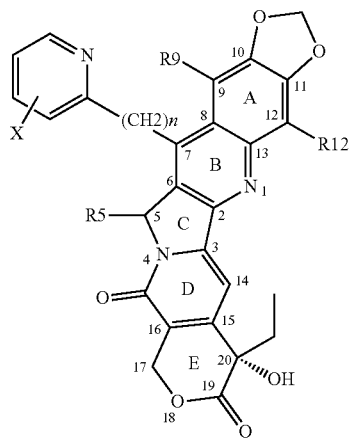

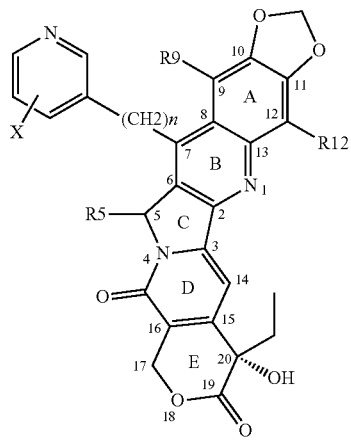

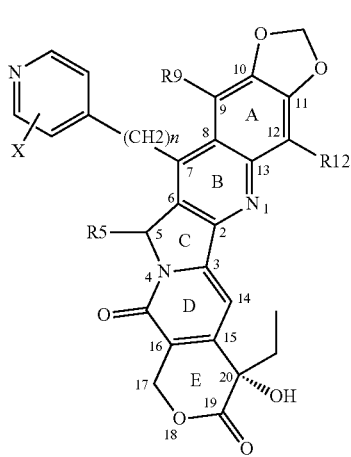

77

-continued

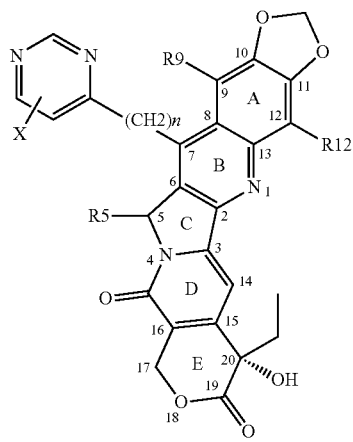

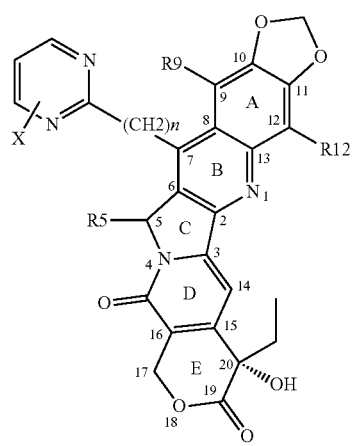

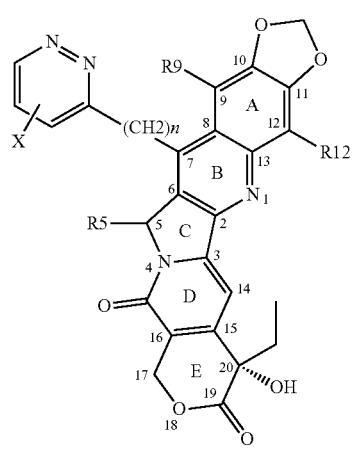

78

-continued

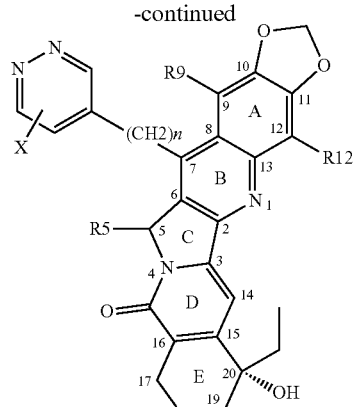

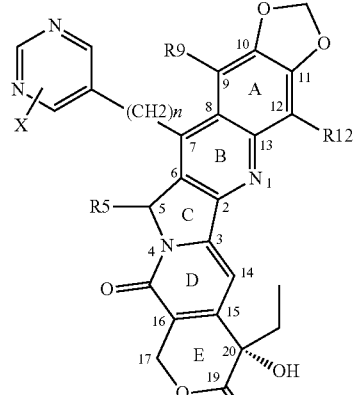

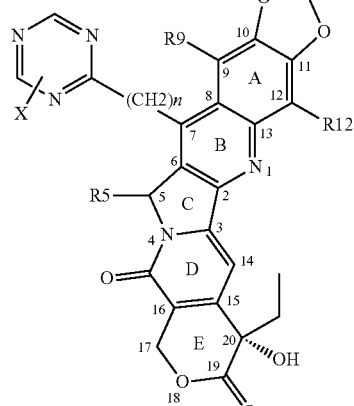

X= H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom on the position 7 is replaced with the chemical group of "X-benzene-based-$(CH_2)n$-", where n is 0 or an integer selected from 1, 2, 3, 4, 5, 6, 7, 8, 9, 10, 11, 12, 13, 14, to 15. The functional groups $R^5$, $R^9$, and $R^{12}$, at respective positions 5, 9 and 12, are any one of the elements selected from H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —$NHC(O)NH_2$, —$C(O)CH_3$, —$CO_2CH_3$, and —$C(O)N(CH_3)_2$, at the 3 positions, while the remaining two functional group positions are H, in some embodiments. In suitable embodiments, the FL118-derived analogs have the following formula:

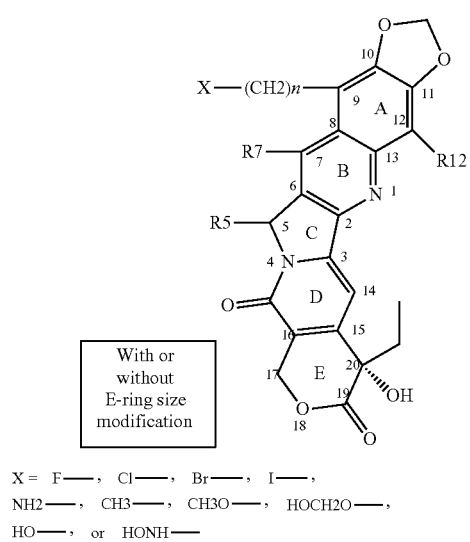

(XVII)

X= F——, Cl——, Br——, I——, NH2——, CH3——, CH3O——, HOCH2O——, HO——, or HONH——

In illustrative embodiments, the hydrogen (H) atom on the position 9 is replaced with the chemical group of "X—(CH₂)n-", where n is 0 or an integer selected from 1, 2, 3, 4, 5, 6, 7, 8, 9, 10, 11, 12, 13, 14, to 15. The functional groups $R^5$, $R^7$, and $R^{12}$, at respective positions 5, 7 and 12, are any one of the elements selected from H—, F—, Cl—, Br—, I—, FCH₂—, ClCH₂—, BrCH₂—, ICH₂—, HO—, HONH—, CH₃O—, HOCH₂—, NH₂—, NH₂CH₂—, CH₃NH—, (CH₃)₂N—, —NHC(O)NH₂, —C(O)CH₃, —CO₂CH₃, and —C(O)N(CH₃)₂, at the 3 positions, while the remaining two functional group positions are H, in some embodiments. In suitable embodiments, the FL118-derived analogs have the following formulas:

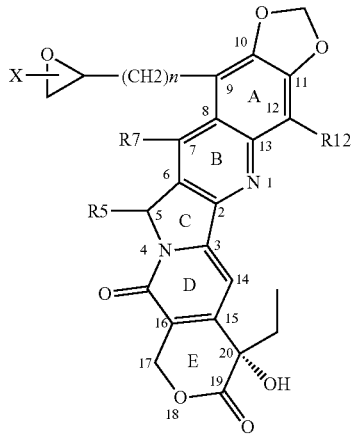

X= H——, F——, Cl——, Br——, I——, ClCH2——, BrCH2——, NH2——, CH3——, CH3O——, HOCH2——, HOCH2O——, NH2CH2——, HO——, or HONH——

In illustrative embodiments, the hydrogen (H) atom on the position 9 is replaced with the chemical group of "X-cyclopropane-based-(CH₂)n-", where n is 0 or an integer selected from 1, 2, 3, 4, 5, 6, 7, 8, 9, 10, 11, 12, 13, 14, to 15. The functional groups $R^5$, $R^7$, and $R^{12}$, at respective positions 5, 7 and 12, are any one of the elements selected from H—, F—, Cl—, Br—, I—, FCH₂—, ClCH₂—, BrCH₂—, ICH₂—, HO—, HONH—, CH₃O—, HOCH₂—, NH₂—, NH₂CH₂—, CH₃NH—, (CH₃)₂N—, —NHC(O)NH₂, —C(O)CH₃, —CO₂CH₃, and —C(O)N(CH₃)₂, at the 3 positions, while the remaining two functional group positions are H, in some embodiments. In suitable embodiments, the FL118-derived analogs have the following formulas:

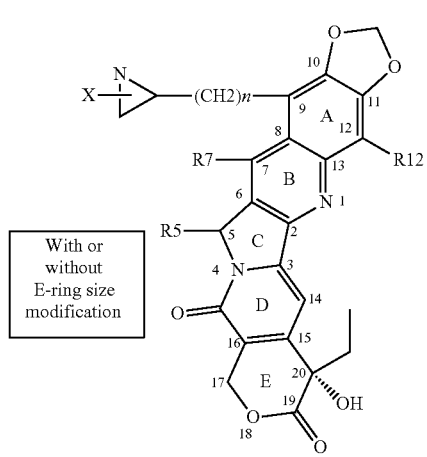

(XVIII)

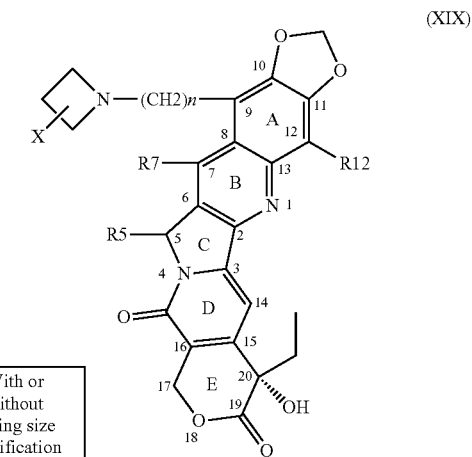

(XIX)

81

-continued

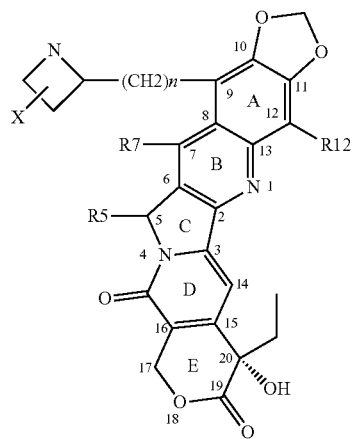

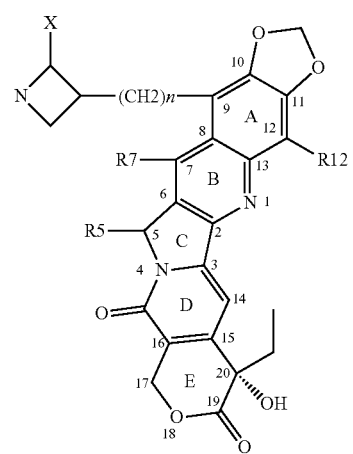

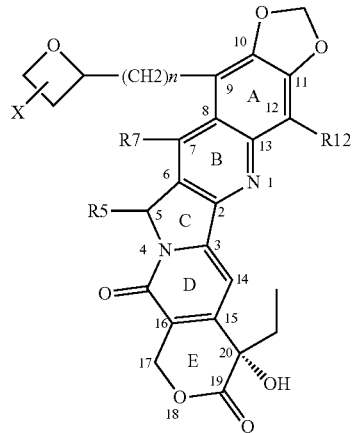

82

-continued

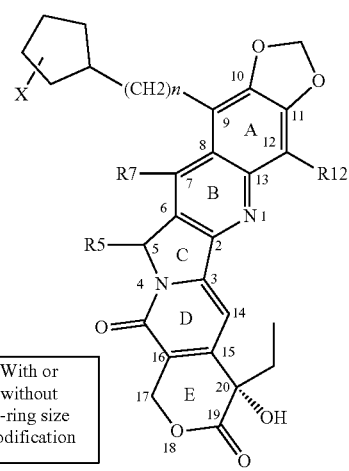

X = H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom on the position 9 is replaced with the chemical group of "X-cyclobutane-based-($CH_2$)n-", where n is 0 or an integer selected from 1, 2, 3, 4, 5, 6, 7, 8, 9, 10, 11, 12, 13, 14, to 15. The functional groups $R^5$, $R^7$, and $R^{12}$, at respective positions 5, 7 and 12, are any one of the elements selected from H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —NHC(O)$NH_2$, —C(O)$CH_3$, —$CO_2CH_3$, and —C(O)N($CH_3$)$_2$, at the 3 positions, while the remaining two functional group positions are H, in some embodiments. In suitable embodiments, the FL118-derived analogs have the following formulas:

(XX)

With or without E-ring size modification

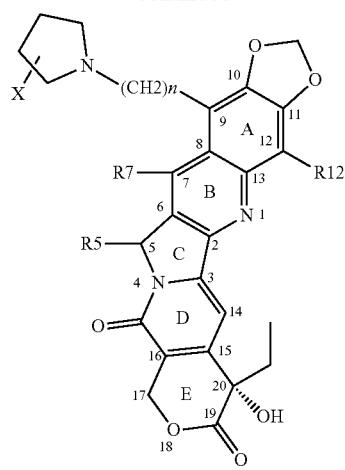
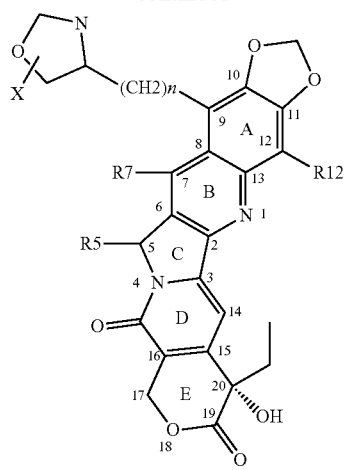
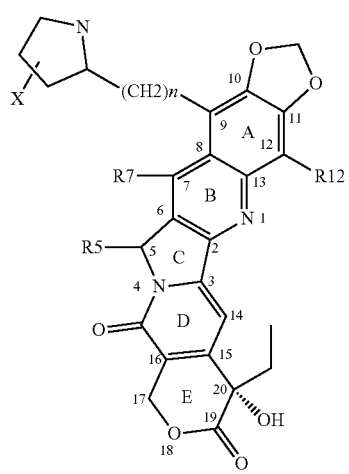
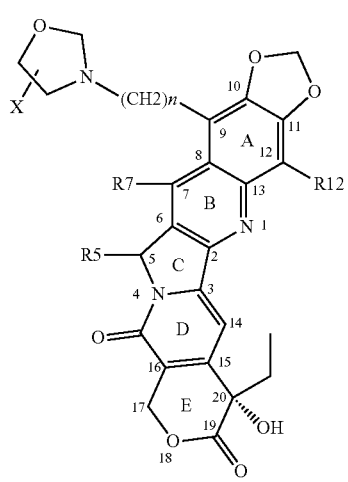
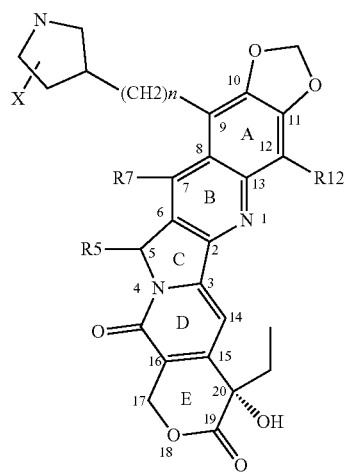
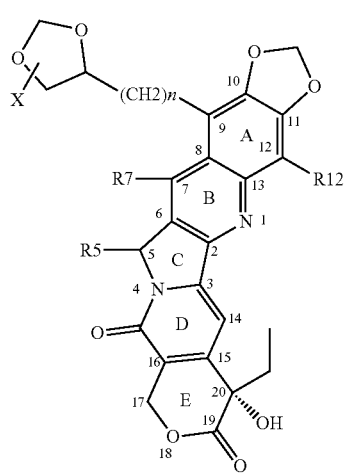

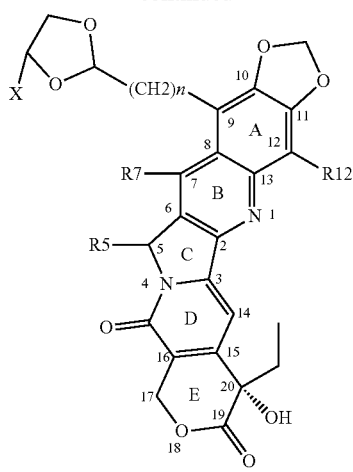

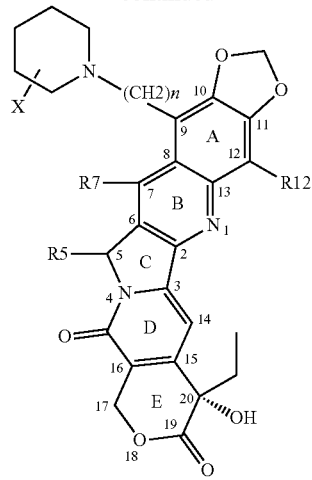

X = H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom on the position 9 is replaced with the chemical group of "X-cyclopentane-based-(CH$_2$)n-", where n is 0 or an integer selected from 1, 2, 3, 4, 5, 6, 7, 8, 9, 10, 11, 12, 13, 14, to 15. The functional groups $R^5$, $R^7$, and $R^{12}$, at respective positions 5, 7 and 12, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

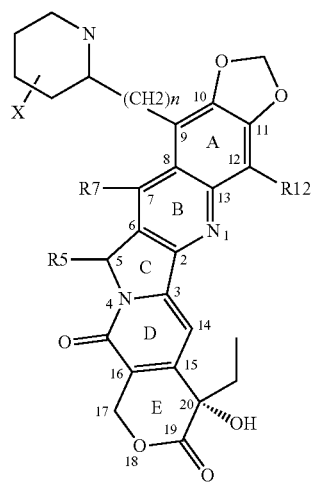

(XXI)

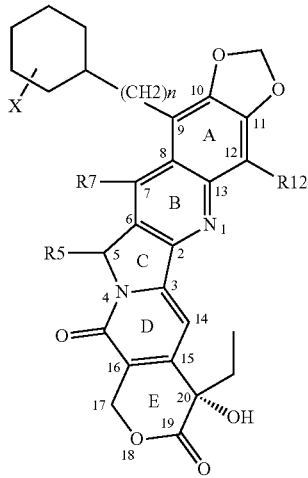

With or without E-ring size modification

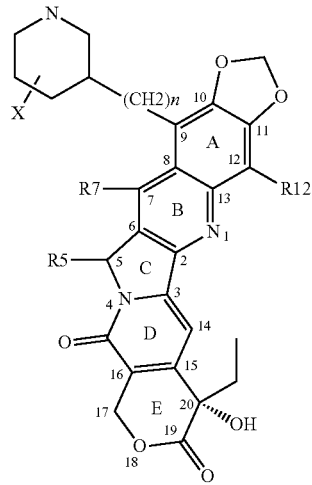

87
-continued
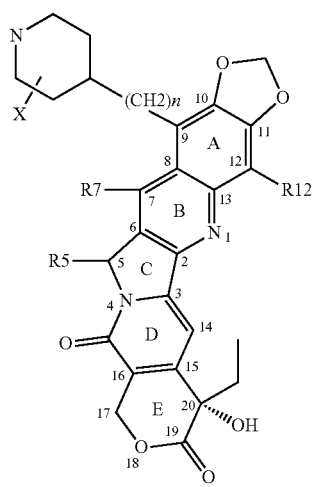
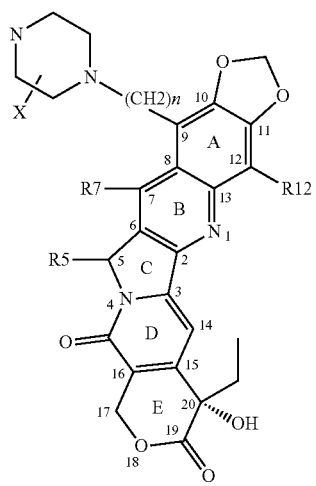
88
-continued
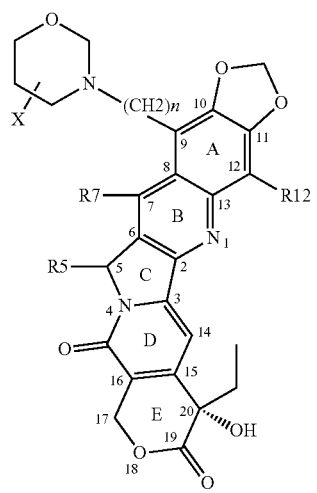

-continued

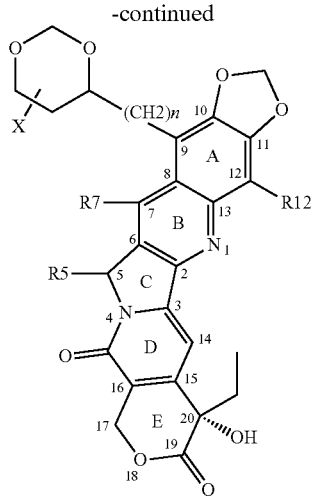

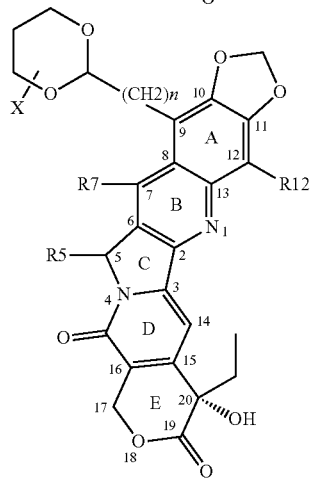

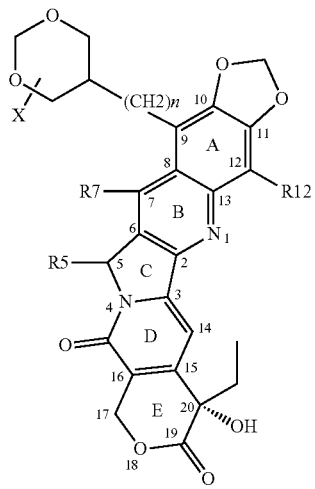

X= H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom on the position 9 is replaced with the chemical group of "X-cyclo-hexane-based-(CH$_2$)n-", where n is 0 or an integer selected from 1, 2, 3, 4, 5, 6, 7, 8, 9, 10, 11, 12, 13, 14, to 15. The functional groups $R^5$, $R^7$, and $R^{12}$, at respective positions 5, 7 and 12, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

(XXII)

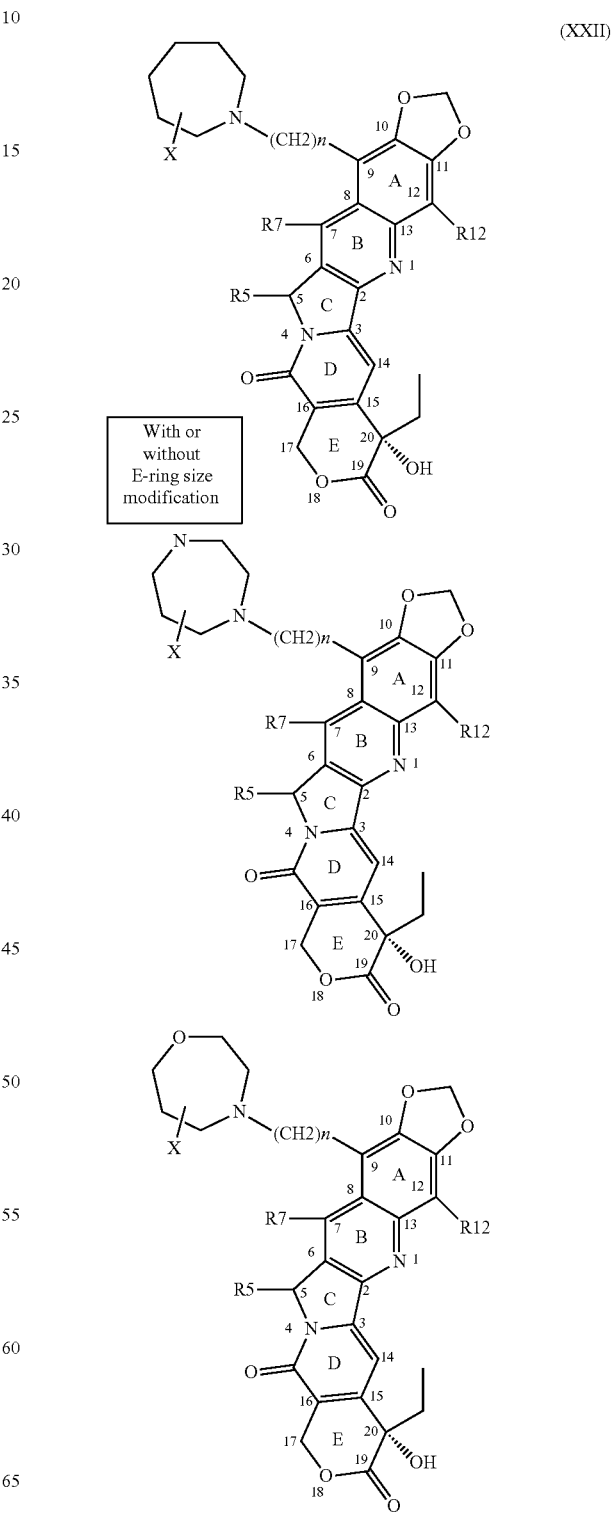

-continued

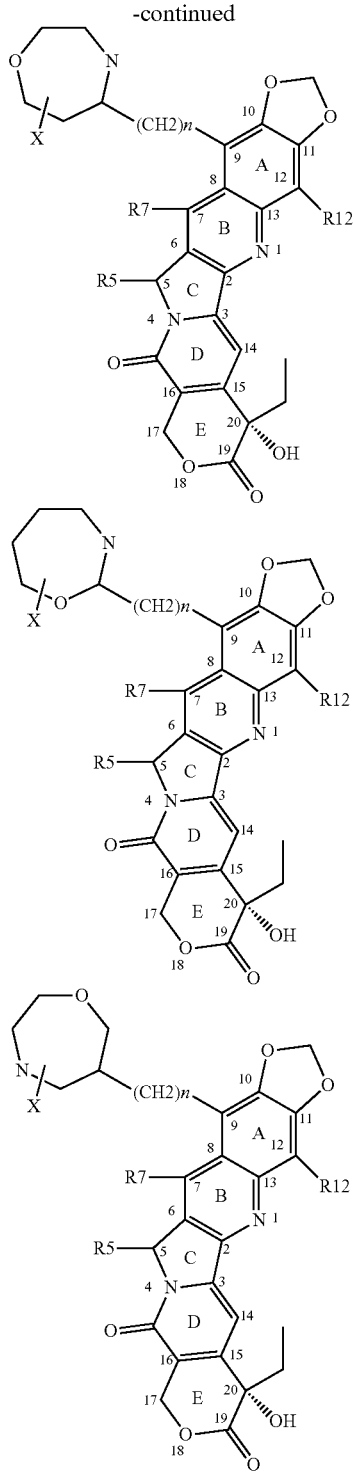

X = H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom on the position 9 is replaced with the chemical group of "X-cycloheptane-based-(CH₂)n-", where n is 0 or an integer selected from 1, 2, 3, 4, 5, 6, 7, 8, 9, 10, 11, 12, 13, 14, to 15. The functional groups $R^5$, $R^7$, and $R^{12}$, at respective positions 5, 7 and 12, are any one of the elements selected from H—, F—, Cl—, Br—, I—, FCH₂—, ClCH₂—, BrCH₂—, ICH₂—, HO—, HONH—, CH₃O—, HOCH₂—, NH₂—, NH₂CH₂—, CH₃NH—, (CH₃)₂N—, —NHC(O)NH₂, —C(O)CH₃, —CO₂CH₃, and —C(O)N(CH₃)₂, at the 3 positions, while the remaining two functional group positions are H, in some embodiments. In suitable embodiments, the FL118-derived analogs have the following formulas:

(XXIII)

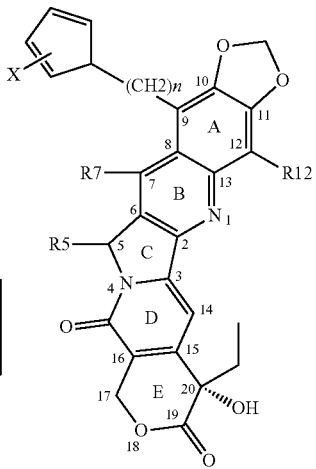

With or without E-ring size modification

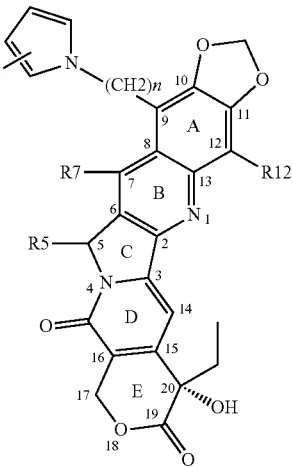

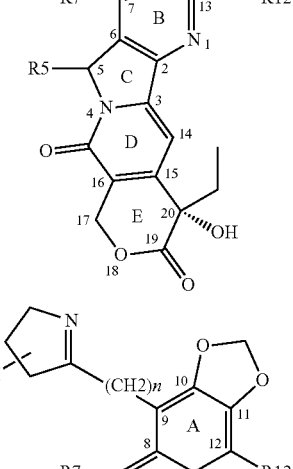

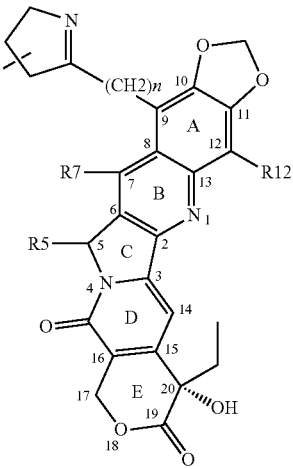

-continued
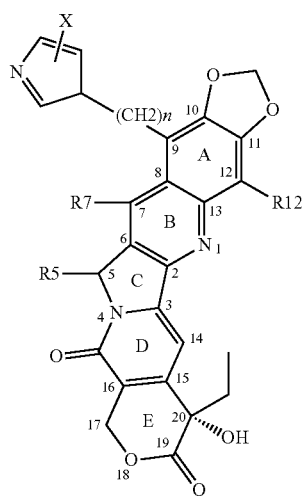
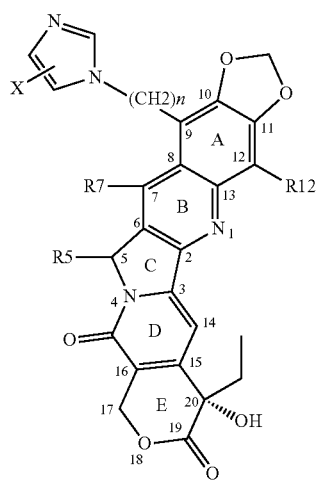
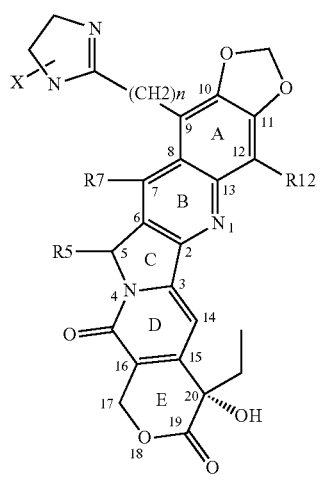
-continued
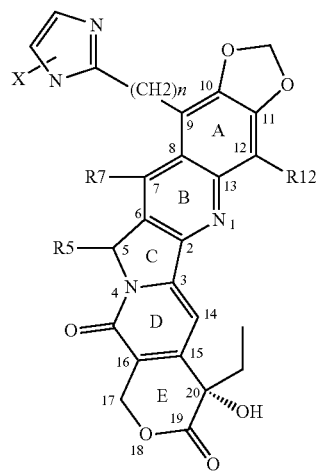
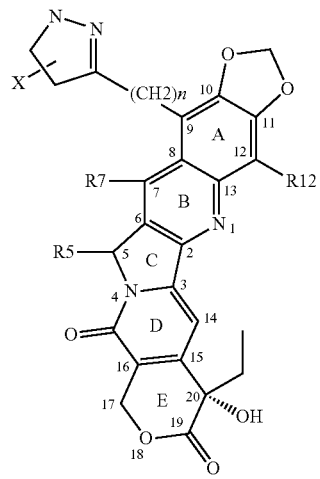
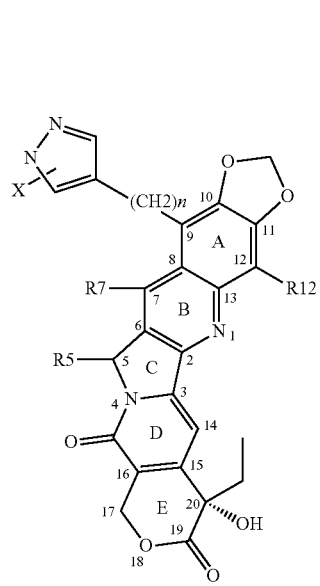

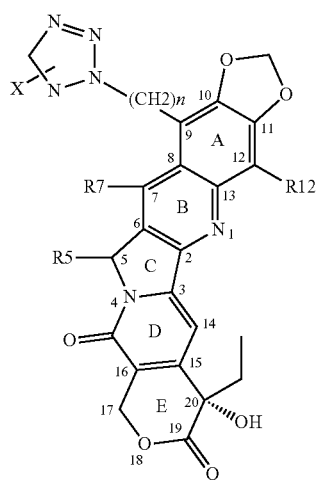

X = H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom on the position 9 is replaced with the chemical group of "X-cyclopentadiene-based-(CH$_2$)n-", where n is 0 or an integer selected from 1, 2, 3, 4, 5, 6, 7, 8, 9, 10, 11, 12, 13, 14, to 15. The functional groups $R^5$, $R^7$, and $R^{12}$, at respective positions 5, 7 and 12, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

(XXIV)

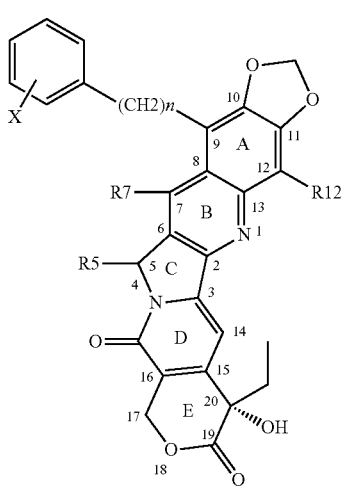

With or without E-ring size modification

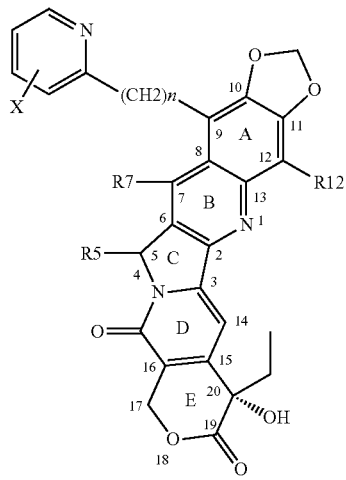

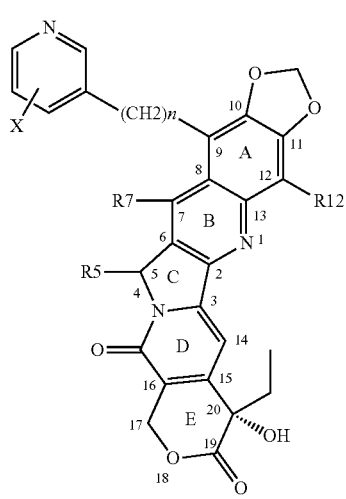

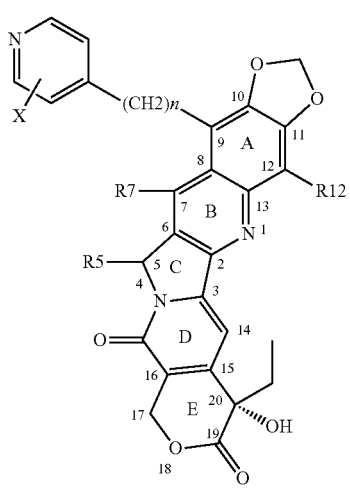

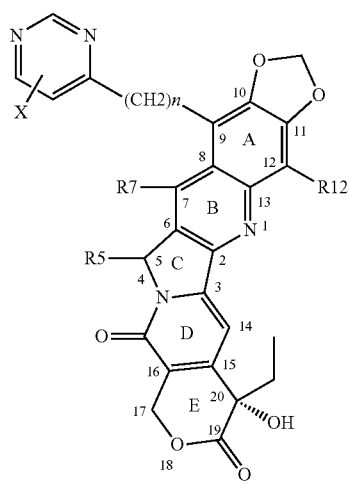
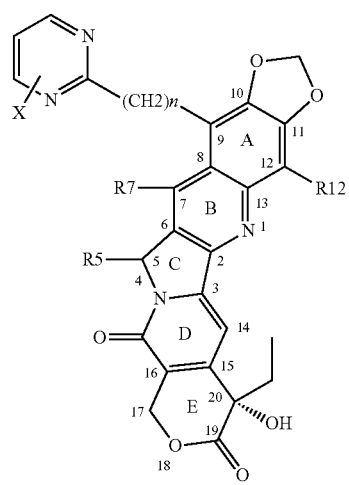
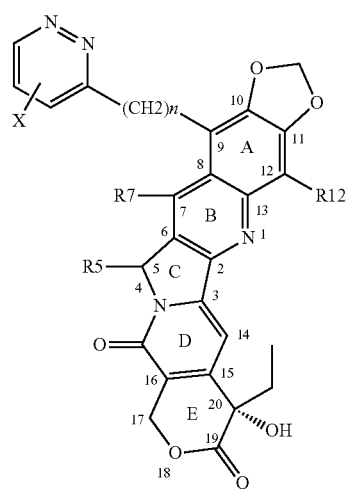
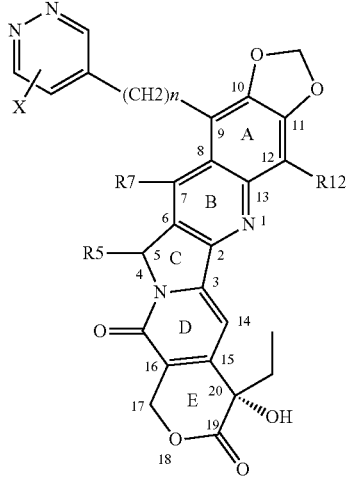
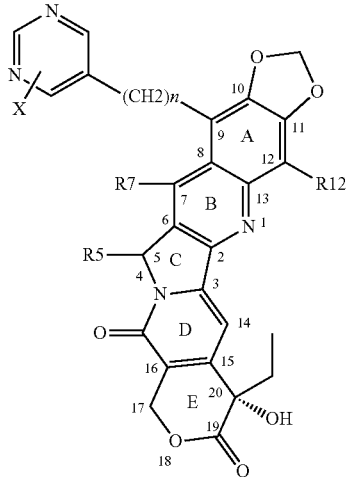
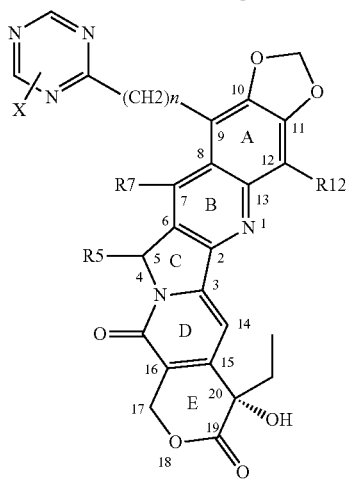
X = H—, F—, Cl—, Br—, I—, ClCH2—, BrCH2—, NH2—, CH3—, CH3O—, HOCH2—, HOCH2O—, NH2CH2—, HO—, or HONH—
In illustrative embodiments, the hydrogen (H) atom on the position 9 is replaced with the chemical group of "X-benzene-based-$(CH_2)n$-", where n is 0 or an integer selected from 1, 2, 3, 4, 5, 6, 7, 8, 9, 10, 11, 12, 13, 14, to 15. The functional groups $R^5$, $R^7$, and $R^{12}$, at respective positions 5, 7 and 12, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formula:

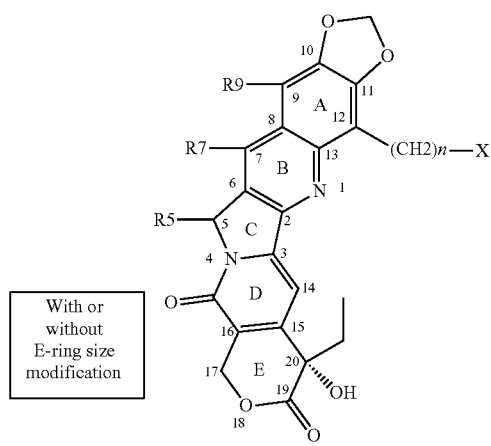

(XXV)

X = F—, Cl—, Br—, I—,
NH2—, CH3—, CH3O—, HOCH2O—,
HO—, or HONH—

In illustrative embodiments, the hydrogen (H) atom on the position 12 is replaced with the chemical group of "X—(CH$_2$)n-", where n is 0 or an integer selected from 1, 2, 3, 4, 5, 6, 7, 8, 9, 10, 11, 12, 13, 14, to 15. The functional groups R$^5$, R$^7$, and R$^9$, at respective positions 5, 7 and 9, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

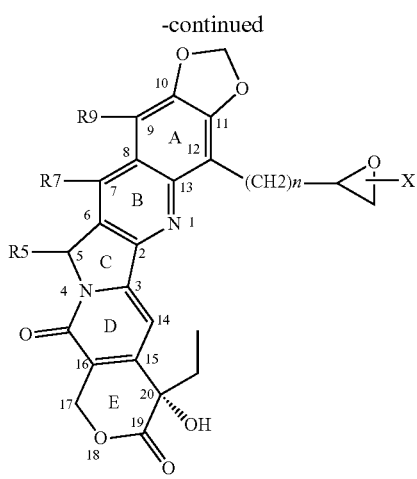

X = H—, F—, Cl—, Br—, I—, ClCH2—, BrCH2—,
NH2—, CH3—, CH3O—, HOCH2—, HOCH2O—,
NH2CH2—, HO—, or HONH—

In illustrative embodiments, the hydrogen (H) atom on the position 12 is replaced with the chemical group of "X-cyclopropane-based-(CH$_2$)n-", where n is 0 or an integer selected from 1, 2, 3, 4, 5, 6, 7, 8, 9, 10, 11, 12, 13, 14, to 15. The functional groups R$^5$, R$^7$, and R$^9$, at respective positions 5, 7 and 9, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

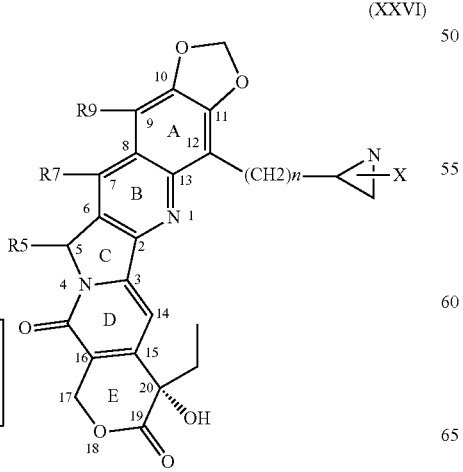

(XXVI)

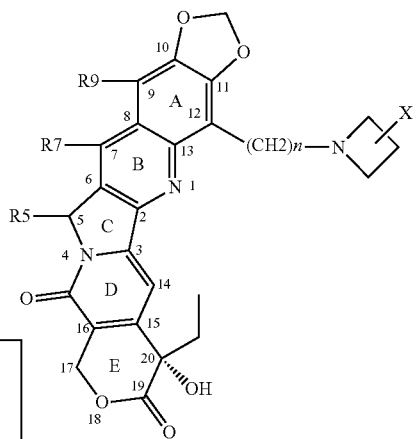

(XXVII)

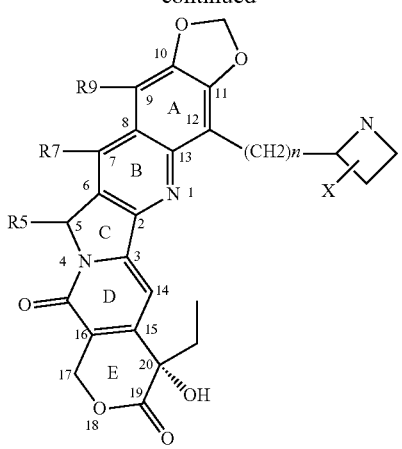

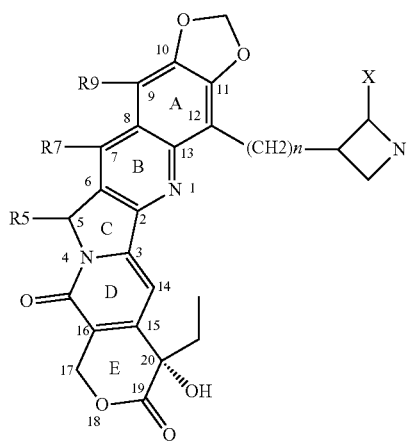

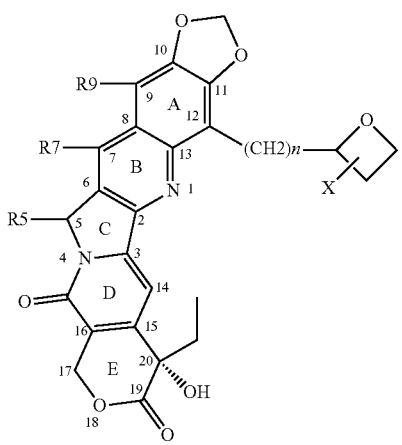

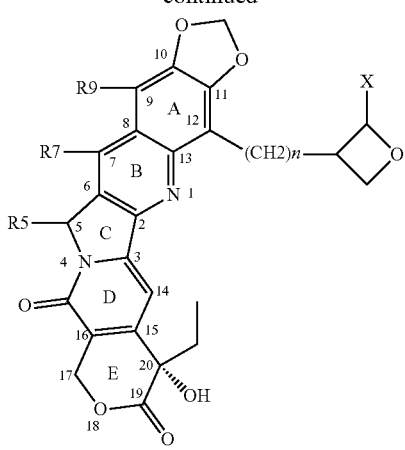

X = H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom on the position 12 is replaced with the chemical group of "X-cyclobutane-based-(CH₂)n, where n is 0 or an integer selected from 1, 2, 3, 4, 5, 6, 7, 8, 9, 10, 11, 12, 13, 14, to 15. The functional groups $R^5$, $R^7$, and $R^9$, at respective positions 5, 7 and 9, are any one of the elements selected from H—, F—, Cl—, Br—, I—, FCH₂—, ClCH₂—, BrCH₂—, ICH₂—, HO—, HONH—, CH₃O—, HOCH₂—, NH₂—, NH₂CH₂—, CH₃NH—, (CH₃)₂N—, —NHC(O)NH₂, —C(O)CH₃, —CO₂CH₃, and —C(O)N(CH₃)₂, at the 3 positions, while the remaining two functional group positions are H, in some embodiments. In suitable embodiments, the FL118-derived analogs have the following formulas:

(XXVIII)

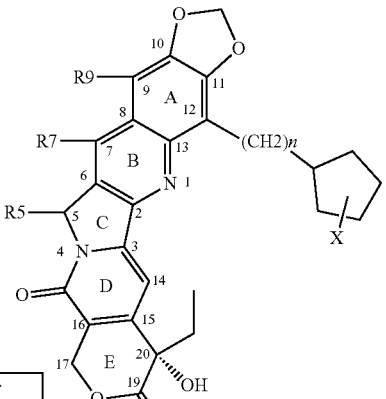

With or without E-ring size modification

103
-continued
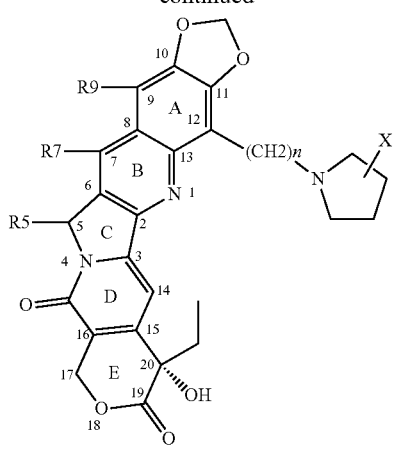
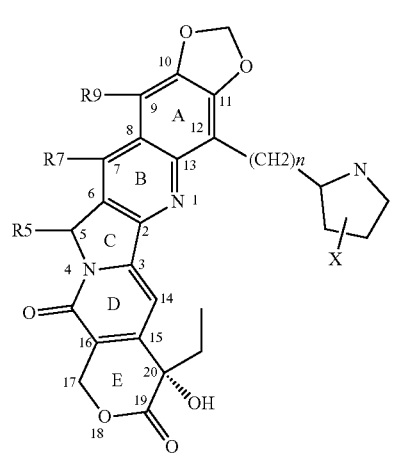
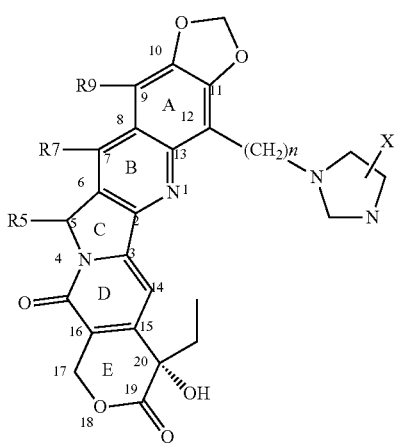
104
-continued
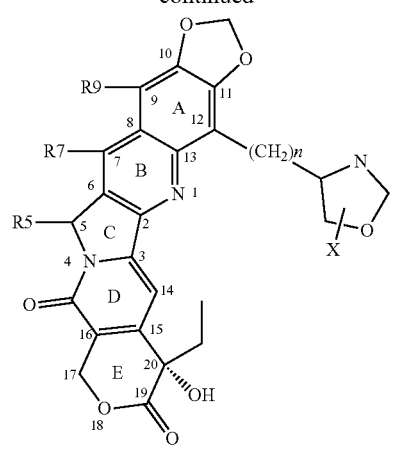
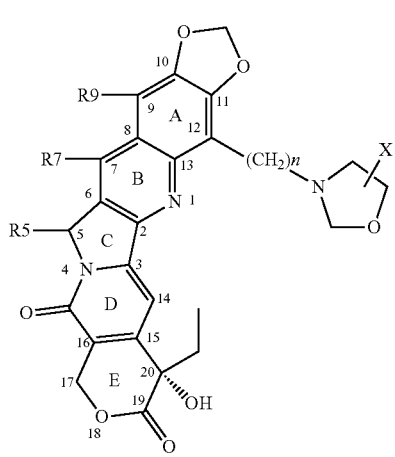
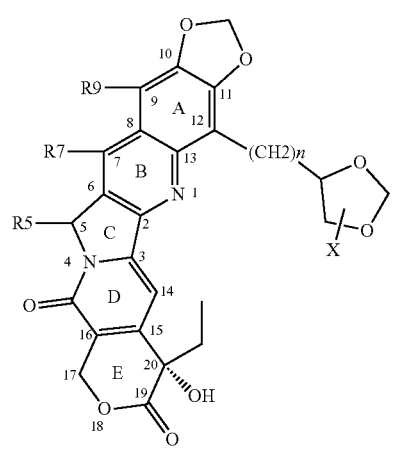

-continued

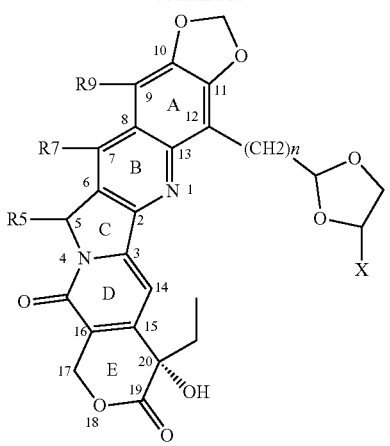

X = H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom on the position 12 is replaced with the chemical group of "X-cyclopentane-based-(CH₂)n-", where n is 0 or an integer selected from 1, 2, 3, 4, 5, 6, 7, 8, 9, 10, 11, 12, 13, 14, to 15. The functional groups R⁵, R⁷, and R⁹, at respective positions 5, 7 and 9, are any one of the elements selected from H—, F—, Cl—, Br—, I—, FCH₂—, ClCH₂—, BrCH₂—, ICH₂—, HO—, HONH—, CH₃O—, HOCH₂—, NH₂—, NH₂CH₂—, CH₃NH—, (CH₃)₂N—, —NHC(O)NH₂, —C(O)CH₃, —CO₂CH₃, and —C(O)N(CH₃)₂, at the 3 positions, while the remaining two functional group positions are H, in some embodiments. In suitable embodiments, the FL118-derived analogs have the following formulas:

(XXIX)

With or without E-ring size modification

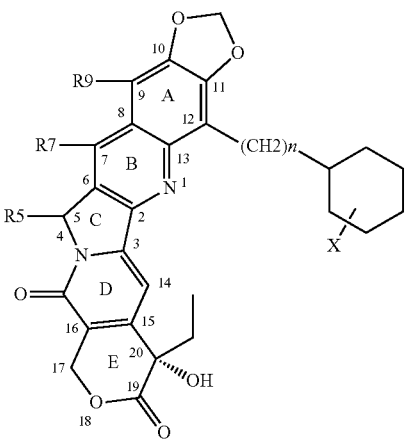

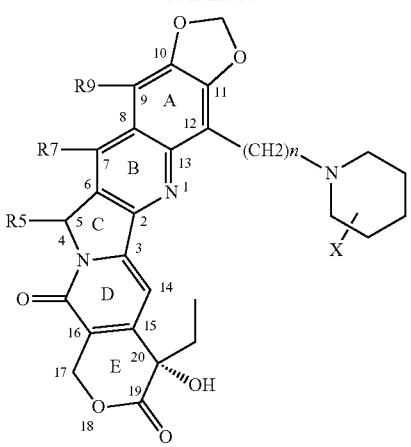

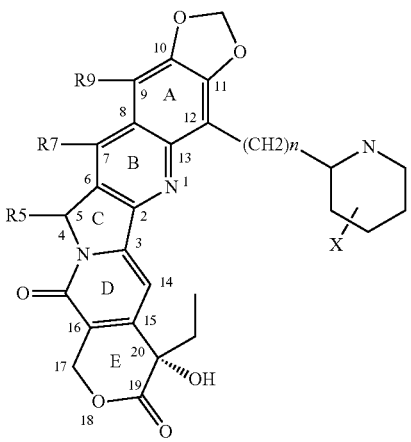

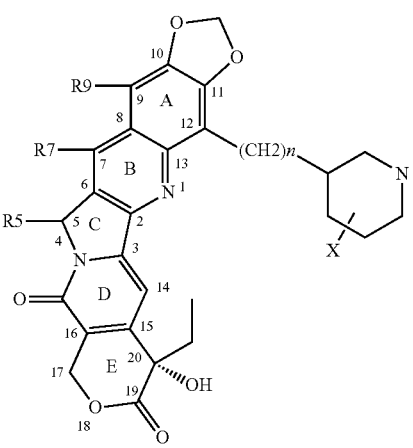

107
-continued
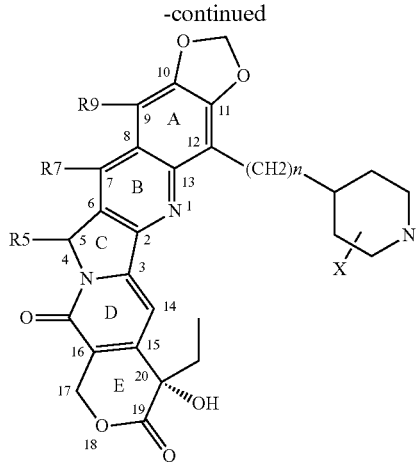
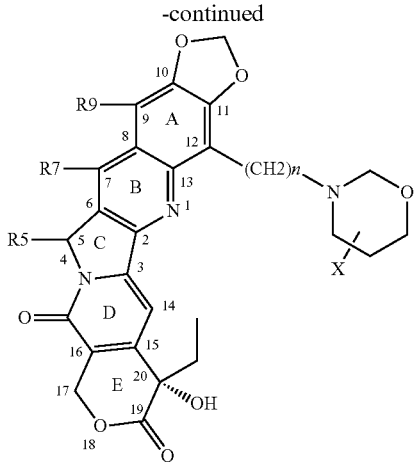
108
-continued

-continued

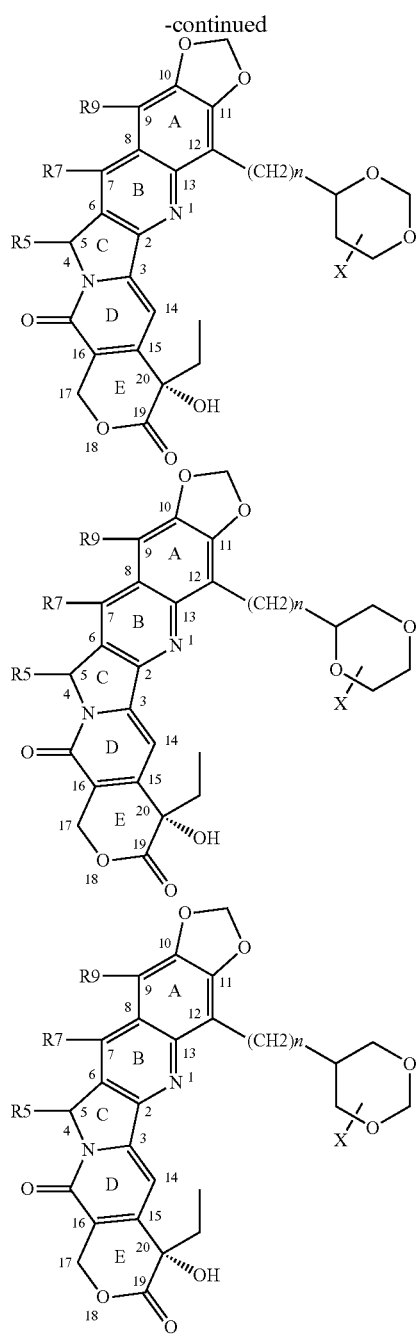

X = H—, F—, Cl—, Br—, I—,
ClCH2—, BrCH2—, NH2—, CH3—,
CH3O—, HOCH2—, HOCH2O—,
NH2CH2—, HO—, or HONH—

In illustrative embodiments, the hydrogen (H) atom on the position 12 is replaced with the chemical group of "X-cyclohexane-based-($CH_2$)n-", where n is 0 or an integer selected from 1, 2, 3, 4, 5, 6, 7, 8, 9, 10, 11, 12, 13, 14, to 15. The functional groups $R^5$, $R^7$, and $R^9$, at respective positions 5, 7 and 9, are any one of the elements selected from H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —NHC(O)$NH_2$, —C(O)$CH_3$, —$CO_2CH_3$, and —C(O)N($CH_3$)$_2$, at the 3 positions, while the remaining two functional group positions are H, in some embodiments. In suitable embodiments, the FL118-derived analogs have the following formulas:

(XXX)

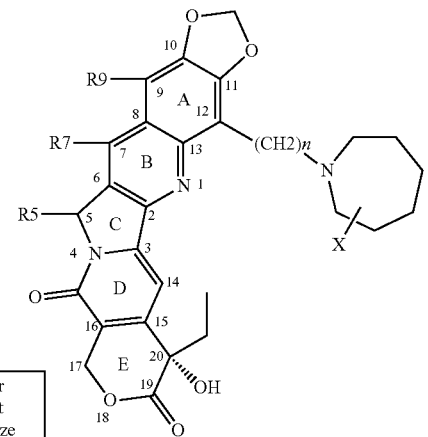

With or without E-ring size modification

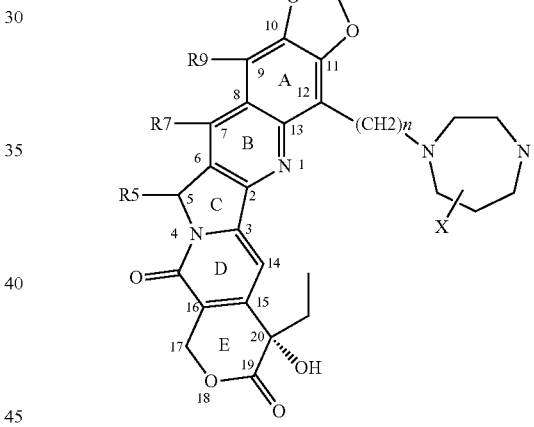

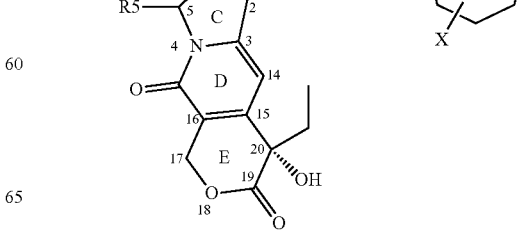

-continued

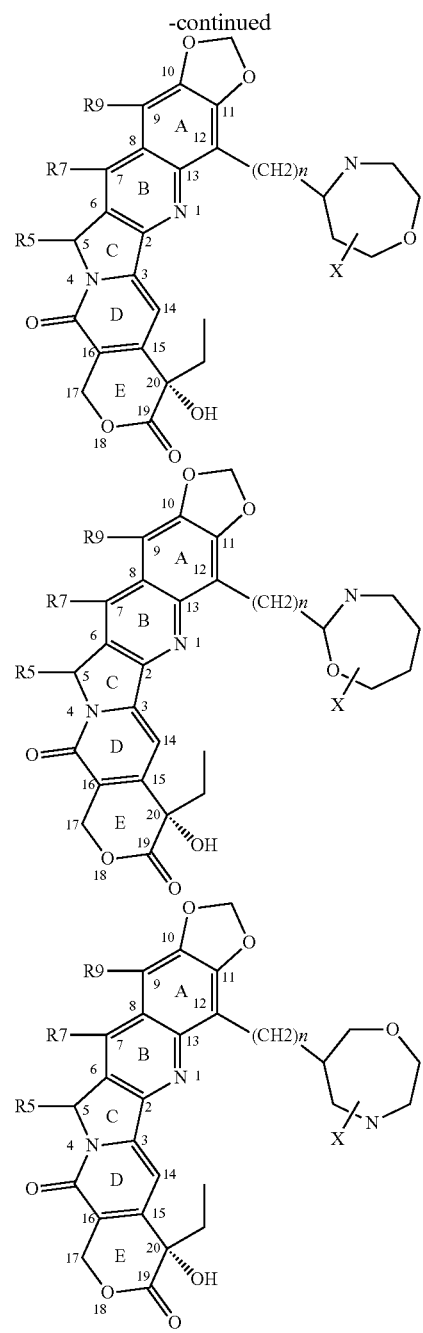

X = H—, F—, Cl—, Br—, I—, ClCH2—, BrCH2—, NH2—, CH3—, CH3O—, HOCH2—, HOCH2O—, NH2CH2—, HO—, or HONH—

In illustrative embodiments, the hydrogen (H) atom on the position 12 is replaced with the chemical group of "X-cycloheptane-based-($CH_2$)n-", where n is 0 or an integer selected from 1, 2, 3, 4, 5, 6, 7, 8, 9, 10, 11, 12, 13, 14, to 15. The functional groups $R^5$, $R^7$, and $R^9$, at respective positions 5, 7 and 9, are any one of the elements selected from H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —NHC(O)$NH_2$, —C(O)$CH_3$, —$CO_2CH_3$, and —C(O)N($CH_3$)$_2$, at the 3 positions, while the remaining two functional group positions are H, in some embodiments. In suitable embodiments, the FL118-derived analogs have the following formulas:

(XXXI)

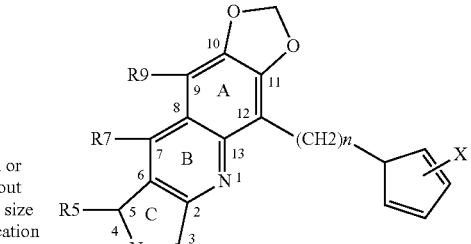

With or without E-ring size modification

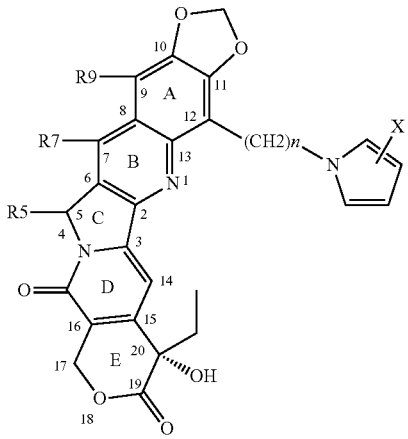

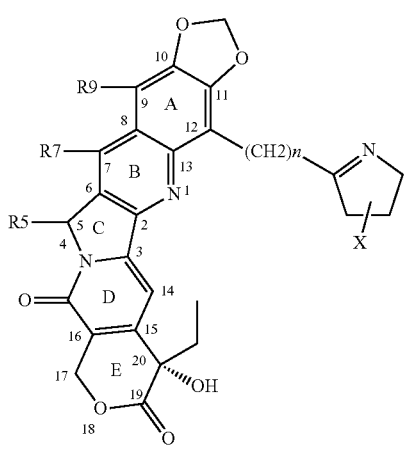

113
-continued
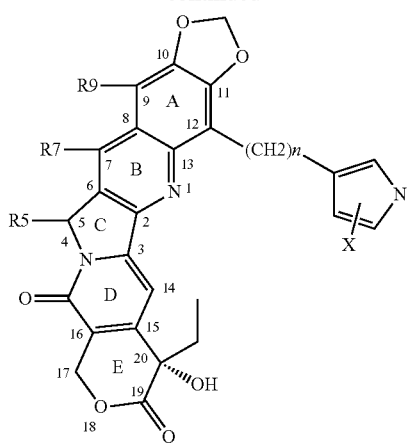
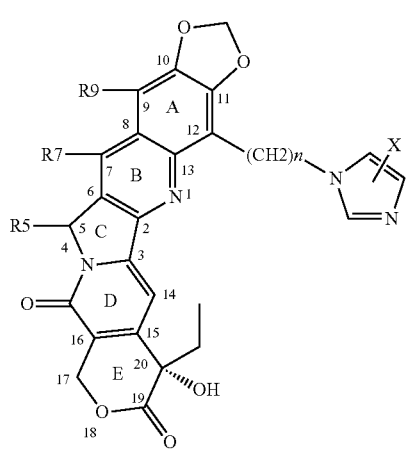
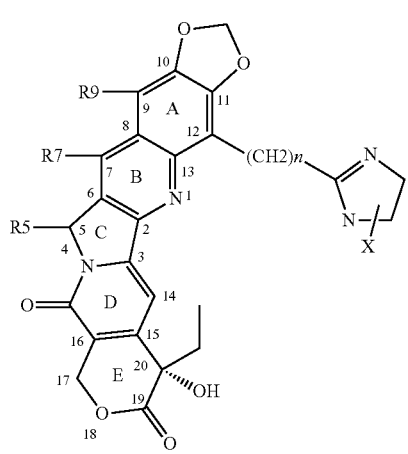
114
-continued
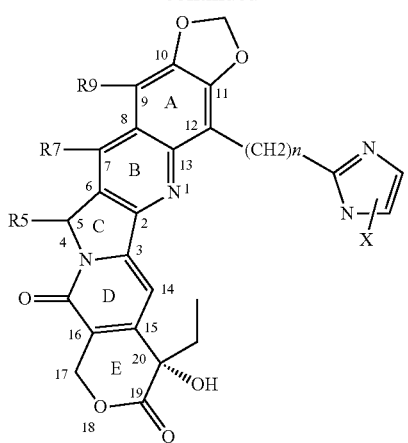
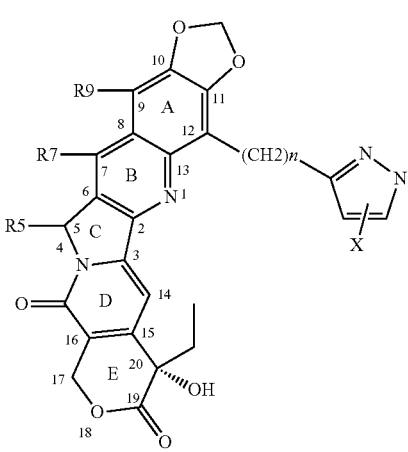
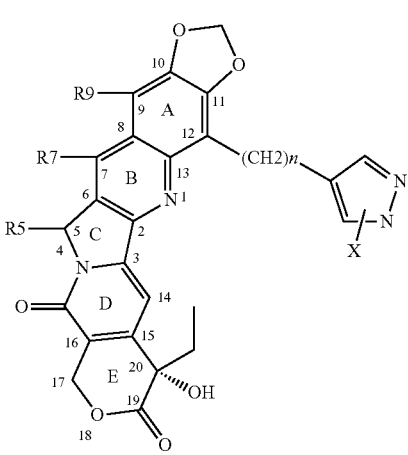

-continued

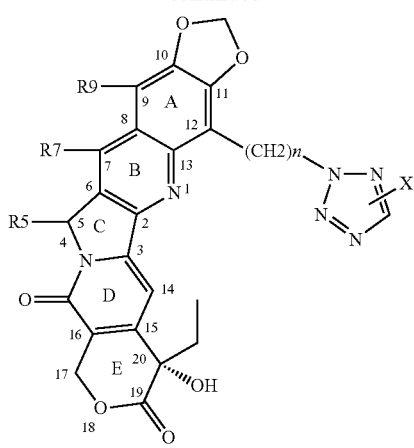

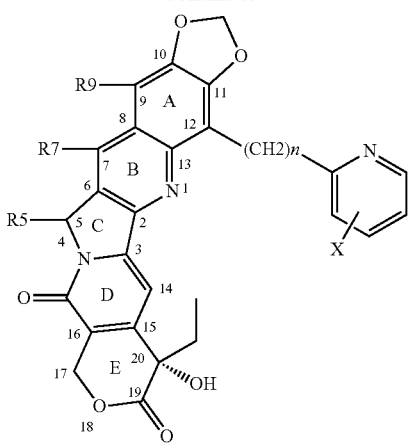

X = H—, F—, Cl—, Br—, I—,
ClCH2—, BrCH2—, NH2—, CH3—,
CH3O—, HOCH2—, HOCH2O—,
NH2CH2—, HO—, or HONH—

In illustrative embodiments, the hydrogen (H) atom on the position 12 is replaced with the chemical group of "Aryl-(CH$_2$)n-"X-cyclopentadiene-based-(CH$_2$)n-", where n is 0 or an integer selected from 1, 2, 3, 4, 5, 6, 7, 8, 9, 10, 11, 12, 13, 14, to 15. The functional groups R$^5$, R$^7$, and R$^9$, at respective positions 5, 7 and 9, are any one of the elements selected from H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_3$)$_2$, at the 3 positions, while the remaining two functional group positions are H, in some embodiments. In suitable embodiments, the FL118-derived analogs have the following formulas:

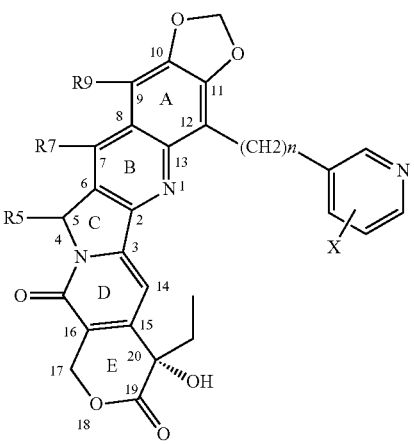

(XXXII)

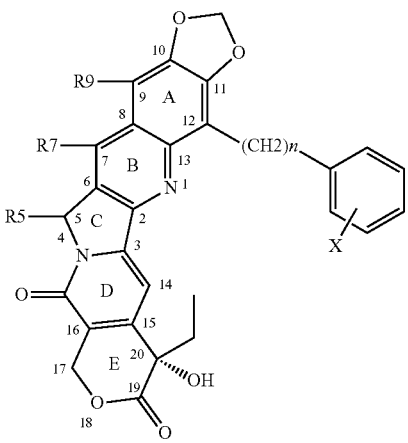

With or without E-ring size modification

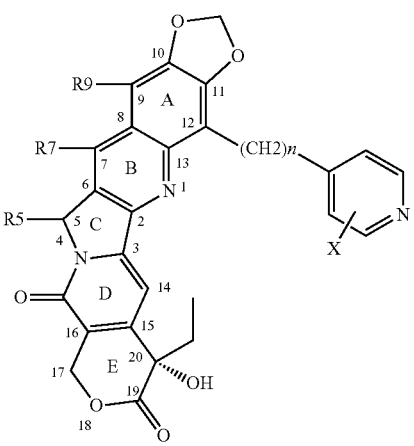

117
-continued
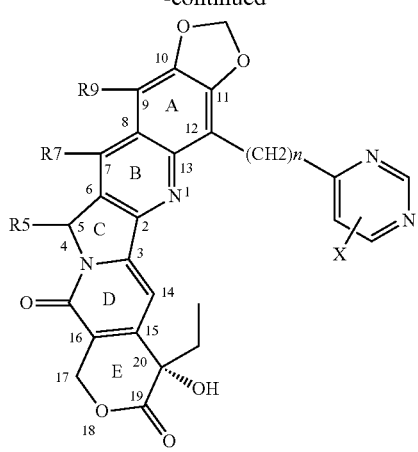
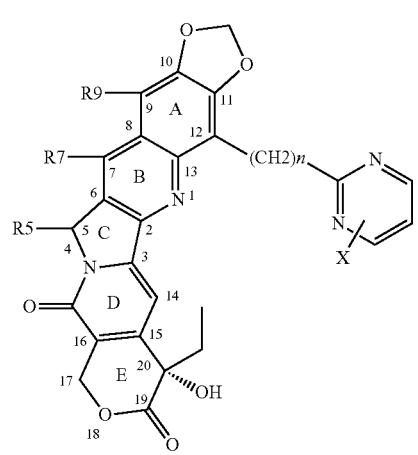
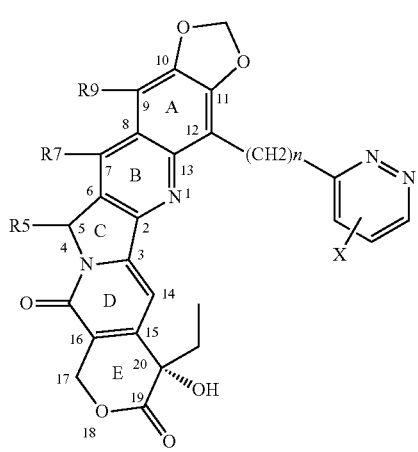
118
-continued
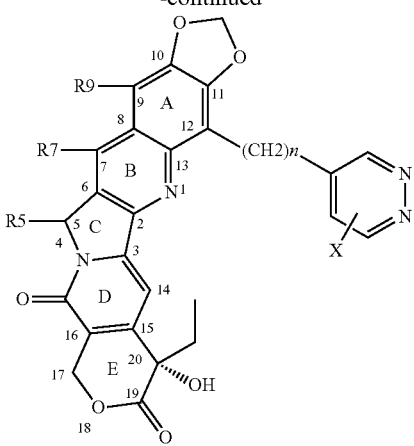
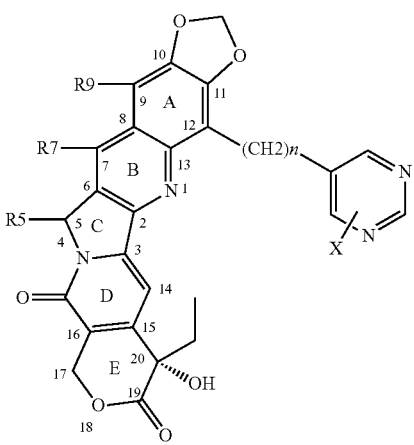
X = H—, F—, Cl—, Br—, I—,
ClCH2—, BrCH2—, NH2—, CH3—,
CH3O—, HOCH2—, HOCH2O—,
NH2CH2—, HO—, or HONH—

In illustrative embodiments, the hydrogen (H) atom on the position 12 is replaced with the chemical group of "X-benzene-based-$(CH_2)n$-", where n is 0 or an integer selected from 1, 2, 3, 4, 5, 6, 7, 8, 9, 10, 11, 12, 13, 14, to 15. The functional groups $R^5$, $R^7$, and $R^9$, at respective positions 5, 7 and 9, are any one of the elements selected from H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —$NHC(O)NH_2$, —$C(O)CH_3$, —$CO_2CH_3$, and —$C(O)N(CH_3)_2$, at the 3 positions, while the remaining two functional group positions are H, in some embodiments.

In illustrative embodiments, FL118 core chemical structure platform-derived analogs described herein, function to overcome or bypass various cancer treatment resistance as well as potential for other human disease such as autoimmune diseases or as combinational use with immunotherapy. Simply out, the compounds, compositions, methods and uses described herein, lay the foundation for human disease treatment including human cancer treatment with (personalized cancer treatment) or without (general cancer treatment) performing the personalized biomarker testing.

Synthesis of the FL118 Platform-Derived Compounds

Approaches used to synthesize the FL118 core structure platform-based analogs are described below. For detailed description of each of the individual FL118 platform-derived analogues, see this patent's sister patent entitled "synthesis and application of FL118 core structure platform-derived analogues for human disease treatment". In illustrative embodiments, FL118 or a FL118 analog is synthesized using a Friedlander condensation method same as in our recent publication for FL118 synthesis (Zhao J, et al.: Antitumor activity of FL118, a survivin, Mcl-1, XIAP, cIAP2 selective inhibitor, is highly dependent on its primary structure and steric configuration, Molecular Pharmaceutics 2014; 11: 457-467). Then through multiple know-how reactions to convert FL118 into different FL118 analogs or convert simple FL118 analogs into more complex FL118 analogs in the presence of appropriate chemical groups. Scheme 1 is outlined below.

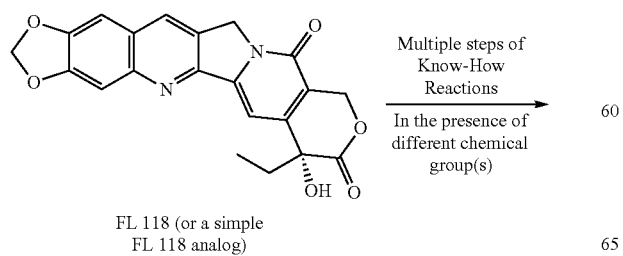

FL 118 (or a simple FL 118 analog)

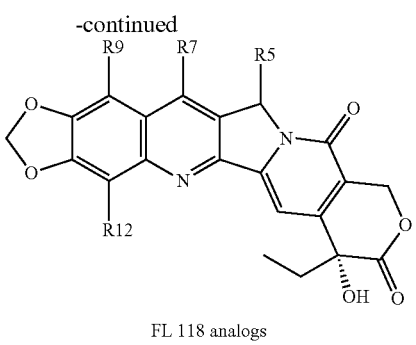

FL 118 analogs

In another embodiment, a method similar to the synthesis of FL118 (Zhao J, et al., Molecular Pharmaceutics 2014; 11: 457-467) is used for the synthesis of FL118 analogs as shown in Scheme 2 below.

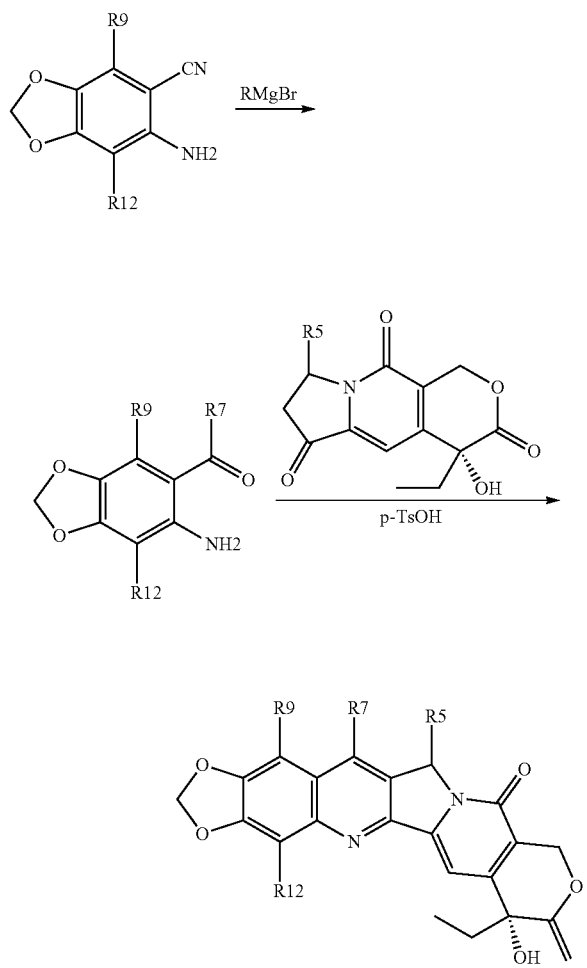

Modification of the E-Ring Structure of the FL118-Derived Analogs

The modification of the E-ring structure of the FL118 platform-derived analogs is shown in Scheme 3 below.

Scheme 3: Modification of the E-ring structure

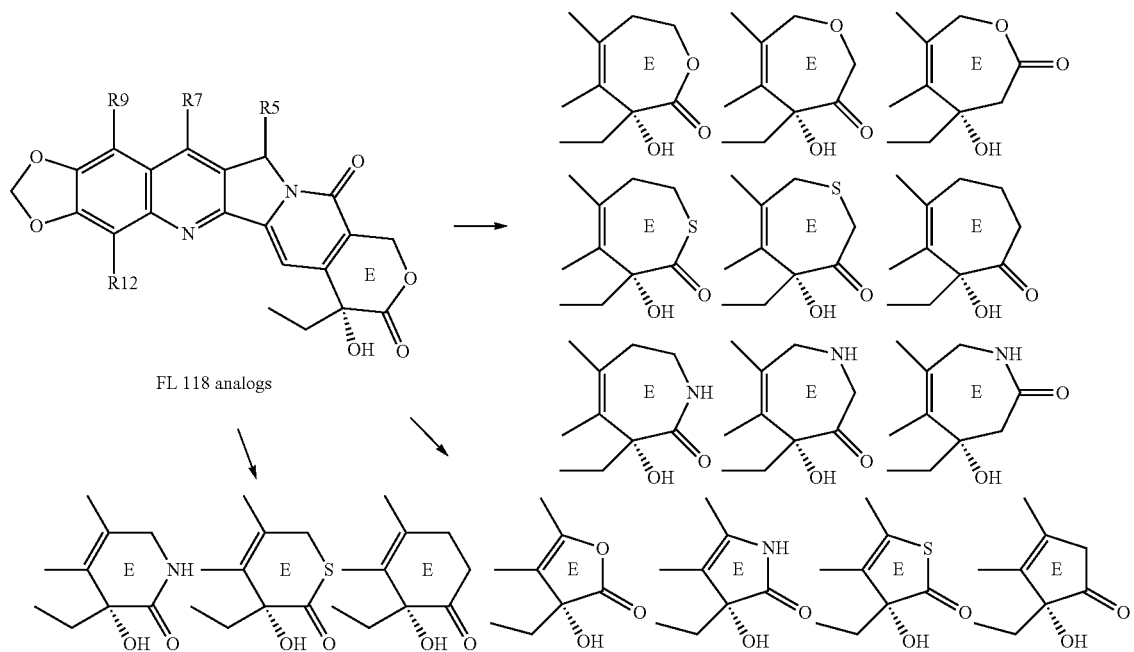

FL 118 analogs

Pharmaceutical Compositions

In one aspect, the present disclosure provides pharmaceutical compositions which include at least one of the compounds of Formula 1 and a pharmaceutically acceptable carrier. The compositions of the present invention may contain other therapeutic agents as described below, and may be formulated, for example, by employing conventional or specialized solid or liquid vehicles or diluents, as well as pharmaceutical additives of a type appropriate to the mode of desired administration, for example, excipients, binders, preservatives, stabilizers, flavors, etc., according to techniques such as those well known in the art of pharmaceutical formulation. See, e.g., Remington: The Science and Practice of Pharmacy, 21st Ed., Lippincott Williams & Wilkins (2005).

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents in the presence of a low percentage (0-10%) of a type of cyclodextrin such as β cyclodextrin, hydroxypropyl-β-cyclodextrin, sulfobutylether-β-cyclodextrin but not limited to, which are incorporated into the solvent formulation to increase drug solubility; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course.

The compounds of the present disclosure are administered by any suitable means, for example, orally, such as in the form of suspension, thick soup, tablets, capsules, granules or powders; sublingually; buccally; parenterally, such as by subcutaneous, intravenous, intramuscular, intra(trans)dermal, or intracisternal injection or infusion techniques, e.g., as sterile injectable aqueous or non-aqueous solutions or suspensions, nasally such as by inhalation spray or insufflation, topically, such as in the form of a cream or ointment ocularly in the form of a solution or suspension, vaginally in the form of pessaries, tampons or creams, or rectally such as in the form of suppositories, in unit dosage formulations containing nontoxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, particularly in the case of extended release, by the use of certain natural, synthetic or modified thickening agents such as tragacanth, acacia, hydroxypropyl methylcellulose (HPMC), Methyl cellulose, carboxymethyl cellulose, sodium carboxymethyl cellulose, gelatin, xanthium gum or use of devices such as subcutaneous implants or osmotic pumps.

The pharmaceutical compositions for the administration of the compounds of Formula 1 are presented in unit dosage form and may be prepared by any of the methods well known in the art of pharmacy, in some embodiments. These methods typically include bringing the Formula 1 compound into association with the carrier which constitutes one or more accessory ingredients. In some embodiments, the pharmaceutical compositions are prepared by uniformly and intimately bringing the compound of Formula 1 into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the compound of Formula 1, in some embodiments, are in a form suitable for oral use, for example, as suspension, thick soup, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents such as sweetening agents, flavoring agents, coloring agents, thickening agents, and preserving agents, e.g., to provide pharmaceutically stable and palatable preparations. Tablets contain the compound of Formula 1 in admixture with nontoxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. In some embodiments, the tablets are further coated to form osmotic therapeutic tablets for control release.

Formulations for oral use may also be presented as hard gelatin capsules wherein the compound of Formula 1 is mixed with an inert solid diluent, for example, calcium carbonate, calcium phosphate or kaolin, or as soft gelatin capsules wherein the compound of Formula 1 is mixed with water or an oil medium, for example peanut oil, liquid paraffin, or olive oil.

Aqueous suspensions contain the active materials in admixture with excipients suitable for the manufacture of aqueous suspensions in the presence of a low percentage (0-10%) of a cyclodextrin such as β cyclodextrin, hydroxypropyl-β-cyclodextrin, sulfobutylether-β-cyclodextrin but not limited to, which are incorporated into the solvent formulation to increase drug suspension. Such excipients are suspending agents, for example sodium carboxymethylcellulose, methylcellulose, hydroxy-propylmethylcellulose (HPMC), sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more surface-active agents, for example sodium lauryl sulfate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the compound of Formula 1 in a vegetable oil, for example arachis oil, olive oil, sesame oil or coconut oil, or in a mineral oil such as liquid paraffin. The oily suspensions may contain a thickening agent, for example beeswax, hard paraffin, cetyl alcohol, tragacanth, acacia, hydroxypropyl methylcellulose, Methyl cellulose, carboxymethyl cellulose, sodium carboxymethyl cellulose, gelatin, xanthium gum. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compound of Formula 1 in admixture with a dispersing or wetting agent, suspending agent and one or more preservatives in the presence of a low percentage (0-10%) of a cyclodextrin such as β cyclodextrin, hydroxypropyl-β-cyclodextrin, sulfobutylether-β-cyclodextrin but not limited to, which are incorporated into the solvent formulation to increase drug dispersing. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions in the presence of a low percentage (0-10%) of a cyclodextrin such as β cyclodextrin, hydroxypropyl-β-cyclodextrin, sulfobutylether-β-cyclodextrin but not limited to, which are incorporated into the solvent formulation to increase drug emulsion. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, flavoring and coloring agent in the presence of a low percentage (0-10%) of a cyclodextrin such as β cyclodextrin, hydroxypropyl-β-cyclodextrin, sulfobutylether-β-cyclodextrin but not limited to, which are incorporated into the solvent formulation. This formulation may also present of one or more thickening agents such as certain natural, synthetic or modified thickening agents such as tragacanth, acacia, hydroxypropyl methylcellulose (HPMC), xanthium gum In some embodiments, the pharmaceutical compositions are sterile injectable solutions of aqueous or oleagenous suspension in the presence of a low percentage (0-10%) of a cyclodextrin such as β cyclodextrin, hydroxypropyl-β-cyclodextrin, sulfobutylether-β-cyclodextrin but not limited to, which are incorporated into the solvent formulation. This suspension may be formulated according to the known art using those suitable dispersing or wetting agents and suspending agents which have been mentioned above. The sterile injectable preparation is a sterile injectable solution or suspension in a non-toxic parenterally-acceptable diluent or solvent, for example, as a solution in 1,3-butane diol, in some embodiments. In some embodiments, vehicles and solvents that are employed, include, but are not limited to, water, Ringer's solution and isotonic sodium chloride solution. Additionally, sterile, fixed oils are conventionally employed as a solvent or suspending medium. For this purpose any bland fixed oil may be employed including synthetic mono- or diglycerides. In addition, fatty acids such as oleic acid find use in the preparation of injectable formulations.

For administration to the respiratory tract, e.g., inhalation, including intranasal administration, the active compound may be administered by any of the methods and formulations employed in the art for administration to the respiratory tract. Thus, the active compound may be administered in the form of a solution, suspension, or as a dry powder, in some embodiments.

The agents according to this aspect of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The propellant-driven inhalation aerosols which may be used according to the invention may also contain other ingredients such as co-solvents, stabilizers, surfactants, antioxidants, lubricants and pH adjusters. The propellant-driven inhalation aerosols according to the invention which may be used according to the invention may be administered using inhalers known in the art, e.g., metered dose inhalers.

As another alternative, the agents of the present invention may be administered to the airways in the form of a lung surfactant formulation. The lung surfactant formulation can include exogenous lung surfactant formulations (e.g., Infasurf® (Forest Laboratories), Survanta® (Ross Products), and Curosurf®) (DEY, California, USA) or synthetic lung surfactant formulations (e.g., Exosurf® (GlaxoWellcome Inc.) and ALEC). These surfactant formulations are typically administered via airway instillation (i.e., after intubation) or intratracheally.

As a further alternative, the agents of the present invention may be administered to the airways in the form of an inhalable powder. The powder formulation may include physiologically acceptable excipients such as monosaccharides (e.g. glucose or arabinose), disaccharides (e.g. lactose, saccharose, maltose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates.

Within the scope of the inhalable powders according to the invention the excipients have a maximum average particle size of up to 250 µm, preferably between 10 and 150 µm, most preferably between 15 and 80 µm. It may sometimes seem appropriate to add finer excipient fractions with an average particle size of 1 to 9 µm to the excipients mentioned above. These finer excipients are also selected from the group of possible excipients listed hereinbefore. Finally, in order to prepare the inhalable powders according to the invention, micronized formulations, preferably with an average particle size of 0.5 to 10 µm is added to the excipient mixture. Processes for producing the inhalable powders according to the invention by grinding and micronizing and by finally mixing the ingredients together are well known.

Inhalable powders according to the invention which contain a physiologically acceptable excipient in addition to the active formulation may be administered, for example, by means of inhalers which deliver a single dose from a supply using a measuring chamber as described in U.S. Pat. No. 4,570,630, or by other means as described in DE 36 25 685 A, each of which is hereby incorporated by reference in its entirety.

As a still further alternative, the agents of the present invention may be administered to the airways in the form of a propellant-free inhalable solution and suspension. The solvent used may be an aqueous or alcoholic, preferably an ethanolic solution. The solvent may be water on its own or a mixture of water and ethanol. The relative proportion of ethanol compared with water is not limited but the maximum is up to 70 percent by volume, more particularly up to 60 percent by volume and most preferably up to 30 percent by volume. The remainder of the volume is made up of water. The solutions or suspensions containing the active formulation are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g., as flavorings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions which may be used according to the invention. Preferred co-solvents are those which contain hydroxyl groups or other polar groups, e.g., alcohols-particularly isopropyl alcohol, glycols-particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavorings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 mL, more preferably between 5 and 20 mg/100 mL.

Solutions and suspensions will generally be aqueous in the presence of a low percentage (0-10%) of a cyclodextrin such as β cyclodextrin, hydroxypropyl-β-cyclodextrin, sulfobutylether-β-cyclodextrin but not limited to, which are incorporated into the solvent formulation, for example prepared from water alone, e.g., sterile or pyrogen-free water, or water and a physiologically acceptable co-solvent, e.g., ethanol, propylene glycol or polyethylene glycols such as PEG300 or PEG 400. Such solutions or suspensions may or may not additionally contain other excipients, e.g., preservatives such as benzalkonium chloride, solubilizing agents/surfactants such as polysorbates, e.g., Tween 80, Span 80, and benzalkonium chloride, buffering agents, isotonicity-adjusting agents, e.g., sodium chloride, absorption enhancers and viscosity enhancers. Suspensions may additionally contain suspending agents, e.g., microcrystalline cellulose and carboxymethyl cellulose sodium.

Solutions or suspensions are applied directly to the nasal cavity by conventional means, e.g., with a dropper, pipette or spray, in some embodiments. The formulations are provided in single or multidosing form in some embodiments. Insofar as a dropper or pipette is employed, administration is achieved by appropriate, predetermined volume of the solution or suspension. In some embodiments, spray administration is achieved, e.g., via metering atomising spray pump.

Inhalation administration to the respiratory tract is achieved using an aerosol formulation in which the compound is provided in a pressurized pack with a suitable propellant, such as a chlorofluorocarbon (CFC), e.g., dichlorodifluoromethane, trichlorofluoromethane, dichlorotetrafluoroethane, carbon dioxide or other suitable gas, in some embodiments. The aerosol may also contain a surfactant such as lecithin. In some embodiments, the active compound dose is controlled by a valve. In other embodiments, the active compound is provided in the form of a dry powder, e.g., a powder mix of the compound in a suitable powder base such as lactose, starch, starch derivatives, e.g., hydroxypropylmethyl cellulose and/or polyvinylpyrrolidine (PVP). The powder carrier forms a gel in the nasal cavity in some embodiments. The powder composition is administered in unit dose form, e.g., in capsules or cartridges of, e.g., gelatin or blister packs from which the powder may be administered by means of an inhaler, in some embodiments.

In formulations intended for administration to the respiratory tract, including intranasal formulations, the active compound is typically configured to have a small particle size, e.g., approximately 5 microns or less, via micronisation techniques and the like. Sustained release formulations of the active compound are employed in some embodiments. The active compound, in other embodiments, is administered by oral inhalation as a free-flow powder using an aerosol inhaler.

The compounds of the present disclosure are administered in the form of suppositories for rectal administration in some embodiments. Such compositions are prepared by mixing the compound formulation with a suitable non-irritating excipient, which is solid at room temperature, but liquid at body temperature, and will therefore be released subsequent to supposition. Compositions suitable for vaginal administration, moreover, are configured as pessaries, tampons, creams, gels, pastes, foams or sprays containing, in addition to the active ingredient, suitable carriers known in the art. For topical use, creams, ointments, jellies, solutions or suspensions, etc., containing the compounds of the present disclosure, are employed.

For application to the eye, the active compound may be in the form of a solution or suspension in a suitable sterile aqueous or non-aqueous vehicle in the presence of a low percentage (0-5%) of a cyclodextrin such as β cyclodextrin, hydroxypropyl-β-cyclodextrin, sulfobutylether-β-cyclodextrin but not limited to, which are incorporated into the solvent formulation with or without a thicken agent as mentioned earlier. Additives, for instance buffers, preservatives including bactericidal and fungicidal agents, such as phenyl mercuric acetate or nitrate, benzalkonium chloride, or chlorohexidine and thickening agents such as hypromellose may also be included.

The compounds of the present disclosure are administered in liposome form in some embodiments. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. Suitable lipids, in some embodiments, are phospholipids and phosphatidyl cholines, both natural and synthetic.

The pharmaceutical composition and method of the present disclosure further include additional therapeutically active compounds (second agents), as noted herein and/or known in the art, which are typically employed for treating one or more pathological conditions in concert with the compositions comprising compounds of Formula 1 of the present disclosure. The combination of therapeutic agents acts synergistically to effect the treatment or prevention of the various diseases, disorders, and/or conditions described herein. Such second agents, include, but are not limited to, chemotherapeutic and/or chemopreventive agents from plants or non-plants such as curcumin, resveratrol, vitamin D3, isothiocyanates (ITCs), e.g., allyl isothiocyanate (AITC), prostanoids, endothelin antagonists, cytoplasmic kinase inhibitors, receptor kinase inhibitors, endothelin receptor antagonists, e.g., ambrisentan, bosentan, and sitaxsentan, PDE5 (PDE-V) inhibitors, e.g., sildenafil, tadalafil, and vardenafil, calcium channel blockers, e.g., amlodipine, felodipine, varepamil, diltiazem, and menthol, prostacyclin, treprostinil, iloprost, beraprost, nitric oxide, oxygen, heparin, warfarin, diuretics, digoxin, cyclosporins, e.g., cyclosporin A, CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39, i.e., CD 154, fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal anti-inflammatory drugs (NSAIDs) such as ibuprofen, aspirin, acetaminophen, leflunomide, deoxyspergualin, cyclooxygenase inhibitors such as celecoxib, steroids such as prednisolone or dexamethasone, gold compounds, beta-agonists such as salbutamol, LABAs such as salmeterol, leukotriene antagonists such as montelukast, antiproliferative agents such as methotrexate, FK506 (tacrolimus, Prograf), mycophenolate mofetil, cytotoxic drugs such as azathioprine, VP-16, etoposide, fludarabine, doxorubin, adriamycin, amsacrine, camptothecin, cytarabine, gemcitabine, fluorodeoxyuridine, melphalan and cyclophosphamide, antimetabolites such as methotrexate, topoisomerase inhibitors such as camptothecin, DNA alkylators such as cisplatin, kinase inhibitors such as sorafenib, microtubule poisons such as paclitaxel, TNF-α inhibitors such as tenidap, anti-TNF antibodies or soluble TNF receptor, hydroxy urea and rapamycin (sirolimus or Rapamune) or derivatives thereof.

The compounds of the invention may also be prepared as salts which are pharmaceutically acceptable, but it will be appreciated that non-pharmaceutically acceptable salts also fall within the scope of the present disclosure at least to the extent that such salts are useful as intermediates in the preparation of pharmaceutically acceptable salts. Examples of pharmaceutically acceptable salts include, but are not limited to, sulfates, phosphates, mesylates, bismesylates, tosylates, lactates, tartrates, malates, bis-acetates, citrates, bishydrochloride salts, salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety. The salts may be formed by conventional means, such as by reacting the free base form of the compound with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin. In some embodiments, the salt is a chloride, sulfate, phosphate, mesylate, bismesylate, tosylate, lactate, tartrate, malate, bis-acetate, citrate, or bishydrochloride salt.

Where a compound possesses a chiral center the compound can be used as a purified enantiomer or diastereomer, or as a mixture of any ratio of stereoisomers. It is however preferred that the mixture comprises at least 1, 5, 10, 20, 30, 40, 50, 60, 70, 80, 90% of the preferred isomer. The compound may also exist as tautomers, as described herein. In some embodiments, the mixture can comprise up to 99% of the preferred isomer.

In some embodiments, the compounds of the present disclosure are formulated as prodrugs of the compounds of Structure I. For example, compounds of Formula 1 having free amino, amido, hydroxy or carboxylic acid groups can be converted into prodrugs. Prodrugs include compounds wherein an amino acid residue, or a polypeptide chain of two or more amino acid residues which are covalently joined through peptide bonds to free amino, hydroxy and carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of compounds of the present invention through the carbonyl carbon prodrug sidechain. Prodrugs also include phosphate derivatives of compounds (such as acids, salts of acids, or esters) joined through a phosphorus-oxygen bond to a free hydroxyl of the Formula 1 compounds. Prodrugs may also include N-oxides, and S-oxides of the appropriate nitrogen and sulfur atoms in Formula 1.

In some embodiments, the compounds of the present disclosure are administered in a therapeutically effective amount. Such an administration imparts that a compound of Formula 1 will elicit a response associated with, e.g., cells, tissues, fluids, of a subject being sought by the clinician. In some embodiments, from about 0.01 to 5 mg/kg of subject body weight per day is administered in single or multiple doses. In accord, dosage levels are from about 0.1 to about 2.5 mg/kg per day in some embodiments, while in other embodiments from about 0.5 to about 5 mg/kg per day is administered to the subject. Suitable dosage levels include, for example, from about 0.01 to 5 mg/kg per day, from about 0.05 to 1 mg/kg per day, or from about 0.1 to 0.5 mg/kg per day. Within this range, in some embodiments, the dosage is from about 0.05 to 0.2, 0.2 to 1 or 1 to 5 mg/kg per day or weekly. For oral administration, the compositions are provided in the form of tablets per a thicken soup containing 1.0 to 50 mg of the active ingredient, including, but not limited to, 1, 5, 10, 15, 20, 25, 30, 35, 40, 45 and 50 mg of the active ingredient. The dosage may be selected, for example, to any dose within any of these ranges, for therapeutic efficacy and/or symptomatic adjustment of the dosage to the subject being treated.

Based on our pharmacokinetics studies with some of compounds of Formula 1, in some embodiments, the unit dose is sufficient to provide one or more of: (a) a $C_{max}$ of about 10 to 400 ng/mL of the compound In a subject's plasma or a $C_{max}$ of about 10 to 400 ng/mL of the compound In the subject's blood when it is administered to the subject; (b) about 1 to 50 ng/mL of the compound in a subject's plasma 12 hours after administration or about 1 to 50 ng/mL of the compound in the subject's blood 12 hours after administration to the subject; (c) about 0 to 1 ng/mL of the compound in a subject's plasma 24 hours after administration; and (d) active gradients of Formula 1 sustain ≥1-25 ng/mL in tumor within 48 hours after administration to the subject.

It will be understood that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods and Uses

The present inventor identified unique therapeutic indications with respect to treatment (chemotherapy, radiation) resistance factors, which are targeted for overcoming cancer resistance through the use of a FL118 platform-derived anticancer agent to target or bypass two or more of the defined set of treatment resistant factors for cancer control. This set of treatment resistant factors includes aberrant expression of survivin, Mcl-1, XIAP, cIAP2, ATP-binding cassette (ABC) transporter proteins (such as ABCG2, ABCC4, MDR1, MRP1), hypoxia inducing factor 1α (HIF-1α), HdmX and Hdmx in the Hdm2/HdmX complex, wild-type, null or mutation of p53 and/or p53 related pathways. As detailed herein, the present inventor has developed a set of treatment resistant factors are critical targets or bypassing gene products for FL118 and FL118 platform-derived compounds to show high effectiveness to control various cancer types.

EXAMPLES

The present invention is further illustrated by the following examples, which should not be construed as limiting in any way. The following is a description of the materials and methods used throughout the examples.

MTT assays.

Cancer cell viability and growth are determined by MTT assay. MTT is a tetrazolium salt with a full chemical name of 3-[4,5-dimethylthiazol-2-yl]-2,5-diphenyltetrazolium bromide. MTT is used as a colorimetric substrate for measuring cell viability and growth. When cell growth is inhibited, there is an alteration of cellular redox activity, and thus rendering cells unable to reduce the MTT dye. Cells are seeded in 96 well plates overnight and then treated with or without a compound/drug in the presence or absence of an protein molecule inhibitor (e.g. ABCG2 inhibitor ko143) for 48-72 hours, MTT is added to a final concentration 0.5 mg/ml. Cells are continuously incubated in a 5% $CO_2$ incubator at 37° C. for 4 h with MTT and then lysed with a cell lysis buffer (20% SDS, 50% N,N-dimethylformamide, pH 4.7), 100 µl per well, for 4 h in the incubator. Subsequently, cell absorbance in each well is measured at 570 nm with an Ultra Microplate Reader (Bio-Tek Instruments). Results are reported as the mean±SD from 3-5 independent assays at each point. Alternatively, for FIG. 16, FIG. 17 and FIG. 19, cells are plated at a density of 300,000 cells/well in 6-well plates; cells are allowed to attach on the plate overnight. Cells are then treated in triplicate with escalating doses of FL118, SN-38, or DMSO (vehicle) with or without Ko143 as indicated. After 72 hours, media is removed and cells are harvested using 0.5 ml of 0.25% Trypsin-EDTA. Cells are counted and viability is analyzed on a Vi-CELL XR Cell Viability Analyzer (Beckman Coulter).

Luciferase Activity Assay.

Cancer cells are seeded in 48-well plates at about 50% confluent overnight in complete cell culture medium. Cells are either stably transfected with the pLuc-4080 survivin promoter-luciferase construct or transiently transfected with relevant luciferase reporter vectors. For transient transfection, 245 ng of targeting luciferase reporter construct plus 5 ng of internal control vector, pRK-tk in 30 µl serum-free DMEM, is mixed in a 1.5 ml tube containing 30 µl serum-free DMEM containing 0.4 µl Lipofectamine™ 2000. After incubation at room temperature for 20-25 minutes, the DNA/Lipofectamine complex is added to each well of 48-well plates, which already contain 300 µl corresponding complete growth medium in each well. The DNA/Lipofectamine complex is replaced after incubation for 16 hours by complete growth medium with relevant treatment such as containing either DMSO or FL118. Cells are further incubated for an additional 24-48 hours in a normoxia and/or hypoxia condition, followed by processing luciferase assays. For luciferase assay, a Dual-Luciferase Reporter Assay System (Promega) is used. Cells in 48-well plates are washed with PBS and lysed with 80 µl 1× passive lysis buffer on a shaker for up to 1 hour at 4° C. Twenty µl cell lysate per well is used to measure the Firefly and *Renilla* luciferase activity in triplicates in a Luminometer by subsequently adding 20 µl luciferase assay reagent and 20 µl Stop-Glo reagent. Data are normalized to *Renilla* luciferase activity (internal control) as arbitrary units to show relative promoter activity. For use of stable cell lines, total protein will be used as internal control.

Western Blotting/Immunoblotting.

Cancer cells with or without FL118 treatment are washed with PBS (50 mM phosphate pH 7.4, 100 mM NaCl, 10 mM KCl) and lysed on ice for 30 minutes in PBS containing 1% Nonidet P-40, 0.5% sodium deoxycholate, 0.1% SDS, 10 µg/ml PMSF, and 20 µM leupeptin. After the lysates are cleared by centrifugation at 15,000 g for 20 minutes at 4° C., the total protein is determined using Bio-Rad protein assay solution. Up to 50 µg of total protein is denatured in 2×SDS sample loading buffer for 5 minutes at 95° C., separated on 10-15% SDS-PAGE gels, and electrotransferred to the Pure Nitrocellulose Membrane (Bio-Rad, Hercules, Calif.) using semi-dry electrophoretic transfer. After the nonspecific binding sites on the membranes are blocked with 5% skim milk in TBS-T (20 mM Tris-HCl pH 7.5, 0.137 M NaCl, and 0.01% Tween 20) for 3 hours at room temperature with constant shaking, the membranes are incubated in TBS-T containing the relevant primary antibody (1: 500-1000) and 5% BSA overnight at 4° C. After washing with TB S-T three times, the membrane is incubated in 5% skim milk in TBS-T buffer containing the appropriate secondary anti-IgG antibody (1:5000) at room temperature for 1 h with constant shaking. The protein of interest is detected using Western Lightning®-ECL (Perkin Elmer, Waltham, Mass.) and visualized by exposure for various times (5-60 seconds). For normalization of protein loading, the same membranes are stripped with stripping buffer (100 mM 2-mercaptoethanol, 2% sodium dodecyl sulphate, 62.5 mM Tris-HCl pH 6.7) and used for Western blot by the same procedure with actin antibody (1:1000 dilution). The actin result is used as an internal control.

Computer-Directed Identification of Gene Promoter.

Using the UCSC Human Genome Bioinformatics website, individual gene sequences are isolated. A 2 kb promoter for individual genes is arbitrarily selected based on their transcription start site (TSS) region identified via NCBI EST Database.

Cancer Cell Colony Formation Assays (Clonogenic Assays).

Cancer cells are infected with or without lentivirus particles expressing control shRNA or shRNA for p53 knockdown (pLKO.1) followed by selection with puromycin for one week at 5 µg/ml. The cells are plated at 200 cells/well in 6-well plates for no-treatment group or 1000 cells/well for FL118 treatment groups in order to have sufficient numbers of colonies in drug-treated groups for accurate colony counting. Cells are treated with FL118 at concentrations of 0.15-20 nM for 3 days followed by two washes with PBS and replenished with drug-free cell culture medium. Then the cells are cultured in an incubator at 37° C., 5% CO2 for another two weeks before fixation and staining with crystal violet solution. Colonies are defined as more than 50 cells and/or images are then digitally taken.

Senescence-Associated (SA) β-Gal Assay.

Cancer cells (e.g. HCT-8) are either treated with 10 nM FL118 for 72 h or left untreated, followed by additional 7-day culture. Then the cells were fixed and stained for SA-β-gal activity with a commercial kit performed according to manufacturer's instructions (Calbiochem, catalog no QIA117).

In Vivo Ubiquitination Assay.

In vivo p53 or MdmX ubiquitination assay was carried out with HCT-8 cells. Briefly, whole cell lysates were denatured by adding SDS to a final concentration of 1% followed by boiling for 5 min. The samples were diluted 10 times with a buffer containing 20 mM Tris, pH7.5, 0.5% NP40 and 120 mM NaCl followed by centrifugation at 22,000×g for 10 minutes. Ubiquitinated proteins were pulled down with an anti-ubiquitin antibody coupled with Western blotting for p53 or HdmX.

In Vitro Ubiquitination Assay.

Reactions are carried out at 30° C. for 1 h in a volume of 20 μl containing 40 mM Tris/HCl (pH 7.5), 2 mM DTT, 5 mM MgCl2, 10 μM of ubiquitin, 40 nM E1, 350 nM UbCH5c, 5 mM ATP, 100 nM p53, 200 nM Hdm2, 200 nM HdmX and different concentrations of FL118 or vehicle solvent DMSO. The reaction products are resolved by SDS-PAGE followed by immunoblotting with p53 antibody DO-1. For HdmX ubiquitination in vitro, reactions are performed in a 50-μl volume. After completion of the reactions, 10 μl is used for direct immunoblotting to reveal HdmX ubiquitination (a smearing pattern) with FLAG antibody. 40 μl reactions are used for denaturing with 1% SDS followed by dilution with 800 μl of 20 mM Tris, pH7.5, 0.5% NP40, and 120 mM NaCl. The processed reaction products are used for immunoprecipitation with ubiquitin antibody followed by immunoblotting for FLAG-HdmX using anti-FLAG antibodies.

Flow Cytometry Analysis.

Subconfluent cancer cells are suspended in 1 mL complete media (RPMI 1640) in 15 mL conical tubes (400,000 cells/tube) in the presence of FL118, SN38, or vehicle (1% DMSO), with or without 1 μM Ko143 (ABCG2 inhibitor). Cells are then incubated for 3 h in 37 C and 5% $CO_2$, with manual agitation every 30 min. After incubation, cells are pelleted and supernatant is removed. Cell pellets are washed twice with ice-cold PBS, and then suspended in 300 uL ice-cold PBS, and placed on ice until analysis. Cells are analyzed on a LSR II flow cytometer (BD Biosciences, San Jose Calif.) with a 355 nm laser and a 540 nm band-pass filter to detect emission. Median fluorescence intensity (MFI) of each drug+/−Ko143 is compared.

Formulation of FL118 and its Analogues for In Vitro and In Vivo Studies.

For in vitro studies, FL118 or its analogues are initially dissolved in DMSO at 1 mM as a stock solution. Prior to addition of FL118 or its analogues to the cells, the stock solution is further diluted with DMSO to a concentration of a 1000× of the final concentration used for the experiment. The 1000× working stock solution is directly diluted into experiment-relevant buffers or cancer cell type-relevant medium. For in vivo studies, FL118 or its analogues are formulated using a know-how method as below.

Below is a newly invented formulation method, which is the further to the development of related indications. See, e.g., PCT/US2011/058558 (Formulations of Water-Insoluble Chemical Compounds and Methods of Using a Formulation of Compound FL118 For Cancer Therapy); U.S. patent application Ser. No. 13/881,785; Canadian Patent Application 2,816,418; Chinese Patent Application 201180063530.5; and European Patent Organization Application 11837250.7, all of which are hereby incorporated by reference in their entirety.

All aqueous solutions or suspensions or any other forms of formulation which contain Formula 1 for administration are invented to be prepared in the following ways: 1) dissolve a solvent A (e.g. CD, βCD, HPβCD, SBEβCD) into a solvent B (e.g. DMSO, ethanol), and dissolve the Formula 1 compound into the solvent A/B mixture. Then the resultant solution and/or suspension is lyophilized to get rid of the solvent B. The remained substance mixture after lyophilizing is then resuspended using an aqueous solution in the presence of one or more co-solvents such as propylene glycol, polyethylene glycols with or without a thickening agents such as tragacanth, acacia, hydroxypropyl methylcellulose, Methyl cellulose, carboxymethyl cellulose, sodium carboxymethyl cellulose, gelatin, xanthium gum.

The formulation for FL118 or an analogue of FL118 in the basic formulation recipe for in vivo studies contains FL118 (0.1-2.5 mg/ml), DMSO (<5%), and hydroxypropyl-β-cyclodextrin (0.1-2.5%, w/v) in saline, and the corresponding vehicle solution in the basic formulation recipe contains DMSO (<5%), and hydroxypropyl-β-cyclodextrin (0.1-2.5%, w/v) in saline without FL118. The alternative advanced formulation for FL118 or its analogues in the DMSO-free formulation recipe for in vivo studies contains FL118 (0.1-5.0 mg/ml) and hydroxypropyl-β-cyclodextrin (0.1-5%, w/v) in saline with up to 10% propylene glycol (PG) or up to 10% polyethylene glycol 400 (PEG400) or the combination of PG and PEG400 with total percentage up to 10%, and the corresponding vehicle solution in the DMSO-free formulation recipe is the corresponding solution without FL118.

Method for the formulation of DMSO-free solution/suspension containing FL118 or other water-insoluble compounds derived from Formula 1 for administration: A certain amount of hydroxypropyl-β-cyclodextrin or another type of cyclodextrin (Solvent A) was dissolved in DMSO (solvent B) to make a 1-20% Solvents A/B mixture. Then, FL118 or another water-insoluble compound derived from Formula 1 was dissolved into Solvents A/B mixture to make a concentration of 1-20 mg/ml for FL118 or the other water-insoluble compound. A typical example was to use a 10% Solvents A/B mixture (w/v) to dissolve FL118 or another compound derived from Formula 1 to 10 mg/ml. The resultant solution/suspension was then lyophilized for getting rid of DMSO (solvent B). The resultant substance was then resuspended with saline containing one or two co-solvents such as propylene glycol (1-10%) or polyethylene glycol 300 or 400 (1-10%) alone or in combination. A typical formulation is containing FL118 0.1-2 mg/ml, 0.1-2% hydroxypropyl-β-cyclodextrin, and 1% propylene glycol in saline for administration. A typical oral administration is to use a solution that contains FL118 0.1-2 mg/ml, 0.1-2% hydroxypropyl-β-cyclodextrin, 1% propylene glycol and 1-4% thickening agents such as hydroxypropyl methylcellulose (a typical concentration is 2-3%) in saline. This solution is typically formulated as follows using 100 ml solution containing 2% hydroxypropyl methylcellulase (HPMC) and 1% propylene glycol as an example: weigh 2 g HPMC and put in a 50 ml sterile tube:

1. Add 90° C. saline to less than 40 ml and shake well and then incubate the tube in 90° C. water bath for 3-5 hours (shaking 4-6 time)
2. Then put the 50 ml tube on a room temperature rotator (25-50 rpm) for rotating overnight (become thick solution with a lot bubbles).
3. 2000 rpm×2 min to eliminate air bobbles
4. Add room temperature saline to 40 ml and rotating 15 rpm×2 h, at RT
5. After 2000 rpm×2 min, divide 20 ml to a new 50 ml sterile tube.
6. Add 0.5 ml PG into each 50 ml tube that contains 20 ml above solution, and then add saline in the 50 ml tube to 50 ml for each tube. Then rotating 13-15 rpm×2-3 h at RT for 2 h to overnight to obtain (HPMC 2%, PG 1% in saline).
7. 2000 rpm×2 min to get rid of bobbles (if any) and store at 4° C. Now the solution (HPMC 2%, PG 1% in saline) is ready for formulating lyophilized FL118 or another compound derived from Formula 1.

Animal Models of Human Tumor Xenografts.

Three types of human cancer xenografts are used in the studies: 1) from human head-&-neck cancer cell line (FaDu)-established xenografts; 2) from human colon cancer cell line (SW620)-established xenografts; and 3) from human acute lymphocytic leukemia cell line (EU-4)-established xenografts. All in vivo experiments use either nude or severe combined immunodeficiency (SCID) mice. Human tumor cell line-derived xenografts are initially established by subcutaneously injecting $1 \times 10^6$ cultured cancer cells. The derived tumors are then passed several generations in mice by transplanting 40-50 mg non-necrotic tumor mass via a trocar after the xenograft tumor reached ~1000 mm$^3$. Treatment is initiated 7 days after tumor transplantation when the tumor reached 200-250 mm$^3$, at which time the treatment was designated as Day 0. Six to 12-week-old female SCID mice used in the studies. All animal experiments are performed in accordance with IACUC-approved animal protocols. Mice were housed 5 mice per cage with water and food ad libitum. For the data shown in FIG. 28C, athymic nude mice are xenografted with human FaDu (head and neck cancer) and SW620 (colon cancer) tumors. After tumor mass grows to their maximal sizes allowed by IACUC (1500-2000 mg), mice are treated with FL118 solutions, which are prepared more than 6 months ago and stored at +4° C. refrigerator, at a dose of 1.5 mg/kg weekly for 4 contiguous weeks as indicated by arrows.

Pharmacokinetics Analysis.

Figure 1:
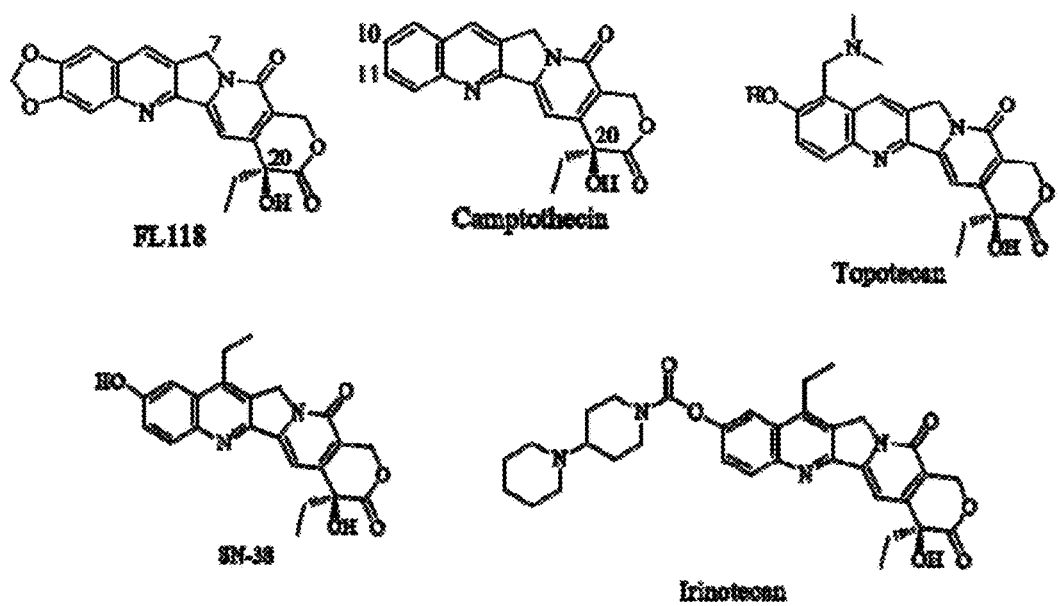
FIG. 1 shows that FL118 has structural similarity to camptothecin (CPT), topotecan, SN-38 (active form/metabolite of irinotecan), and irinotecan (pro-drug of SN-38).

FL118 in plasma is extracted with acidified methanol. A 800 µl aliquot of ice cold acidified methanol is added to 200 µl plasma and vortexed for 15 sec. In parallel, FL118 in mouse tissue or human xenograft tumor tissue is first homogenized in 1×PBS (WN=1 g tissue/3 ml 1×PBS) and then extracted with acidified methanol. A 800 µl aliquot of ice cold acidified methanol is added to 200 µl homogenized tissue and then vortexed for 1 min. The samples are then centrifuged at 13,000 rpm for 5 min. and the supernatant is transferred to a clean 13×100 mm glass tube. Samples are dried under vacuum and stored at −20° C. until analysis. Dried samples were then reconstituted in 200 µl of mobile phase (80% 3% TEA and 20% acetonitrile pH 5.5) and 15 µl is injected. Analysis is carried out using an Acquity UPLC system with Fluorescence detection interfaced with Empower software. Separation is carried out on a Acquity BEH Shield RP18 1.7 µm, 2.1 mm×100 mm column (Waters). Of note, using a gradient method FL118 and its internal standard (IS) can be resolved in less than 10 minutes with the following relative retentions: FL118 3.8 min and CPT-11 (IS) 2.7 min (FIG. 1). CPT-11 is used as the internal standard (IS); a 10 µl aliquot of a 1.3 µg/ml solution is added to each 200 µl sample. The fluorescence detector is set at the following Excitation (Ex) and Emissions (Em) wavelengths: Ex 370 nm Em 510 nm. The calibration standards are prepared by spiking plasma with FL118; the calibration curve range is 5 ng/ml-500 ng/ml. To ensure quality assurance, quality control samples are prepared in plasma at 25 and 250 ng/ml aliquoted and stored at −20° C. The QC's are injected in duplicate at the beginning and end of the assay. Assay has been validated. Validation consists of running twelve standard curves over the course of 5 days. QC samples are analyzed with each curve. The overall precision (% CV=6.4) and overall accuracy (101%) of the assay calibrators is shown to be excellent. QC precision measured as % CV is equal to 7.5% and overall QC accuracy is 96%.

Cardiac Measurements.

Cardiac imaging is performed using a 55 MHz ultrasound transducer system. Calculations are made based on the Simpson's method. Three short axis images and one long axis image of the left ventricle are acquired and used to determine cardiac output, ejection fraction, and stroke volume. Cardiac measurements are used to determine potential cardiotoxic effects of FL118. Measurements are made with a 55 MHz ultrasound probe. Step (a): cardiac output is a measurement of the total volume of blood pumped by the left ventricle per minute. Step (b) ejection fraction measures the percentage of blood that leaves the left ventricle every time it contracts. Step (c) stroke volume measures the volume of blood pumped from the left ventricle with each contraction.

Metabolic Toxicity Analysis Using Serum.

Changes of 16 parameters (GLU, BUN, CREA, PHOS, CA, TP, ALB, GLOB, ALB/GLOB, ALT, ALKP, GGT, TBIL, CHOL, AMYL, LIPA) that reflect the toxicity of FL118 treatment in blood after vehicle or FL118 treatment are analyzed using Catalyst Dx® Chemistry Analyzer (IDEXX BioResearch) following the manufacturer's protocol. The Catalyst Dx® Chemistry Analyzer is a real-time result analyzer at the push of a button processing to measure multiple parameters from a small volume of 50-100 µl of whole blood, plasma, serum or urine from multiple species including mouse, rat, monkey, dog, cat, rabbit, guinea pig, cow, pig, mini pig, horse, etc. The Catalyst Dx® Chemistry Analyzer can run only the tests required (up to 25 tests per sample can be done) by using Chem 10 CLIP, Chem 17 CLIP, NSAID 6 CLIP or by using single slides with custom CLIPs for research use.

Mass Spectrometry Analysis.

Mass spectrometry (MS) parameters are used as follows. Bruker Esquire, ion trap; Infusion Flow Rate, 5 µl/min; Ion Polarity, Positive; Ion Source Type, ESI; Dry Temp, 300 deg C.; Nebulizer, 8.00 psi; Dry Gas, 7.00 Umin; HV Capillary, 4000 V; HV End Plate, −500 V; Scan Begin, 100.00 m/z; Average, 30; Max Acc Time, 400 us; and ICC Target, 50000. MS scan is in both negative ion mode and positive ion mode.

Combination Index Analysis.

Effects of Drug A and Drug B combination on growth inhibition are analyzed by the Combination Index (CI) equation developed by Chou-Talalay (Chou T C and Talalay P. Quantitative analysis of dose-effect relationships: the combined effects of multiple drugs or enzyme inhibitors. Adv Enzyme Regul 1984; 22: 27-55) using a CalcuSyn program (Biosoft, Cambridge, UK). The general equation for the classic isobologram is given by: $CI=(D)_1/(D_x)_1+(D)_2/(D_x)_2$ where $CI<1$ indicates synergism; $CI=1$ indicates additive effect, and CI>1 indicates antagonism; $(Dx)_1$ and $(Dx)_2$ in the denominators are the doses (or concentrations) of Drug A [$(D)_1$] and Drug B [$(D)_2$] alone that gives x % inhibition, whereas $(D)_1$ and $(D)_2$ in the numerators are the doses of $D_1$ and $D_2$ in combination that also inhibits x % (i.e. isoeffective). The (Dx)1 and (Dx)2 can be readily calculated from the Meridian-effect equation of Chou (Chou T C. Preclinical versus clinical drug combination studies. Leuk Lymphoma 2008; 49: 2059-2080): $D_x = D_m [f_a/(1-f_a)]^{1/m}$ where $D_x$ is the median-effect dose, $f_a$ is the fraction affected, Dm is the median-effect dose signifying potency and m is the kinetic order signifying the shape of dose-effect curve. A 3-D plot of CI versus concentrations of both Drug A and Drug B is obtained for each treated cell line as descried before (Soriano A F, et al., Synergistic effects of new chemopreventive agents and conventional cytotoxic agents against human lung cancer cell lines. Cancer Res 1999; 59: 6178-6184).

TKO MEF Cell Transection.

TKO MEFs are transfected with HA-HdmX (200 ng/6 cm plate) together with or without Hdm2 (200 ng/6 cm plate). Cells are treated with FL118 at 10 and 100 nM for 8 h and WB for Hdm2 and HA-HdmX was performed. Actin, Tubulin or GFP is used as an internal control for equal protein loading.

The present invention is further illustrated by the following examples, which should not be construed as limiting in any way. The following is a description of the examples.

FL118 as a Platform is Distinct from the FDA-Approved Camptothecin Analogs, Irinotecan, SN-38 (Active Metabolite of Irinotecan) and Topotecan, which are Topoisomerase 1 (Top1) Inhibitors.

Figure 2:
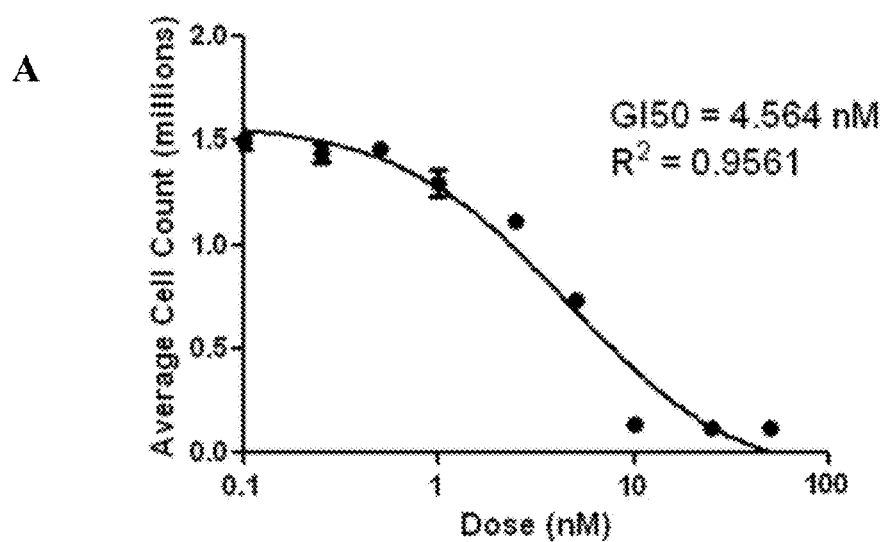
FIG. 2 shows the determination of 50% of the growth inhibition (GI50) values of FL118 in the parental DU145 prostate cancer cells and in DU145-derived two sub-lines with topoisomerase 1 (Top1) mutations (RC0.1, RC1). Three cell lines (DU145, RC0.1, RC1) grown at sub-confluence are treated with a series of FL118 concentrations in triplicate for 72 hours as shown. Cell numbers are then counted at the condition of individual FL118 concentrations used. Data are shown as a curve of cell number changes over FL118 concentrations. Each dot is the mean±SD derived from 3 independent assays.
Figure 2:
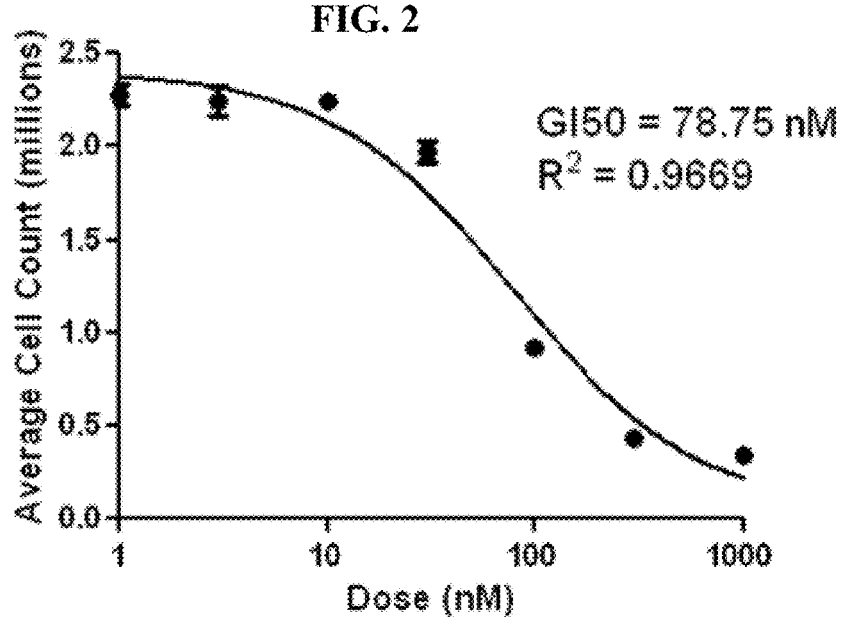
Figure 2:
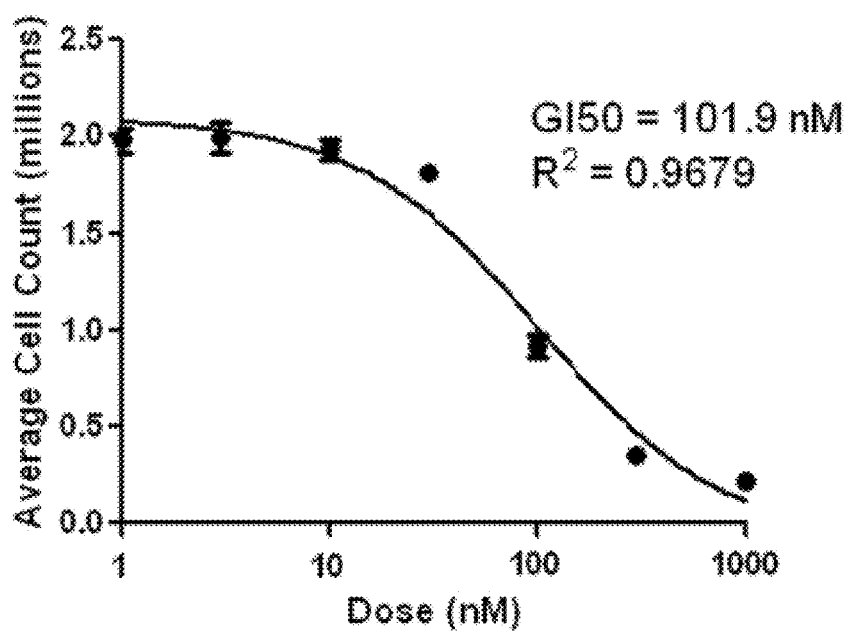

Irinotecan and topotecan are the only two analogs derived from direct modification of camptothecin (CPT) that are approved by the FDA for cancer treatment in clinical practice. The mechanism of action for irinotecan and topotecan has been identified as Top1 inhibitors. Therefore, if FL118 can be qualified to be a novel platform for generation of novel FL118 platform-based analogs, FL118 should have a mechanism of action distinct from irinotecan and topotecan. Structurally, FL118 has similarity with irinotecan, SN-38 (active metabolite of irinotecan), and topotecan, which are structurally classified as camptothecin (CPT) derivatives (FIG. 1). First, we have demonstrated that the antitumor efficacy of FL118 is much superior to the antitumor efficacy of irinotecan in animal model of both human colon and head-&-neck tumors (Ling X, et al.: A Novel Small Molecule FL118 That Selectively Inhibits Survivin, Mcl-1, XIAP and cIAP2 in a p53-Independent Manner, Shows Superior Antitumor Activity, PLOS ONE 2012, 7:e45571). However, it is possible that FL118 is actually a better Top1 inhibitor. In this regard, we obtain one DU145 parental prostate cancer cell line and two DU145-derived sub-lines with Top1 mutations (DU145-RC0.1, DU145-RC1). We then compare the required concentration of 50% growth inhibition (GI50) among FL118, SN-38 (active metabolite of irinotecan) and topotecan. If the main target of FL118 is not on Top1, mutation of the Top 1 gene product would show much less effects on FL118 function than those of irinotecan, SN38 and topotecan in cancer cell growth inhibition. Based on this logical thought, we first determine the GI50 for FL118 in the defined three DU-145 cell lines (FIG. 2). Then we compare the GI50 of FL118 with the GI50 of SN-38 and topotecan; the data from this experiment is exciting. As shown in Table 1, the Du145 prostate cancer cell line-derived two sub-cell lines with Top1 mutations (RC0.1, RC1) strikingly increase resistance to CPT, SN-38 and topotecan in comparison with their parental Du145 cell line (Table 1). In other words, in the parental Du145 cell line, FL118 is only about 10-40 fold more effective than CPT, SN-38 and topotecan to inhibit cancer cell growth. In contract, after Top1 is mutated in Du145-derived RC0.1 and RC1 cell lines, FL118 is up to 800 folds more effective than CPT, SN-38 and topotecan (Table 1). Specifically, RC0.1 and RC1 are 778 and 572 times more resistant to topotecan, respectively, in comparison with FL118 (Table 1). Altogether, these observations indicate that although FL118 structurally has similarity to topotecan, SN-38 and CTP (FIG. 1), FL118's anticancer activity is unlikely through the inhibition of Top1 activity as its major mechanism of action. FL118 should have its unique mechanisms of action that are different from the Top1 inhibitors, irinotecan, SN-38 and topotecan.

TABLE 1

Comparison of the relative potency (RP) of FL118 with topotecan, SN-38 (active form of irinotecan) and camptothecin (CPT): RP was calculated by dividing the IC50 of topotecan with the IC50 of CPT, SN-38 and FL118 in each line.*

| | DU-145 | | RC0.1 | | RC1 | |
|---|---|---|---|---|---|---|
| | IC50(nM) | RP | IC50(nM) | RP | IC50(nM) | RP |
| CPT | 60 | 3.17 | 63300 | 0.97 | 21700 | 2.69 |
| SN-38 | 40 | 4.75 | 11670 | 5.24 | 4430 | 13.2 |
| Topotecan | 190 | 1 | 61200 | 1 | 58300 | 1 |
| FL118 | 4.56 | 41.7 | 78.7 | 778 | 102 | 572 |

*The IC50 data for CPT, SN-38, topotecan is adopted from Urasaki Y et al., Characterization of a novel Topoisomerase I mutation from a camptothecin-resistant human prostate cancer cell line. Cancer Res (2001) 61: 1964-1969

The High Selectivity of FL118 to Inhibit IAP and Bcl-2 Family Antiapoptotic Proteins Suggests that 1) FL118 Acts as a Novel Derivative Producing Platform and 2) these FL118 Target Genes are Important for Both FL118 and its Derivatives' Function.

Figure 3:
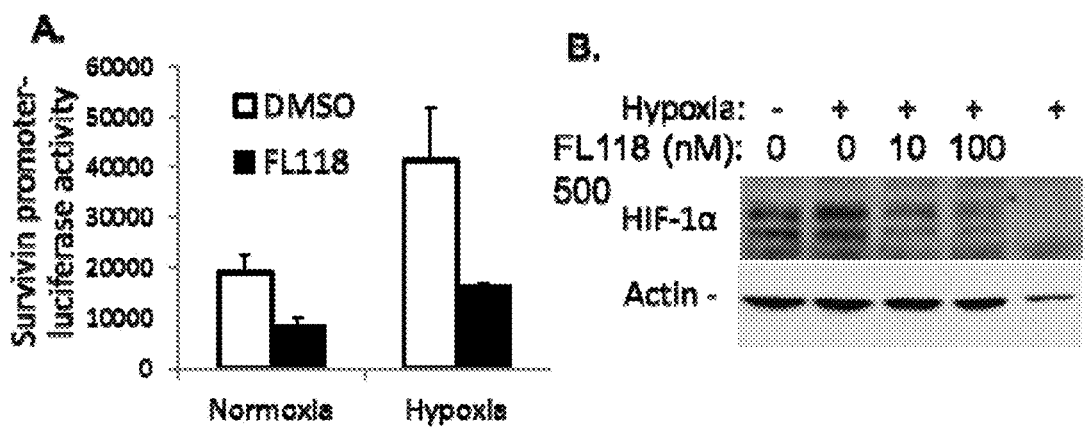
FIG. 3 shows that hypoxia induces survivin promoter activity (A) and HIF-1α expression (B), which are abrogated by FL118 treatment: A. HCT116 colon cancer cells that stably express a full-length survivin promoter (6309 bp)-luciferase construct are treated with and without FL118 for 24 h under normoxia or hypoxia, followed by luciferase activity assay. B. FaDu cancer cells are treated with and without FL118 for 36 h under normoxia or hypoxia, followed by Western blot analysis for HIF-1α expression. Actin is an internal control.
Figure 4:
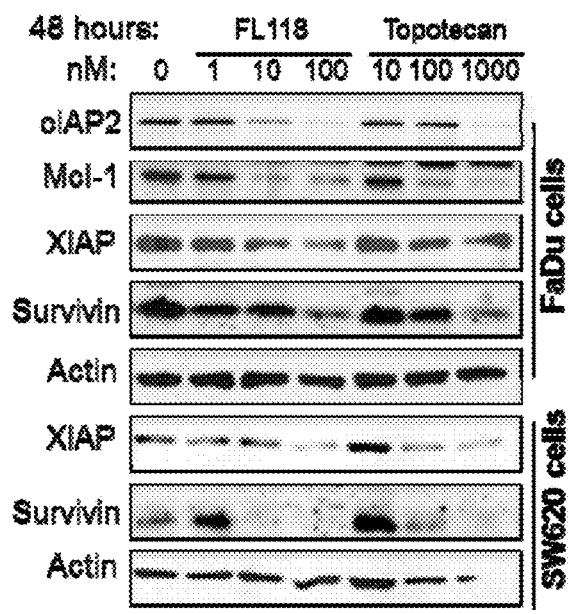
FIG. 4 shows that although FL118 has structural similarity to camptothecin (CPT), topotecan, SN-38 (active form of irinotecan) and irinotecan (pro-drug of SN-38), FL118 is at least 10-time more effective than topotecan in the inhibition of FL118 targets (survivin, Mcl-1, XIAP, cIAP2). Subconfluent FaDu (head-&-neck) and SW620 (colon) cancer cells are treated with FL118 or topotecan as shown. Cells were then analyzed for FL118 target gene expression using western blots. Actin is used as an internal control for equal protein loading. Of note, based on the PK data in FIG. 25, the dose used here is highly relevant to the in vivo situation (10 ng/ml (g)=25 nM).
Figure 5:
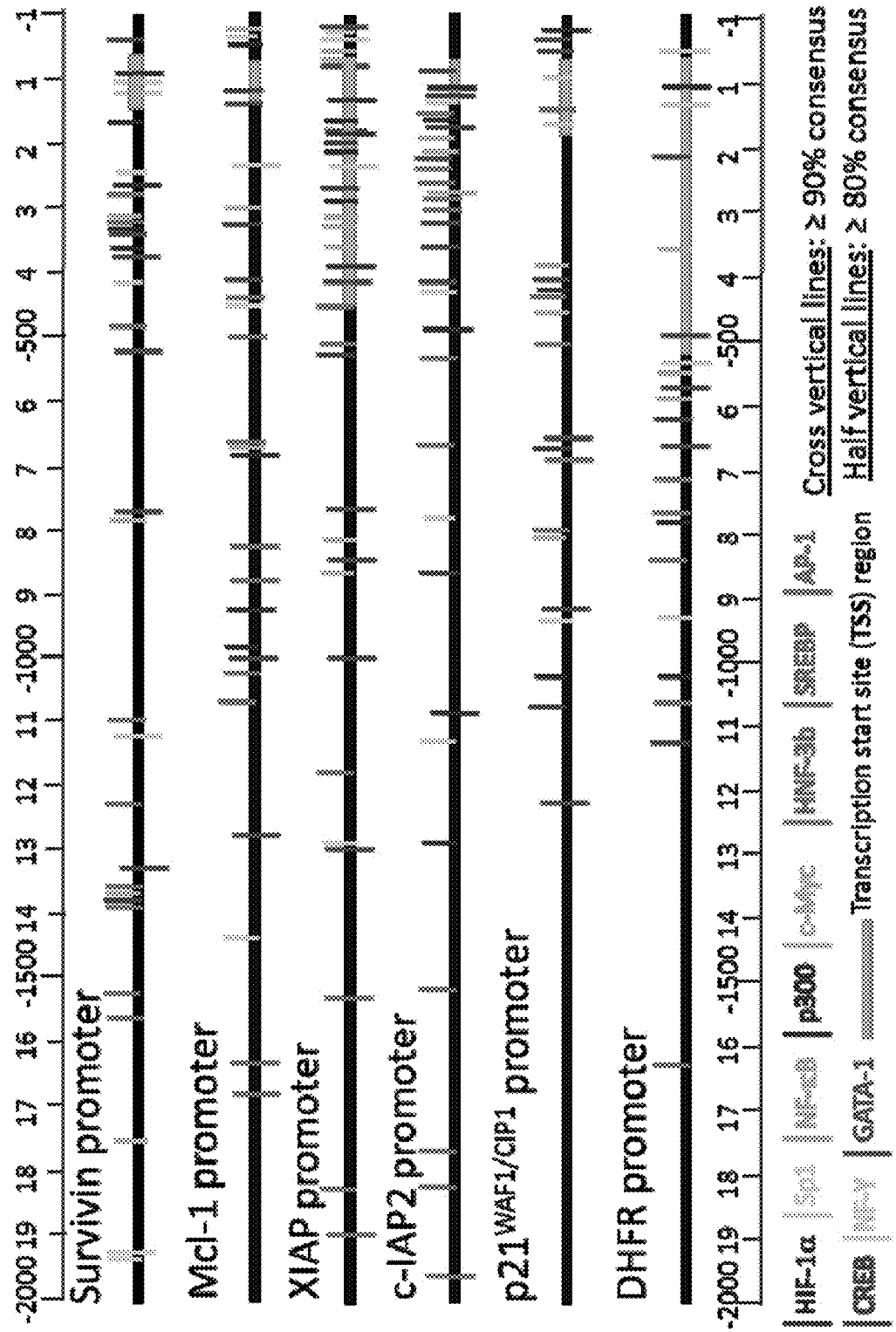
FIG. 5 shows major transcription factor (TF) binding sites on FL118 target gene promoters (survivin, Mcl-1, XIAP, cIAP2) and control promoter (dhfr, p21). The 3'-end for each promoter is the location including an additional 60 bp downstream of the TSS region (the defined 3'-end is designated as −1 bp). If the 60 bp overlaps with translation start site (ATG), we select the sequence available upstream of ATG (only survivin is the case, 49 bp left). Interestingly, while the individual promoters for survivin, Mcl-1, XIAP and cIAP2 contain more than 50% repeat DNA sequences, the DHFR and p21 promoters contain less than 15% repeat sequences.

It was discovered that FL118 by serendipity when we used genetically engineered cancer cell models in which the survivin gene is used as a target and biomarker, to find survivin inhibitors through high throughput screening (HTS), followed by in vitro and in vivo characterization of hit and lead compounds (Ling X, et al.: A Novel Small Molecule FL118 That Selectively Inhibits Survivin, Mcl-1, XIAP and cIAP2 in a p53-Independent Manner, Shows Superior Antitumor Activity, PLOS ONE 2012, 7:e45571). FL118 shows high selectivity to inhibit the survivin gene promoter activity and endogenous survivin expression. Specifically, FL118 at a concentration of 1-10 nM can effectively inhibit survivin promoter activity, while FL118 at 10 nM shows no inhibitory effects on promoter activity of the cell cycle regulator p21 gene, the dihydrofolate reductase (DHFR) gene, the human thrombin receptor (HTR) gene and the thymidine kinase (TK) gene, indicating high selectivity. However, in addition to survivin, FL118 selectively inhibits the expression of XIAP and cIAP2 (IAP family), Mcl-1 (Bcl-2 family) and hypoxia-inducing factor 1α (HIF-1α, FIG. 3), while inducing the expression of pro-apoptotic proteins Bax and Bim in various cancer cell types. Importantly, inhibition of survivin, Mcl-1, XIAP, cIAP2 by FL118 is at least 10-time more effective than irinotecan and topotecan (FIG. 4), indicating the unique mechanism of action for FL118. Intriguingly, FL118-mediated inhibition of survivin, Mcl-1, XIAP, and cIAP2 can be partially explained by the fact that the transcription factor (TF) pattern of the promoter region for the survivin, Mcl-1, XIAP, and cIAP2 genes shows similarity, which are significantly different from the promoter region of p21 and DHFR genes (FIG. 5). Of course, this is not the entire story, since modulation of the expression of these genes by FL118 may not be entirely through transcriptional regulation. Importantly, inhibition of survivin, Mel-1, XIAP, and cIAP2 by FL118 is independent events, since genetic knockdown of survivin shows no inhibitory effects on the expression of Mel-1, XIAP and cIAP2. We have further validated the selectivity of FL118 on the expression of its downstream targets using the Affymetrix GeneChip® Human Gene 1.0 ST Array. We hybridize the DNA microarray with FL118-treated and untreated PC3 cells-derived biotinylated CRNA probes. The results show that IAP and Bcl-2 family genes are the major targets. Specifically, in the IAP family, FL118 decreases (2 fold cutoff) NAIP, cIAP2, XIAP and Bruce, and shows no effects on cIAP1, Livin and hILP2. In the Bcl-2 family, FL118 slightly decreases Mcl-1 and Bcl-XL, and shows no effect on Bcl-2, Bcl2A1, Bcl-w, Bcl-B, Bcl2L12, Bcl2L13, Bcl-G and Bcl2L15. In contrast, FL118 increases proapoptotic proteins Bax, Bad, Bim, Hrk, and Bmf without affecting the expression of Bid, Bik, Bak and Bok. Taken these observations together, FL118 selectively modulates the expression of multiple antiapoptotic and proapoptotic proteins in the IAP and Bcl-2 families. In contrast, our studies reveal that SN-38 and topotecan are at least 10 times less effective to inhibit the expression of survivin, Mel-1, XIAP, and cIAP2 (FIG. 4). We should point out that inhibition of the expression of survivin, Mcl-1, XIAP, cIAP2, and HIF-1α by FL118 does not mean that FL118 is able to always inhibit all of these genes in all types of cancer cells. Instead, inhibition of these genes by FL118 can vary among different cancer cell types. However, induction of cancer cell death usually does not need to inhibit all of these genes, since cancer cell survival requires the concurrent overexpression of multiple genes, interference of two or more of these genes can be sufficient to trigger cancer cell death.

Genetically Knocked-Down or Overexpression of FL118 Target Genes (Survivin, Mcl-1, XIAP, and cIAP2) Demonstrates a Role of these Genes in FL118 Efficacy, Suggesting the Importance of these Genes in FL118 and its Derivatives' Function.

This is important because without demonstration of a role of survivin, Mcl-1, XIAP, and cIAP2 in FL118 function, we cannot claim these genes are the FL118 downstream targets. Our studies showed that genetic knockdown of survivin increases FL118-mediated inhibition of cancer cell growth and induction of apoptosis (Annexin V positive cells) (Ling X, et al.: A Novel Small Molecule FL118 That Selectively Inhibits Survivin, Mcl-1, XIAP and cIAP2 in a p53-Independent Manner, Shows Superior Antitumor Activity, PLOS ONE 2012, 7:e45571); in contrast, Tet-on induced survivin expression decreases FL118 ability to inhibit cancer cell growth and induce DNA fragmentation (a hallmark of apoptosis) (Zhao J, et al.: Antitumor activity of FL118, a survivin, Mcl-1, XIAP, cIAP2 selective inhibitor, is highly dependent on its primary structure and steric configuration, Molecular Pharmaceutics 2014; 11: 457-467). Similarly, genetic knockdown of Mcl-1 increases the cleavage of PARP, another hallmark of apoptosis; vice versa, forced expression of Mcl-1 in cancer cells shows resistance to FL118-mediated inhibition of cancer cell growth. Our studies also reveal similar results about XIAP and cIAP2. Forced expression of XIAP decreases FL118-mediated PARP cleavage and resists FL118-induced apoptosis (Annexin V positive cells). Forced expression of cIAP2 decreases caspase-3 activation (a hallmark of apoptosis). Together, these studies have demonstrated that each of the four FL118 downstream targets (survivin, Mcl-1, XIAP, cIAP2) plays a role in FL118 function.

While p53 Status Apparently Plays No Roles in FL118-Mediated Inhibition of its Downstream Targets (Survivin, Mcl-1, XIAP, cIAP2), Wild Type p53 Plays a Role in FL118-Induced Cancer Cell Senescence. However, FL118 Uses p53-Independent Mechanisms to Induce Cancer Cell Death when Cancer Cells have Null or Mutated p53.

It is known that p53 is a pivotal tumor suppressor; various stress signals such as DNA damage can activate p53. Activated p53 participates many important cellular processes including arrest of cell cycle and induction of senescence or apoptosis. This is mainly through control of p53 downstream target genes in the p53 transcriptional networks and thus p53 realizes its tumor suppression function (Bieging K T, Attardi L D: Deconstructing p53 transcriptional networks in tumor suppression, Trends Cell Biol 2012, 22:97-106). Therefore, cancer cells with wild type p53 is essential for many anticancer drugs to show their effectiveness to inhibit cancer cell growth and induce apoptosis and/or senescence, especially for those that interfere DNA synthesis, repair and cell cycle. In other words, loss of functional p53 (p53 mutated or null) will make cancer cells acquire treatment resistance to many chemotherapeutic drugs that are currently used in clinical practice. We have demonstrated that FL118 effectively inhibits cancer cell growth and induce apoptosis regardless of p53 status (wild type, mutant or null) (Ling X, Cao S, Cheng Q, Keefe J T, Rustum Y M, Li F: A Novel Small Molecule FL118 That Selectively Inhibits Survivin, Mcl-1, XIAP and cIAP2 in a p53-Independent Manner, Shows Superior Antitumor Activity, PLOS ONE 2012, 7:e45571). Our in vivo studies revealed that FL118 effectively eliminates human colon and head-&-neck tumor xenografts in animal models, no matter the tumor contains wild type p53 or mutant p53. This is consistent with the observation that inhibition of survivin, Mcl-1, XIAP, and cIAP2 by FL118 is p53 status-independent. FL118 can effectively inhibit the expression of survivin, Mcl-1, XIAP, and cIAP2 in cancer cells with wild type p53, mutant p53 or null p53.

Figure 6:
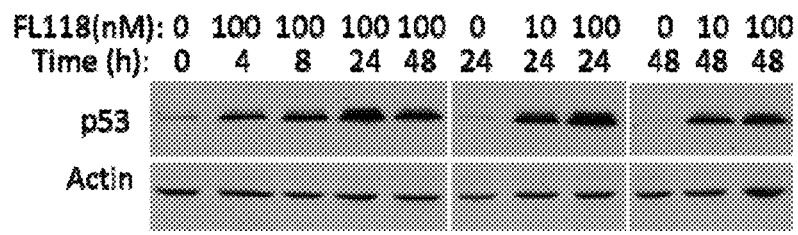
FIG. 6 shows the strong and rapid induction of p53 expression by FL118 in cancer cells with wild type p53. Subconfluent colon cancer cells are treated with FL118 with the time points and concentrations as shown, followed by Western blots (WB) to determine p53 protein expression with p53 protein antibodies. Actin is an internal control for total protein loading.
Figure 6:
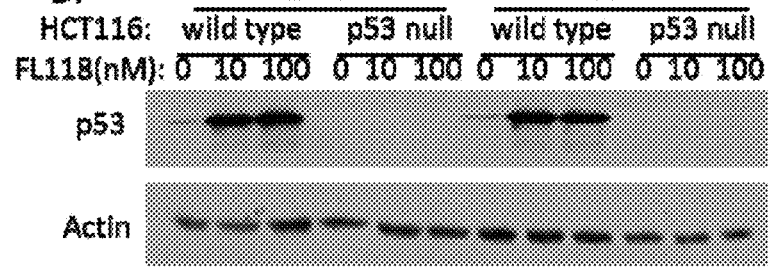
Figure 7:
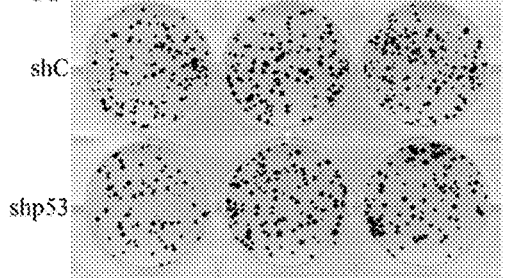
FIG. 7 shows that FL118 inhibits clonogenic growth independent of p53 status. A. Effects of FL118 on clonogenic growth of HCT-8 cells. HCT-8 cells are infected with either control lentivirus (shC) or lentivirus expressing shRNA against human p53 (shp53). Puromycin-selected cells are treated with FL118 at 0.3 or 10 nM for 3 days followed by three washes with PBS and replenished with fresh medium. Cell colonies are stained with crystal violet solution after 14-days culture. B. Histograms of relative colony numbers after FL118 treatment. Colonies larger than 50 cells are counted and normalized against non-treatment control group. Inset, WB for p53 protein levels in the two groups of cells (shC versus shp53) before and after FL118 treatment at 10 and 100 nM.
Figure 7:
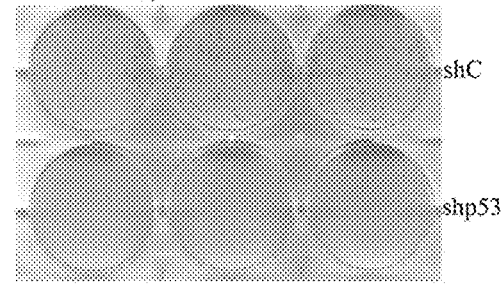
Figure 7:
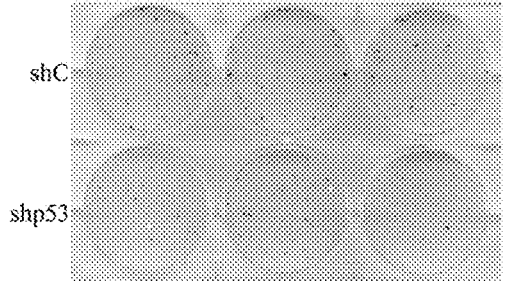
Figure 7:
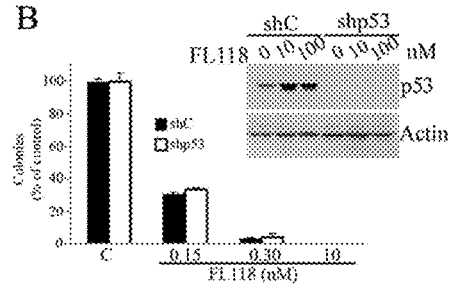
Figure 8:
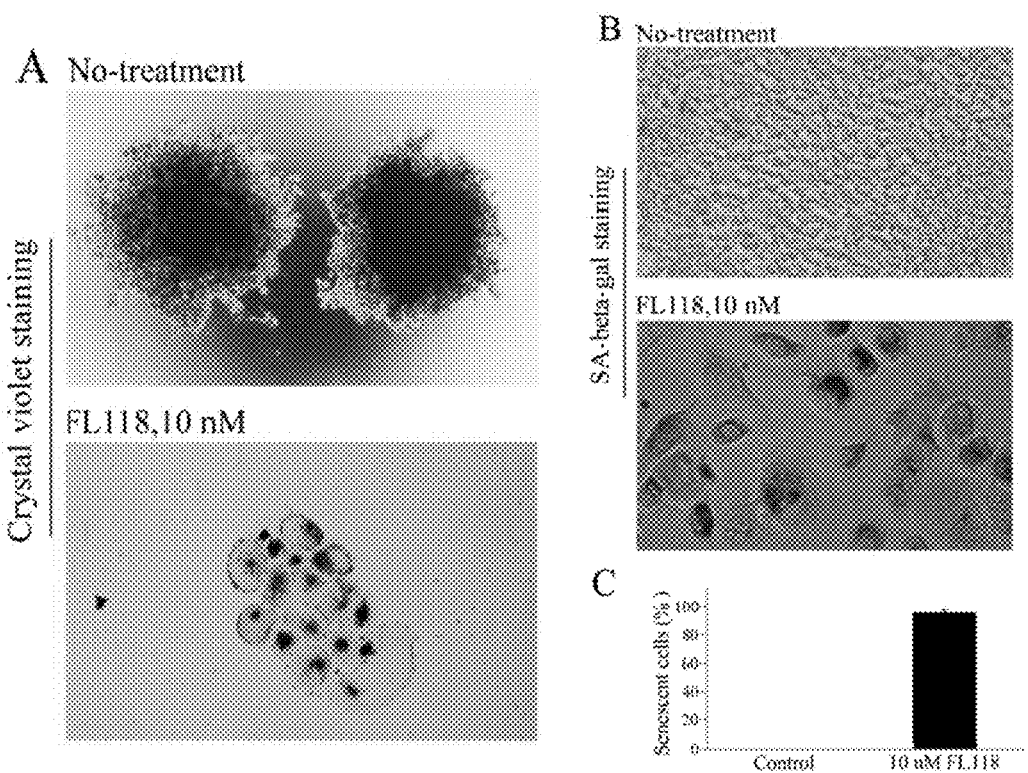
FIG. 8 shows that FL118 induces p53-dependent senescence. A. Morphology of colonies of HCT-8 cells in non-treated control and cell clusters of HCT-8 cells after 10 nM FL118 for 10 days stained with crystal violet solution. HCT-8 cells in colonies are small, round and stacking on each other whereas HCT-8 cells after 10 nM FL118 treatment show enlarged cell size and are adherent to the surface of plate in a loose morphology without stacking on each other. B. Effects of FL118 on SA-β-gal positivity. HCT-8 cells without treatment or treated with 10 nM FL118 for 3 days followed by another 10-day culture in drug-free medium. The cells are stained for SA-b-gal activity. C. Histogram of senescent HCT-8 cells in percentage of total cells after 10 nM FL118 treatment is shown for the experiments performed in B.
Figure 9:
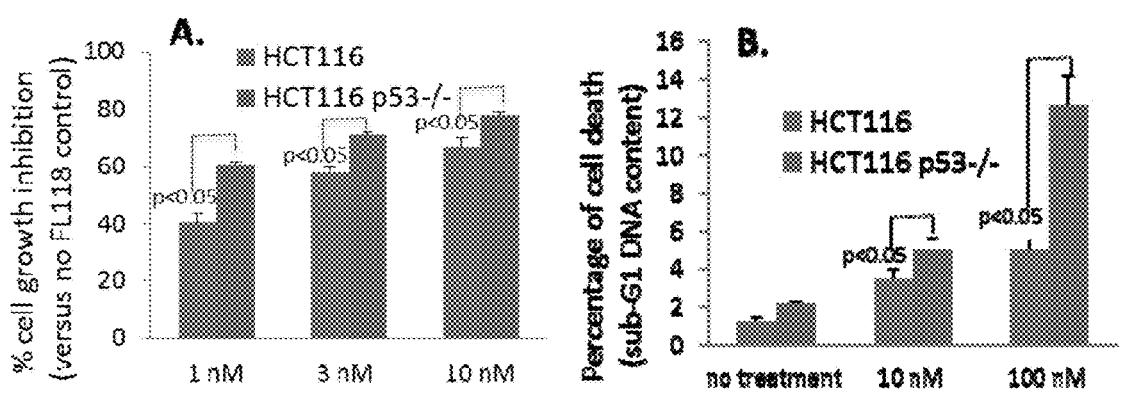
FIG. 9 shows that FL118 is more effective to inhibit cell growth (A) and induce cell killing (B) in p53-null HCT116 cells than in wild type HCT116. Subconfluent cells are treated with and without FL118 for 72 h, followed by measuring cell growth inhibition using MTT assays (A) or by measuring sub-G1 DNA content (death cells) using flow cytometry (B). Data are the mean±SD from three independent experiments at least in triplicate.
Figure 10:
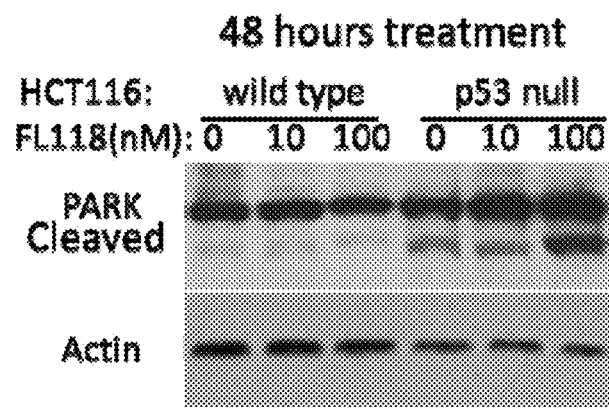
FIG. 10 shows that FL118 is more effective to induce PARP cleavage in p53 null HCT116 colon cancer cells than in p53 wild type HCT116 cells. Actin is used as internal controls for total protein loading.
Figure 11:
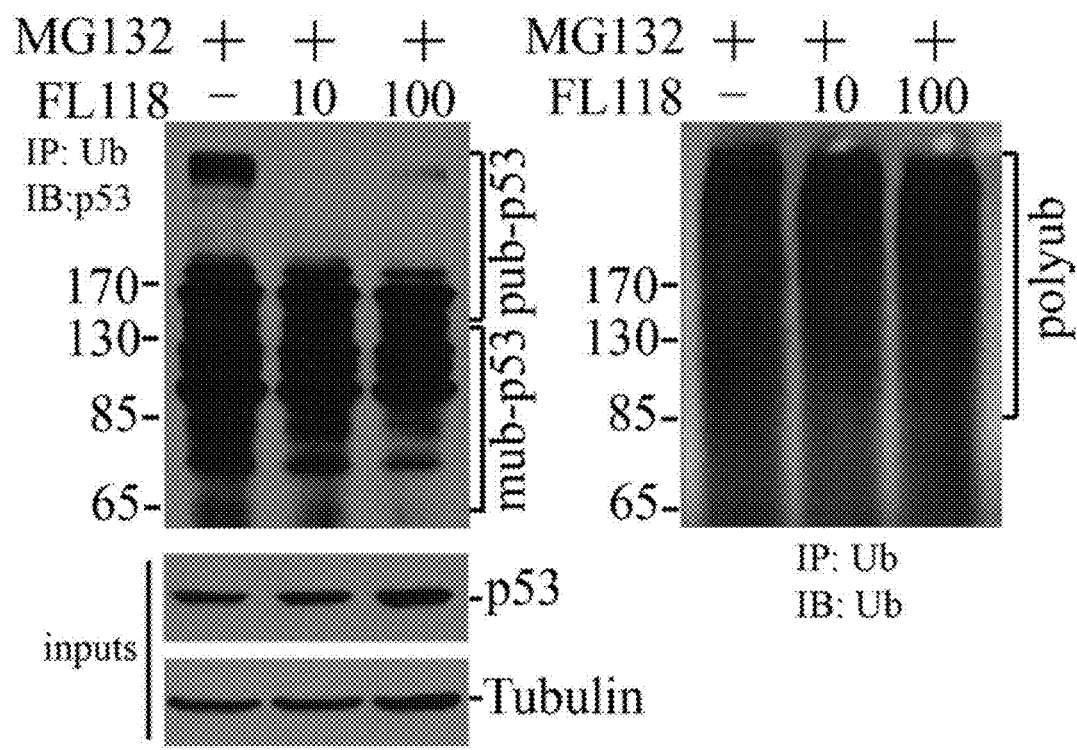
FIG. 11 shows that FL118 inhibits Hdm2-mediated p53 ubiquitination in cells. HCT-8 cells are treated with 10, and 100 nM FL118 for 24 h followed by 4 h treatment with 25 µM MG132. SDS-denatured cell lysates are used for in vivo ubiquitination assays by immunoprecipitation with anti-ubiquitin antibody followed by immunoblotting for p53 (left panel). Equal anti-ubiquitinin immunoprecipitation is monitored through re-probing the membrane with anti-ubiquitin antibody (right panel). Inputs for p53 and tubulin expression are used as internal controls (lower panel). Ubiquitination Assay: Whole cell lysates are denatured by adding SDS to final concentration of 1% followed by boiling for 5 min. The samples are diluted 10 times with 20 mM Tris, pH7.5-0.5% NP40-120 mM NaCl buffer followed by centrifugation at 22,000×g for 10 minutes. Ubiquitinated proteins are pulled down with an anti-ubiquitin antibody coupled with Western blotting for p53.

While p53 status does not affect FL118-mediated inhibition of cancer cell growth and induction of cancer cell death in vitro and in vivo overall, the mechanisms of action of FL118 to inhibit cancer cell growth and induce cancer cell death appear to be distinct. This nation is based on many observations. Some of the observations are presented here. First, FL118 is a strong wild type p53 inducer/activator in p53 wild type cancer cells (FIG. 6). Second, inhibition of cancer cell colony formation by FL118 in colony formation assay is independent of p53 status. Specifically, FL118 effectively inhibits cancer cell colony formation in both p53-intact cancer cells and cancer cells with p53 knockdown by p53-specific shRNA (FIG. 7). However, in the presence of wild type p53, FL118 inhibits colony formation through induction of cancer cell senescence (FIG. 8). In contrast, in the absence of wild type p53, FL118 inhibits colony formation through induction of cancer cell death. While the induction of cancer cell death by FL118 in cancer cells with different p53 status needs further investigation, it appears that cancer cells without p53 (p53 null) shows more sensitive to FL118 treatment in terms of cancer cell growth inhibition (FIG. 9A), cell death (FIG. 9B) and PARP cleavage, a hallmark of apoptosis (FIG. 10). It is rare for a drug that can be more sensitive to cancer cells without a functional p53. However, this may be partially because FL118-induced senescence is a much slower process than FL118 induced apoptosis. In any case, this is an exciting observation to make FL118 stand out for an important platform for making novel FL118 derivatives. Our recent studied reveal that FL118 inhibits p53 ubiquitination by HdM2 in cancer cells. As shown in FIG. 11, FL118 treatment for 8 h in the presence of proteasome inhibitor MG132 significantly reduced polyubiquitination of endogenous p53 (pub-p53) in HCT-8 cells (FIG. 11, top left panel), accompanied with evident reduction in multi-monoubiquitinated p53 (mub-p53, FIG. 11, top left panel). Re-probing the same membrane with anti-ubiquitin antibody after stripping indicated the immunoprecipitation efficiencies are comparable between the non-treated and treated samples (FIG. 11, top right panel, polyub).

FL118 Downregulates HdmX (Human MdmX), which Involves HdmX Protein Degradation, which Provides a Bright Window for FL118 Derivatives to Selectively Target Cancer.

Figure 12:
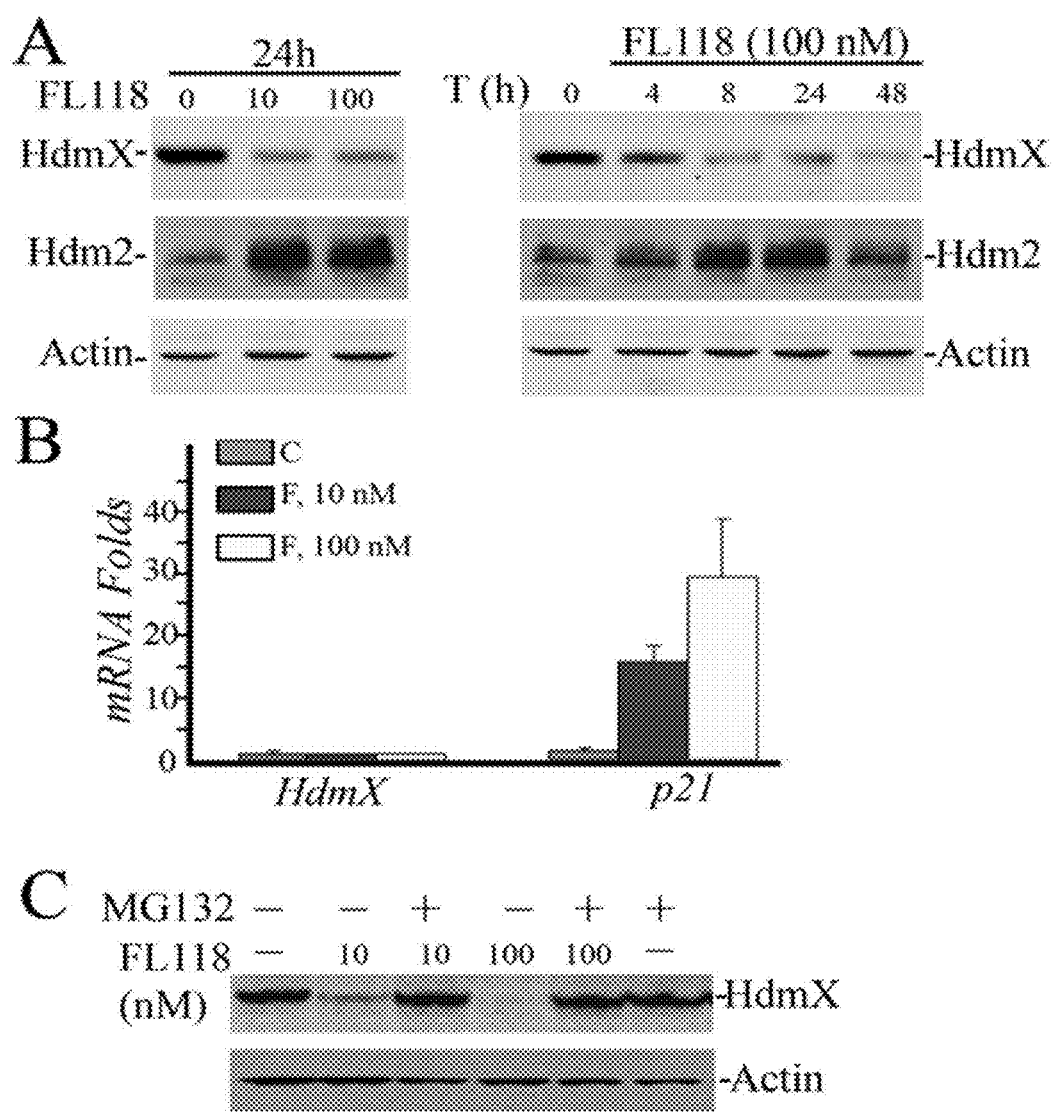
FIG. 12 shows that FL118 promotes proteasomal degradation of HdmX but not Hdm2. A. Western blot analysis of the effects of FL118 at different concentrations on HdmX and Hdm2. HCT-8 cells are treated with FL118 at 10 and 100 nM for 24 h (left panel) or treated at 100 nM and sampled at various time points (right panel). The changes in HdmX and Hdm2 protein levels are revealed by immunoblotting. B. Effects of FL118 on transcription of HdmX analyzed by quantitative PCR with p21 as a positive control using RNA samples prepared from FL118-treated HCT-8 cells. C. Rescue of HdmX degradation by proteasome inhibitor MG132. HCT-8 cells are treated at the indicated concentrations of FL118 for 24 h followed by 4 h treatment with or without 25 µM MG132 as shown. Cell lysates are then analyzed by immunoblotting of HdmX. Actin expression is used as an internal control.

Since p53 polyubiquitination is mediated by Hdm2 (human Mdm2)-HdmX complex and is required for degradation of p53, we determine the inhibitory effects of FL118 on p53 ubiquitination is mediated by inhibition of Hdm2-HdmX activity. As shown in FIG. 12A (left panel), FL118 treatment induces expression of Hdm2 protein but inhibits expression of HdmX protein after treatment at 10 nM and 100 nM for 24 h. Results from time course experiment indicated that HdmX downregulation by FL118 is a rapid event occurring within as short as 4 h after FL118 treatment (FIG. 12A, right panel). We further determine whether HdmX is downregulated at transcriptional level or post-transcriptional level, we performed quantitative real time PCR. Our results indicate that FL118 treatment does not significantly alter the mRNA levels of HdmX but increases the control gene p21 mRNA levels after FL118 treatment for 8 h (FIG. 12B), indicating that modulation of HdmX by FL118 is post-transcriptional event and FL118-mediated p53 accumulation increased p21 transcription. However, the presence of MG132 during 8 h treatment with FL118 rescues HdmX downregulation (FIG. 12C), indicating that a proteasomal degradation mechanism is involved in HdmX downregulation induced by FL118 treatment.

FL118-Induced HdmX Protein Degradation is Independent of ATM, p53 and p21 Status, but Requires Hdm2, which Revealed the Unique Features of FL118 and its Derivatives in Comparison with Camptothecin-Derived Analogs, Irinotecan, SN-38 and Topotecan.

Figure 13:
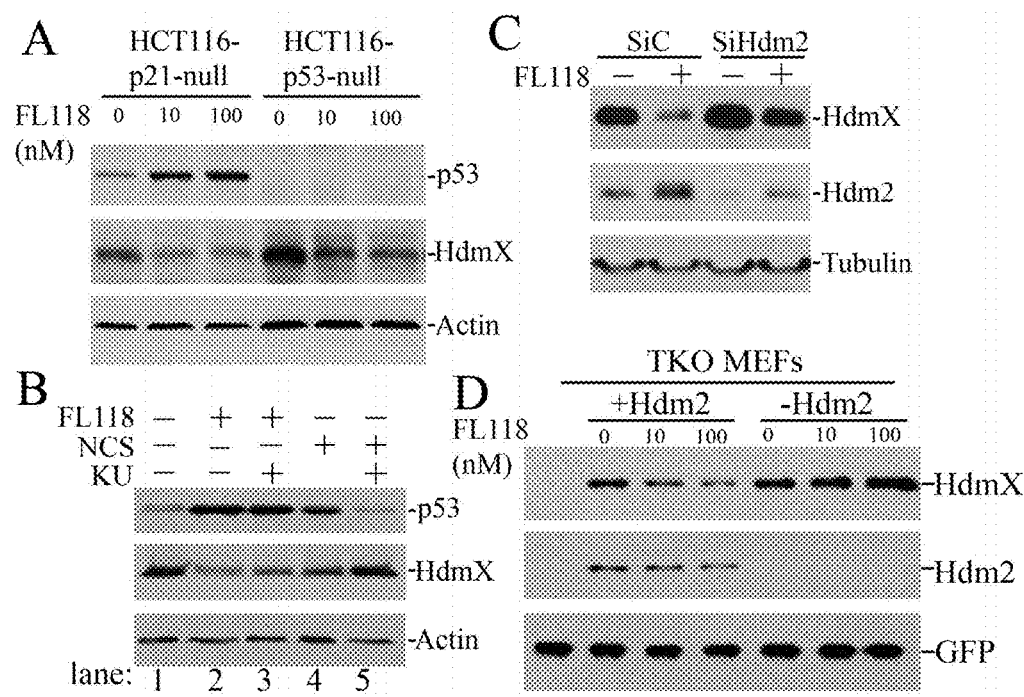
FIG. 13 shows the role of p53, p21, ATM and Hdm2 on FL118-induced HdmX degradation. A. Western blot analysis of the effects of p21 and p53 on FL118-induced HdmX degradation. HCT116-p21-null or HCT116-p53-null cells are treated with FL118 at 10 and 100 nM for 24 h and cell lysates are used for WB analysis for p53 and HdmX expression. B. Western blot analysis of the effects of inhibition of ATM on the FL118-induced HdmX degradation. HCT-8 cells are treated for 8 h with FL118 (100 nM) or neocarzinostatin (NCS, 40 µM) in the presence or absence of ATM inhibitor KU55933 (KU, 10 µM). Cell lysates are used for WB for p53 and HdmX expression. C. Western blot analysis of the effects of Hdm2 knockdown on the FL118-induced HdmX degradation. HCT-8 cells are transfected with control siRNA (SiC) or siRNA for Hdm2 (SiHdm2) followed by 100 nM FL118 treatment for 24 h. Cell lysates are used for WB for HdmX expression. D. FL118 down regulates HdmX via Hdm2.

Furthermore, experiments using HCT116 cells with p53-null or p21-null status were performed. We find that FL118-induced HdmX downregulation does not require p53 or p21 since FL118 induced HdmX degradation was not affected by p53 or p21 status (FIG. 13A). Next, we use an ATM-specific inhibitor KU55933 to inhibit ATM activity and examined the requirement of ATM-dependent DNA damage signaling in this process. We find that inhibition of ATM with KU55933 has minimal effect on FL118-induced HdmX degradation or p53 accumulation (FIG. 13B, compare lane 2 with 3). As a positive control of KU55933 treatment, we use neocarzinostatin, a radiation-mimicking DNA damage agent for treatment. Our results show that HdmX downregulation by neocarzinostatin is strictly dependent on ATM thus completely rescued by the presence of KU55933 (FIG. 13B, compare lane 4 with 5). These results indicate that FL118-induced HdmX degradation involves an ATM-independent process. This is a distinct feature from other camptothecin analogs, irinotecan, SN-38 and topotecan.

Next, we determine whether FL118 induced HdmX degradation is also mediated by Hdm2. We use siRNA to knockdown Hdm2 in HCT-8 cells and look at the HdmX levels after FL118 treatment. Our results indicate that knockdown of Hdm2 at least partially rescues FL118-induced HdmX degradation even Hdm2 is not completely knocked down (FIG. 13C), indicating that Hdm2 plays an important role in the proteasomal degradation of HdmX after FL118 treatment. Since the Hdm2 knockdown is not complete, we next address the role of Hdm2 in an unambiguously way. We use p53/mdm2/mdmx triple knockout (TKO) MEF cells to test the dependence of HdmX degradation induced by FL118. Our results indicate that presence of Hdm2 in HdmX-co-transfected cells is required for FL118-induced HdmX degradation, since absence of Hdm2 totally abolishes the effect of FL118 on HdmX degradation (FIG. 13D).

FL118 Inhibits Hdm2-Mediated p53 Ubiquitination in the Hdm2-HdmX Complex but Promotes Hdm2-Mediated HdmX Ubiquitination and Degradation, which Provides a Strategy for FL118 and its Derivatives to Control Both p53-Dependent and p53-Independent Cancer Cell Signaling for Treatment of Human Disease.

Figure 14:
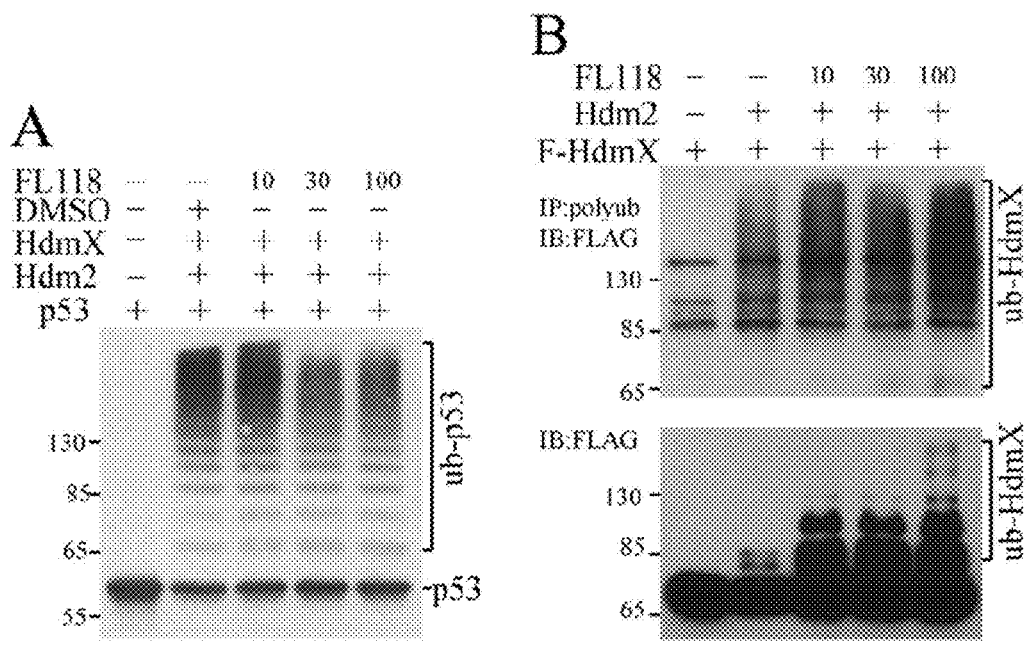
FIG. 14 shows that FL118 inhibits Hdm2-mediated p53 ubiquitination but promotes HdmX ubiquitination in the Hdm2/HdmX complex. A. FL118 effects on p53 ubiquitination in vitro. Proteins for 100 nM p53, 200 nM Hdm2 and FLAG-HdmX are included in the in vitro ubiquitination reaction in the presence of indicated concentrations of FL118 or DMSO followed by Western blots for detecting p53 expression. The ubiquitinated p53 (Ub-p53) bands are detected as shown. B. FL118 effects on HdmX ubiquitination in vitro. The experiments are performed as in A followed by Western blots for detecting FLAG-HdmX (IB: FLAG, lower panel) or followed by immunoprecipitation with polyubiquitin antibody followed by WB for FLAG (IP: polyub, IB: FLAG, upper panel). IB: immuno-blotting, IP: immunoprecipitation.
Figure 15:
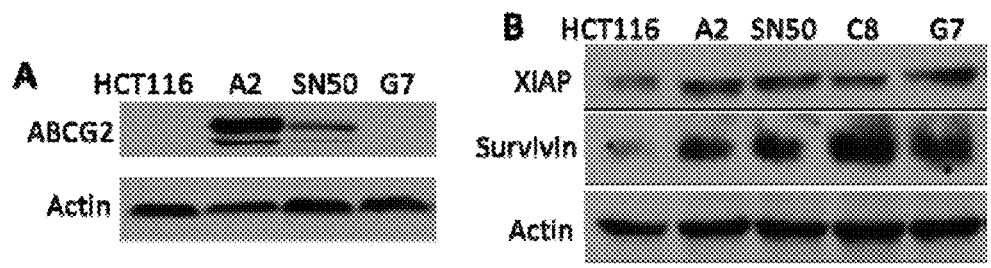
FIG. 15 shows the association of topoisomerase 1 (Top1) mutation and/or ABCG2 overexpression with increased survivin and XIAP expression among the HCT116 colon cancer cell lines and HCT116-derived four sub-lines with Top1 mutations (A2, SN50, C8, G7) and ABCG2 overexpression (A2, SN50): Subconfluent cells grown in culture as shown are lysed for Western blot analysis with corresponding antibodies. A. ABCG2 expression in HCT116-derived sublines with Top1 mutation (A2, SN50, G7). B. Expression of survivin and XIAP is increased in Top1-mutated colon cancer cell lines with or with ABCG2 overexpression. Actin is an internal control for equal protein loading. No significant changes for Mcl-1 and cIAP2 expression are observed (data not shown).

To assess whether FL118 has the ability to shift Hdm2-mediated p53 ubiquitination to Hdm2-mediated HdmX ubiquitination in the Hdm2-HdmX E3 complex and thus, FL118 stabilizes p53 and destabilizes HdmX, we have performed in vitro p53 ubiquitination by Mdm2-MdmX using recombinant proteins in the presence or absence of FL118. We find that FL118 moderately inhibits Mdm2-MdmX mediated p53 polyubiquitination reaction in vitro (FIG. 14A). Since FL118-induced proteasomal degradation of HdmX requires Hdm2 (FIG. 13C, D), it is possible that FL118 affects the Mdm2-MdmX E3 ligase activity in a way that makes HdmX a preferential substrate for polyubiquitination. To test this possibility, we examine the effects of FL118 on Hdm2-mediated HdmX ubiquitination in an in vitro reaction. Our results indicate that FL118 stimulates Hdm2-mediated HdmX ubiquitination in a concentration-dependent manner (FIG. 14B), contrasting the FL118 effects of inhibiting p53 ubiquitination by Hdm2-HdmX (compare FIG. 14A with B). These results indicate that FL118 treatment switches substrate preference of the Mdm2-MdmX E3 complex from p53 to MdmX for ubiquitination that results in proteasomal degradation of HdmX and consequently leading to p53 accumulation. This finding possesses significant clinical applications for treatment of human diseases including cancer by using FL118. This is because the center cross road of cell signaling through specific ubiquitination of downstream target proteins by the Hdm2/HdmX complex does not only include p53. Therefore, this provides a strategy to use FL118 to affect the central Hdm2/HdmX complex and thus, realizing FL118 to control p53-dependent and p53-independent signaling to treat human disease including cancer. In term, use of FL118 platform to generate FL118 analogs will diversify the clinical application of the FL118 derived chemical compounds for personalized medicine.

Another Evidence that FL118 is an Important Platform for Producing Novel FL118 Analogs is the Fact that FL118 is not a Substrate of the ATP-Binding Cassette (ABC) Efflux Transporter ABCG2 (BCRP) and Possible Others Such as ABCC4 (MRP4), P/MDR1 (ABCB1), ABCC10 (MRP7), ABCC4 (MRP4) and ABCC5 (MRP5).

The drug efflux pump ABCG2/BCRP (breast cancer resistant protein) is an important member in the ATP-binding cassette (ABC) transporter family. ABCG2 is considered as a major cancer stem cell marker, functional molecule and drug resistant factor. Previous studies revealed that ABCG2 is a SN-38 and topotecan resistant factor. Cancer cells with high ABCG2 expression significantly increase SN-38 and topotecan resistance.

Figure 16:
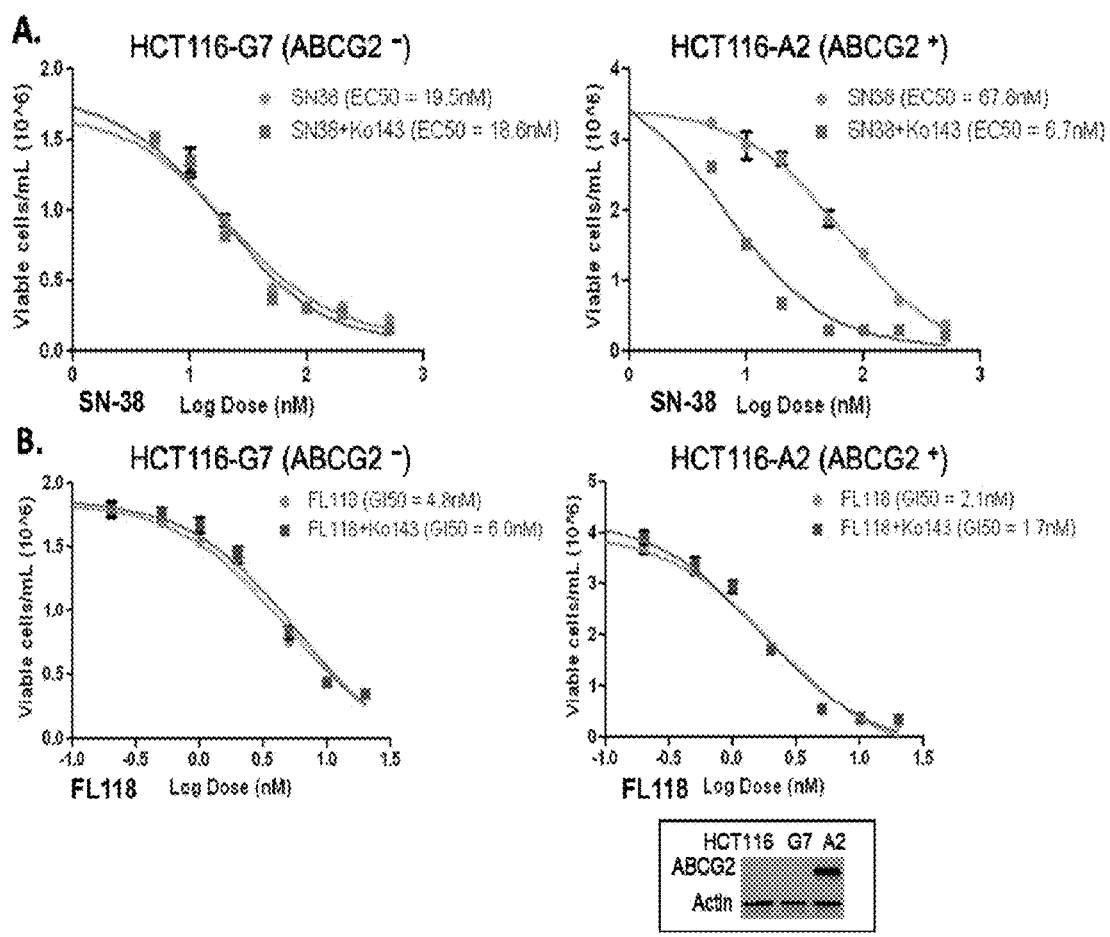
FIG. 16 shows the differential role of ABCG2 in resistance to SN-38 (active metabolite of irinotecan) and FL118. Sub-confluent ABCG2 positive (A2) and negative (G7) HCT116-derived colon cancer cells are treated with a series of SN-38 (A) or FL118 (B) concentrations in triplicate for 72 hours in the presence or absence of Ko143 at 1 µM concentrations as shown. Cell numbers are then counted at each drug concentration used. Data are shown as a curve of cell numbers over SN-38 (A) or FL118 (B) concentrations with or without Ko142. Cell numbers at each dot is the mean±SD derived from 3 independent assays. Data are plotted graphically and $EC_{50}$ values are calculated using GraphPad Prism 6.0.
Figure 17:
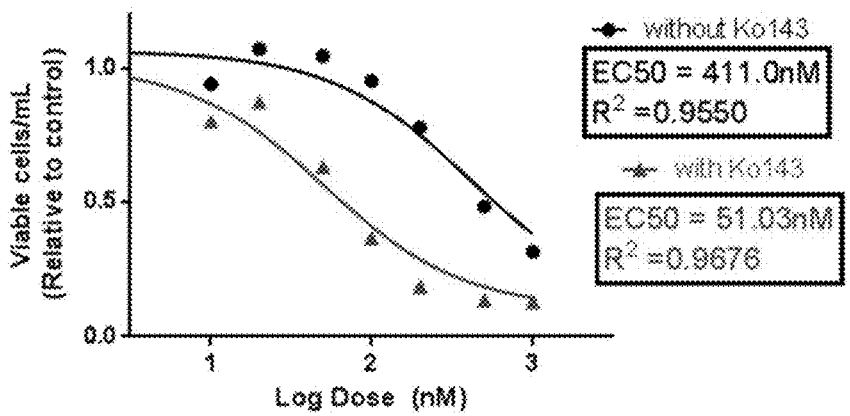
FIG. 17 shows the role of ABCG2 in topotecan resistance. ABCG2 positive HCT116-derived colon cancer cells (HCT116-A2) grown at sub-confluence are treated with a series of concentrations of topotecan in triplicate for 72 hours in the presence or absence of Ko143 at 1 µM concentrations as shown. Cell numbers are then counted at each topotecan concentration used. Data are shown as a curve of cell numbers over FL118 concentrations with or without Ko142. Cell numbers at each dot is the mean±SD derived from 3 independent assays. Data are plotted graphically and $EC_{50}$ values and R-values are calculated using GraphPad Prism 6.0.
Figure 18:
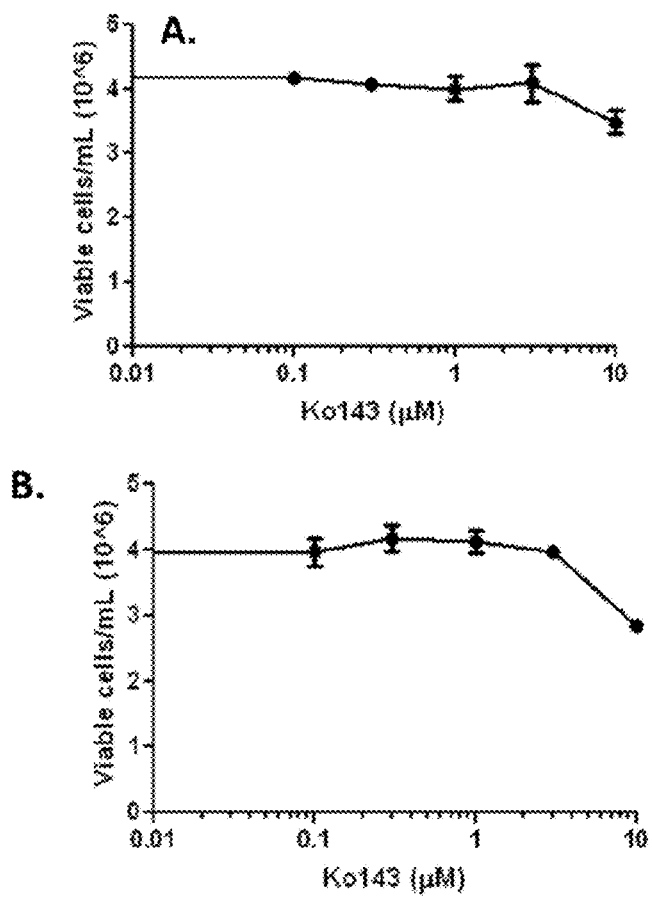
FIG. 18 shows the determination of non-toxic concentration range of Ko143, an ABCG2 selective inhibitor, on cancer cells. SW620 (A) and HCT116-A2 (B) colon cancer cells grown at sub-confluence are treated with a series of Ko143 concentrations in triplicate for 72 hours as shown. Cell numbers are then counted at each Ko143 concentration used. Data are shown as a curve of cell numbers over Ko143 concentrations. Cell numbers at each dot is the mean±SD derived from 3 independent assays.
Figure 19:
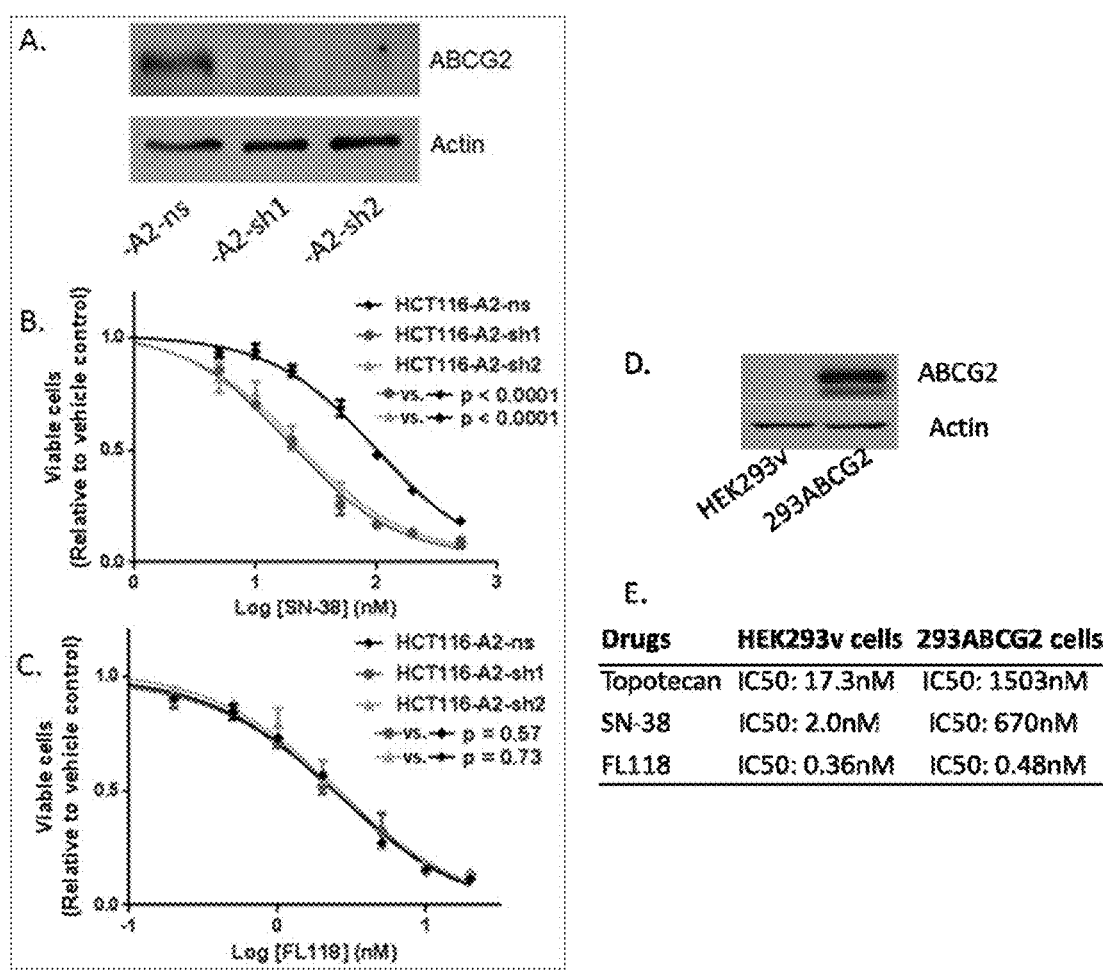
FIG. 19 shows the silencing or overexpression of ABCG2 does not affect the effectiveness of FL118 but significantly modulates SN-38 (active metabolite of irinotecan) and topotecan sensitivity. A. Silencing of ABCG2 expression in HCT116-A2 colon cancer cells by ABCG2 shRNA ((sh1=V3LHS 380805, sh2=V3LHS 380806).) was shown in western blots. Actin is internal control. B and C. Silencing of ABCG2 in HCT116-A2 cells significantly sensitizes SN-38 to inhibit cell growth but shows no effect to FL118. Cells at sub-confluence are infected with lentiviral particles containing nonsense shRNA (ns), or AGCG2-specific shRNA (sh1, sh2) to silence ABCG2 expression in the cells. Then infected cells are treated with a series of SN-38 (B) or FL118 (C) concentrations in triplicate for 72 hours as shown. Viability for each dose was determined using a ViCELL XR cell viability analyzer and normalized to that of DMSO control. Error bars=SEM, n=3 independent experiments. Data are plotted graphically and $EC_{50}$ values are calculated using GraphPad Prism 6.0. D. Stable overexpression of ABCG2 in HEK293 cells by transfection of pcDNA3-ABCG2 (393ABCG2) or pcDNA3 vector (HEK293v) was shown using western blots. E. Overexpression of ABCG2 in HEK293 cells significantly increases IC50 for topotecan and SN-38 but shows no resistant effects on FL118 IC50 for inhibition of cell growth.
Figure 20:
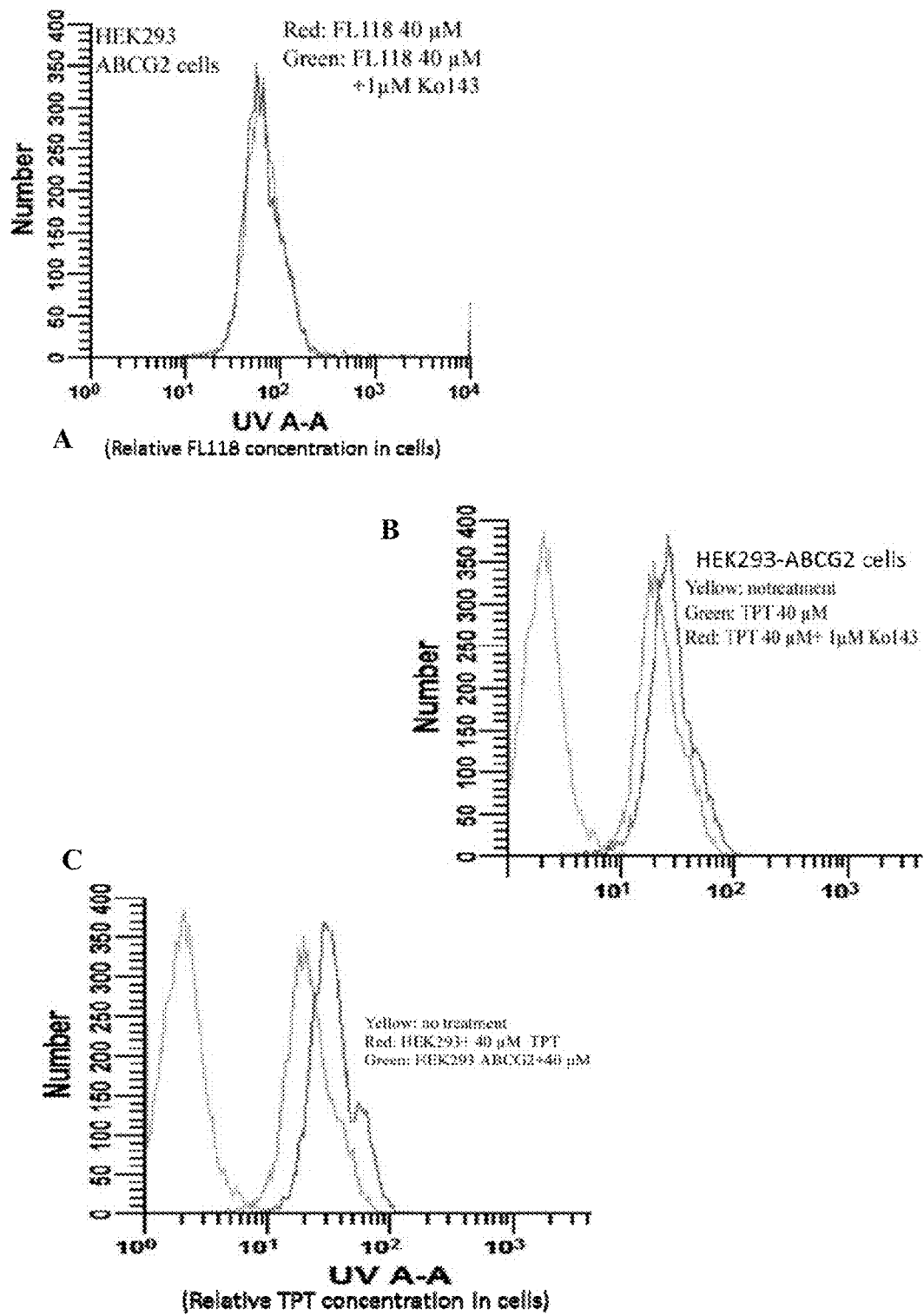
FIG. 20 shows the effects of forced expression of ABCG2 in HEK293 cells on the intracellular concentrations of topotecan (TPT) and FL118. HEK293 or HEK293-ABCG2 cells are treated with or without TPT or FL118 in the presence or absence of the ABCG2 inhibitor Ko143 for 8 hours. Then cells at the different treatment conditions are subject to flow cytometry to test the intracellular concentration of FL118 or TPT through UV light fluorescence over cell numbers as shown.
Figure 21:
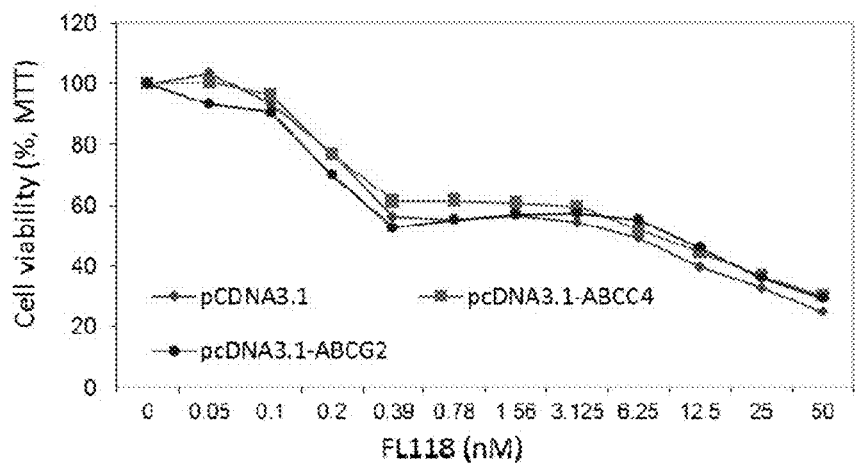
FIG. 21 shows that both ABCG2 and ABCC4 do not possess resistance to FL118-mediated cancer cell growth inhibition. HCT-8 colon cancer cells are transfected with empty vector (pcDNA3.1), ABCC4 or ABCG2 expression vectors as shown. Transfected cells are selected with G418 (800 µg/ml) for one week and then maintained at 400 µg/ml G418 for additional 3 days, cells are then treated with FL118 at 0, 0.05, 0.1 0.2 0.39, 0.78, 1.56, 3.125, 6.25, 12.5, 25 and 50 nM for 72 hours. Cell growth/viability is then determined by MTT assay. Cell viability mean curves over the FL118 concentration ranges are shown, which is derived from 5 independent wells in parallel with a variation of <10%.
Figure 22:
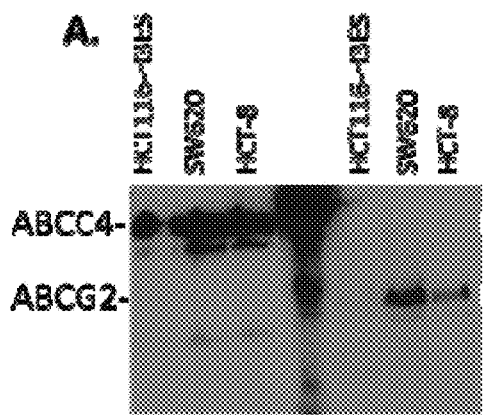
FIG. 22 shows the expression of ABCC4/MRP4 and ABCG2/BCRP in three types of colon cancer cells using Western blots (A) and the MTT assay results after FL118 treatment with or without inhibitors of MDR1, ABCG2 or ABCC4 (B). In A, sub-confluent cells are lysed and the cell lysates are analyzed using western blots with antibodies for ABCC4 or ABCG3. In B, sub-confluent SW620 colon cancer cells are treated for 3 days with or without a series of concentrations of FL118 in the presence and absence of various inhibitors as shown. Cell viability is then analyzed using MTT assays. The cell survival curves are the mean from three independent assays. Variations are within 10%. Of note, Sulindac: An ABCC4 inhibitor; Losartan: a MDR1 and ABCC4 inhibitor; KO143: An ABCG2 inhibitor; and Sildenafil: an inhibitor for MDR1, ABCG2, and ABCC4, and possible for ABCC4 (MRP4) and ABCC5 (MRP5) as well.
Figure 22:
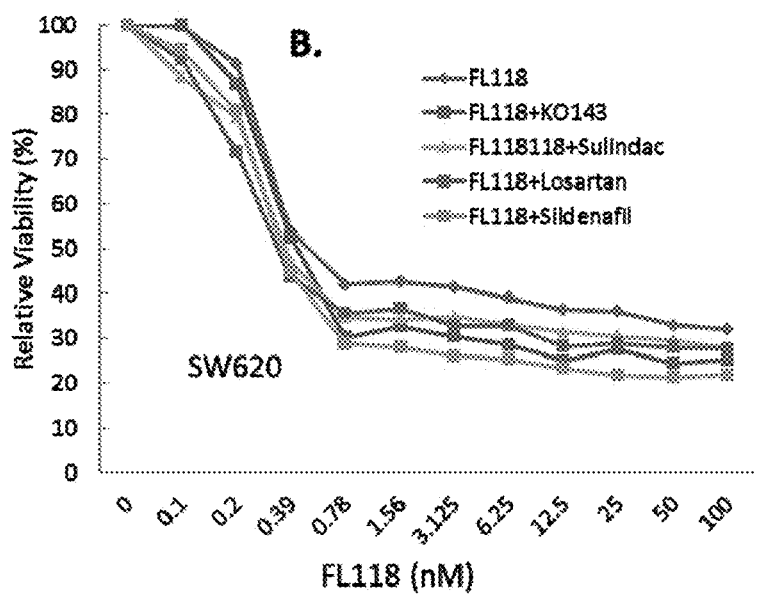
Figure 23:
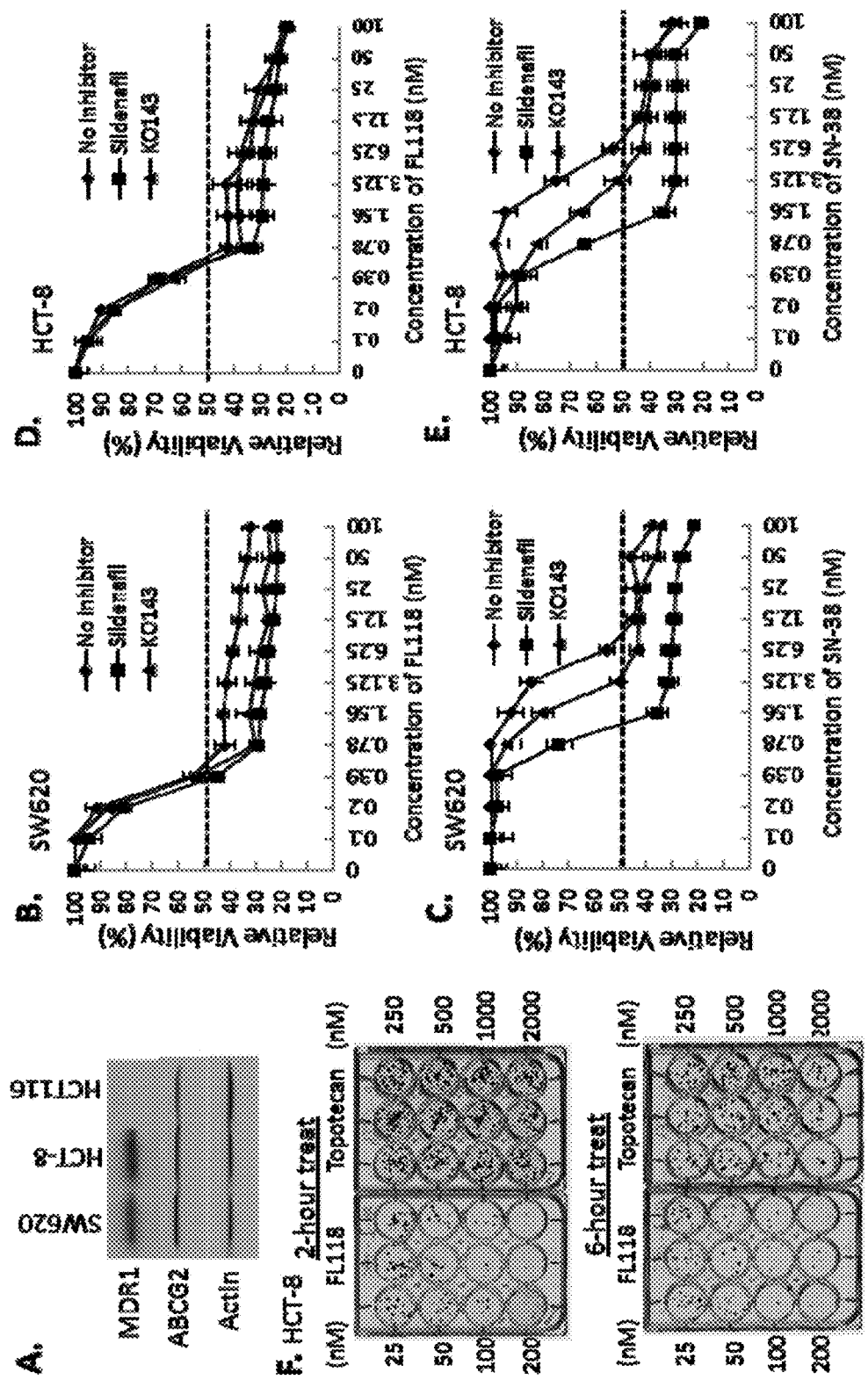
FIG. 23 shows that different from SN-38 and topotecan, FL118 can bypass drug resistance from ABCG2 and possible other efflux pump ATP-binding cassette (ABC) transporter proteins: A. Expression of MDR1 and ABCG2 in CRC cells. Subconfluent SW620, HCT-8, and HCT-116 cells were lysed and analyzed for the expression of MDR1 and ABCG2 using western blots (WB). Actin is the internal control. B to E. FL118 bypasses not only ABCG2 efflux pump protein-induced treatment resistance, but also other ABC transporter-induced treatment resistance. Subconfluent SW620 and HCT-8 colon cancer cells were treated with FL118 (B, D) or with SN-38 (C, E) at a series of concentrations as shown in the presence or absence of a multi-efflux pump protein inhibitor (sildenafil, 50 µM) or an ABCG2-specific inhibitor (KO143, 2 µM) for 3 days. Cell growth/viability was then analyzed by MTT assays. Each time point in the individual curve is the mean±SD from 3 to 5 independent assays. The dash lines cross individual IC50 values. F. FL118 is over a 100 time more effective to inhibit colony formation than topotecan. After seeding HCT-8 cells in 12-well plates at 100 cells per well overnight, cells were then treated with either FL118 or topotecan for 2 h (up panel) or 6 h (low panel) at a series of concentrations as shown. Drugs were then washed out and cells were allowed to grow in new medium without drugs for 2 weeks. Cell colonies were stained with crystal violet solution; images were digitally taken. Triplicate results are shown.

Clinically, development of resistance to irinotecan and topotecan occurs commonly during treatment, often involving the upregulation of ABCG2. By increasing the rate of drug export, ABCG2 decreases the amount of SN-38, irinotecan or topotecan that accumulates intracellularly, thereby protecting cancer cells from the cytotoxic effects of these chemotherapeutic drugs. Therefore, if FL118 can be proved not to be an ABCG2 substrate or is even an ABCG2 inhibitor, FL118 will bypass or inhibit the ABCG2-mediated drug resistance and thus, FL118 may overcome irinotecan and topotecan resistance due to ABCG2 overexpression. In this regard, using several HCT116-derived irinotecan-resistant colon cancer cell lines with or without ABCG2 overexpression (FIG. 15A), we have observed a decrease in the potency of SN-38 in irinotecan-resistant cells that overexpressed ABCG2 compared to cells that do not overexpress ABCG2; in contrast, this loss of potency is not observed for FL118. To confirm the decrease in potency was ABCG2-dependent, HCT116-A2, an ABCG2 overexpressing cell line, is treated with SN-38 or FL118 in the presence or absence of Ko143, an ABCG2 inhibitor. It was observed that Ko143 restores potency to SN-38 in HCT116-A2 cells (FIG. 16A), confirming that irinotecan resistance in HCT116-A2 cells is dependent on ABCG2. However, Ko143 does not modulate the potency of FL118 (FIG. 16B), further suggesting that FL118 is not affected by ABCG2 activity. Using the same approach, it was further demonstrated that ABCG2 is also a topotecan resistance factor (FIG. 17). Of note, the nontoxic concentration of Ko143 used in the experiment is identified carefully through testing a series of Ko142 concentration in cancer cell viability testing (FIG. 18). Alternatively, genetic knockdown of ABCG2 expression with anti-ABCG2 shRNA obtains similar results (FIG. 19A-C) as the use of the pharmacological ABCG2 inhibitor (Ko143) approach (FIG. 16). In contract, overexpression of ABCG2 in HEK293 cells significantly increases topotecan and SN-38 resistance but showed no resistant effects on FL118 (FIG. 19D, E). This is consistent with the data obtained via flow cytometry analysis of the intracellular concentration of topotecan and FL118 while overexpression of ABCG2 decreases intracellular concentration of topotecan but not FL118 (FIG. 20). Based on these observations, it can be concluded that FL118 is not a substrate of ABCG2 and can bypass ABCG2-mediated drug resistance. Furthermore, the inventor's genetic approach of forced expression of ABCG2 or ABCC4 in cancer cells demonstrates that overexpression of ABCC4 or ABCG2 fails to increase FL118 resistance (FIG. 21). Further studies indicate that FL118 may not be a substrates for many other ABC transporter proteins including, ABCB2, ABCC4, MDR1, Pgp, etc, which are suggested by the data shown in FIG. 22. Consistently, comparison studies between FL118 and SN-38 with and without ABC transporter-selective inhibitors in both SW620 and HCT-8 (FIG. 23) support the same conclusion obtained from FIG. 22. As a further proving, 2 hours or 6 hours of treatment of HCT-8 cells with FL118 obtained similar inhibition of colony formation (FIG. 23F); however, 6 hours of topotecan treatment showed significantly better colony formation inhibition than 2 hours topotecan treatment, suggesting that ABC transporters play a role in it (FIG. 23F). Since it has been reported that sildenafil can selectively reverse multiple ABC transporters-mediated drug resistance, including ABCB1 (P-glycoprotein/MDR1) and ABCG2 (BCRP), ABCC10 (MRP7) and possibly others such as ABCC4 (MRP4) and ABCC5 (MRP5), and in contrast to SN-38, sildenafil does not sensitize FL118 (FIG. 23), it is reasonable to interpret that FL118 can bypass multiple ABC transporters-induced resistance. Intriguingly, since all of the HCT116-derived A2, SN50 (also named C4), C8 and G7 have at least one site mutation in the topoisomerase 1 (Top1) protein, it is clear that Top1 mutation with or without ABCG2 overexpression is associated with enhanced survivin and XIAP expression (FIG. 15B).

FL118 and its Core Structure-Based Analogs Show Favorable Toxicology Profile in Animal Models, which Provides Further Evidence that FL118 is a Platform for Generation of Novel Anticancer Drugs.

Figure 24:
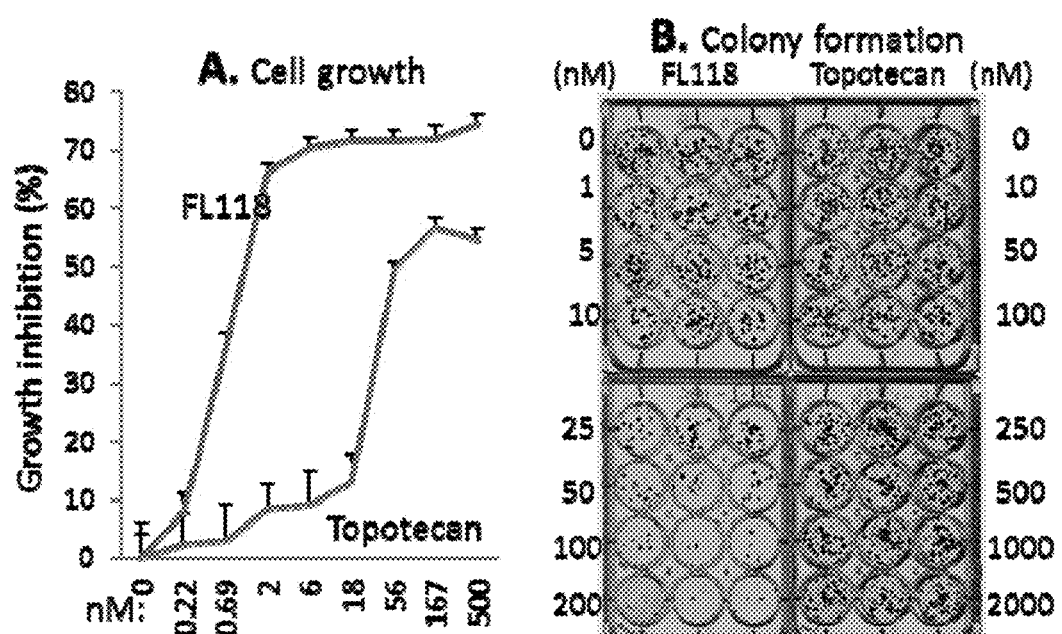
FIG. 24 shows that FL118 is at least 25-time more sensitive to colon cancer cells than topotecan. A. Cell growth: Subconfluent HCT-8 colon cancer cells are treated with either FL118 or topotecan as shown for 72 hours. Cell growth is then measured and the data are plotted as percentage of growth inhibition (no drug treatment was set at 0%). B. Colony formation: After seeding HCT-8 cells in 12-well plates for 100 cells per well for overnight, cells are then treated with either FL118 or topotecan for two hours at a series of concentrations as shown. C. Comparison of the effectiveness of SN-38, topotecan and FL118 in cancer growth inhibition and killing. Subconfluent SW620 cancer cells were treated with SN-38, topotecan and FL118 for 72 hours at 1 µM as shown. Representative cancer cell images were taken with a digital camera under phase-contrast microscope.
Figure 24:

A drug candidate toxicology profile is a critical issue that needs to be addressed before a drug being moved into clinical trials. While a complete profile of FL118 toxicology data is under investigation, there is a favorable toxicology profile basis for FL118 and highly promising for FL118-derive analogs as well. Several aspects support this conclusion. Firstly, FL118 selectively inhibits cancer-associated antiapoptotic proteins (survivin, Mcl-1, XIAP, cIAP2). These proteins are well known to be good therapeutic targets for keeping minimal toxicity to normal tissues, since these proteins, especially survivin, are expressed at a very low or an undetectable level in normal tissue and highly expressed in cancer. Secondly, cancer cells are usually addictive to the presence of these proteins for survival; interference of one or more of these proteins would inhibit tumor cell growth and induce apoptosis. However, normal tissues are relatively less sensitive to the modulation of these proteins. For example, studies revealed that FL118 is highly effective to inhibit cancer cell growth but much less effective to inhibit normal cell growth (Ling X, et al.: A Novel Small Molecule FL118 That Selectively Inhibits Survivin, Mcl-1, XIAP and cIAP2 in a p53-Independent Manner, Shows Superior Antitumor Activity, PLOS ONE 2012, 7:e45571); this is at least in part because normal cells showing low or negative expression of the targeted proteins as in the case of survivin. Thirdly, all normal cells have wild type p53; our studies indicated that cancer cells with mutant or null p53 are more sensitive to FL118 treatment than cancer cells with wild type p53 (FIG. 9). This provides a possibility that both p53-dependent and p53-independent pathways are involved in FL118 function to kill cancer cells. Our recent studies indicate that FL118 mainly induces cancer cell senescence when cancer cells with wild type 53 (FIGS. 7 and 8). Thus, it appears that FL118 mainly induces cancer cell apoptosis using a wild type p53-independent pathway if cancer cells with null or mutant p53. Importantly, the activated p53 can either induce cell death or arrest cell cycle, which depends on p53 downstream target activation. For example, p53 activation of cell cycle regulator p21 may result in cell cycle arrest without cell killing, while p53 activation of proapoptotic proteins Bax and/or Puma may result in cell killing. Therefore, FL118 may exhibit the use of differential pathways between cancer cells and normal cells in the case of wild type p53 in the cells. Therefore, while FL118 can effectively kill cancer cells, FL118 may show relative non-toxic to normal cells. Fourthly, although FL118 structurally has similarity to irinotecan, SN-38 and topotecan (FIG. 1), in contrast to these antitumor agents, FL118 is a poor Top1 inhibitor. While Top1 mutation significantly increases resistance to SN-38 and topotecan, FL118 is largely not affected (Table 1). In this regard, FL118 is much more effective to inhibit cancer cell growth and colony formation (FIG. 24) and effectively overcomes topotecan and irinotecan resistance in vivo (FIG. 25). Additionally, different from SN-38 and topotecan, FL118 is not an ABCG2 substrate, while SN-38 and topotecan are ABCG2 substrates (FIGS. 16, 17, 19). Furthermore, the results from our recent studies indicate that it appears that many ABC transporter efflux proteins may not be able to use FL118 as a substrate (FIGS. 21, 22, 23). Thus, FL118 can effectively kill cancer cells, while sparing normal cells. These and other (yet to be explored) characteristics appear to make FL118 stand out not only to be a much better antitumor agent with less toxicity to normal tissues in comparison with irinotecan, SN-38 and topotecan, but also to be an ideal platform for generation of novel FL118 platform-derived analogues. Finally, it appears that good formulation of FL118 could further decrease FL118 toxicity and increase its efficacy (Ling X, Li F: An intravenous (i.v.) route-compatible formulation of FL118, a survivin, Mcl-1, XIAP, and cIAP2 selective inhibitor, improves FL118 antitumor efficacy and therapeutic index (TI), American Journal of Translational Research 2013, 5:139-154, and other evidence shown in this invention). Our recent studies reveal that FL118 intravenous injection is rapidly accumulated in tumor but cleared from blood stream; while FL118 can be maintained in tumor over 48 hours, FL118 is cleared from blood within 12 hours (FIG. 26, Table 2). This may also contribute FL118 low toxicity to normal tissue and high efficacy to tumor. Again, all these features point to FL118 not only a good anticancer candidate for further development but also a good platform for generation of novel FL118 analogous compounds.

(CACNB1), Probable G-protein coupled receptor 1 (PG-PCR1), ubiquitin specific peptidase 2 (USP2), melanocortin 2 receptor (MC2R), Fibroblast growth factor 18 (FGF18), tumor protein p53 inducible protein 3 (TP53I3), CCHC-type zinc finger, nucleic acid binding protein (CNBP), WD repeat domain 22 (WDR22), Potassium voltage-gated channel subfamily E member 1 (PVGCSE-M1), ubiquitin-conjugating enzyme E2T (putative) (UBE2T), Ubiquitin-like protein 7 (ULP7), RNA binding motif, single stranded interacting protein 2 (RBMS2), Cytoplasmic tyrosine-protein kinase (BMX), and cyclin B1 interacting protein 1 (CCNB1IP1).

Cardiac Measurements and Analysis of a Comprehensive Panel of Chemical Parameters to Evaluate Toxicity of FL118 Using Blood Sample from SCID Mice Shows No Cardiac and Metabolic Toxicity in Comparison Vehicle Control, which Provide Additional Evidence for FL118 to be a Good Platform for Generation of Novel Derivatives.

Intravenously (IV), half of the maximal tolerated dose (½MTD) of FL118 (0.75 mg/kg) was administered via a schedule of q2d×4, followed by analysis of cardiac function, our experiments indicate that there is no difference between vehicle control and FL118-treated SCID mice in terms of the parameters of cardiac output, ejection fraction and stroke volume (FIG. 27). On the other hand, we have analyzed a comprehensive panel of chemical parameters to determine the potential chemical toxicity including renal and liver toxicity using blood samples from vehicle-treated SCID mice and FL118-treated mice. The analyzed parameters

TABLE 2

Pharmacokinetics (PK) parameters of FL118 in human tumor and mouse plasma following iv administration.

| Sample | $T_{1/2}$ (hr) | $T_{max}$ (hr) | $C_{max}$ (ng/g, ml) | AUC (hr*ng/g) | AUC∞ (hr*ng/g) | AUC % Extrap % | Vz (g/kg) (ml/kg) | Cl (g/hr/kg (ml/hr/kg) |
|---|---|---|---|---|---|---|---|---|
| FaDu | 6.852 | 0.167 | 115 | 413 | 448 | 7.74 | 33052 | 3343 |
| SW620 | 12.75 | 0.167 | 158 | 842 | 897 | 6.17 | 30742 | 1671 |
| Plasma | 1.788 | 0.167 | 43 | 82 | 104 | 21.7 | 36849 | 14287 |

FL118 Affinity Column Chromatography Purification Revealed Novel FL118 Biochemical Targets (Human Proteins).

These human protein targets include, but not limited to, heat shock protein 60 (HSP60), stress-70 protein (GRP75), ATP-dependent RNA helicase DDX5 (p68), nucleolar RNA helicase 2 (DDX21), elongation factor 2 (EF2), pre-mRNA-splicing factor ATP-dependent RNA helicase (DHX15), Transitional endoplasmic reticulum ATPase (TERA), Transferrin receptor protein (TFR1), MAP kinase-activated protein kinase 2 (MAPK2), Catenin beta-1 (CTNB1), Early endosome antigen 1 (EEA1), Guanine nucleotide-binding protein subunit beta-2-like 1 (GBLP), Electron transfer flavoprotein subunit alpha (ETFA), Proteasome activator complex subunit 3 (PSME3), UPF0368 protein Cxorf26 (CX026), Peroxiredoxin-2 (PRDX2), Peroxiredoxin-1 (PRDX1), Thioredoxin-dependent peroxide reductase (PRDX3), Serine/arginine-rich splicing factor 3 (SRSF3), Proteasome subunit beta type-2 (PSB2), and Glutathione S-transferase P (GSTP1).

Protein Microarray (ProtoArray) Analysis of Over 9,000 Human Proteins Using FL118 as a Probe Revealed Novel FL118 Biochemical Targets.

These targets include, but not limited to, MAP/microtubule affinity-regulating kinase 3 (MARK3), DNA-damage inducible 1 (DDI1), tumor protein D52-like 2 (TPD52L2), calcium channel, voltage-dependent, beta 1 subunit include glucose (GLU), blood urea nitrogen (BUN), creatinine (CREA), inorganic phosphate (PHOS), calcium (CA), total protein (TP), albumin (ALB), alanine aminotransferase (ALT), alkaline phosphatase (ALKP), Gamma-glutamyl transferase (GGT), total bilirubin (TBIL), cholesterol (CHOL), and amylase (AMYL), lipase (LIPA). The analysis indicates that the parameters of FL118-treated blood samples have similar to or even better than the parameters obtained from vehicle-treated SCID mice-collected blood samples (FIG. 28).

The E-Ring of FL118 is not in an Opening State and its Core Structure is Highly Stable, the Feature of which Gives FL118 to be an Ideal Platform for Generating Derivatives.

One critic question for FL118 to be used as a platform is whether the core structure and antitumor activity of FL118 is stable in solution. Our studies indicate that FL118 shows highly stable in solution, and the E-ring of FL118 is not in an opening state in solution (FIG. 29B). Furthermore, our studies indicate that FL118 formulated in the ready-to-use solution is stored in the 4° C. refrigerator for 6 months; then the FL118 solutions are used in animal model work to test FL118 antitumor activity, the 6-month-stored FL118 solution is as effective as the newly formulated solution (FIG. 29C). This provides further support for FL118 as a platform-based composition for deriving additional antitumor compounds.

FL118 Effectively Inhibits Ascites Production Induced by Leukemia and Extend Mouse Survival Time, which Provide an Additional Evidence for FL118 and Possible its Derivatives to be Used as Broad-Spectrum Drugs for Treatment of Human Cancer.

In a human leukemia animal model, we demonstrate that FL118 effectively inhibits ascites production and extends animal survival in an aggressive human EU-4 acute lymphocytic leukemia (ALL) mouse model (FIG. 30). As shown, mice without FL118 treatment get weight and enlarge belly rapidly (indicating the production of ascites), which cause mouse death within 4 weeks. However, mice with FL118 treatment do not show rapid body weight increase and no belly enlargement is observed throughout the experiment period without further FL118 treatment, suggesting no ascites production. Of note, "died with ascites" means mice at a moribund/dying state and then being euthanized. This is because moribund mice need to be euthanized based on the animal protocol rule.

Consistent with the Fact that FL118 is not a Substrate of Both ABCG2 and Possible Other ABC Transporter Proteins (FIGS. 16-23), Our Developed Oral Formulation of FL118 Demonstrated that Oral Administration of FL118 Increase FL118 MTD in Comparison with IV Injection (10 mg/kg for Oral Weekly×4 Versus 5 mg/kg IV Injection Weekly×4) with Minimal Body Weight Loss (FIG. 31).

Oral administration of FL118 can result in significant inhibition of SW620 tumor growth in comparison with saline or vehicle control. FL118 shows efficacy as low as 0.625 mg/kg (FIG. 32). Based on the stringent TI definition: complete inhibition of tumor growth for at least 7 days after FL118 treatment (not tumor grows larger than the size on Day 0), we obtain a therapeutic index (TI) as about 4.

The Data Shown in FIG. 33 Suggest that FL118 Itself May be Developed for Personalized Cancer Treatment (Personalized Medicine) in Clinical Practice.

The definition of personalized cancer treatment is that a targeted drug will show super-effective to a particular group of cancer patients' tumor with special genetic alterations. As we know, cancer is highly heterogeneity. Individual tumor for the same type of cancer in different individuals could have much different sensitivity to a targeted anticancer agent due to different genetic background/alterations. In this regard, our studies showed that FL118 exhibits very similar antitumor activity to the same tumor on different SCID mice (FIG. 33A, B). In contrast, FL118 exhibits much different efficacy to different tumors of the same type (e.g. pancreatic cancer shown here in FIG. 33C). This means that FL118 will show super effectiveness for a sub-group of cancer with matched genetic alternations. Therefore, our future studies will reveal what genetic alternations are sensitive to FL118 and what genetic alterations are resistant to FL118 by characterizing each of the individual PDX genetic changes using next generation sequencing (NGS) technology.

Screening of 146 Camptothecin Analogs in Our Selection Processes Provides Additional Evidence that FL118 Platform-Derived Compounds are Highly Promising Both for Cancer Treatment in General and for Personalized Medicine.

Screening of 146 camptothecin analogs was performed. After testing the targeting profile of these compounds as well as their anticancer cell growth versus anti-normal cell growth, we have identified 19 best compounds and find that all of these 19 compounds possess the core structure of FL118, which provides additional evidence that FL118 is a great platform for generating novel anticancer compounds.

Compounds Derived from the FL118 Core Structure Platform are Promising Anticancer Drugs for Personalized Cancer Treatment (Personalized Medicine).

In addition to the evidence provided above, our studies also reveal that while most (if not all) FL118 core structure platform-derived compounds exhibit high antitumor activity, the antitumor specificity of individual compounds shows cancer types and/or cancer genetic background-selectivity. In other words, (i) one compound may be very effective to certain human cancer but shows much less effective in control of other types of cancer or the same type of cancer with different genetic alterations; and (ii) different FL118 platform-derived compounds show distinct antitumor activity for the same type of cancer xenograft used in the testing. This finding has significant applications in clinical practice for treatment of human disease in a way that is called personalized or individualized medicine.

In one set of experiments using the parental HCT116 colon cancer cell line and five HCT116-derived colon cancer cell lines with topoisomerase 1 (Top1) mutations (NS6, G7, C8) or both Top1 mutation and ABCG2 overexpression (NS50/C4, A2), we find that FL118 shows much more effective to inhibit cancer cell growth in comparison with SN-38 and topotecan (Table 3). Together, these and other observations clearly provide strong evidence for us to have new perspectives that structurally very similar compounds derived from the FL118 core structure platform may exhibit distinct antitumor selectivity to cancer of different types of cancer of the same type but with different genetic backgrounds.

TABLE 3

Comparison of the relative potency (RP) of FL118 with topotecan and SN-38 in six colon cancer cell lines: Parental cell line (HCT116); HCT116-derived topoisomerase 1 (Top1) mutated cell line (SN6, C4/SN50, A2, G7, C8) with (C4, A2) or without (HCT116, SN6, G7, C8) ABCG2 overexpression. RP was calculated by dividing the IC50 of topotecan with the IC50 of other corresponding individual drugs as shown.

| Cell lines | HCT116 | | HCT116-NS6 | | HCT116-C4 | | HCT116-A2 | | HCT116-G7 | | HCT116-C8 | |
|---|---|---|---|---|---|---|---|---|---|---|---|---|
| Drug | IC50 | RP | IC50 | RP | IC50 | RP | IC50 | RP | IC50 | RP | IC50 | RP |
| SN-38 | 0.1915 | 2.474 | 1.115 | 5.055 | 25.71 | 3.337 | 43.41 | 2.499 | 4.765 | 4.048 | 8.472 | 44.69 |
| Topotecan | 0.7473 | 1 | 5.636 | 1 | 85.8 | 1 | 108.5 | 1 | 19.29 | 1 | 378.6 | 1 |
| FL118 | 0.0477 | 15.67 | 0.1379 | 40.87 | 0.1521 | 564.1 | 0.1628 | 666.5 | 1.189 | 16.22 | 0.0937 | 4041 |

Targeting or Bypassing of the Aberrant Expression of Survivin, Mcl-1, XIAP, cIAP1, HIF-1, ATP-Binding Cassette (ABC) Transporters (e.g. ABCG2, ABCC4, MDR1), HdmX in the Hdm2/HdmX Complex or Loss of Functional p53 are Important for FL118 Platform-Derived Anticancer Drugs to Exhibit High Efficacy for Treatment of Human Disease.

Overcoming treatment resistance is challenging because cancer cells always develop multiple treatment resistance mechanisms. Currently, researchers have mainly developed molecular targeting drugs that attack a single mechanism of resistance. Therefore, combination of one targeting agent with one or more classical cytotoxic agents is the current trend in modern clinical practice for treatment of cancer. While this approach has balanced efficacy versus toxicity with up-to-date technologies, this approach may not ultimately solve the issue due to its efficacy and toxicity limitation. In contract, FL118 and FL118 platform-derived compounds target or bypass a set of treatment resistant factors (survivin, Mcl-1, XIAP, cIAP2, HIF-1α, ABCG2, MRP1, MDR1, ABCC4, HdmX and wild type, mutant or null p53) to overcome the challenge of resistance during cancer treatment. We employ the FL118 core structure platform to generate a series of FL118 platform-derived analogous compounds through 32 different approaches by modifying FL118 core structure. Thus, we will have a series of novel anticancer compounds to deal with resistant cancer types induced by combinational different resistant factors listed above (please refer to this patent's sister patent entitled "synthesis and application of FL118 core structure platform-derived analogues for human disease treatment", which will further demonstrate the application of these FL118 platform-derived compounds to realize personalized medicine (personalized cancer treatment) by targeting multiple treatment resistant factors at the same time.

FL118 Produces Synergistic Effects in Combination of Curcumin on Colon Cancer in Terms of Efficacy, which Provide a Basis for Combinational Treatment of FL118 or FL118 Analogs with Other Anticancer Agents.

Colorectal cancer is the third most commonly diagnosed cancer in the United States and may cause about 50,830 deaths in 2013. There is an unmet need for new therapeutic strategies. Combination of natural compounds with pharmacological small molecular inhibitors to increase anticancer efficacy while minimizing toxicity is an attractive approach for management of cancer. Curcumin, a natural dietary compound, has been shown to inhibit multiple cancer cell signaling pathways involved in survival, proliferation, apoptosis, angiogenesis and metastasis. FL118, a novel camptothecin derivative and an IAP (inhibitor of apoptosis) inhibitor, significantly attenuates colon cancer cell growth in vitro and tumor growth in vivo. We find that curcumin enhances FL118 anti-cancer efficacy to induce colon cancer cell death (FIG. 34). The synergistic effect of FL118 in combination with curcumin treatment on colon cancer growth inhibition is further analyzed by the Combination Index (CI) equation developed by Chou-Talalay using a CalcuSyn program (Biosoft, Cambridge, UK). Our data demonstrate that FL118 shows a synergistic growth-inhibitory effect in combination with curcumin in colon cancer cells (FIG. 35). In conclusion, 1) combination of FL118 with curcumin might provide a novel therapeutic strategy in colon cancer treatment; and 2) FL118 platform-derived analog might be good for combinational treatment.

The Opposite Effect of Crolibulin, a Vascular Disruptive Agent (VDA), and FL118 on Survivin Expression in Cancer Cells Makes the Two Drugs be Ideal Candidates for Combinational Treatment, which Suggest FL118 Analogs May have Similar Potential for Combinational Treatment.

Crolibulin is an anticancer drug that targets endothelial cells of the cancer vasculature system. Therefore, crolibulin is considered as a vascular disrupt agent (VDA). Our ex vivo cell level studies reveal that crolibulin strongly induce survivin expression in cancer cells, and in contrast, FL118 inhibits survivin expression in cancer cells (FIG. 36A). This is consistent with our new finding that the human umbilical vein endothelial cells (HUVECS) is sensitive to crolibulin inhibition, while cancer cells are resistant to crolibulin inhibition (FIG. 36B). In contrast, HUVEC cells are insensitive to FL118 treatment, while cancer cells are sensitive to FL118 treatment. The oppose effect of crolibulin and FL118 could make these two agents be ideal candidates for combinational treatment.

Combination of FL118 with the Mutant K-Ras-Targeting Agent is Promising for Treatment of Pancreatic Cancer with K-Ras Mutation.

Currently, there are no effective therapies for pancreatic cancer with mutant K-ras. Using a novel screening approach with K-ras mutant cells versus normal cells, 15 chemical constituents are identified from the medicinal plant *Amoora rohituka*, and structurally analyzed by spectroscopic analyses. Over 50 derivatives, each with different side chain groups of the initial 15-hit compounds, are then semi-synthesized using diverse chemical reactions. Next, using ovarian K-Ras mutant T29Kt1 cells versus normal ovarian epithelial T29 cells as a system via synthetic lethality screening, we identified, among these derivatives, AMR-Me and AMR-MeOAc as the most potent compounds selected against the K-ras mutant cells (FIG. 37). Since AMR-Me and AMR-MeOAc show the best selectivity to cells with K-ras mutations (FIG. 37B), FL118 in combination with AMR-Me or AMR-MeOAc appear to be synergistic for pancreatic cancer.

Newly Developed Formulation May Improve FL118 and FL118 Analog Efficacy.

One approach to make FL118 or FL118 nanoparticles is as follows: Drug is dissolved in chloroform with pluronic F127. Pluronic acid and drug is mixed at a weight ratio of 5 to 1 (or at other ratios) in a glass vial and the organic solvent is removed with a rotary evaporator. The dried film is rehydrated using D5W (Pharmaceutical grade). When power is completely rehydrated, the mixture is then vortexed and sonicated in ice-cold water with a sonicator. The milky solution is vortexed and sonicated for s few cycles until a homogeneous colloidal solution is obtained. FL118-F127 nanoparticles are used for experiments.

Another approach to make nanoparticles for FL118 or FL118 analogs is through using a nanoprecipitation technique with assistance of DSPE-PEG [N-(Carbonyl-methoxypolyethyleneglycol 2000)-1,2-distearoyl-sn-glycero-3-phosphoethanolamine, sodium salt] and PLGA [poly(lactic-co-glycolic acid)]. A drug and PLGA are dissolved in DMSO or other organic solvent. DSPE-PEG was dissolved in 4% ethanol and preheated to 65° C. Then organic solution (Drug/PLGA/DMSO) is dropwise added into 4% ethanol solution (4 ml 100% ethanol in 96 ml dH2O) of DSPE-PEG-MAL (MAL is the maleimide end group of PEG) under stirring. The solution was vortexing for 3 min and then stirred for 2 h allowing for nanoparticle formation by self-assembly. Afterwards the solution is via dialysis (MWCO: 12-14 kDa) against water for 2 d to remove DMSO and excess amount of DSPE-PEG. Spray Dry formulations for oral administration of FL118 or FL118 analogs is an aspect of the present invention.

Development of DMSO-Containing Formulation into DMSO-Free Formulation for FL118 and FL118 Platform-Derived Analogues for Both Further Increase of MTD of FL118 or One of FL118 Platform-Based Analogues and Clinically Convenient Administration of FL118 or its Core Structure Platform-Derived Analogues.

All aqueous solutions or suspensions or any other forms of formulation which contain Formula 1 for administration are invented to be prepared in the following ways: 1) dissolve a solvent A (e.g. β cyclodextrin, hydroxypropyl-β-cyclodextrin, sulfobutylether-β-cyclodextrin) into a solvent B (e.g. DMSO, ethanol), and dissolve the Formula 1 compound into the solvent AB mixture. Then the resultant solution and/or suspension is subject to a process of lyophilization. The lyophilized substance mixture is then resuspended using an aqueous solution in the presence of one or more co-solvents such as propylene glycol, polyethylene glycols with or without a thickening agents such as tragacanth, acacia, hydroxypropyl methylcellulose, Methyl cellulose, carboxymethyl cellulose, sodium carboxymethyl cellulose, gelatin, xanthium gum. This process is a further enrichment of the previous invention See, e.g., PCT/US2011/058558 (Formulations of Water-Insoluble Chemical Compounds and Methods of Using a Formulation of Compound FL118 For Cancer Therapy); U.S. patent application Ser. No. 13/881,785; Canadian Patent Application 2,816,418; Chinese Patent Application 201180063530.5; and European Patent Organization Application 11837250.7, all of which are hereby incorporated by reference in their entirety.

The formulation for FL118 or an analogue of FL118 in a basic formulation recipe for in vivo studies contains FL118 or a FL118 analogue (0.1-2.5 mg/ml), DMSO (≤5%), and hydroxypropyl-β-cyclodextrin (0.1-2.5%, w/v) in saline, and the corresponding vehicle solution in the basic formulation recipe contains DMSO (≤5%), and hydroxypropyl-β-cyclodextrin (0.1-2.5%, w/v) in saline without FL118 or a FL118 analogue. The alternative advanced formulation for FL118 or its analogues in the DMSO-free formulation recipe for in vivo studies contains FL118 or a FL118 analogue (0.1-5.0 mg/ml) and hydroxypropyl-β-cyclodextrin (0.1-5%, w/v) in saline with up to 10% propylene glycol (PG) or up to 10% polyethylene glycol 400 (PEG400) or the combination of PG and PEG400 with total percentage up to 10%, and the corresponding vehicle solution in the DMSO-free formulation recipe is the corresponding solution without FL118.

Method for the formulation of DMSO-free solution/suspension containing FL118 or other compounds derived from Formula 1 for administration: A certain amount of hydroxypropyl-β-cyclodextrin or another type of cyclodextrin (Solvent A) was dissolved in DMSO (solvent B) to make a 1-30% Solvents A/B mixture. Then, FL118 or another compound derived from Formula 1 was dissolved into the Solvent A/B mixture to make a concentration of 1-30 mg/ml. A typical example was to use a 10-20% Solvent A mixed with Solvent B (w/v) to dissolve FL118 or another compound derived from Formula 1 to 10-20 mg/ml with aqueous solution. The resultant solution/suspension was then lyophilized for getting rid of DMSO. The resultant substance from the lyophilization process was then resuspended with saline containing one or two co-solvents such as propylene glycol (1-10%), polyethylene glycol 300 or 400 (1-10%) alone or in combination. A typical end formulation for drug administration is containing FL118 or a FL118 analogue 0.1-3 mg/ml, 0.1-3% hydroxypropyl-β-cyclodextrin, and 1% propylene glycol in saline. A typical oral administration is to use a solution that contains FL118 or a FL118 analogue 0.1-3 mg/ml, 0.1-3% hydroxypropyl-β-cyclodextrin, 1% propylene glycol and 2-5% thickening agents such as hydroxypropyl methylcellulose (a typical concentration is 2-3%) in saline. This solution is typically formulated as follows using 100 ml solution containing 2% hydroxypropyl methylcellulase (HPMC) and 1% propylene glycol as an example:

1. Weigh 2 g HPMC and put in a 50 ml sterile tube
2. Add 90° C. saline to less than 40 ml and shake well and then incubate the tube in 90° C. water bath for 3-5 hours (shaking 4-6 time)
3. Then put the 50 ml tube on a room temperature rotator (25-50 rpm) for rotating overnight (become thick solution with a lot bubbles).
4. 2000 rpm×2 min to eliminate air bobbles
5. Add room temperature saline to 40 ml and rotating 15 rpm×2 h, at RT
6. After 2000 rpm×2 min, divide 20 ml of the above solution to a new 50 ml sterile tube.
7. Add 0.5 ml PG into each 50 ml tube containing 20 ml above solution, and then add saline in the 50 ml tube to 50 ml for each tube. Then rotating 13-15 rpm×2-3 h at RT for 2 h to overnight to obtain (HPMC 2%, PG 1% in saline).
8. 2000 rpm×2 min to get rid of bobbles (if any) and store at 4° C. Now the solution (HPMC 2%, PG 1% in saline) is ready for formulating lyophilized FL118 or another compound derived from Formula 1.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting. In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

While various aspects and illustrative embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference herein in their entireties and for all purposes to the same extent as if each individual publication, patent, or patent application is specifically and individually incorporated by reference in its entirety for all purposes.

What is claimed is:

1. A compound of Formula 1, a tautomer of the compound, an isomer of the compound, a pharmaceutically acceptable salt of the compound, a pharmaceutically acceptable salt of the tautomer, a pharmaceutically acceptable salt of the isomer, or a mixture thereof, wherein Formula 1 has the following formula:

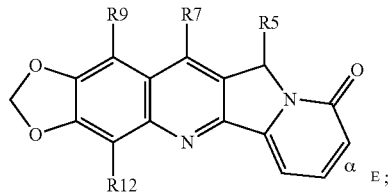

Formula 1 and wherein fused ring E is in the α position, and further wherein E is independently selected from the group consisting of group I structures, group II structures and group III structures:

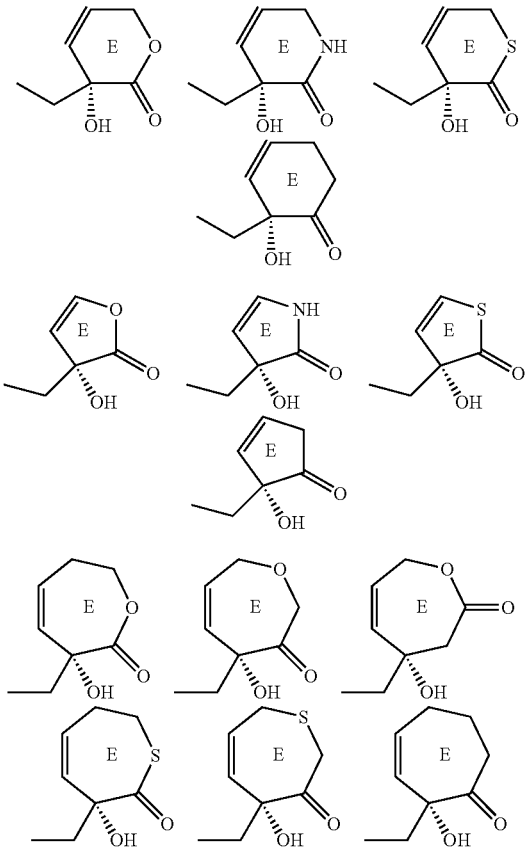

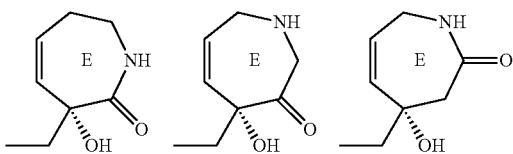

wherein $R^5$, $R^7$, $R^9$ and $R^{12}$ are selected from the group consisting of H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —$NHC(O)NH_2$, —$C(O)CH_3$, —$CO_2CH_3$, —$C(O)N(CH_2)_2$, and group IV structures:

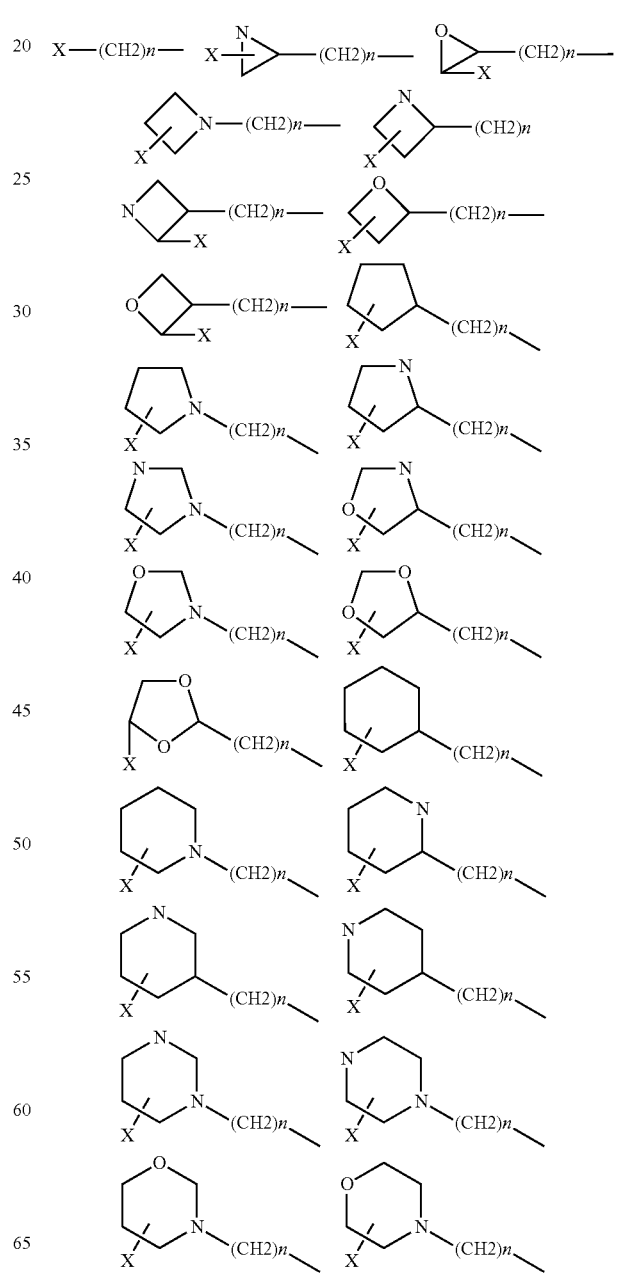

IV

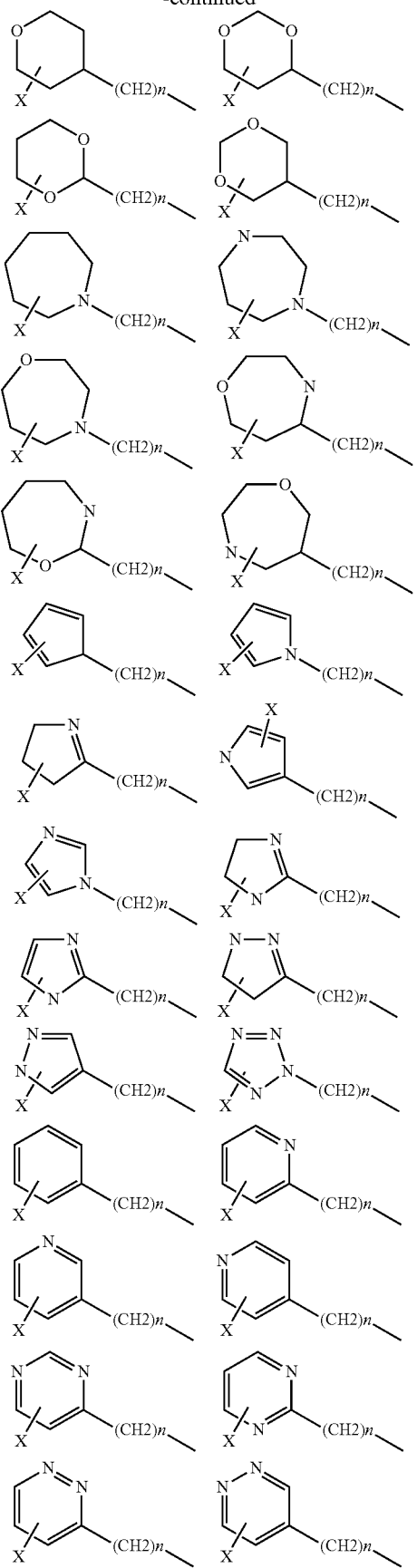

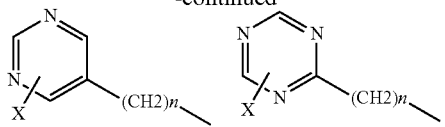

wherein X is independently selected from the group consisting of H—, F—, Cl—, Br—, I—, ClCH$_2$—, BrCH$_2$—, HO—, HONH—, CH$_3$O—, HOCH$_2$—, NH$_2$—, NH$_2$CH$_2$—, CH$_3$, —HOCH$_2$O, and wherein n is 0 or any integer from 1-15, wherein n is any integer from 1-15 when X is H;

wherein R$^5$, R$^7$, R$^9$ and R$^{12}$ cannot be simultaneously H—, and wherein when any of R$^5$, R$^7$, or R$^9$ is H—, then R$^{12}$ is selected from the group consisting of F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, —C(O)N(CH$_2$)$_2$, and the group IV structures, or wherein when R$^7$ is

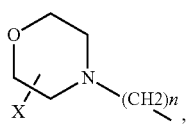

n is 2 and X is H, then each of R$^5$, R$^9$, and R$^{12}$ are H.

2. The compound of claim 1, wherein at least one functional group selected from the group consisting of R$^5$, R$^7$, and R$^9$ is H, and wherein at least one functional group selected from the group consisting of R$^5$, R$^7$, R$^9$ and R'$^2$ is selected from the group consisting of group IV structures, and further wherein at least one functional group selected from the group consisting of R$^5$, R$^7$, and R$^9$ is selected from the group consisting of H—, F—, Cl—, Br—, I—, FCH$_2$—, ClCH$_2$—, BrCH$_2$—, ICH$_2$—, HO—, HONH—, CH$_3$O—, HOCH$_2$—, NH$_2$—, NH$_2$CH$_2$—, CH$_3$NH—, (CH$_3$)$_2$N—, —NHC(O)NH$_2$, —C(O)CH$_3$, —CO$_2$CH$_3$, and —C(O)N(CH$_2$)$_2$.

3. A pharmaceutical composition comprising a compound of claim 1 for use with a subject or a disease in the subject, wherein the disease is a neoplastic, recurrent or metastatic disease, wherein the neoplastic, recurrent or metastatic disease comprises expression of one or more drug resistance targets, surrogates and/or biomarkers selected from the group consisting of survivin, Mcl-1, XIAP, cIAP2, ABCG2, ABCC4, MDR1, ABCC10, ABCC5, hypoxia inducing factor 1α (HIF-1α), Hdm2, HdmX, wild type p53, mutant p53, null p53, HSP60, GRP75, DDX5 (p68), DDX21, EF2, DHX15, TERA, TFR1, MAPK2, CTNB1, EEA1, GBLP, ETFA, PSME3, CX026, PRDX1, PRDX2, PRDX3, SRSF3, PSB2, GSTP1, MARK3, DDI1, TPD52L2, CACNB1, PGPCR1, USP2, MC2R, FGF18, TP53I3, CNBP, WDR22, PVGCSE-M1, UBE2T, ULP7, RBMS2, BMX, and CCNB1IP1.

4. The pharmaceutical composition of claim 3, wherein the pharmaceutical composition is configured to administer to a subject separately, sequentially or simultaneously with one or more agents selected from the group consisting of chemotherapeutic agents, chemopreventive agents, derived from natural plants, derived from non-plants and combinations thereof.

5. A formulation of the compound of claim 1, wherein the formulation comprises DMSO from about 0.1 to about 5% (w/v) in saline and hydroxypropyl-β-cyclodextrin from about 0.1 to about 5% (w/v) in saline in final concentration for administration.

6. A formulation of the compound of claim 1, wherein the formulation is DMSO free.

7. A formulation of the compound of claim 1, wherein the formulation comprises hydroxypropyl-β-cyclodextrin from 0.1 to 5% (w/v) in saline and from 0.1 to 10% propylene glycol (w/v) or polyethylene glycol 400 (w/v), or both, wherein the combination of the propylene glycol and polyethylene glycol is from 0.1 to 10% total (w/v).

8. The compound of claim 1, wherein at least two functional groups selected from the group consisting of $R^5$, $R^7$, and $R^9$ are H.

9. The compound of claim 1 wherein at least one functional group selected from the group consisting of $R^5$, $R^7$, $R^9$ and $R^{12}$ is selected from the group IV structures.

10. The compound of claim 1 wherein at least one functional group selected from the group consisting of $R^5$, $R^7$, and $R^9$ is selected from the group consisting of H—, F—, Cl—, Br—, I—, $FCH_2$—, $ClCH_2$—, $BrCH_2$—, $ICH_2$—, HO—, HONH—, $CH_3O$—, $HOCH_2$—, $NH_2$—, $NH_2CH_2$—, $CH_3NH$—, $(CH_3)_2N$—, —$NHC(O)NH_2$, —$C(O)CH_3$, —$CO_2CH_3$, and —$C(O)N(CH_2)_2$.

11. The pharmaceutical composition of claim 4, wherein the one or more agents derived from natural plants is selected from the group consisting of curcumin, resveratrol, vitamin D3, vitamin A, vitamin E, vitamin C, isothiocyanates (ITCs), allyl isothiocyanate (AITC), silibinin (silybin), Sulindac, selenium-containing compounds, Methylseleninic acid, *Amoora rohituka*-derived AMR analogs, AMR-Me, AMR-MeOAc, quercetin, Epigallocatechin-3-gallate (EGCG), Deguelin, 3,3'-Diindolylmethane (DIM), Emodin, Genistein, Gambogic acid, Docosahexaenoic acid, Ursolic acid, Oleanolic acid, Sulforaphane, Noscapine, Lupeol, Decursin, Avicin D, crolibulin, Baicalein, Paxilline, Anacardic acid, Diterpenes, Withaferin A, Plumbagin, Flavokawain A, Flavokawain B, Escin, Kuguacin J, Crotepoxide, Kuguaglycoside C, Evodiamine, and Sesamin.

12. The pharmaceutical composition of claim 4, wherein the one or more agents derived from non-plants is selected from the group consisting of terameprocol, celecoxib, imatinib, Tolfenamic acid, Simvastatin, Bufalin, Indomethacin (indomethacin), Ciglitazone, Bevacizumab (Avastin), Purvalanol A, NU6140, Ardisianone, NVP-BGT226, HDAC inhibitors, MS-275/Entinostat, SAHA, Bufotalin, Ponicidin, LQB-118, and Destruxin B.

* * * * *